United States Patent
Chen et al.

(10) Patent No.: US 11,673,892 B2
(45) Date of Patent: Jun. 13, 2023

(54) BICYCLIC COMPOUNDS FOR USE AS RIP1 KINASE INHIBITORS

(71) Applicant: Genentech, Inc., South San Francisco, CA (US)

(72) Inventors: Huifen Chen, Burlingame, CA (US); Gregory Hamilton, San Mateo, CA (US); Snahel Patel, Foster City, CA (US); Guiling Zhao, San Mateo, CA (US); Blake Daniels, Oakland, CA (US); Craig Stivala, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/844,952

(22) Filed: Apr. 9, 2020

(65) Prior Publication Data
US 2020/0283446 A1  Sep. 10, 2020

Related U.S. Application Data

(63) Continuation of application No. PCT/EP2018/077656, filed on Oct. 10, 2018.

(60) Provisional application No. 62/570,892, filed on Oct. 11, 2017.

(51) Int. Cl.
| C07D 487/04 | (2006.01) |
| C07D 519/00 | (2006.01) |
| A61P 25/28 | (2006.01) |
| A61K 31/4196 | (2006.01) |
| A61P 25/16 | (2006.01) |

(52) U.S. Cl.
CPC ............ *C07D 487/04* (2013.01); *A61P 25/28* (2018.01); *C07D 519/00* (2013.01); *C07B 2200/05* (2013.01)

(58) Field of Classification Search
CPC ..... C07D 487/04; C07D 519/00; A61P 25/28; A61P 25/16; C07B 2200/05; A61K 31/4196
See application file for complete search history.

(56) References Cited

U.S. PATENT DOCUMENTS

| 9,115,143 B2 | 8/2015 | Minne et al. |
| 11,149,019 B2 | 10/2021 | Kim et al. |
| 2017/0008877 A1 | 1/2017 | Patel et al. |
| 2020/0223821 A1 | 7/2020 | Kim et al. |

FOREIGN PATENT DOCUMENTS

| JP | 2012-051806 A | 3/2012 |
| JP | 2014-518286 A | 7/2014 |
| WO | 98/027092 A1 | 6/1998 |
| WO | 98/56376 A1 | 12/1998 |
| WO | 2002/012242 A2 | 2/2002 |
| WO | 2002/094833 A1 | 11/2002 |
| WO | 2008/096260 A1 | 8/2008 |
| WO | 2010/098495 A1 | 9/2010 |
| WO | 2011/006903 A1 | 2/2011 |
| WO | 2014/125444 A1 | 8/2014 |
| WO | 2016/027253 A1 | 2/2016 |
| WO | 2017/004500 A1 | 1/2017 |
| WO | 2017/136727 A2 | 8/2017 |
| WO | 2019/074275 A1 | 4/2019 |

OTHER PUBLICATIONS

Chemical Abstracts Service CAS Registry Nos. 2104558-36-1 (2017), 1545019-33-7 (2014), 1553451-22-1 (2014), p. 1-3.*
Harnisch, F-X., "Combined intra-intermolecular criss-cross cycloaddition reactions leading to perfluoroalkylated fused tricyclic nitrogen heterocycles." Journal of Fluorine Chemistry 158 (2014): 38-43.*
Bertrand et al., "cIAP1 and cIAP2 facilitate cancer cell survival by functioning as E3 ligases that promote RIP1 ubiquitination," Mol. Cell 30(6):689-700 (2008).
Chen, "Ubiquitination in signaling to and activation of IKK," Immunol. Rev. 246(1):95-106 (2012).
Cho et al., "Phosphorylation-driven assembly of the RIP1-RIP3 complex regulates programmed necrosis and Virus-induced inflammation," Cell 137(6):1112-1123 (2009).
De Almagro et al., "Necroptosis: Pathway diversity and characteristics," Semin. Cell Dev. Biol. 39:56-62 (2015).
Degterev et al., "Chemical inhibitor of nonapoptotic cell death with therapeutic potential for ischemic brain injury," Nat. Chem. Biol. 1(2):112-119 (2005).
Edegterev et al., "Identification of RIP1 kinase as a specific cellular target of necrostatins," Nat. Chem. Biol. 4(5):313-321 (2008).
Feoktistova et al., "cIAPs block Ripoptosome formation, a RIP1/caspase-8 containing intracellular cell death complex differentially regulated by cFLIP isoforms," Mol. Cell 43(3):449-463 (2011).
Harris et al., "Discovery of Small Molecule RIP1 Kinase Inhibitors for the Treatment of Pathologies Associated with Necroptosis," ACS Med. Chem. Lett. 4(12):1238-1243 (2013).

(Continued)

*Primary Examiner* — John M Mauro
(74) *Attorney, Agent, or Firm* — Jelena Libby

(57) ABSTRACT

The invention provides novel compounds having the general formula I:

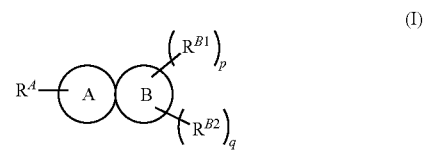

or pharmaceutically acceptable salts thereof, wherein $R^A$, $R^{B1}$, $R^{B2}$, the A ring and the B ring are as described herein, pharmaceutical compositions including the compounds, and methods of using the compounds.

29 Claims, No Drawings

(56) References Cited

OTHER PUBLICATIONS

Harris et al., "Discovery of a First-in-Class Receptor Interacting Protein 1 (RIP1) Kinase Specific Clinical Candidate (GSK2982772) for the Treatment of Inflammatory Diseases," J Med. Chem. 60(4):1247-1261 (2017).
He et al., "Receptor interacting protein kinase-3 determines cellular necrotic response to TNF-alpha," Cell 137(6):1100-1111 (2009).
Kaiser et al., "Toll-like receptor 3-mediated necrosis via TRIF, RIP3, and MLKL," J. Biol. Chem. 288(43):31268-31279 (2013).
Linkermann et al., "Necroptosis," N. Engl. J. Med. 370(5):455-465 (2014).
Najjar et al., "Structure Guided Design of Potent and Selective Ponatinib-Based Hybrid Inhibitors for RIPK1" Cell Rep. 10(11):1850-60 (2015).
Newton et al., "Activity of protein kinase RIPK3 determines whether cells die by necroptosis or apoptosis," Science 343(6177):1357-1360 (2014).
Newton, "RIPK1 and RIPK3: critical regulators of inflammation and cell death," Trends Cell Biol. 25(6):347-353 (2015).
O'Donnell et al., "Ubiquitination of RIP1 regulates an NF-kappaB-independent cell-death switch in TNF signaling," Curr. Biol. 17(5):418-424 (2007).
Sun et al., "Mixed lineage kinase domain-like protein mediates necrosis signaling downstream of RIP3 kinase," Cell 148(1-2):213-227 (2012).
Takahashi et al., "Necrostatin-1 analogues: critical issues on the specificity, activity and in vivo use in experimental disease models," Cell Death Dis. 3(11):e437 (2012).
Vanden Berghe et al., "Regulated necrosis: the expanding network of non-apoptotic cell death pathways," Nat. Rev. Mol. Cell Biol. 15(2):135-147 (2014).
Wang et al., "TNF-α induces two distinct caspase-8 activation pathways," Cell 133(4):693-703 (2008).
Zhao et al., "Mixed lineage kinase domain-like is a key receptor interacting protein 3 downstream component of TNF-induced necrosis," Proc. Natl. Acad. Sci. USA 109(14):5322-5327 (2012).
PCT International Search Report and Written Opinion for PCT/EP2018/077656, dated Nov. 16, 2018, 15 pages.
PCT International Preliminary Report on Patentability for PCT/EP2018/077656, dated Apr. 23, 2020, 9 pages.
Aurora Fine Chemicals et al., CAS Registry Database, 1547153-77-4, pp. 1Creation Date Feb. 17, 2014.
Aurora Fine Chemicals et al., CAS Registry Database, 1556249-42-3, pp. 1Creation Date Feb. 26, 2014.
Belikov et al. Pharmaceutical Chemistry (Textbook pages in Russian with English translation attached), Moscow:MEDpress-inform,:pp. 27-29 (2007).
Dyson, G., et al. Chmistry of Synthetic Medicinal Substances (Russian w/Eng. Translation), Moscow::12-19 (Jan. 1, 1964).
Kummerer, K., "Pharmaceuticals in the Environment" Ann Rev Environ Res 35:57-55 (Nov. 1, 2010).
Mashkovskiy, M.D. et al. [Meditisina] "Pharmaceuticals" (Russian with English translation attached), Moscow: vol. 1:8 (Jan. 1, 2002).
Rackham, D.M., "Spectroscopic Studies of Some Imidazo[1,2-a]pyridine and Imidazo[1,2-a]pyrimidine Derivatives" Applied Spectroscopy 33(6):561-563 (Nov. 1, 1979).

* cited by examiner

BICYCLIC COMPOUNDS FOR USE AS RIP1 KINASE INHIBITORS

CROSS REFERENCE TO RELATED APPLICATIONS

This application is a continuation of International Application No. PCT/EP2018/077656, filed Oct. 10, 2018, which claims priority to U.S. Provisional Application No. 62/570,892, filed Oct. 11, 2017, each of which is incorporated herein by reference in its entirety.

FIELD OF THE INVENTION

The present invention relates to organic compounds useful for therapy and/or prophylaxis in a mammal, and in particular to inhibitors of RIP1 kinase useful for treating diseases and disorders associated with inflammation, cell death and others.

BACKGROUND OF THE INVENTION

Receptor-interacting protein-1 ("RIP1") kinase is a serine/threonine protein kinase. RIP1 is a regulator of cell signaling that is involved, among other things, in the mediation of programmed cell death pathways, e.g., necroptosis. The best studied form of necroptotic cell death is initiated by TNFα (tumor necrosis factor), but necroptosis can also be induced by other members of the TNFα death ligand family (Fas and TRAIL/Apo2L), interferons, Toll-like receptors (TLRs) signaling and viral infection via the DNA sensor DAI (DNA-dependent activator of interferon regulatory factor) [1-3]. Binding of TNFα to the TNFR1 (TNF receptor 1) prompts TNFR1 trimerization and formation of an intracellular complex, Complex-I. TRADD (TNF receptor associated death domain protein) binds to the intracellular death domain of TNFR1 and recruits the protein kinase RIP1 (receptor-interacting protein 1) through the death domain present in both proteins [4]. Following initial recruitment into TNFR1-associated signaling complex, RIP1 translocates to a secondary cytoplasmatic complex, Complex-II [5-7]. Complex-II is formed by the death domain containing protein FADD (Fas-associated Protein), RIP1, caspase-8 and cFLIP. If caspase-8 is not fully activated or its activity is blocked, the protein kinase RIP3 gets recruited to the complex, forming a necrosome, which will lead to necroptotic cell death initiation [8-10]. Once the necrosome is formed, RIP1 and RIP3 engage in a series of auto and cross phosphorylation events that are essential for necroptotic cell death. Necroptosis can be completely blocked either by the kinase inactivating mutation in any of the two kinases, or chemically by RIP1 kinase inhibitors (necrostatins), or RIP3 kinase inhibitors [11-13]. Phosphorylation of RIP3 allows the binding and phosphorylation of pseudokinase MLKL (mixed lineage kinase domain-like), a key component of necroptotic cell death [14, 15].

Necroptosis has crucial pathophysiological relevance in myocardial infarction, stroke, atherosclerosis, ischemia-reperfusion injury, inflammatory bowel diseases, retinal degeneration and a number of other common clinical disorders [16]. Therefore, selective inhibitors of RIP1 kinase activity are therefore desired as a potential treatment of diseases mediated by this pathway and associated with inflammation and/or necroptotic cell death.

Inhibitors of RIP1 kinase have been previously described. The first published inhibitor of RIP1 kinase activity was necrostatin 1 (Nec-1) [17]. This initial discovery was followed by modified versions of Nec-1 with various abilities to block RIP1 kinase activity [11, 18]. Recently, additional RIP1 kinase inhibitors have been described that differ structurally from necrostatin class of compounds [19, 20, 21].

References cited above, each of which is hereby incorporated by reference in its entirety:

1) Vanden Berghe, T., Linkermann, A., Jouan-Lanhouet, S., Walczak, H. and Vandenabeele, P. (2014) Regulated necrosis: the expanding network of non-apoptotic cell death pathways. Nature reviews. Molecular cell biology. 15, 135-147.
2) Newton, K. (2015) RIPK1 and RIPK3: critical regulators of inflammation and cell death. Trends in cell biology. 25, 347-353.
3) de Almagro, M. C. and Vucic, D. (2015) Necroptosis: Pathway diversity and characteristics. Semin Cell Dev Biol. 39, 56-62.
4) Chen, Z. J. (2012) Ubiquitination in signaling to and activation of IKK. Immunological reviews. 246, 95-106.
5) O'Donnell, M. A., Legarda-Addison, D., Skountzos, P., Yeh, W. C. and Ting, A. T. (2007) Ubiquitination of RIP1 regulates an NF-kappaB-independent cell-death switch in TNF signaling. Curr Biol. 17, 418-424.
6) Feoktistova, M., Geserick, P., Kellert, B., Dimitrova, D. P., Langlais, C., Hupe, M., Cain, K., MacFarlane, M., Hacker, G. and Leverkus, M. (2011) cIAPs block Ripoptosome formation, a RIP1/caspase-8 containing intracellular cell death complex differentially regulated by cFLIP isoforms. Molecular cell. 43, 449-463.
7) Bertrand, M. J., Milutinovic, S., Dickson, K. M., Ho, W. C., Boudreault, A., Durkin, J., Gillard, J. W., Jaquith, J. B., Morris, S. J. and Barker, P. A. (2008) cIAP1 and cIAP2 facilitate cancer cell survival by functioning as E3 ligases that promote RIP1 ubiquitination. Mol Cell. 30, 689-700.
8) Wang, L., Du, F. and Wang, X. (2008) TNF-alpha induces two distinct caspase-8 activation pathways. Cell. 133, 693-703.
9) He, S., Wang, L, Miao, L., Wang, T., Du, F., Zhao, L and Wang, X. (2009) Receptor interacting protein kinase-3 determines cellular necrotic response to TNF-alpha. Cell. 137, 1100-1111.
10) Cho, Y. S., Challa, S., Moquin, D., Genga, R., Ray, T. D., Guildford, M. and Chan, F. K. (2009) Phosphorylation-driven assembly of the RIP1-RIP3 complex regulates programmed necrosis and virus-induced inflammation. Cell. 137, 1112-1123.
11) Degterev, A., Hitomi, J., Germscheid, M., Ch'en, I. L., Korkina, O., Teng, X., Abbott, D., Cuny, G. D., Yuan, C., Wagner, G., Hedrick, S. M., Gerber, S. A., Lugovskoy, A. and Yuan, J. (2008) Identification of RIP1 kinase as a specific cellular target of necrostatins. Nat Chem Biol. 4, 313-321.
12) Newton, K., Dugger, D. L, Wickliffe, K. E., Kapoor, N., de Almagro, M. C., Vucic, D., Komuves, L, Ferrando, R. E., French, D. M., Webster, J., Roose-Girma, M., Warming, S. and Dixit, V. M. (2014) Activity of protein kinase RIPK3 determines whether cells die by necroptosis or apoptosis. Science. 343, 1357-1360.
13) Kaiser, W. J., Sridharan, H., Huang, C., Mandal, P., Upton, J. W., Gough, P. J., Sehon, C. A., Marquis, R. W., Bertin, J. and Mocarski, E. S. (2013) Toll-like receptor 3-mediated necrosis via TRIF, RIP3, and MLKL The Journal of biological chemistry. 288, 31268-31279.
14) Zhao, J., Jitkaew, S., Cai, Z., Choksi, S., U, Q., Luo, J. and Liu, Z. G. (2012) Mixed lineage kinase domain-like is a key receptor interacting protein 3 downstream component of TNF-induced necrosis. Proceedings of the National Academy of Sciences of the United States of America. 109, 5322-5327.
15) Sun, L., Wang, H., Wang, Z., He, S., Chen, S., Liao, D., Wang, L., Yan, J., Liu, W., Lei, X. and Wang, X. (2012) Mixed Lineage Kinase Domain-like Protein Mediates Necrosis Signaling Downstream of RIP3 Kinase. Cell. 148, 213-227.
16) Linkermann, A. and Green, D. R. (2014) Necroptosis. The New England journal of medicine. 370, 455-465.
17) Degterev, A., Huang, Z., Boyce, M., Li, Y., Jagtap, P., Mizushima, N., Cuny, G. D., Mitchison, T. J., Moskowitz, M. A. and Yuan, J. (2005) Chemical inhibitor of nonapoptotic cell death with therapeutic potential for ischemic brain injury. Nat Chem Biol. 1, 112-119.
18) Takahashi, N., Duprez, L., Grootjans, S., Cauwels, A., Nerinckx, W., DuHadaway, J. B., Goossens, V., Roelandt, R., Van Hauwermeiren, F., Libert, C., Declercq, W., Callewaert, N., Prendergast, G. C., Degterev, A., Yuan, J. and Vandenabeele, P. (2012) Necrostatin-1 analogues: critical issues on the specificity, activity and in vivo use in experimental disease models. Cell Death Dis. 3, e437.
19) Harris, P. A., Bandyopadhyay, D., Berger, S. B., Campobasso, N., Capriotti, C. A., Cox, J. A., Dare, L, Finger, J. N., Hoffman, S. J., Kahler, K. M., Lehr, R., Lich, J. D., Nagilla, R., Nolte, R. T., Ouellette, M. T., Pao, C. S., Schaeffer, M. C., Smallwood, A., Sun, H. H., Swift, B. A., Totoritis, R. D., Ward, P., Marquis, R. W., Bertin, J. and Gough, P. J. (2013) Discovery of Small Molecule RIP1 Kinase Inhibitors for the Treatment of Pathologies Associated with Necroptosis. ACS medicinal chemistry letters. 4, 1238-1243.
20) Najjar, M., Suebsuwong, C., Ray, S. S., Thapa, R. J., Maki, J. L, Nogusa, S., Shah, S., Saleh, D., Gough, P. J., Bertin, J., Yuan, J., Balachandran, S., Cuny, G. D. and Degterev, A. (2015) Structure Guided Design of Potent and Selective Ponatinib-Based Hybrid Inhibitors for RIPK1. Cell Rep.
21) International Patent Publication No. WO 2014/125444.
22) International Patent Publication No. WO 2017/004500.

SUMMARY OF THE INVENTION

Provided herein are compounds of formula I:

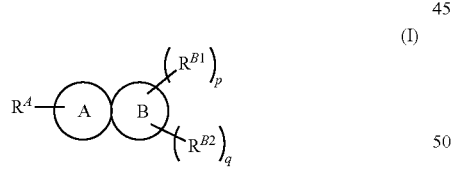

or pharmaceutically acceptable salts thereof, wherein $R^4$ is selected from the group consisting of:

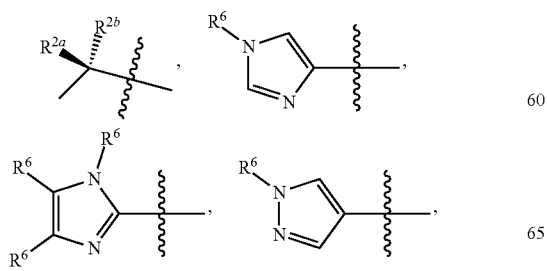

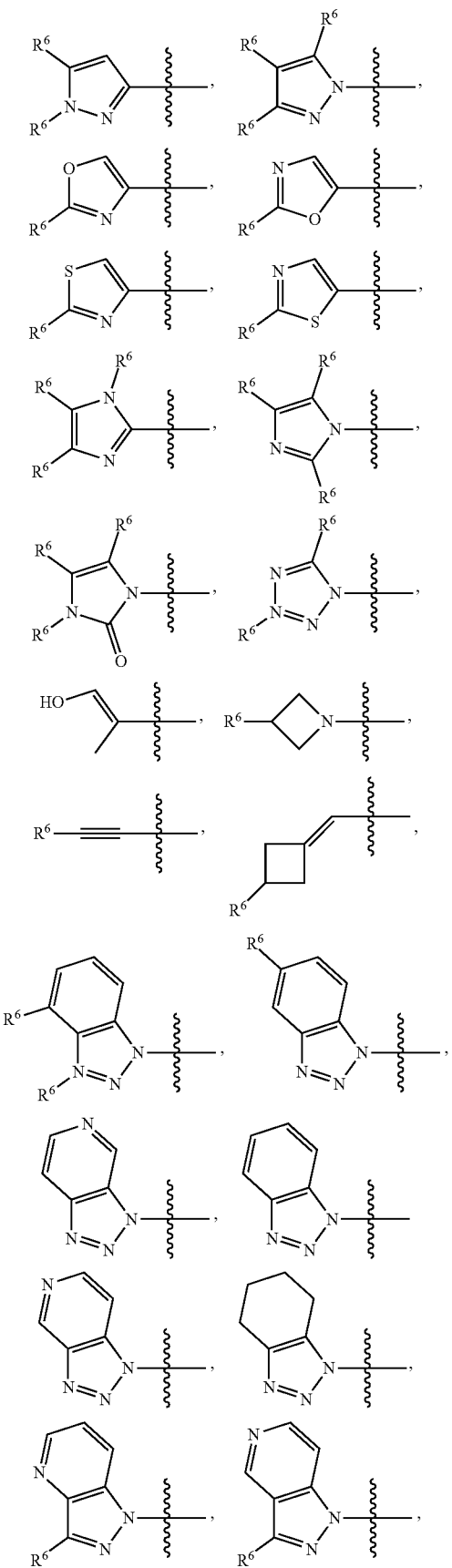

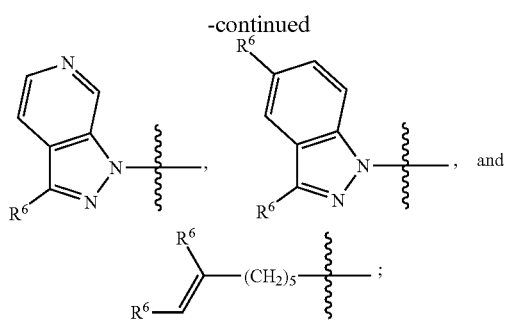

s is 0 or 1;
R¹ is selected from the group consisting of hydrogen, deutero, fluoro, hydroxyl, cyano, $C_1$-$C_6$ alkyl, $C_3$-$C_6$ cycloalkyl, $C_1$-$C_6$ alkoxy, $C_1$-$C_6$ haloalkyl, $C_1$-$C_6$ haloalkoxy, $C_1$-$C_6$ alkyl substituted with one $(R^N)_2N$ substituent, $C_1$-$C_6$ cyanoalkyl, $C_1$-$C_6$ alkylsulfonyl, phenyl, benzyl, 4 to 6 membered heterocyclyl, and 5 to 6 membered heteroaryl;
wherein, when R¹ is phenyl, benzyl, $C_1$-$C_6$ alkyl, $C_1$-$C_6$ alkoxy or $C_3$-$C_6$ cycloalkyl, the phenyl, $C_1$-$C_6$ alkoxy or cycloalkyl ring is optionally substituted with 1 to 2 substituents selected from the group consisting of fluoro, chloro, cyano, $C_1$-$C_3$ alkyl, cyclopropyl, $C_1$-$C_3$ alkoxy, $C_1$-$C_3$ hydroxyalkyl, $C_1$-$C_3$ haloalkyl, $C_1$-$C_6$ alkoxycarbonyl, $C_1$-$C_3$ alkoxy-$C_1$-$C_3$ alkyl and $C_1$-$C_3$ haloalkoxy; $R^{2a}$ and $R^{2b}$ are each independently selected from the group consisting of hydrogen, deutero, fluoro, hydroxyl, $C_1$-$C_3$ alkyl, and $C_1$-$C_3$ fluoroalkyl; provided that both $R^{2a}$ and $R^{2b}$ cannot be hydroxyl; or
R¹ is selected from the group consisting of hydrogen, deutero, fluoro, methyl, and cyano; and
$R^{2a}$ and $R^{2b}$ together with the carbon atom to which they are both attached form a 4 to 6 membered heterocyclic ring or a 3 to 5 membered carbocyclic ring, each optionally substituted by 1 to 2 substituents selected from the group consisting of fluoro, chloro, hydroxyl, cyano, $C_1$-$C_3$ alkyl, hydroxymethyl, methoxymethyl, $C_1$-$C_4$ alkoxycarbonyl, trifluoromethyl, difluoromethoxy, and trifluoromethoxy;
each $R^N$ is independently selected from the group consisting of $C_1$-$C_6$ alkyl, $C_3$-$C_6$ cycloalkyl, $C_1$-$C_6$ alkoxy, and $C_1$-$C_6$ haloalkyl; or two $R^N$ together with the nitrogen atom to which they are both attached form a 4-6 membered heterocyclic ring;
each $R^6$ is independently selected from the group consisting of hydrogen, halogen, $C_1$-$C_6$ alkyl, $C_3$-$C_6$ cycloalkyl, $C_1$-$C_3$ cyanoalkyl. $C_1$-$C_3$ alkylcarbonyl. $C_1$-$C_3$ methylsulfonyl. $C_1$-$C_6$ alkoxy, $C_1$-$C_6$ haloalkyl, formyl, $C_1$-$C_6$ haloalkoxy, cyano, 1-methyl-pyrazol-4-yl and pyrimidinyl; and
the A ring and the B ring are fused to form a polycyclic ring system, wherein
the A ring is a 5 membered heteroaromatic ring having as its only heteroatoms, either (i) two or three nitrogen atoms, (ii) one nitrogen atom and one oxygen atom, or (iii) one nitrogen atom and one sulfur atom; wherein the A ring is optionally substituted at a carbon atom by one substituent selected from the group consisting of fluoro, chloro, methyl, and trifluoromethyl; and
the B ring is a 4 to 8 membered carbocyclic ring, or a 4 to 8 membered heterocyclic ring having 1 to 3 heteroatoms selected from the group consisting of nitrogen, oxygen, and sulfur;

p is 1 or 2, and q is 0 or 1; or p is 0, and q is 1;
each $R^{B1}$ is independently selected from the group consisting of halogen, deutero, hydroxyl, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-$N(R^N)_2$, and cyano; wherein two $C_1$-$C_6$ alkyl substituents may together form a bridged or spirocyclic ring; and wherein if a nitrogen atom in the B ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom;
$R^{B2}$ is selected from the group consisting of $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-$N(R^N)_2$, phenyl, benzyl, $CH_2$—$(C_3$-$C_6$ cycloalkyl), $CH_2CH_2$—$(C_3$-$C_6$ cycloalkyl), $CH_2$-(4 to 6 membered heterocyclyl), $CH_2CH_2$-(4 to 6 membered heterocyclyl), 5 to 6 membered heteroaryl, and $CH_2$-(5 to 6 membered heteroaryl); wherein when $R^{B2}$ is phenyl or benzyl the phenyl ring is optionally substituted by 1 to 3 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano;
provided that, when $R^A$ is

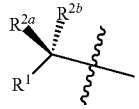

and $R^{2a}$ and $R^{2b}$ are each hydrogen, R¹ is not hydrogen, halogen or methyl; and
further provided that, when the B ring is substituted by $C_1$-$C_6$ alkyl-$N(R^N)_2$ and phenyl, and each $R^N$ is hydrogen,

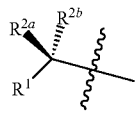

is not methyl, tert-butyl, N-ethylmorpholino, or methoxyethyl.

Also provided herein are pharmaceutical compositions comprising a compound of formula I, or a pharmaceutically acceptable salt thereof, and one or more pharmaceutically acceptable carriers or excipients. Specific embodiments include pharmaceutical compositions suitable for oral delivery.

Also provided herein are oral formulations of a compound of formula I, or a pharmaceutically acceptable salt thereof, and one or more pharmaceutically acceptable carriers or excipients suitable for oral delivery.

Also provided herein are methods of treatment of diseases and disorders associated with inflammation, cell death, and others related to RIP1 kinase, as described further below.

Also provided herein are compounds or pharmaceutical compositions for use as therapeutically active substances.

Also provided herein are uses of compounds or pharmaceutical compositions for use in the treatment of diseases and disorders associated with inflammation, cell death, and others related to RIP1 kinase, as described further below.

Also provided herein are uses of compounds or pharmaceutical compositions for the preparation of a medicament for the treatment of diseases and disorders associated with inflammation, cell death, and others related to RIP1 kinase, as described further below.

Also provided herein are compounds or pharmaceutical compositions for use in the treatment of diseases and disorders associated with inflammation, cell death, and others related to RIP1 kinase, as described further below.

Also provided herein are uses of compounds or pharmaceutical compositions for use in the treatment of diseases and disorders associated with inflammation, cell death, and others related to RIP1 kinase, as described further below.

Also provided herein are uses of compounds or pharmaceutical compositions for the preparation of a medicment for the treatment of diseases and disorders associated with inflammation, cell death, and others related to RIP1 kinase, as described further below.

DETAILED DESCRIPTION OF THE INVENTION

Definitions

As provided herein, all chemical formulae and generic chemical structures should be interpreted to provide proper valence and chemically stable bonds between atoms as understood by one of ordinary skill in the art. Where appropriate, substituents may be bonded to more than one adjacent atom (e.g., alkyl includes methylene where two bonds are present).

In the chemical formulae provided herein, "halogen" or "halo' refers to flurorine, chlorine, and bromine (i.e., F, Cl, Br).

Alkyl, unless otherwise specifically defined, refers to an optionally substituted, straight-chain or branched $C_1$-$C_{12}$ alkyl group. In some embodiments, alkyl refers to a $C_1$-$C_6$ alkyl group. Exemplary alkyl groups include methyl, ethyl, propyl, iso-propyl, n-butyl, iso-butyl, tert-butyl, sec-butyl, n-pentyl, n-hexyl, n-heptyl, and n-oxtyl. Substituted alkyl groups provided herein are substituted by one or more substituents selected from the group consisting of halogen, cyano, trifluoromethyl, methoxy, ethoxy, difluoromethoxy, trifluoromethoxy, $C_3$-$C_6$ cycloalkyl, phenyl, OH, $CO_2H$, $CO_2(C_1$-$C_4$ alkyl), $NH_2$, $NH(C_1$-$C_4$ alkyl), $N(C_1$-$C_4$ alkyl)$_2$, $NH(C=O)C_1$-$C_4$ alkyl, $(C=O)NH(C_1$-$C_4$ alkyl), $(C=O)N(C_1$-$C_4$ alkyl)$_2$, $S(C_1$-$C_4$ alkyl), $SO(C_1$-$C_4$ alkyl), $SO_2(C_1$-$C_4$ alkyl), $SO_2NH(C_1$-$C_4$ alkyl), $SO_2N(C_1$-$C_4$ alkyl)$_2$, and $NHSO_2(C_1$-$C_4$ alkyl). In some embodiments, the substituted alkyl group has 1 or 2 substituents. In some embodiments, the alkyl group is unsubstituted.

Cycloalkyl, unless otherwise specifically defined, refers to an optionally substituted $C_3$-$C_{12}$ cycloalkyl group and includes fused, spirocyclic, and bridged bicyclic groups, wherein the substituents are selected from the group consisting of halogen, cyano, trifluoromethyl, methoxy, ethoxy, difluoromethoxy, trifluoromethoxy, $C_3$-$C_6$ cycloalkyl, phenyl, OH, $CO_2H$, $CO_2(C_1$-$C_4$ alkyl), $NH_2$, $NH(C_1$-$C_4$ alkyl), $N(C_1$-$C_4$ alkyl)$_2$, $NH(C=O)C_1$-$C_4$ alkyl, $(C=O)NH(C_1$-$C_4$ alkyl), $(C=O)N(C_1$-$C_4$ alkyl)$_2$, $S(C_1$-$C_4$ alkyl), $SO(C_1$-$C_4$ alkyl), $SO_2(C_1$-$C_4$ alkyl), $SO_2NH(C_1$-$C_4$ alkyl), $SO_2N(C_1$-$C_4$ alkyl)$_2$, and $NHSO_2(C_1$-$C_4$ alkyl). In some embodiments, cycloalkyl refers to a $C_3$-$C_6$ cycloalkyl group. In some embodiments, the $C_3$-$C_6$ cycloalkyl group is optionally substituted with 1 to three halogen atoms. In some embodiments, the $C_3$-$C_6$ cycloalkyl group is optionally substituted with 1 to three fluorine atoms. Exemplary $C_3$-$C_6$ cycloalkyl groups include cyclopropyl, cyclobutyl, cyclopentyl and cyclohexyl. Exemplary $C_3$-$C_{12}$ cycloalkyl groups further include bicyclo[3.1.0]hexyl, bicyclo[2.1.1]hexyl, cycloheptyl, bicycle[4.1.0]heptyl, spiro[4.2]heptyl, cyclooctyl, spiro [4.3]octyl, spiro[5.2]octyl, bicyclo[2.2.1]heptanyl, bicycle [2.2.2]octanyl, adamantanyl, decalinyl, and spiro[5.4] decanyl. Where appropriate, cycloalkyl groups may be fused to other groups such that more than one chemical bond exists between the cycloalkyl group and another ring system (e.g., the C ring of formula I). In some embodiments, the cycloalkyl group is unsubstituted.

Haloalkyl, unless otherwise specifically defined, refers to a straight-chain or branched $C_1$-$C_{12}$ alkyl group, wherein one or more hydrogen atoms are replaced by a halogen. In some embodiments, haloalkyl refers to a $C_1$-$C_6$ haloalkyl group. In some embodiments, 1 to 3 hydrogen atoms of the haloalkyl group are replaced by a halogen. In some embodiments, every hydrogen atom of the haloalkyl group is replaced by a halogen (e.g., trifluoromethyl). In some embodiments, the haloalkyl is as defined herein wherein the halogen in each instance is fluorine. Exemplary haloalkyl groups include fluoromethyl, difluoromethyl, trifluromethyl, trifluoroethyl, and pentafluoroethyl.

Alkoxy, unless otherwise specifically defined, refers to a straight-chain or branched $C_1$-$C_{12}$ alkyl group, wherein one or more oxygen atoms are present, in each instance between two carbon atoms.

In some embodiments, alkoxy refers to a $C_1$-$C_6$ alkoxy group. In some embodiments, $C_1$-$C_6$ alkoxy groups provided herein have one oxygen atom. Exemplary alkoxy groups include methoxy, ethoxy, $CH_2OCH_3$, $CH_2CH_2OCH_3$, $CH_2OCH_2CH_3$, $CH_2CH_2OCH_2CH_3$, $CH_2OCH_2CH_2CH_3$, $CH_2CH_2CH_2OCH_3$, $CH_2OCH(CH_3)_2$, $CH_2OC(CH_3)_3$, $CH(CH_3)OCH_3$, $CH_2CH(CH_3)OCH_3$, $CH(CH_3)OCH_2CH_3$, $CH_2OCH_2OCH_3$, $CH_2CH_2OCH_2CH_2OCH$, and $CH_2OCH_2OCH_2OCH_3$.

Cycloalkoxy, unless otherwise specifically defined, refers to a $C_4$—C or a $C_4$-$C_6$ alkoxy group as defined above wherein the group is cyclic and contains one oxygen atom. Exemplary cycloalkoxy groups include oxetanyl, tetrahydrofuranyl, and tetrahydropyranyl.

Haloalkoxy, unless otherwise specifically defined, refers to a $C_1$-$C_6$ haloalkyl group as defined above, wherein one or two oxygen atoms are present, in each instance between two carbon atoms. In some embodiments, $C_1$-$C_6$ haloalkoxy groups provided herein have one oxygen atom. Exemplary haloalkoxy groups include $OCF_3$, $OCHF_2$ and $CH_2OCF_3$.

Thioalkyl, unless otherwise specifically defined, refers to a $C_1$-$C_6$ alkoxy group as defined above wherein the oxygen atom is replaced by a sulfur atom. In some embodiments, thioalkyl groups may include sulfur atoms substituted by one or two oxygen atoms (i.e., alkylsulfones and alkylsulfoxides). Exemplary thioalkyl groups are those exemplified in the definition of alkoxy above, wherein each oxygen atom is replaced by a sulfur atom in each instance.

Alkoxycarbonyl, unless otherwise specifically defined, refers to a $C_1$-$C_6$ alkoxy group as defined above wherein the oxygen atom is bonded to a carbonyl group to form an ester. Exemplary alkoxycarbonyl groups include $CH_3OC(O)$— and $CH_3CH_2OC(O)$—.

Acyl, alkanoyl or alkylcarbonyl unless otherwise defined refers to a group of formula —C(=O)R wherein R is hydrogen or lower alkyl as defined herein. Formyl refers to a group of formula —C(=O) wherein R=H. Arylcarbonyl or aroyl refers to a group of formula —C(=O)R wherein R is an aryl group; the term "benzoyl" as used herein an "arylcarbonyl" or "aroyl" group wherein R is phenyl.

Cyanoalkyl, unless otherwise specifically defined, refers to a $C_1$-$C_6$ alkyl group as defined above wherein one hydrogen atom is replaced by a cyano group ("—CN"). Exemplary cyanoalkyl groups include CNCH$_2$— and CNCH$_2$CH$_2$—.

Alkylsulfonyl, unless otherwise specifically defined, refers to a C$_1$-C$_6$ alkyl group as defined above wherein a carbon atom is bonded to a sulfone group ("SO$_2$"), which is in turn bound to a C$_1$-C$_6$ alkyene. Exemplary alkylsulfonyl groups include CH$_3$SO$_2$CH$_2$— and CH$_3$SO$_2$CH$_2$CH$_2$—.

Heterocyclyl, unless otherwise specifically defined, referes to a single saturated or partially unsaturated 4 to 8 membered ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems have from 7 to 12 atoms and are further described below. Thus, the term includes single saturated or partially unsaturated rings (e.g., 3, 4, 5, 6, 7 or 8 membered rings) from about 1 to 7 carbon atoms and from about 1 to 4 heteroatoms selected from the group consisting of oxygen, nitrogen and sulfur in the ring. The ring may be C-branched (i.e., substituted by C$_1$-C$_4$ alkyl). The ring may be substituted with one or more (e.g., 1, 2 or 3) oxo groups and the sulfur and nitrogen atoms may also be present in their oxidized forms. Exemplary heterocycles include but are not limited to azetidinyl, tetrahydrofuranyl and piperidinyl. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system. It is also to be understood that the point of attachment for a heterocycle or heterocycle multiple condensed ring system can be at any suitable atom of the heterocyclyl group including a carbon atom and a nitrogen atom. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one N-methylpiperidine, imidazolidine, pyrazolidine, butyrolactam, valerolactam, imidazolidinone, hydantoin, dioxolane, phthalimide, 1,4-dioxane, thiomorpholine, thiomorpholine-S-oxide, thiomorpholine-S,S-oxide, pyran, 3-pyrroline, thiopyran, pyrone, tetrahydrothiophene, quinuclidine, tropane, 2-azaspiro[3.3]heptane, (1R,5S)-3-azabicyclo[3.2.1]octane, (1s,4s)-2-azabicyclo[2.2.2]octane, (1R, 4R)-2-oxa-5-azabicyclo[2.2.2]octane and pyrrolidin-2-one.

In some embodiments, the heterocyclyl is a C$_4$-C$_{10}$ heterocyclyl having 1 to 3 heteroatoms selected from the group consisting of nitrogen, oxygen and sulfur. In some embodiments, the heterocyclyl group is neither bicyclic nor spirocyclic. In some embodiments, the heterocyclyl is a C$_5$-C$_6$ heterocylcyl having 1 to 3 heteroatoms, wherein at least 2 are nitrogen if 3 heteroatoms are present.

Aryl, unless otherwise specifically defined, refers to a single all carbon aromatic ring or a multiple condensed all carbon ring system wherein at least one of the rings is aromatic and wherein the aryl group has 6 to 20 carbon atoms, 6 to 14 carbon atoms, 6 to 12 carbon atoms, or 6 to 10 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Exemplary aryl groups include phenyl, indenyl, naphthyl, 1, 2, 3, 4-tetrahydronaphthyl, anthracenyl, and the like.

Heteroaryl, unless otherwise specifically defined, refers to a 5 to 6 membered aromatic ring that has at least one atom other than carbon in the ring, wherein the atom is selected from the group consisting of oxygen, nitrogen and sulfur; "heteroaryl" also includes multiple condensed ring systems having 8 to 16 atoms that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2 or 3 rings) wherein a heteroaryl group, as defined above, is condensed with one or more rings selected from heteroaryls (to form for example a naphthyridinyl such as 1,8-naphthyridinyl), heterocycles, (to form for example a 1, 2, 3, 4-tetrahydronaphthyridinyl such as 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has 1 to 15 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system. It is also to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo

[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclo-penta[1,2-c]pyrazole.

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein a wavy line "⁓" that intersects a bond in a chemical structure indicates the point of attachment of the bond that the wavy bond intersects in the chemical structure to the remainder of a molecule.

As used herein, the term "C-linked" means that the group that the term describes is attached the remainder of the molecule through a ring carbon atom.

As used herein, the term "N-linked" means that the group that the term describes is attached to the remainder of the molecule through a ring nitrogen atom.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95% the absolute stereoisomer depicted. In another embodiment, the compound may be at least 97% the absolute stereoisomer depicted. In another embodiment, the compound may be at least 98% the absolute stereoisomer depicted. In another embodiment, the compound may be at least 99% the absolute stereoisomer depicted.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4$^{th}$ edition, Wiley-Interscience, New York, 2006.

As used herein, the term "mammal" includes, but is not limited to, humans, mice, rats, guinea pigs, monkeys, dogs, cats, horses, cows, pigs, and sheep.

As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as ($C_{1-6}$)alkanoyloxymethyl, 1-(($C_{1-6}$)alkanoyloxy)ethyl, 1-methyl-1-(($C_{1-6}$)alkanoyloxy)ethyl, ($C_{1-6}$)alkoxycarbonyloxymethyl, N—($C_{1-6}$)alkoxycarbonylaminomethyl, succinoyl, ($C_{1-6}$)alkanoyl, alpha-amino($C_{1-4}$)alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "therapeutically effective amount" or "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. For cancer therapy, efficacy can, for example, be measured by assessing the time to disease progression (TTP) and/or determining the response rate (RR).

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

Inhibitors of RIP1 Kinase

All embodiments described herein can be combined.

The present invention provides novel compounds having the general formula I:

Provided herein are compounds of formula I:

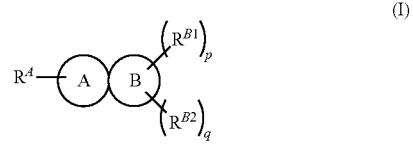

or pharmaceutically acceptable salts thereof, wherein $R^A$ is selected from the group consisting of

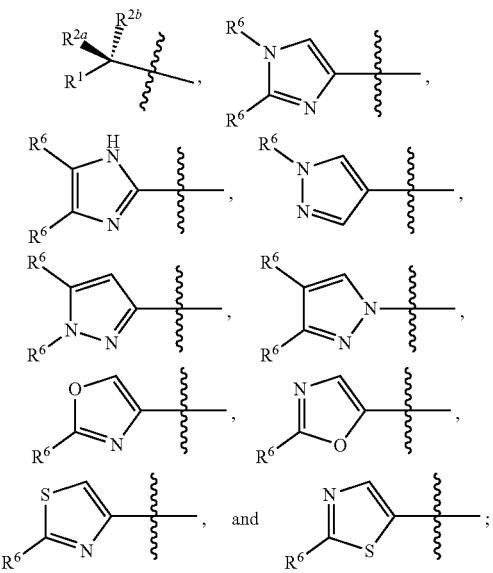

$R^1$ is selected from the group consisting of hydrogen, deutero, fluoro, hydroxyl, cyano, $C_1$-$C_6$ alkyl, $C_3$-$C_6$ cycloalkyl, $C_1$-$C_6$ alkoxy, $C_1$-$C_6$ haloalkyl, $C_1$-$C_6$ haloalkoxy, $C_1$-$C_6$ alkyl substituted with one $(R^N)_2N$ substituent, $C_1$-$C_6$ cyanoalkyl, $C_1$-$C_6$ alkylsulfonyl, phenyl, benzyl, 4 to 6 membered heterocyclyl, and 5 to 6 membered heteroaryl;

wherein, when $R^1$ is phenyl or benzyl, the phenyl ring is optionally substituted with 1 to 2 substituents selected from the group consisting of fluoro, chloro, cyano, $C_1$-$C_3$ alkyl, cyclopropyl, $C_1$-$C_3$ alkoxy, $C_1$-$C_3$ haloalkyl, and $C_1$-$C_3$ haloalkoxy;

$R^{2a}$ and $R^{2b}$ are each independently selected from the group consisting of hydrogen, deutero, fluoro, hydroxyl, $C_1$-$C_3$ alkyl, and $C_1$-$C_3$ fluoroalkyl; provided that both $R^{2a}$ and $R^{2b}$ cannot be hydroxyl; or $R^1$ is selected from the group consisting of hydrogen, deutero, fluoro, methyl, and cyano; and $R^{2a}$ and $R^{2b}$ together with the carbon atom to which they are both attached form a 4 to 6 membered heterocyclic ring or a 3 to 5 membered carbocyclic ring, each optionally substituted by 1 to 2 substituents selected from the group consisting of fluoro, chloro, hydroxyl, cyano, $C_1$-$C_3$ alkyl, hydroxymethyl, methoxymethyl, $C_1$-$C_4$ alkoxycarbonyl, trifluoromethyl, difluoromethoxy, and trifluoromethoxy;

each $R^N$ is independently selected from the group consisting of $C_1$-$C_6$ alkyl, $C_3$-$C_6$ cycloalkyl, $C_1$-$C_6$ alkoxy, and $C_1$-$C_6$ haloalkyl; or two $R^N$ together with the nitrogen atom to which they are both attached form a 4-6 membered heterocyclic ring;
each $R^6$ is independently selected from the group consisting of hydrogen, $C_1$-$C_6$ alkyl, $C_3$-$C_6$ cycloalkyl, $C_1$-$C_6$ alkoxy, $C_1$-$C_6$ haloalkyl, and $C_1$-$C_6$ haloalkoxy; and
the A ring and the B ring are fused to form a polycyclic ring system, wherein
the A ring is a 5 membered heteroaromatic ring having as its only heteroatoms, either (i) two or three nitrogen atoms, (ii) one nitrogen atom and one oxygen atom, or (iii) one nitrogen atom and one sulfur atom; wherein the A ring is optionally substituted at a carbon atom by one substituent selected from the group consisting of fluoro, chloro, methyl, and trifluoromethyl; and
the B ring is a 4 to 8 membered carbocyclic ring, or a 4 to 8 membered heterocyclic ring having 1 to 3 heteroatoms selected from the group consisting of nitrogen, oxygen, and sulfur;
  p is 1 or 2, and q is 0 or 1; or p is 0, and q is 1;
  each $R^{B1}$ is independently selected from the group consisting of halogen, deutero, hydroxyl, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-$N(R^N)_2$, and cyano; wherein two $C_1$-$C_6$ alkyl substituents may together form a bridged or spirocyclic ring; and wherein if a nitrogen atom in the B ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom;
  $R^{B2}$ is selected from the group consisting of $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-$N(R^N)_2$, phenyl, benzyl, $CH_2$—($C_3$-$C_6$ cycloalkyl), $CH_2CH_2$—($C_3$-$C_6$ cycloalkyl), $CH_2$-(4 to 6 membered heterocyclyl), $CH_2CH_2$-(4 to 6 membered heterocyclyl), 5 to 6 membered heteroaryl, and $CH_2$-(5 to 6 membered heteroaryl); wherein when $R^{B2}$ is phenyl or benzyl the phenyl ring is optionally substituted by 1 to 3 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano;
provided that, when $R^A$ is

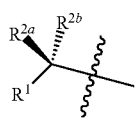

and $R^{2a}$ and $R^{2b}$ are each hydrogen, $R^1$ is not hydrogen, halogen or methyl; and
further provided that, when the B ring is substituted by $C_1$-$C_6$ alkyl-$N(R^N)_2$ and phenyl, and each $R^N$ is hydrogen,

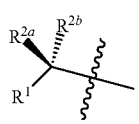

is not methyl, tert-butyl, N-ethylmorpholino, or methoxyethyl.

In some embodiments of the invention $R^A$ is selected from the group consisting of:

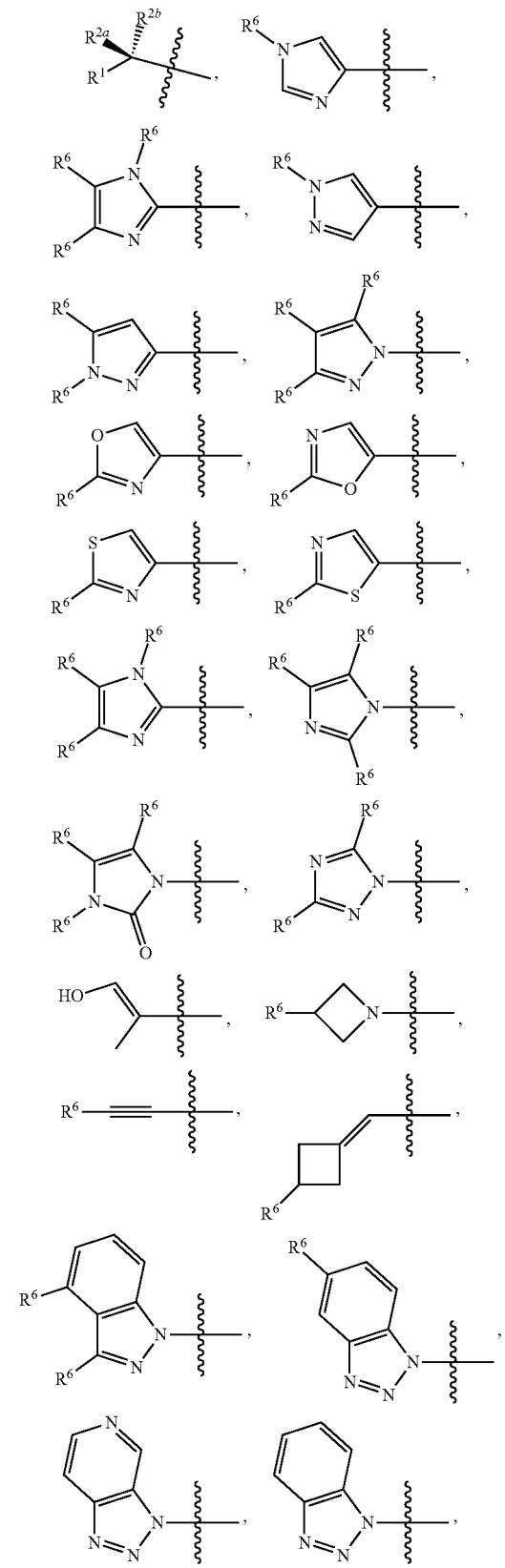

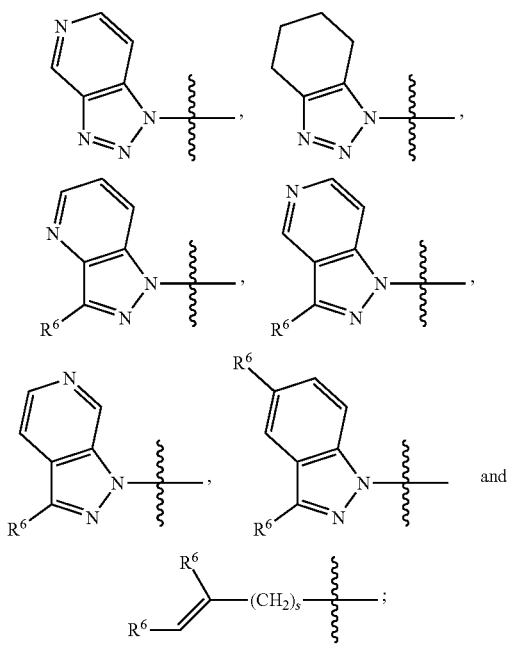
wherein s is 0 or 1.
In some embodiments $R^4$ is
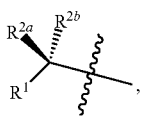
wherein $R^1$, $R^{2a}$ and $R^{2b}$ are as described herein.
In some embodiments of formula (I), $R^4$ is as defined above, and the A ring and the B ring together (including substituents, p, q, $R^{B1}$ and $R^{B2}$) are selected from the group consisting of:
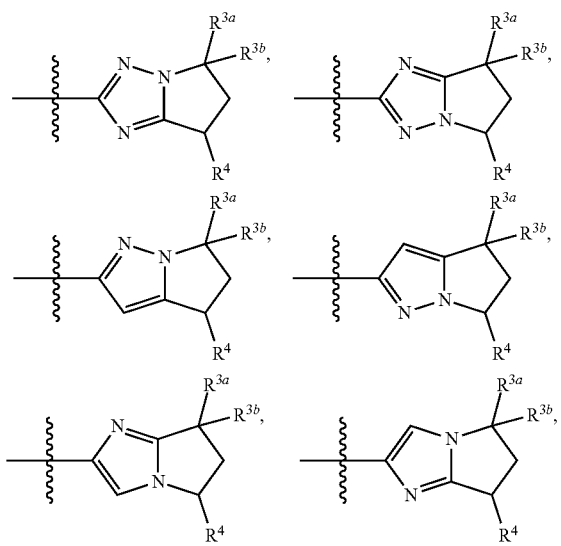
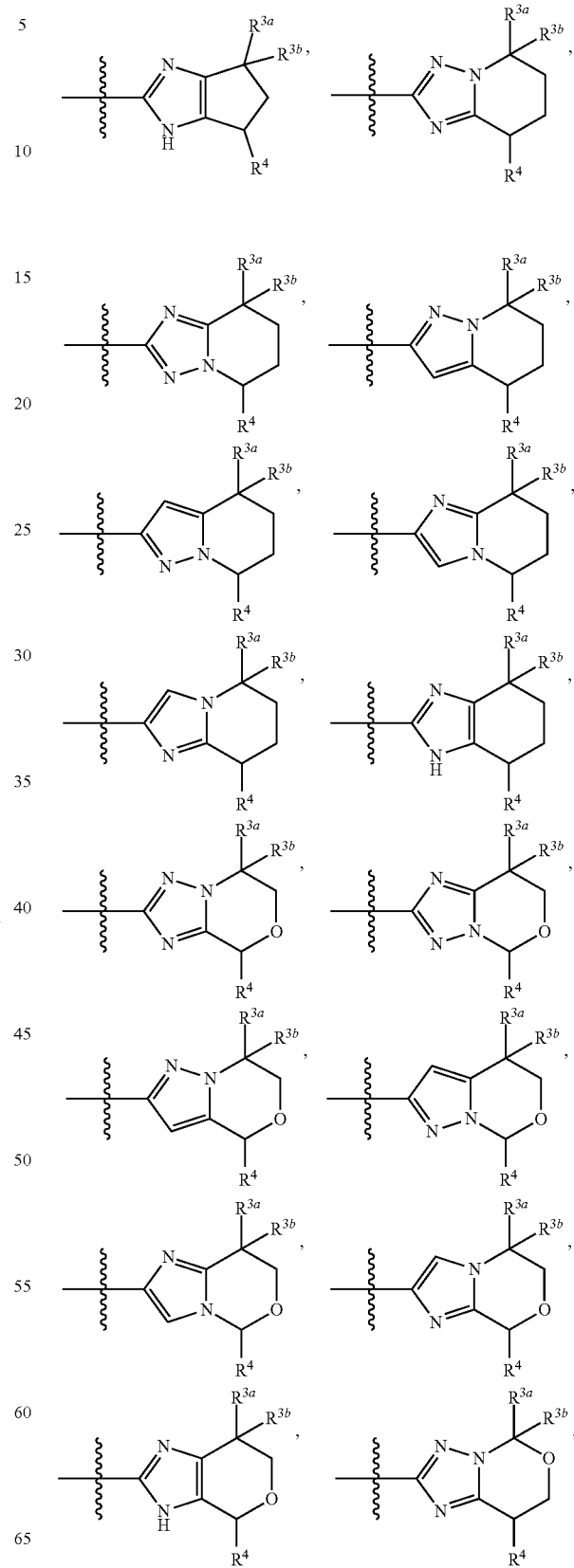

-continued

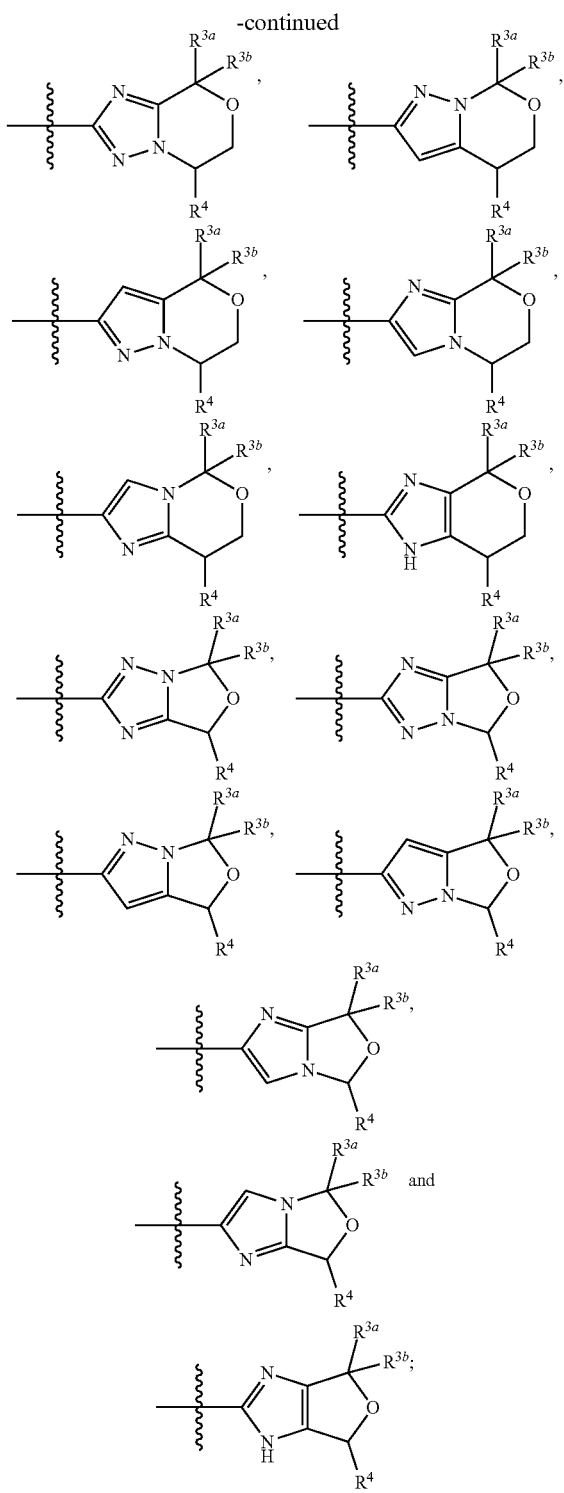

wherein
$R^{3a}$ and $R^{3b}$ are selected as follows:
(i) one of $R^{3a}$ and $R^{3b}$ is H, and the other is selected from the group consisting of H, D, F, Cl, OH, CN, $C_1$-$C_4$ alkyl, $C_1$-$C_4$ haloalkyl, cyclopropyl, $C_1$-$C_4$ alkoxy and $C_1$-$C_4$ haloalkoxy;
(ii) each of R and R is independently selected from the group consisting of D, F, Cl, OH, CN and methyl, provided that $R^{3a}$ and $R^{3b}$ cannot both be OH or CN; or
(iii) $R^{3a}$ and $R^{3b}$, together with the adjacent carbon atom, form cyclopropyl; and $R^4$ is selected from the group consisting of $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, phenyl, benzyl, $CH_2$—($C_3$-$C_6$ cycloalkyl), $CH_2CH_2$—($C_3$-$C_6$ cycloalkyl), $CH_2$-(4 to 6 membered heterocyclyl), $CH_2CH_2$-(4 to 6 membered heterocyclyl), 5 to 6 membered heteroaryl, and $CH_2$-(5 to 6 membered heteroaryl); wherein when a phenyl ring is present it may be substituted by 1 to 3 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano.

In some embodiments of formula (I), $R^4$ is as defined above, and the A ring and the B ring together are

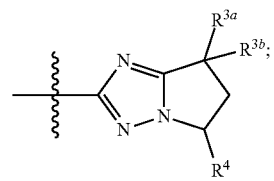

wherein
$R^{3a}$ and $R^{3b}$ are selected as follows:
(i) one of $R^{3a}$ and $R^{3b}$ is H, and the other is selected from the group consisting of H, D, F, Cl, OH, CN, $C_1$-$C_4$ alkyl, $C_1$-$C_4$ haloalkyl, cyclopropyl, $C_1$-$C_6$ alkoxy and $C_1$-$C_4$ haloalkoxy;
(ii) each of $R^{3a}$ and $R^{3b}$ is independently selected from the group consisting of D, F, Cl, OH, CN and methyl, provided that $R^{3a}$ and $R^{3b}$ cannot both be OH or CN; or
(iii) $R^{3a}$ and $R^{3b}$, together with the adjacent carbon atom, form cyclopropyl; and $R^4$ is selected from the group consisting of $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, phenyl, benzyl, $CH_2$—($C_3$-$C_6$ cycloalkyl), $CH_2CH_2$—($C_3$-$C_6$ cycloalkyl), $CH_2$-(4 to 6 membered heterocyclyl), $CH_2CH_2$-(4 to 6 membered heterocyclyl), 5 to 6 membered heteroaryl, and $CH_2$-(5 to 6 membered heteroaryl); wherein when a phenyl ring is present it may be substituted by 1 to 3 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano.

In some embodiments of formula (I), $R^4$ is as defined above, and the A ring and the B ring together are selected from the group consisting of:

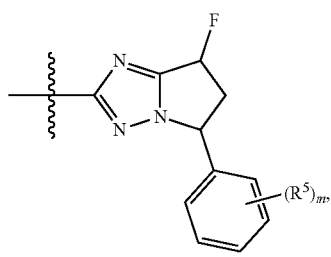

-continued

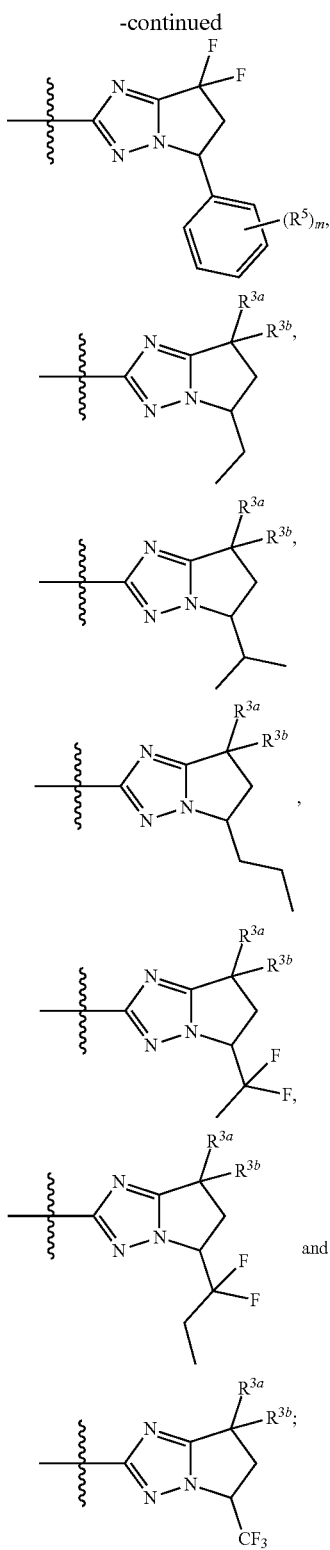

wherein
$R^{3a}$ and $R^{3b}$ are selected as follows:
(i) one of $R^{3a}$ and $R^{3b}$ is H, and the other is selected from the group consisting of H, D, F, Cl, OH, CN, $C_1$-$C_4$ alkyl, $C_1$-$C_4$ haloalkyl, cyclopropyl, $C_1$-$C_4$ alkoxy and $C_1$-$C_4$ haloalkoxy;

(ii) each of $R^{3a}$ and $R^{3b}$ is independently selected from the group consisting of D, F, Cl, OH, CN and methyl, provided that $R^{3a}$ and $R^{3b}$ cannot both be OH or CN; or
(iii) $R^{3a}$ and $R^{3b}$ together form cyclopropyl;
each $R^5$ is independently selected from the group consisting of H, F, Cl, $C_1$-$C_6$ alkyl, $C_1$-$C_6$ haloalkyl, $C_1$-$C_6$ alkoxy and $C_1$-$C_6$ haloalkoxy; and
m is 1, 2 or 3.

In some embodiments of formula (I), $R^4$ is as defined above, and the A ring and the B ring together are:

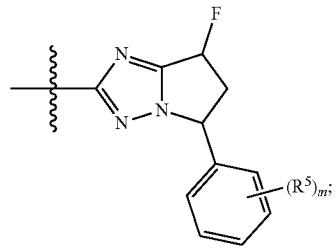

wherein
each $R^5$ is selected from the group consisting of H, F, Cl, $C_1$-$C_6$ alkyl, $C_1$-$C_6$ haloalkyl, $C_1$-$C_6$ alkoxy and $C_1$-$C_5$ haloalkoxy; and
m is 0, 1, 2 or 3.

In other embodiments m is 1, 2, 3.

In some embodiments of formula (I), $R^4$ is as defined above, and the A ring and the B ring together are:

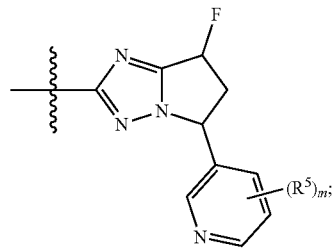

wherein
each $R^5$ is selected from the group consisting of H, F, Cl, $C_1$-$C_6$ alkyl, $C_1$-$C_6$ haloalkyl, $C_1$-$C_6$ alkoxy and $C_1$-$C_6$ haloalkoxy; and
m is 0, 1, 2 or 3.

In some of the above embodiments, $R^4$ is

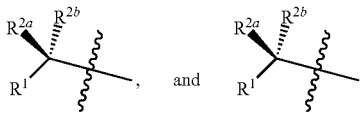

is selected from the group consisting of:

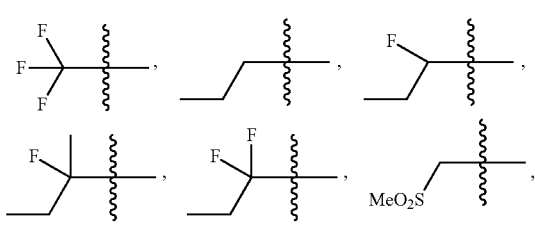

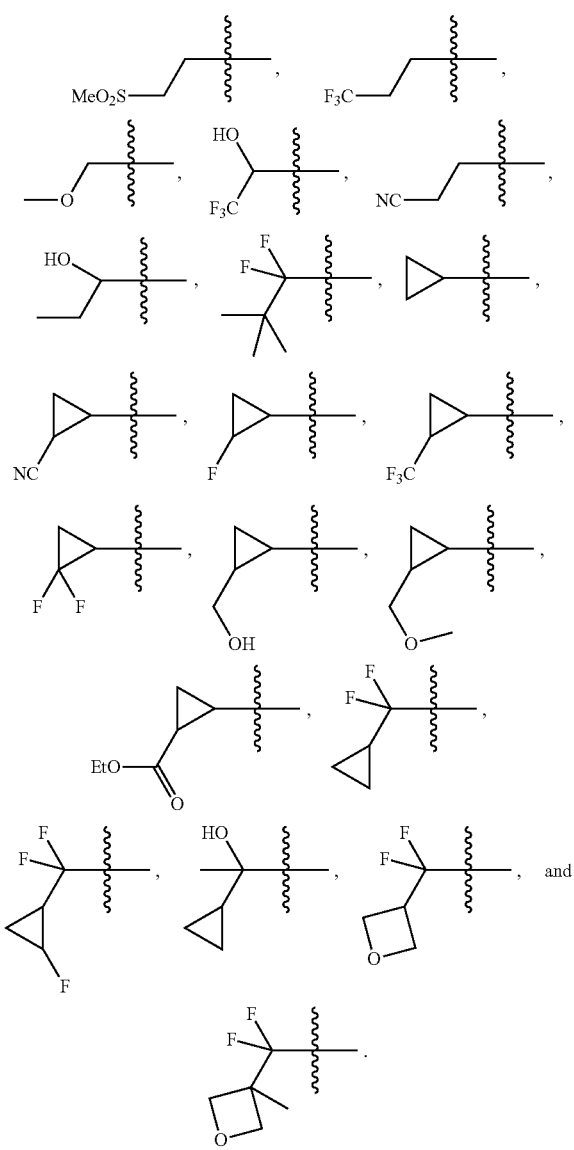
In some of the above embodiments, R$^A$ is
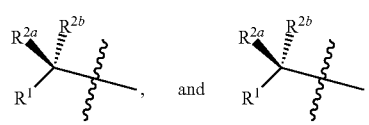
is selected from the group consisting of:
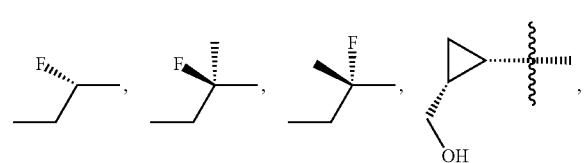
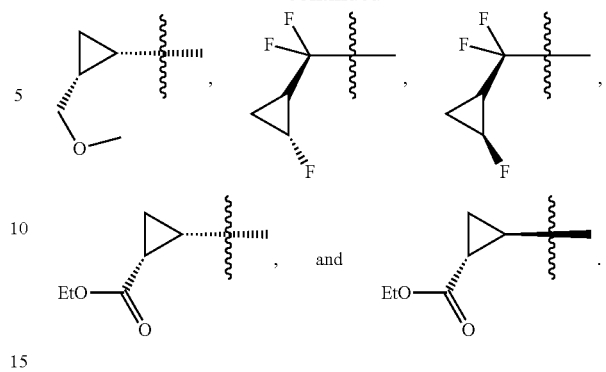
In some of the above embodiments R$^A$ is
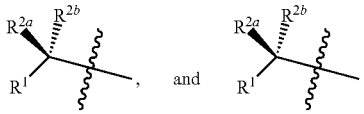
is selected from the group consisting of:
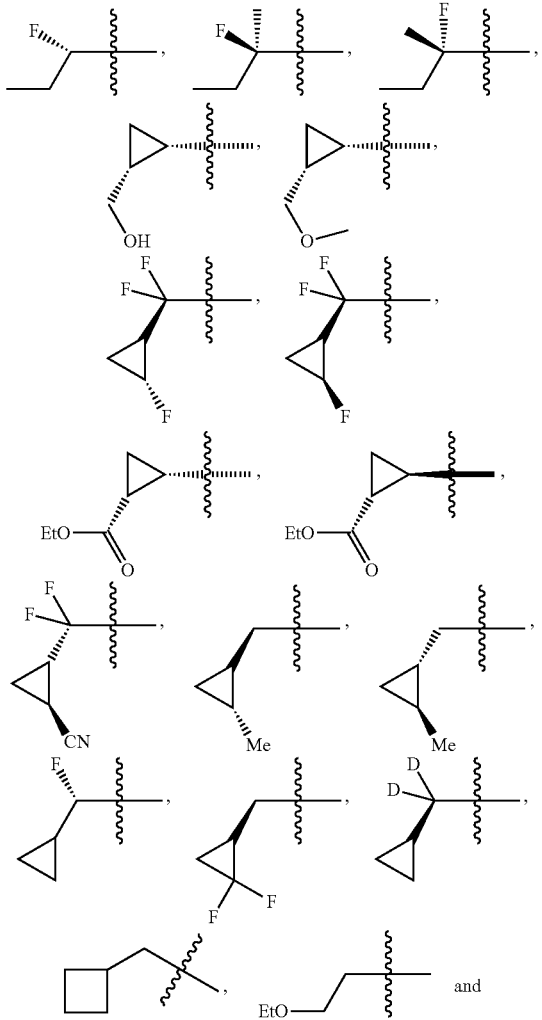

-continued

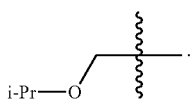

In some of the above embodiments, $R^4$ is selected from the group consisting of:

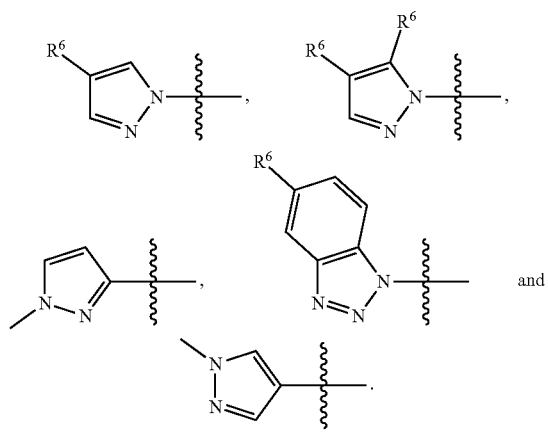

In some of the above embodiments, $R^4$ is selected from the group consisting of:

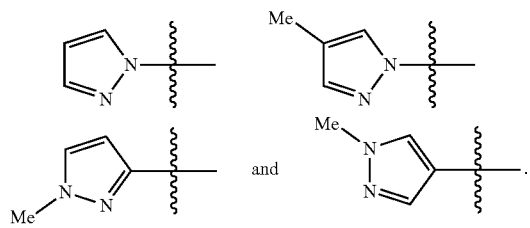

In some of the above embodiments, $R^4$ is selected from the group consisting of:

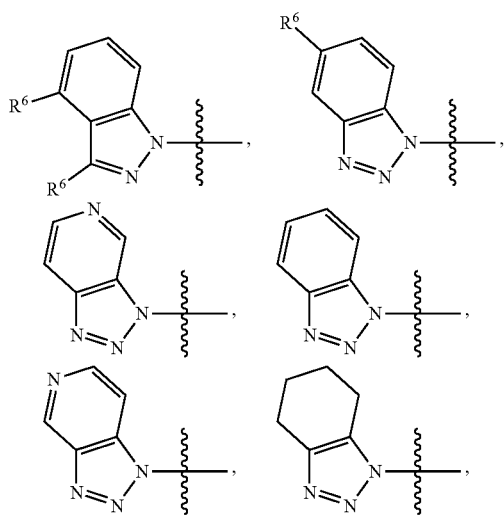

-continued

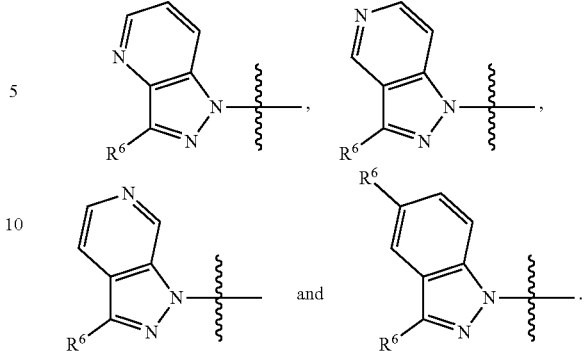

In some of the above embodiments, $R^1$ is selected from the group consisting of hydrogen, fluoro, hydroxyl, cyano, $CH_2CN$, $C_1$-$C_6$ alkyl, $C_3$-$C_6$ cycloalkyl, $C_1$-$C_6$ alkoxy, $C_1$-$C_6$ haloalkyl, $C_1$-$C_6$ haloalkoxy, and 4 to 5 membered heterocyclyl; n is 0, 1, 2 or 3; $R^{2a}$ and $R^{2b}$ are each independently selected from the group consisting of hydrogen, deutero, fluoro, hydroxyl, $C_1$-$C_3$ alkyl, $C_1$-$C_3$ fluoroalkyl; or when $R^1$ is hydrogen, deutero, fluoro, methyl or cyano; $R^{2a}$ and $R^{2b}$, together with the adjacent carbon atom, may form a cyclopropyl that is optionally substituted by one or two substituents selected from the group consisting of F, $C_{1-3}$ alkyl, hydroxyl, hydroxymethyl, methoxymethyl, cyano, $CO_2$—$C_{1-3}$ alkyl, trifluoromethyl, difluoromethoxy and trifluoromethoxy.

In some of the above embodiments, $R^1$ is selected from the group consisting of hydrogen, deutero, fluoro, hydroxyl, cyano, $C_1$-$C_6$ alkyl, $C_3$-$C_6$ cycloalkyl, $C_1$-$C_6$ alkoxy, $C_1$-$C_6$ haloalkyl, $C_1$-$C_6$ haloalkoxy, $C_1$-$C_6$ alkyl substituted with one $(R^N)_2N$ substituent, $C_1$-$C_6$ cyanoalkyl, $C_1$-$C_6$ alkylsulfonyl, phenyl, benzyl, 4 to 6 membered heterocyclyl, and 5 to 6 membered heteroaryl;
  wherein, when $R^1$ is phenyl, benzyl, $C_1$-$C_6$ alkyl, $C_1$-$C_6$ alkoxy or $C_3$-$C_6$ cycloalkyl, the phenyl, $C_1$-$C_6$ alkoxy or cycloalkyl ring is optionally substituted with 1 to 2 substituents selected from the group consisting of fluoro, chloro, cyano, $C_1$-$C_3$ alkyl, cyclopropyl, $C_1$-$C_3$ alkoxy, $C_1$-$C_3$ hydroxyalkyl, $C_1$-$C_3$ haloalkyl, $C_1$-$C_6$ alkoxycarbonyl, $C_1$-$C_3$ alkoxy-$C_1$-$C_3$ alkyl and $C_1$-$C_3$ haloalkoxy;

In some of the above embodiments, $R^{3a}$ and $R^{3b}$ are each H. In some of the above embodiments, $R^{3a}$ is H and $R^{3b}$ is D. In some of the above embodiments, $R^{3a}$ is H and $R^{3b}$ is F. In some of the above embodiments, $R^{3a}$ is H and $R^{3b}$ is Cl. In some of the above embodiments, $R^{3a}$ and $R^{3b}$ are each D. In some of the above embodiments, $R^{3a}$ and $R^{3b}$ are each F. In some of the above embodiments, $R^{3a}$ and $R^{3b}$ are each Cl. In some of the above embodiments, $R^{3a}$ and $R^{3b}$ are each methyl. In some of the above embodiments, $R^{3a}$ is methyl and $R^{3b}$ is F. In some of the above embodiments, $R^{3a}$ is methyl and $R^{3b}$ is Cl. In some of the above embodiments, $R^{3a}$ is methyl and $R^{3b}$ is OH. In some of the above embodiments, $R^{3a}$ is methyl and $R^{3b}$ is CN.

In some of the above embodiments, $R^4$ is phenyl. In some embodiments, $R^4$ is mono- or difluorophenyl. In some embodiments, $R^4$ is monofluorophenyl. In some embodiments, $R^4$ is mono- or dichlorophenyl. In some embodiments, $R^4$ is monochlorophenyl.

In some of the above embodiments, $R^5$ is selected from the group consisting of H, F, Cl, $CH_3$, $CH_2CH_3$, $OCH_3$, $CF_3$, $OCF_3$, $CF_2H$, and $OCF_2H$. In some of the above embodiments, $R^5$ is H. In some of the above embodiments, $R^5$ is F.

In some of the above embodiments, $R^5$ is Cl. In some of the above embodiments, $R^5$ is $CH_3$. In some of the above embodiments, $R^5$ is $CF_3$.

In some of the above embodiments, each $R^N$ is independently selected from the group consisting of H and $C_1$-$C_6$ alkyl. In some embodiments, each $R^N$ is a $C_1$-$C_4$ alkyl. In some embodiments, each $R^N$ is methyl.

In some of the above embodiments, n is 0. In some of the above embodiments, n is 1. In some embodiments, n is 2. In some embodiments, n is 3.

In some of the above embodiments, m is 0. In some embodiments, m is 1. In some embodiments, m is 2.

In some of the above embodiments, m is 1 and $R^5$ is F. In some embodiments, m is 2 and $R^5$ is F. In some of the above embodiments, m is 1 and $R^5$ is Cl. In some embodiments, m is 2 and $R^5$ is Cl.

In some of the above embodiments, each $R^1$ is independently selected from the group consisting of hydrogen and $C_1$-$C_6$ alkyl. In some of the above embodiments, each $R^1$ is hydrogen or methyl.

In some of the above embodiments, $R^6$ is independently selected from the group consisting of hydrogen, halogen, $C_1$-$C_6$ alkyl, $C_3$-$C_6$ cycloalkyl, $C_1$-$C_3$ cyanoalkyl, $C_1$-$C_3$ alkylcarbonyl, $C_1$-$C_3$ methylsulfonyl, $C_1$-$C_6$ alkoxy, $C_1$-$C_6$ haloalkyl, formyl, $C_1$-$C_6$ haloalkoxy, cyano, 1-methyl-pyrazol-4-yl and pyrimidinyl.

Also provided herein is a compound selected from the compounds of Table 1 below or a pharmaceutically acceptable salt thereof. In another embodiment, provided herein is a compound of Table 1 having a $K_i$ of less than 100 nM in a RIP1K biochemical or cell-based assay, including as herein described. In another embodiment, the compound of Table 1 has a $K_i$ of less than 50 nM in a RIP1K biochemical or cell-based assay, including as herein described. In yet another embodiment, the compound of Table 1 has a K. of less than 25 nM in a RIP1K biochemical or cell-based assay, including as herein described. In yet another embodiment, the compound of Table 1 has a $K_i$ of less than 10 nM in a RIP1K biochemical or cell-based assay, including as herein described.

In some embodiments, provided herein is a single stereoisomer of a compound of Table 1, as characterized by reference to its chiral separation and isolation (e.g., as described in the Examples by chiral SFC).

In some embodiments, provided herein are pharmaceutical compositions comprising a compound of formula I as described in any one of the above embodiments, or a pharmaceutically acceptable salt thereof, and one or more pharmaceutically acceptable carriers or excipients. Specific embodiments include pharmaceutical compositions suitable for oral delivery.

Also provided herein are oral formulations of a compound of formula I as described in any one of the above embodiments, or a pharmaceutically acceptable salt thereof, and one or more pharmaceutically acceptable carriers or excipients suitable for oral delivery.

In some embodiments, provided herein are uses of a compound of formula I as described in any one of the above embodiments, or a pharmaceutically acceptable salt thereof, for the treatment of neurodegenerative diseases and disorders. In some embodiments, the diseases and disorders to be treated are synucleopathies such as Parkinson's Disease, Lewy body dementia, multiple system atrophy, Parkinson-plus syndromes. In some embodiments, the diseases and disorders to be treated are taupathies such as Alzheimer's Disease and frontotemporal dementia. In some embodiments, the diseases and disorders to be treated are demyelination diseases such as multiple sclerosis.

In some embodiments, the diseases and disorders to be treated are other neurodegenerative diseases such as amyotrophic lateral sclerosis, spinal muscular atrophy, primary lateral sclerosis, Huntington's disease, ischemia, and stroke. Additional exemplary neurodegenerative diseases to be treated as provided herein include, but are not limited to, intracranial hemorrhage, cerebral hemorrhage, muscular dystrophy, progressive muscular atrophy, pseudobulbar palsy, progressive bulbar palsy, spinal muscular atrophy, inherited muscular atrophy, peripheral neuropathies, progressive supranuclear palsy, corticobasal degeneration, and demyelinating diseases.

In some embodiments, the disease or disorder to be treated is Alzheimer's disease. In some embodiments, the disease or disorder to be treated is Parkinson's disease. In some embodiments, the disease or disorder to be treated is Huntington's disease. In some embodiments, the disease or disorder to be treated is multiple sclerosis. In some embodiments, the disease or disorder to be treated is amyotrophic lateral sclerosis (ALS). In some embodiments, the disease or disorder to be treated is spinal muscular atrophy (SMA).

In some embodiments, provided herein are uses of a compound of formula I as described in any one of the above embodiments, or a pharmaceutically acceptable salt thereof, for the treatment of inflammatory diseases and disorders. In some embodiments, the disease or disorder to be treated is selected from the group consisting of inflammatory bowel diseases (including Crohn's disease and ulcerative colitis), psoriasis, retinal detachment, retinitis pigmentosa, macular degeneration, pancreatitis, atopic dermatitis, arthritis (including rheumatoid arthritis, osteoarthritis, spondylarthritis, gout, systemic onset juvenile idiopathic arthritis (SoJIA), psoriatic arthritis), systemic lupus erythematosus (SLE), Sjogren's syndrome, systemic scleroderma, anti-phospholipid syndrome (APS), vasculitis, liver damage/diseases (non-alcohol steatohepatitis, alcohol steatohepatitis, autoimmune hepatitis autoimmune hepatobiliary diseases, primary sclerosing cholangitis (PSC), acetaminophen toxicity, hepatotoxicity), kidney damage/injury (nephritis, renal transplant, surgery, administration of nephrotoxic drugs e.g. cisplatin, acute kidney injury (AKI), Celiac disease, autoimmune idiopathic thrombocytopenic purpura, transplant rejection, ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, amyotrophic lateral sclerosis (ALS), spinal muscular atrophy (SMA), allergic diseases (including asthma and atopic dermatitis), multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), tumor necrosis factor receptor-associated periodic syndrome (TRAPS), periodontitis, NEMO-deficiency syndrome (F-kappa-B essential modulator gene (also known as IKK gamma or IKKG) deficiency syndrome), HOIL-1 deficiency ((also known as RBCKI) heme-oxidized IRP2 ubiquitin ligase-1 deficiency), linear ubiquitin chain assembly complex (LUBAC) deficiency syndrome, hematological and solid organ malignancies, bacterial infections and viral infections (such as tuberculosis and influenza), and Lysosomal storage diseases (particularly, Gaucher Disease, and including GM2, Gangliosidosis, Alpha-mannosidosis, Aspartylglucosaminuria, Cholesteryl Ester storage disease, Chronic Hexosaminidase A Deficiency, Cystinosis, Danon disease, Fabry disease, Farber disease, Fucosidosis, Galactosialidosis, GM1 gangliosidosis, Mucolipidosis, Infantile Free Sialic Acid Storage Disease, Juvenile Hexosaminidase A Deficiency, Krabbe disease, Lysosomal acid lipase deficiency, Metachromatic Leukodystrophy, Mucopolysaccharidoses disorders, Multiple sulfatase deficiency, Niemann-Pick Disease, Neuronal Ceroid Lipofuscinoses, Pompe disease, Pycnodysostosis, Sandhoff disease, Schindler disease, Sialic Acid Storage Disease, Tay-Sachs and Wolman disease).

In some embodiments, the disease or disorder to be treated is an inflammatory bowel disease. In some embodiments, the disease or disorder to be treated is Crohn's disease. In some embodiments, the disease or disorder to be treated is ulcerative colitis. In some embodiments, the disease or disorder to be treated is glaucoma. In some embodiments, the disease or disorder to be treated is psoriasis. In some embodiments, the disease or disorder to be treated is rheumatoid arthritis. In some embodiments, the disease or disorder to be treated is spondyloarthritis. In some embodiments, the disease or disorder to be treated is juvenile idiopathic arthritis. In some embodiments, the disease or disorder to be treated is osteoarthritis.

In some embodiments, provided herein are methods for the treatment or prevention of a disease or disorder with a therapeutically effective amount of a compound of formula I, or a pharmaceutically acceptable salt thereof, wherein the disease or disorder is associated with inflammation and/or necroptosis. In some embodiments said disease or disorder is selected from the specific diseases and disorders recited herein.

In some embodiments, provided herein are methods of inhibiting RIP1 kinase activity by contacting a cell with a compound of formula I or a pharmaceutically acceptable salt thereof.

Pharmaceutical Compositions and Administration

Provided herein are pharmaceutical compositions or medicaments containing the compounds of the invention (or stereoisomers, geometric isomers, tautomers, solvates, metabolites, isotopes, pharmaceutically acceptable salts, or prodrugs thereof), and a therapeutically inert carrier, diluent or excipient, as well as methods of using the compounds of the invention to prepare such compositions and medicaments. In one example, compounds of formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I is formulated in an acetate buffer, at pH 5. In another embodiment, the compounds of formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. In some embodiments, the "effective amount" of the compound to be administered will be governed by such considerations, and is the minimum amount necessary to inhibit RIP1 kinase activity in order to provide a therapeutic effect in the mammal being treated. In addition, such an effective amount may be below the amount that is toxic to normal cells, or the mammal as a whole.

In one example, the pharmaceutically effective amount of the compound of the invention administered intravenously or parenterally will be in the per dose range of about 0.1 to 100 mg/kg, alternatively about 0.1 to 20 mg/kg of patient body weight per day, or alternatively about 0.3 to 15 mg/kg/day.

In another embodiment, oral unit dosage forms, such as tablets and capsules, preferably contain from about 1 to about 1000 mg (e.g., 1 mg, 5 mg, 10 mg, 15 mg, 20 mg, 25 mg, 30 mg, 40 mg, 50 mg, 100 mg, 200 mg, 250 mg, 400 mg, 500 mg, 600 mg, 700 mg, 800 mg, 900 mg, or 1000 mg) of the compound of the invention. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

In some embodiments, a low dose of the compound of the invention is administered in order to provide therapeutic benefit while minimizing or preventing adverse effects.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration. In specific embodiments, the compound of formula I is administered orally. In other specific embodiments, the compound of formula I is administered intravenously.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., compound of formula I or an embodiment thereof) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) 21$^{st}$ Edition, Lippincott Williams & Wilkins, Philadelphia, Pa.

Sustained-release preparations of a compound of the invention (e.g., compound of formula I or an embodiment thereof) can be prepared. Suitable examples of sustained-release preparations include semipermeable matrices of solid hydrophobic polymers containing a compound of formula I or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(-)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

In one example, compounds of formula I or an embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I (or an embodiment thereof) is formulated in an acetate buffer, at pH 5. In another embodiment, the compounds of formula I or an embodiment thereof are sterile. The compound may be stored, for example, as a solid or amorphous composition, as a lyophilized formulation or as an aqueous solution.

An example of a suitable oral dosage form provided herein is a tablet containing about 1 to about 500 mg (e.g., about 1 mg, 5 mg, 10 mg, 25 mg, 30 mg, 50 mg, 80 mg, 100 mg, 150 mg, 250 mg, 300 mg and 500 mg) of the compound of the invention compounded with suitable amounts of anhydrous lactose, sodium croscarmellose, polyvinylpyrrolidone (PVP) K30, and magnesium stearate. The powdered ingredients are first mixed together and then mixed with a solution of the PVP. The resulting composition can be dried, granulated, mixed with the magnesium stearate and compressed to tablet form using conventional equipment.

Formulations of a compound of the invention (e.g., compound of formula I or an embodiment thereof) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described.

An embodiment, therefore, includes a pharmaceutical composition comprising a compound of formula I, or pharmaceutically acceptable salt thereof. In a further embodiment includes a pharmaceutical composition comprising a compound of formula I, or a pharmaceutically acceptable salt thereof, together with a pharmaceutically acceptable carrier or excipient.

When the binding target is located in the brain, certain embodiments of the invention provide for a compound of formula I (or an embodiment thereof) to traverse the blood-brain barrier. In these embodiments, the compounds provided herein exhibit sufficient brain penetration as potential therapeutics in neurological diseases. In some embodiments, brain penetration is assessed by evaluating free brain/plasma ratio ($B_u/P_u$) as measured in vivo pharmacokinetic studies in rodents or by other methods known to persons skilled in the art (see, e.g., Liu, X. et al., J. Pharmacol. Exp. Therap., 325:349-56, 2008).

Certain neurological diseases are associated with an increase in permeability of the blood-brain barrier, such that a compound of formula I (or an embodiment thereof) can be readily introduced to the brain. When the blood-brain barrier remains intact, several art-known approaches exist for transporting molecules across it, including, but not limited to, physical methods, lipid-based methods, and receptor and channel-based methods. Physical methods of transporting a compound of formula I (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford.

Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula I (or an embodiment thereof) across the blood-brain barrier include, but are not limited to, encapsulating the a compound of formula I or I-I (or an embodiment thereof) in liposomes that are coupled to antibody binding fragments that bind to receptors on the vascular endothelium of the blood-brain barrier (see, e.g., U.S. Patent Publication No. 2002/0025313), and coating a compound of formula I (or an embodiment thereof) in low-density lipoprotein particles (see, e.g., U.S. Patent Publication No. 2004/0204354) or apolipoprotein E (see, e.g., U.S. Patent Publication No. 2004/0131692).

Receptor and channel-based methods of transporting a compound of formula I (or an embodiment thereof) across the blood-brain barrier include, but are not limited to, using glucocorticoid blockers to increase permeability of the blood-brain barrier (see, e.g., U.S. Patent Publication Nos. 2002/0065259, 2003/0162695, and 2005/0124533); activating potassium channels (see, e.g., U.S. Patent Publication No. 2005/0089473), inhibiting ABC drug transporters (see, e.g., U.S. Patent Publication No. 2003/0073713); coating a compound of formula I or I-I (or an embodiment thereof) with a transferrin and modulating activity of the one or more transferrin receptors (see, e.g., U.S. Patent Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

Indications and Methods of Treatment

The compounds of the invention inhibit RIP1 kinase activity. Accordingly, the compounds of the invention are useful for the treatment of diseases and disorders mediated by this pathway and associated with inflammation and/or necroptotic cell death.

In some embodiments, the disease or disorder to be treated is a neurodegenerative disease or disorder. In some embodiments, the diseases and disorders to be treated are synucleopathies such as Parkinson's Disease, Lewy body dementia, multiple system atrophy, Parkinson-plus syndromes. In some embodiments, the diseases and disorders to be treated are taupathies such as Alzheimer's Disease and frontotemporal dementia. In some embodiments, the diseases and disorders to be treated are demyelination diseases such as multiple sclerosis.

In some embodiments, the diseases and disorders to be treated are other neurodegenerative diseases such as amyotrophic lateral sclerosis, spinal muscular atrophy, primary lateral sclerosis, Huntington's disease, ischemia, and stroke. Additional exemplary neurodegenerative diseases to be treated as provided herein include, but are not limited to, intracranial hemorrhage, cerebral hemorrhage, muscular dystrophy, progressive muscular atrophy, pseudobulbar palsy, progressive bulbar palsy, spinal muscular atrophy, inherited muscular atrophy, peripheral neuropathies, progressive supranuclear palsy, corticobasal degeneration, and demyelinating diseases.

In some embodiments, the disease or disorder to be treated is Alzheimer's disease. In some embodiments, the disease or disorder to be treated is Parkinson's disease. In some embodiments, the disease or disorder to be treated is Huntington's disease. In some embodiments, the disease or disorder to be treated is multiple sclerosis. In some embodiments, the disease or disorder to be treated is amyotrophic lateral sclerosis (ALS). In some embodiments, the disease or disorder to be treated is spinal muscular atrophy (SMA).

In some embodiments, the disease or disorder to be treated is an inflammatory disease or disorder. In some embodiments, the disease or disorder to be treated is selected from the group consisting of inflammatory bowel diseases (including Crohn's disease and ulcerative colitis), psoriasis, retinal detachment, retinitis pigmentosa, macular degeneration, pancreatitis, atopic dermatitis, arthritis (including rheumatoid arthritis, osteoarthritis, spondylarthritis, gout, systemic onset juvenile idiopathic arthritis (SoJIA), psoriatic arthritis), systemic lupus erythematosus (SLE), Sjogren's syndrome, systemic scleroderma, anti-phospholipid syndrome (APS), vasculitis, liver damage/diseases (non-alcohol steatohepatitis, alcohol steatohepatitis, autoimmune hepatitis autoimmune hepatobiliary diseases, primary sclerosing cholangitis (PSC), acetaminophen toxicity, hepatotoxicity), kidney damage/injury (nephritis, renal transplant, surgery, administration of nephrotoxic drugs e.g. cisplatin, acute kidney injury (AKI), Celiac disease, autoimmune idiopathic thrombocytopenic purpura, transplant rejection, ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, amyotrophic lateral sclerosis (ALS), spinal muscular atrophy (SMA), allergic diseases (including asthma and atopic dermatitis), multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), tumor necrosis factor receptor-associated periodic syndrome (TRAPS), periodontitis, NEMO-deficiency syndrome (F-kappa-B essential modulator gene (also known as IKK gamma or IKKG) deficiency syndrome), HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections and viral infections (such as tuberculosis and influenza), and Lysosomal storage diseases (particularly, Gaucher Disease, and including GM2, Gangliosidosis, Alpha-mannosidosis, Aspartylglucosaminuria, Cholesteryl Ester storage disease, Chronic Hexosaminidase A Deficiency, Cystinosis, Danon disease, Fabry disease, Farber disease, Fucosidosis, Galactosialidosis, GM1 gangliosidosis, Mucolipidosis, Infantile Free Sialic Acid Storage Disease, Juvenile Hexosaminidase A Deficiency, Krabbe disease, Lysosomal acid lipase deficiency, Metachromatic Leukodystrophy, Mucopolysaccharidoses disorders, Multiple sulfatase deficiency, Niemann-Pick Disease, Neuronal Ceroid Lipofuscinoses, Pompe disease, Pycnodysostosis, Sandhoff disease, Schindler disease, Sialic Acid Storage Disease, Tay-Sachs and Wolman disease).

In some embodiments, the disease or disorder to be treated is an inflammatory bowel disease. In some embodiments, the disease or disorder to be treated is Crohn's disease. In some embodiments, the disease or disorder to be treated is ulcerative colitis. In some embodiments, the disease or disorder to be treated is glaucoma. In some embodiments, the disease or disorder to be treated is psoriasis. In some embodiments, the disease or disorder to be treated is rheumatoid arthritis. In some embodiments, the disease or disorder to be treated is spondyloarthritis. In some embodiments, the disease or disorder to be treated is juvenile idiopathic arthritis. In some embodiments, the disease or disorder to be treated is osteoarthritis.

In some embodiments, the method of treatment provided herein is the treatment of one or more symptoms of a disease or disorder listed above.

Also provided herein is the use of a compound of the invention in therapy. In some embodiments, provided herein is the use of a compound of the invention for use in the treatment or prevention of the above diseases and disorders. Also provided herein is the use of a compound of the invention in the manufacture of a medicament for the treatment or prevention of the above diseases and disorders.

Also provided herein is a method of treating a disease or disorder as provided above in a mammal in need of such treatment, wherein the method comprises administering to said mammal a therapeutically effective amount of a compound of formula I, or a pharmaceutically acceptable salt thereof. In some embodiments, the mammal is a human.

Also provided herein is a method of treating a symptom of a disease or disorder in a mammal in need of such treatment, said disease or disorder being selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cysplatin-induced kidney injury, sepsis, systemic inflammatory response syndrome (SIRS), pancreatits, psoriasis, retinitis pigmentosa, retinal degeneration, chronic kidney diseases, acute respiratory distress syndrome (ARDS), and chronic obstructive pulmonary disease (COPD), wherein the method comprises administering to said mammal a therapeutically effective amount of a compound of formula I, or a pharmaceutically acceptable salt thereof.

Also provided herein is a method of treating a disease or disorder in a human patient in need of such treatment, said disease or disorder being selected from those provided above, wherein the method comprises orally administering a therapeutically effective amount of a compound of formula I, or a pharmaceutically acceptable salt thereof, as an orally acceptable pharmaceutical composition.

Combination Therapy

Compounds of the invention may be combined with one or more other compounds of the invention or one or more other therapeutic agent as any combination thereof, in the treatment of the diseases and disorders provided herein. For example, a compound of the invention may be administered simultaneously, sequentially or separately in combination with other therapeutic agents known to be useful for the treatment of a disease or disorder selected from those recited above.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

In some embodiments, a compound provided herein may be combined with another therapeutically active agent as recited in WO 2016/027253, the contents of which are hereby incorporated by reference in their entirety. In such embodiments, the compound that inhibits RIP1 kinase in the combinations recited in WO 2016/027253 is replaced by a compound of formula I of the present disclosure.

In some embodiments, a compound provided herein may be combined with a DLK inhibitor for the treatment of neurodegenerative diseases and disorders, such as those listed elsewhere herein, and including but not limited to the following: Parkinson's Disease, Lewy body dementia, multiple system atrophy, Parkinson-plus syndromes, Alzheimer's Disease, frontotemporal dementia, demyelination diseases such as multiple sclerosis, amyotrophic lateral sclerosis, spinal muscular atrophy, primary lateral sclerosis, Huntington's disease, ischemia, stroke, intracranial hemorrhage, cerebral hemorrhage, muscular dystrophy, progressive muscular atrophy, pseudobulbar palsy, progressive bulbar palsy, spinal muscular atrophy, inherited muscular atrophy, peripheral neuropathies, progressive supranuclear palsy, and corticobasal degeneration. DLK inhibitors are described, for example, in WO 2013/174780, WO 2014/177524, WO 2014/177060, WO 2014/111496, WO 2015/091889 and WO 2016/142310.

Examples

The invention will be more fully understood by reference to the following examples. They should not, however, be construed as limiting the scope of the invention.

These examples serve to provide guidance to a skilled artisan to prepare and use the compounds, compositions and methods of the invention. While particular embodiment of the present invention are described, the skilled artisan will appreciate that various changes and modifications can be made without departing from the spirit and scope of the inventions.

The chemical reactions in the examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, for example, by appropriately protecting interfering group, by utilizing other suitable reagents known in the art, for example, by appropriately protecting interfering groups by utilizing other suitable reagents known in the art other than those described, and/or by making routine modifications of reaction conditions.

In the examples below, unless otherwise indicated all temperatures are set forth in degrees Celsius. Commercially available reagents were purchased from suppliers such as Aldrich Chemical Company, Lancaster, TCI or Maybridge and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. $^1$H NMR spectra were obtained in deuterated CDCl$_3$, d$_6$-DMSO, CH$_3$OD or d$_6$-acetone solvent solutions (reported in ppm) using or trimethylsilane (TMS) or residual non-deuterated solvent peaks as the reference standard. When peak multiplicities are reported, the following abbreviates are used: s (singlet), d (doublet), t (triplet), q (quartet), m (multiplet, br (broadened), dd (doublet of doublets), dt (doublet of triplets). Coupling constants, when given, ar reported in Hz (Hertz).

All abbreviations used to describe reagents, reaction conditions or equipment are intended to be consistent with the definitions set forth in the following list of Abbreviations. The chemical names of discrete compounds of the invention were typically obtained using the structure naming feature of ChemDraw naming program.

Abbreviations

ACN Acetonitrile
Boc tert-Butoxycarbonyl
DAST Diethylaminosulfur trifluoride
DCE 1,2-dichloroethane
DCM Dichloromethane
DMF N,N-Dimethylformamide
DMSO Dimethyl sulfoxide
DPPH 2,2-Diphenyl-1-picrylhydrazyl
HPLC High Pressure Liquid Chromatography
LCMS Liquid Chromatography Mass Spectrometry
PCC Pyridinium chlorochromate
RP Reverse phase
RT or R$_T$ Retention time
SEM 2-(Trimethylsilyl)ethoxymethyl
SFC Supercritical Fluid Chromatography
TBDMS tert-Butyldimethylsilyl
TFA Trifluoroacetic acid
THF Tetrahydrofuran

Synthetic Schemes
In addition to the specific synthetic methods of the examples below, additional compounds of the present invention may be prepared, for example, according to the following synthetic schemes.
Schemes 1-4 illustrate the preparation of chemical intermediates provided in the examples herein.
Scheme 1
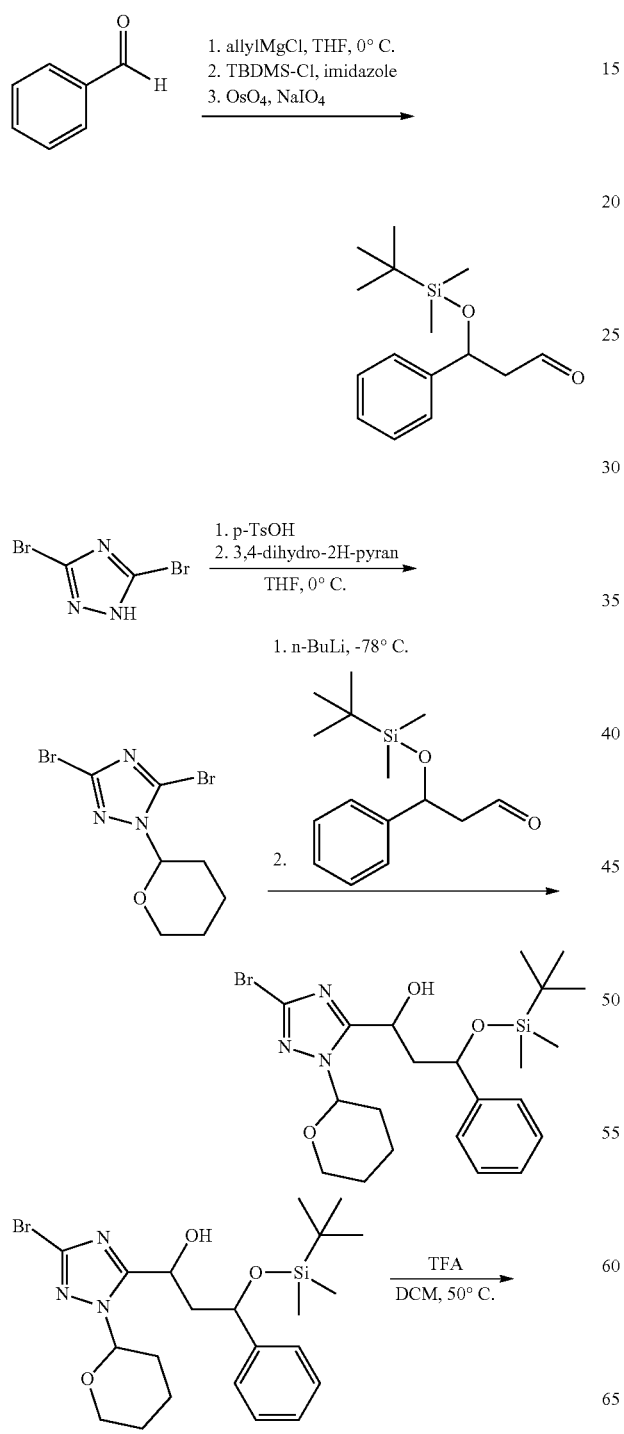
Scheme 2
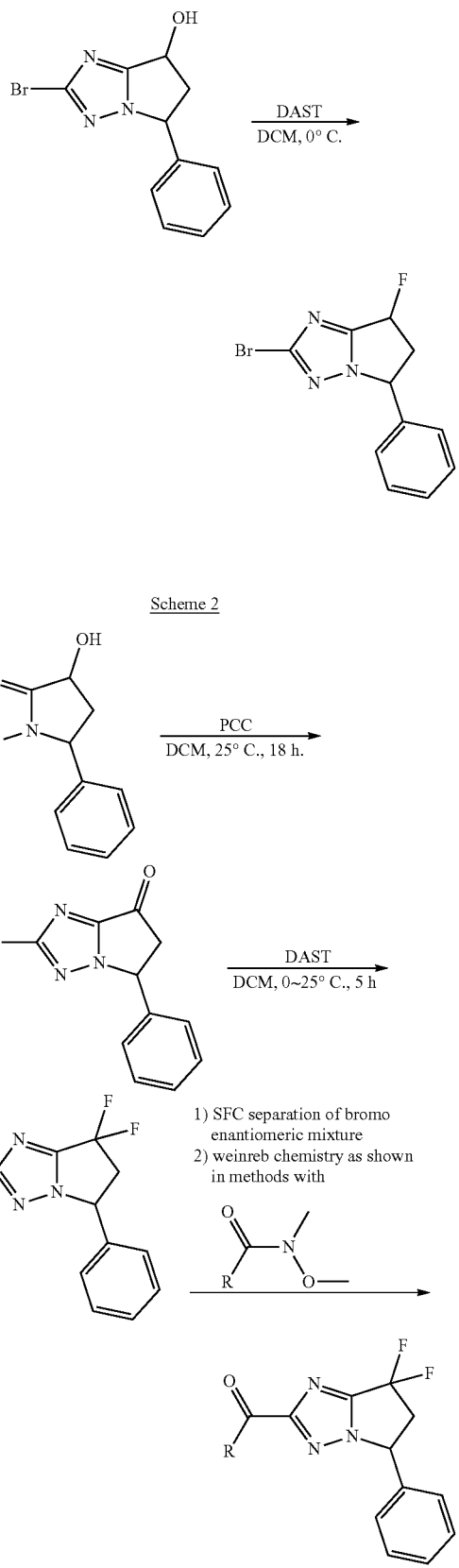

Scheme 3 is followed to prepare additional B ring diversity of compounds of formula I using a variety of nucleophiles including but not limited to halide and cyanide sources:
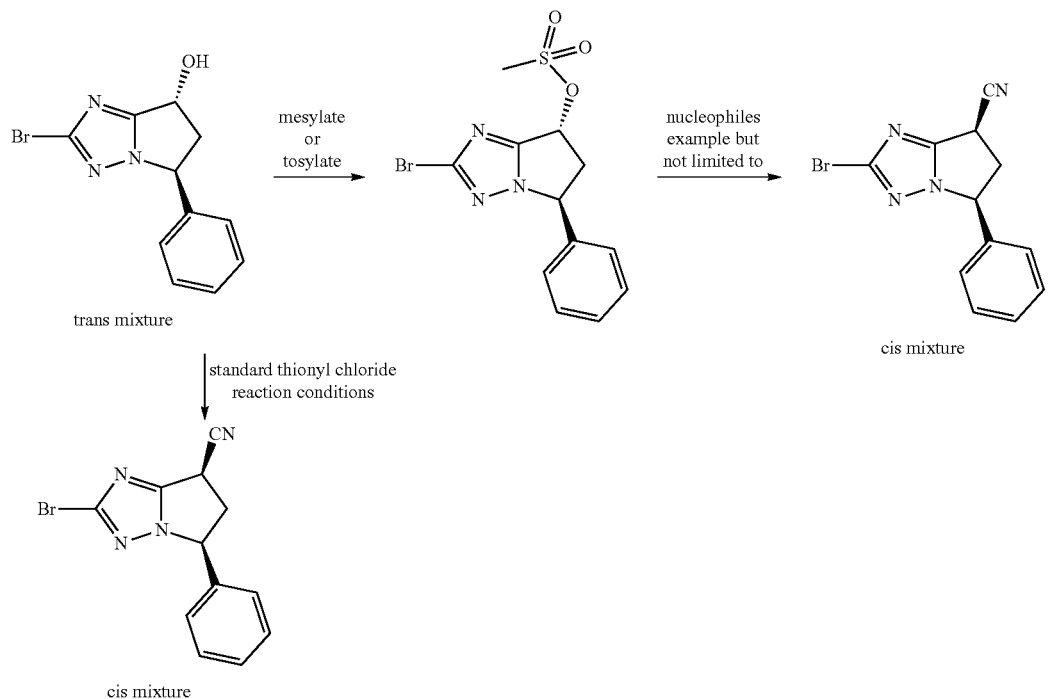
Scheme 4 is followed to prepare gem-dimethyl B ring substituted compounds of formula I:
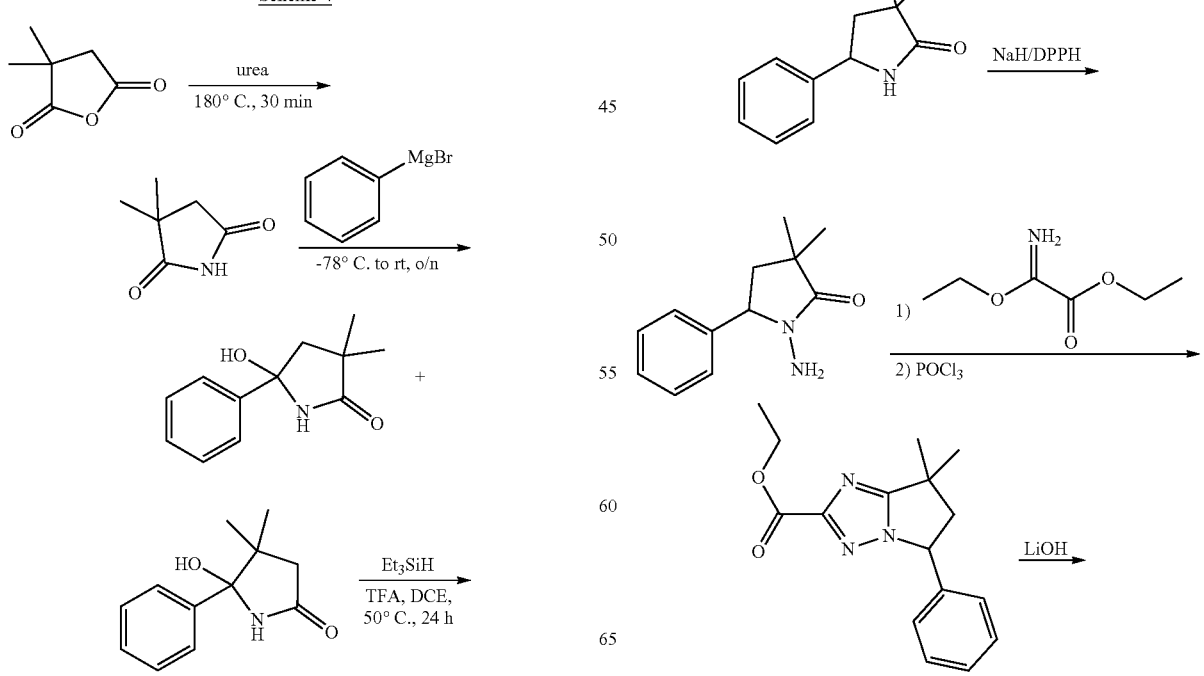

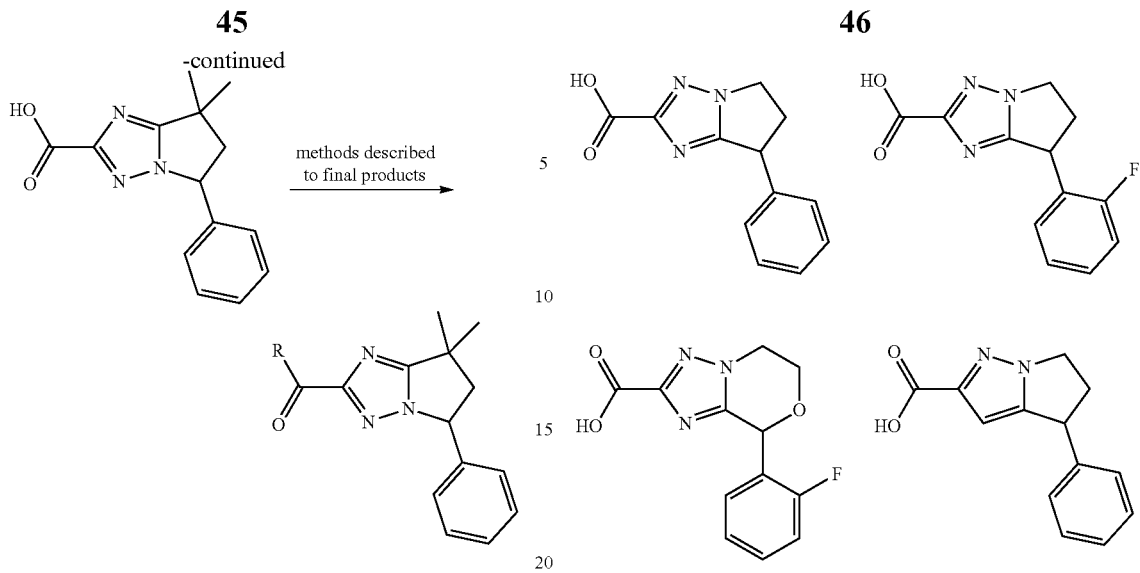
The following intermediates used in the examples below were prepared according to the procedures described in WO 2017/004500 (the entirety of which is incorporated herein by reference):
The following exemplary reactions are then used to prepare certain compounds of Formula I according to Scheme 5:
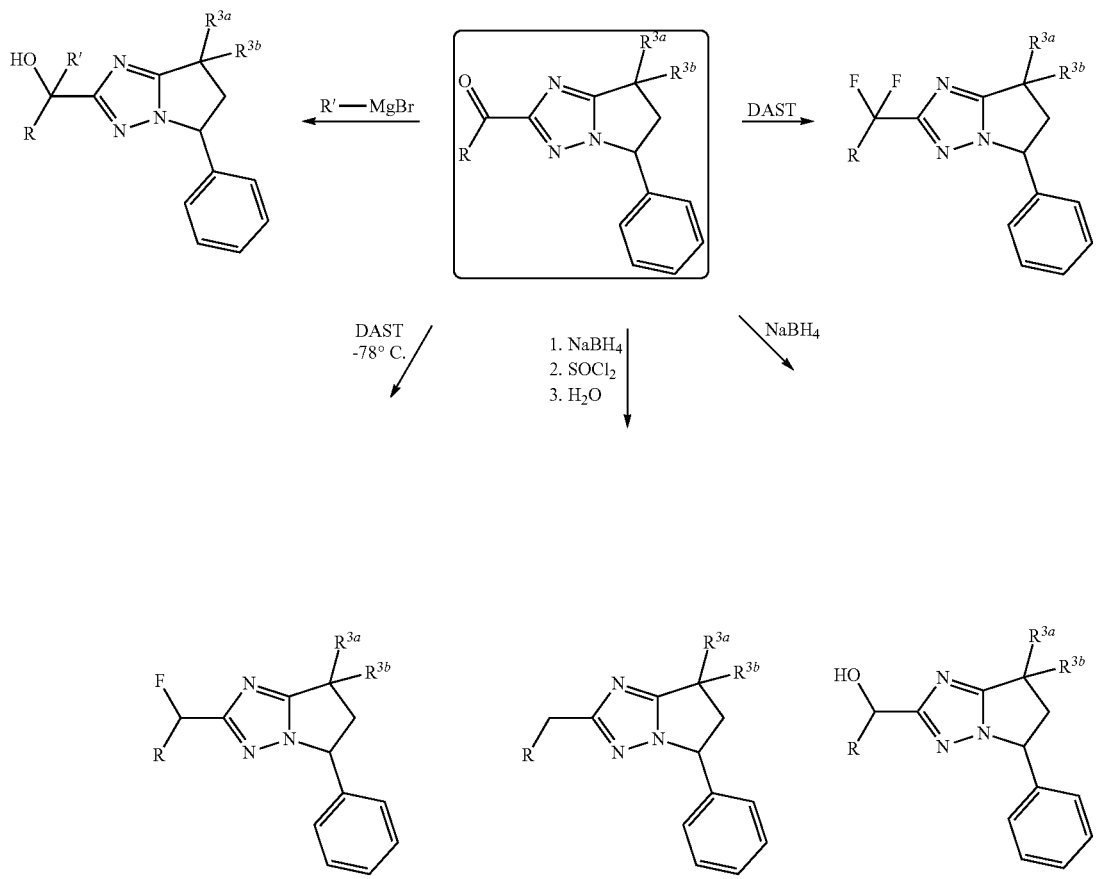

Exemplary Preparation of Mono-Fluorinated Intermediates:

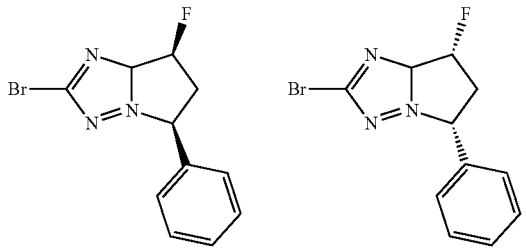

Step 1: 3,5-dibromo-1-(tetrahydro-2H-pyran-2-yl)-1H-1,2,4-triazole

To a solution of 3,5-dibromo-1h-1,2,4-triazole (150.0 g 661.2 mmol) in tetrahydrofuran (1500 mL) was slowly added p-toluenesulfonic acid (17.1 g, 99.2 mmol), followed by 3,4-dihydro-2h-pyran (166.9 g, 1983.6 mmol) at 0° C. After addition, the reaction mixture was heated at 70° C. for 3 h and concentrated under reduced pressure. The residue was poured into water (500 mL) and adjusted to pH=9 by addition of saturated aqueous sodium bicarbonate. The resulting mixture was extracted with ethyl acetate (3×400 mL). The combined organic layers were dried over sodium sulfate and concentrated under reduce pressure. The resulting crude product was washed with methanol (2×50 mL), dried under reduced pressure to give crude 3,5-dibromo-1-tetrahydropyran-2-yl-1,2,4-triazole (155 g, 75%) as a white solid. $^1$H NMR (400 MHz, CDCl$_3$) δ 5.49-5.46 (m, 1H), 4.12-3.99 (m, 1H), 3.72-3.61 (m, 1H), 2.38-2.26 (m, 1H), 2.18-2.07 (m, 1H), 1.98-1.90 (m, 1H), 1.78-1.60 (m, 3H).

Step 2: 1-phenylbut-3-en-1-ol

To a cooled (0° C.) solution of benzaldehyde (130 g, 1.23 mol) in tetrahydrofuran (1000 mL) was added allylmagnesium chloride (2 M in THF, 858 mL, 1.72 mol) over 30 min. After addition, the reaction mixture was allowed to warm to room temperature and stirred for 2 h. The mixture was then quenched by addition of saturated aqueous ammonium chloride (1000 mL) and extracted with ethyl acetate (3×500 mL). The combined organic layers were dried over sodium sulfate and concentrated under reduce pressure. The residue was purified by column chromatography (silica gel, 100-200 mesh, 0 to 5% ethyl acetate in petroleum ether) to give 1-phenylbut-3-en-1-ol (140 g, 77%) as a light yellow oil. $^1$H NMR (400 MHz, CDCl$_3$) δ 7.37-7.34 (m, 4H), 7.29-7.26 (m, 1H), 5.83-5.75 (m, 1H), 5.21-5.08 (m, 2H), 4.76-4.69 (m, 1H), 2.55-2.45 (m, 2H), 2.12 (d, J=2.8 Hz, 1H).

Step 3: tert-butyldimethyl((1-phenylbut-3-en-1-yl)oxy)silane

To a stirred solution of 1-phenyl-3-buten-1-ol (29.0 g, 195.7 mmol) in dichloromethane (400 mL) was added imidazole (27.0 g, 391.6 mmol) and tert-butyldimethylchlorosilane (39.0 g, 254.4 mmol). After addition, the reaction mixture was stirred at 25° C. for 16 h and then quenched by addition of water (200 mL). The mixture was extracted with dichloromethane (2×200 mL). The combined organic layers were washed with brine (100 mL), dried over sodium sulfate and concentrated under reduced pressure. The residue was purified by column chromatography (silica gel, 100-200 mesh, 100% petroleum ether) to afford tert-butyl-dimethyl-(1-phenylbut-3-enoxy)silane (43.0 g, 84%) as colorless oil, used as is in the next step.

Step 4: 3-((tert-butyldimethylsilyl)oxy)-3-phenylpropanal

To a solution of tert-butyl-dimethyl-(1-phenylbut-3-enoxy)silane (50.0 g, 190.5 mmol) in tetrahydrofuran/water (600 mL, 1:1) was added osmium tetraoxide (968 mg, 3.8 mmol). After stirring for 30 min at 15° C., sodium periodate (163 g, 762.0 mmol) was added in small portions over 2 h. The resulting mixture was stirred for another 2 h at 30° C. and then quenched by addition of cold saturated aqueous sodium thiosulfate (500 mL). The mixture was stirred for 30 min and then extracted with ethyl acetate (3×400 mL). The combined organic layers were washed with water (200 mL), brine (200 mL), dried over sodium sulfate and concentrated under reduced pressure. The residue was purified by column chromatography (silica gel, 100-200 mesh, 0 to 10% ethyl acetate in petroleum ether) to afford 3-[tert-butyl(dimethyl)silyl]oxy-3-phenyl-propanal (33.0 g, 65%) as yellow oil. $^1$H NMR (400 MHz, CDCl$_3$) δ 9.94 (t, J=2.4 Hz, 1H), 7.48 (d, J=4.2 Hz, 4H), 7.44-7.39 (m, 1H), 5.37-5.34 (m, 1H), 2.99-2.97 (m, 1H), 2.80-2.75 (m, 1H), 1.01 (s, 9H), 0.19 (s, 3H), 0.00 (s, 3H).

Step 5: 1-(3-bromo-1-(tetrahydro-2H-pyran-2-yl)-1H-1,2,4-triazol-5-yl)-3-((tert-butyldimethylsilyl)oxy)-3-phenylpropan-1-ol To a cooled (−78° C.) solution of 3,5-dibromo-1-tetrahydropyran-2-yl-1,2,4-triazole (39.0 g, 125.4 mmol) in tetrahydrofuran (400 mL) was added n-butyllithium (2.5 M in hexanes, 55.0 mL, 137.5 mmol) dropwise under N$_2$ atmosphere. The mixture was stirred at −78° C. for 30 min, then a solution of 3-[tert-butyl(dimethyl)silyl]oxy-3-phenyl-propanal (33.0 g, 124.2 mmol) in tetrahydrofuran (50 mL) was added dropwise. After addition, the mixture was stirred at −78° C. for 1.5 h and then quenched by addition of saturated aqueous ammonium chloride (500 mL). The resulting mixture was extracted with ethyl acetate (3×300 mL). The combined organic layers were dried over sodium sulfate and concentrated under reduce pressure. The residue was purified by column chromatography (silica gel, 100-200 mesh, 0 to 5% ethyl acetate in petroleum ether) to afford 1-(3-bromo-1-(tetrahydro-2H-pyran-2-yl)-1H-1,2,4-triazol-5-yl)-3-((tert-butyldimethylsilyl)oxy)-3-phenylpropan-1-ol (50.0 g, 80%) as light yellow oil.

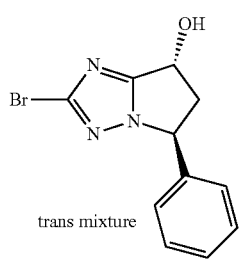 [SMILES: O[C@@H]1C[C@@H](c2ccccc2)n2nc(Br)nc21]

trans mixture

Step 6: trans-2-bromo-5-phenyl-6,7-dihydro-5H-pyrrolo[1,2-b][1,2,4]triazol-7-ol To a stirred solution of 1-(3-bromo-1-(tetrahydro-2H-pyran-2-yl)-1H-1,2,4-triazol-5-yl)-3-((tert-butyldimethylsilyl)oxy)-3-phenylpropan-1-ol (50.0 g, 100.7 mmol) in dichloromethane (150 mL) was slowly added trifluoroacetic acid (150 mL). The resulting mixture was heated at 50° C. for 2 h and then concentrated under reduced pressure. The residue was adjusted to pH=9 with saturated aqueous sodium bicarbonate and extracted with dichloromethane (3×200 mL). The combined organic layers were washed with water (100 mL), brine (100 mL), dried over sodium sulfate and concentrated under reduced pressure. The residue was purified by column chromatography (silica gel, 100-200 mesh, 0 to 32% ethyl acetate in petroleum ether) to afford trans-2-bromo-5-phenyl-6,7-dihydro-5H-pyrrolo[1,2-b][1,2,4]triazol-7-ol (5.5 g, 20%) as a yellow solid (A second fraction (8.5 g, 30%) was also obtained as a 4:3 mixture of trans/cis products). $^1$H NMR (400 MHz, CDCl$_3$) δ7.46-7.32 (m, 3H), 7.15 (d, J=7.6 Hz, 2H), 5.65 (t, J=6.6 Hz, 1H), 5.50 (br s, 1H), 5.45 (d, J=6.4 Hz, 1H), 3.19-3.11 (m, 1H), 3.01-2.92 (m, 1H). LCMS RT=0.682 min, m/z=279.8 [M+H]$^+$. LCMS (5 to 95% acetonitrile in water+ 0.03% trifluoroacetic acid over 1.5 mins) retention time 0.682 min, ESI+ found [M+H]=279.8.

Step 7: (5S,7S)-2-bromo-7-fluoro-5-phenyl-6,7-dihydro-5H-pyrrolo[1,2-b][1,2,4]triazole and (5R,7R)-2-bromo-7-fluoro-5-phenyl-6,7-dihydro-5H-pyrrolo[1,2-b][1,2,4]triazole To a stirred solution of trans-2-bromo-5-phenyl-6,7-dihydro-5H-pyrrolo[1,2-b][1,2,4]triazol-7-ol (3.0 g, 10.71 mmol) in dichloromethane (60 mL) was slowly added diethylaminosulfur trifluoride (7.8 g, 48.19 mmol) at 0° C. The reaction mixture was stirred at 0° C. for 2.5 h and then slowly added into stirred aqueous saturated sodium bicarbonate (100 mL) at 0° C. The mixture was extracted with dichloromethane (3×100 mL). The combined organic layers were washed with water (100 mL), brine (100 mL), dried over sodium sulfate and concentrated under reduced pressure. The residue was purified by column chromatography (silica gel, 100-200 mesh, 0 to 20% ethyl acetate in petroleum ether) to afford racemic cis-2-bromo-7-fluoro-5-phenyl-6,7-dihydro-5H-pyrrolo[1,2-b][1,2,4]triazole (1.5 g, 49%) as a light yellow solid and racemic trans-2-bromo-7-fluoro-5-phenyl-6,7-dihydro-5H-pyrrolo[1,2-b][1,2,4]triazole (650 mg, 21%) as a white solid.

cis-2-bromo-7-fluoro-5-phenyl-6,7-dihydro-5H-pyrrolo[1,2-b][1,2,4]triazole $^1$H NMR (400 MHz, CDCl$_3$) δ 7.31-7.24 (m, 3H), 7.17-7.07 (m, 2H), 5.97-5.77 (m, 1H), 5.37-5.27 (m, 1H), 3.52-3.37 (m, 1H), 2.84-2.70 (m, 1H). LCMS R$_T$=0.632 min, m/z=281.9 [M+H]$^+$. LCMS (5 to 95% acetonitrile in water+ 0.03% trifluoroacetic acid over 1.5 mins) retention time 0.632 min, ESI+ found [M+H]=281.9.

trans-2-bromo-7-fluoro-5-phenyl-6,7-dihydro-5H-pyrrolo[1,2-b][1,2,4]triazole $^1$H NMR (400 MHz, CDCl$_3$) δ 7.58-7.29 (m, 3H), 7.24-7.05 (m, 2H), 6.14-5.93 (m, 1H), 5.70-5.65 (m, 1H), 3.41-3.25 (m, 1H), 3.04-2.87 (m, 1H).

The racemic cis material was further separated by chiral SFC to give arbitrarily assigned:

(5R,7R)-2-bromo-7-fluoro-5-phenyl-6,7-dihydro-5H-pyrrolo[1,2-b][1,2,4]triazole (Peak 1, retention time=2.963 min) (350 mg, 44%) as a white solid.

(5S,7S)-2-bromo-7-fluoro-5-phenyl-6,7-dihydro-5H-pyrrolo[1,2-b][1,2,4]triazole (Peak 2, retention time=3.174 min) (350 mg, 44%) as a white solid.
SFC condition: Column: Chiralpak AD-3 150×4.6 mm I.D., 3 um Mobile phase: A: CO2 B:ethanol (0.05% DEA) Gradient: from 5% to 40% of B in 5 min and hold 40% for 2.5 min, then 5% of B for 2.5 min Flow rate: 2.5 ml/min.

Example 1: Method 1

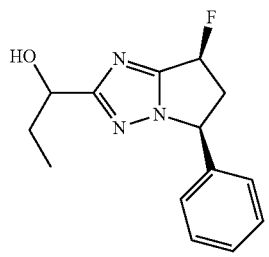 [SMILES: CCC(O)c1nc2n(n1)[C@H](c1ccccc1)C[C@@H]2F]

Cis-7-fluoro-5-phenyl-6,7-dihydro-5H-pyrrolo[1,2-b][1,2,4]triazol-2-yl]propan-1-ol To a cooled solution of 1-[(5S,7S)-7-fluoro-5-phenyl-6,7-dihydro-5H-pyrrolo[1,2-b][1,2,4]triazol-2-yl]propan-1-one (21 mg, 0.08 mmol) in methanol (5 mL) was added sodium borohydride (28 mg, 0.73 mmol) in one portion. The mixture was stirred at 0° C. for 1 h and then quenched by addition of saturated aqueous ammonium chloride (20 mL). The resulting mixture was extracted with ethyl acetate (3×15 mL). The combined organic layers were concentrated under reduce pressure and the residue was purified by RP-HPLC (acetonitrile 22-52%/0.05% hydrochloride in water) to afford arbitrarily assigned cis-7-fluoro-5-phenyl-6,7-dihydro-5H-pyrrolo[1,2-b][1,2,4]triazol-2-yl]propan-1-ol (17 mg, 71%) as a colorless oil. $^1$H NMR (400 MHz, CD$_3$OD) δ 7.40-7.33 (m, 3H), 7.25-7.22 (m, 2H), 6.16-6.13 (m, 0.5H), 6.02-5.98 (m, 0.5H), 5.56-5.52 (m, 1H), 4.65-4.61 (m, 1H), 3.75-3.67 (m, 1H), 2.81-2.74 (m, 1H), 1.93-1.82 (m, 2H), 0.94-0.89 (m, 3H). LCMS R$_T$=0.762 min, m/z=262.0[M+H]$^+$.
LCMS (5 to 95% acetonitrile in water+0.03% trifluoacetic acid over 1.5 mins) retention time 0.762 min, ESI+ found [M+H]=262.0.

Example 2: Method 2

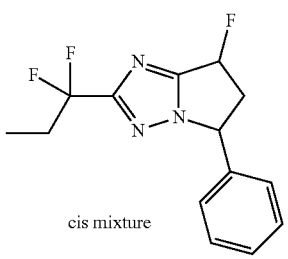 [SMILES: CCC(F)(F)c1nc2n(n1)C(c1ccccc1)CC2F]

cis mixture

Cis-2-(1,1-difluoropropyl)-7-fluoro-5-phenyl-6,7-dihydro-5H-pyrrolo[1,2-b][1,2,4]triazole To a solution of 1-(cis-7-fluoro-5-phenyl-6,7-dihydro-5H-pyrrolo[1,2-b][1,2,4]triazol-2-yl)propan-1-one (40 mg, 0.15 mmol) in dichloromethane (10 mL) was added diethylaminosulfur trifluoride (50 mg, 0.31 mmol) at 0° C. under nitrogen atmosphere. After addition, the mixture was stirred at 25° C. for 2 h, and quenched by slow addition of saturated aqueous sodium bicarbonate (10 mL). The resulting mixture was extracted with dichloromethane (3×20 mL). The combined organic layers were washed with brine (20 mL), dried over anhydrous sodium sulfate and concentrated under reduced pressure. The residue was purified by RP-HPLC (acetonitrile 40-70%/0.05% ammonia hydroxide in water) to afford arbitrarily assigned cis-2-(1,1-difluoropropyl)-7-fluoro-5-phenyl-6,7-dihydro-5H-pyrrolo[1,2-b][1,2,4]triazole (17 mg, 40%) as a white solid. $^1$H NMR (400 MHz, CD$_3$OD) δ 7.41-7.23 (m, 5H), 6.16-6.00 (m, 1H), 5.58 (s, 1H), 3.78-3.69 (m, 1H), 2.80-2.77 (m, 1H), 2.31-2.25 (m, 2H), 1.02 (t, J=7.6 Hz, 3H). LCMS R$_T$=0.859 min, m/z=281.9 [M+H]$^+$.

LCMS (10 to 80% acetonitrile in water+0.03% ammonium bicarbonate over 3.0 mins) retention time 0.859 min, ESI+ found [M+H]=281.9.

Example 3: Method 3

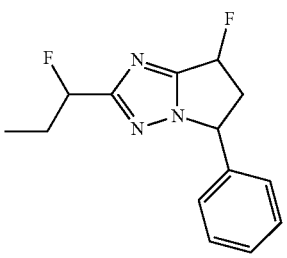 [SMILES: CCC(F)c1nc2n(n1)C(c1ccccc1)CC2F]

Cis-7-fluor-2-(1-fluoropropyl)-5-phenyl-6,7-dihydro-5H-pyrrolo[1,2-b][1,2,4]triazole

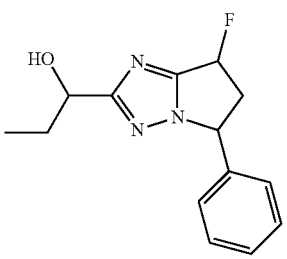 [SMILES: CCC(O)c1nc2n(n1)C(c1ccccc1)CC2F]

Step 1: 1-(cis-5-fluoro-7-phenyl-6,7-dihydro-5H-pyrrolo[1,2-b][1,2,4]triazol-2-yl)propan-1-ol To a solution of 1-(cis-5-fluoro-7-phenyl-6,7-dihydro-5H-pyrrolo[1,2-b][1,2,4]triazol-2-yl)propan-1-one (120 mg, 0.46 mmol) in methanol (10 mL) was added sodium borohydride (21 mg, 0.56 mmol) at 0° C. The resulting solution was stirred for 1 h at 0° C. and then quenched by addition of saturated aqueous ammonium chloride (20 mL). The mixture was extracted with ethyl acetate (3×15 mL). The combined organic layers were concentrated under reduce pressure to afford crude 1-(cis-5-fluoro-7-phenyl-6,7-dihydro-5H-pyrrolo[1,2-b][1,2,4]triazol-2-yl)propan-1-ol (90 mg, 74%) as a white solid. LCMS R$_T$=0.548 min, m/z=262.0 [M+H]$^+$.

LCMS (5 to 95% acetonitrile in water+0.03% trifluoacetic acid over 1.5 mins) retention time 0.548 min, ESI+ found [M+H]=262.0.

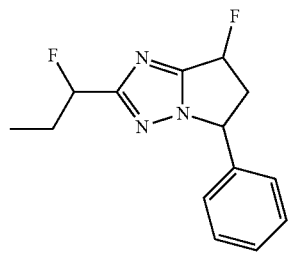 [SMILES: CCC(F)c1nc2n(n1)C(c1ccccc1)CC2F]

Step 2: Cis-(5S,7S)-7-fluoro-2-(1-fluoropropyl)-5-phenyl-6,7-dihydro-5H-pyrrolo[1,2-b][1,2,4]triazole To a solution of 1-(7-fluoro-5-phenyl-6,7-dihydro-5H-pyrrolo[1,2-b][1,2,4]triazol-2-yl)propan-1-ol (90 mg, 0.34 mmol) in dichloromethane (15 mL) was added diethylaminosulfur trifluoride (0.05 mL, 0.36 mmol) dropwise at −78° C. under nitrogen atmosphere. After addition, the mixture was stirred at −78° C. for 2 h and quenched by slow addition of saturated aqueous sodium bicarbonate (10 mL). The mixture was then extracted with dichloromethane (3×20 mL). The combined organic layers were washed with brine (20 mL), dried over anhydrous sodium sulfate and concentrated under reduced pressure. The residue was purified by RP-HPLC (acetonitrile 35-65%/0.05% ammonia hydroxide in water) to afford arbitrarily assigned cis-(5S,7S)-7-fluoro-2-(1-fluoropropyl)-5-phenyl-6,7-dihydro-5H-pyrrolo[1,2-b][1,2,4]triazole (28 mg, 30%) as a white solid. $^1$H NMR (400 MHz, CD$_3$OD) δ 7.40-7.21 (m, 5H), 6.14-5.98 (m, 1H), 5.56-5.34 (m, 2H), 3.77-3.67 (m, 1H), 2.81-2.70 (m, 1H), 2.13-2.03 (m, 2H), 0.98 (t, J=7.6 Hz, 3H). LCMS R$_T$=0.820 min, m/z=263.9 [M+H]$^+$.

LCMS (10 to 80% acetonitrile in water+0.03% ammonium bicarbonate over 3.0 mins) retention time 0.820 min, ESI+ found [M+H]=263.9.

Example 4: Method 4

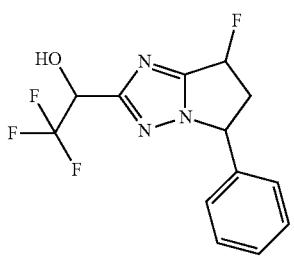 [SMILES: OC(c1nc2n(n1)C(c1ccccc1)CC2F)C(F)(F)F]

cis-(5S,7S)-2,2,2-trifluoro-1-(7-fluoro-5-phenyl-6,7-dihydro-5H-pyrrolo[1,2-b][1,2,4]triazol-2-yl)ethanol

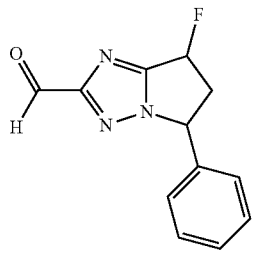 [SMILES: O=Cc1nc2n(n1)C(c1ccccc1)CC2F]

Step 1: Cis-7-fluoro-5-phenyl 6,7-dihydro-5H-pyrrolo[1,2-b][1,2,4]triazole-2-carbaldehyde A mixture of ethyl cis-7-fluoro-5-phenyl-6,7-dihydro-5H-pyrrolo[1,2-b][1,2,4]triazole-2-carboxylate (800 mg, 2.91 mmol) in dichloromethane (30 mL) was added diisobutylaluminum hydride (1.0 M in toluene, 4.36 mL, 4.36 mmol) dropwise at −78° C. After addition, the reaction was stirred at the same temperature for 2 h and then quenched by slow addition of sodium sulfate decahydrate (3 g). The mixture was filtered and the filtrate was concentrated under reduced pressure. The residue was purified by column chromatography (silica gel, 100-200 mesh, 0 to 30% ethyl acetate in petroleum ether) to afford cis-7-fluoro-5-phenyl-6,7-dihydro-5H-pyrrolo [1,2-b][1,2,4]triazole-2-carbaldehyde (520 mg, 77%) as a white solid. $^1$H NMR (400 MHz, CDCl$_3$) δ 9.97 (s, 1H), 7.43-7.26 (m, 5H), 6.14-5.96 (m, 1H), 5.54-5.51 (m, 1H), 3.73-3.63 (m, 1H), 2.99-2.95 (m, 1H).

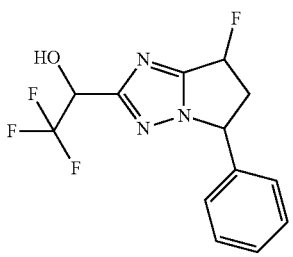 [SMILES: OC(c1nc2n(n1)C(c1ccccc1)CC2F)C(F)(F)F]

Step 2: Cis(5S,7S)-2,2,2-trifluoro-1-(7-fluoro-5-phenyl-6,7-dihydro-5H-pyrrolo[1,2-b][1,2,4]triazol-2-yl)ethanol A mixture of cis-7-fluoro-5-phenyl-6,7-dihydro-5H-pyrrolo[1,2-b][1,2,4]triazole-2-carbaldehyde (50 mg, 0.22 mmol) and cesium fluoride (65 mg, 0.43 mmol) in (trifluoromethyl)trimethylsilane (62 mg, 0.43 mmol) was stirred at 25° C. for 12 h and then diluted with added methanol (5 mL). The solid was removed by filtration and the filtrate was concentrated under reduced pressure. The residue was purified by RP-HPLC (acetonitrile 30-60%/0.05% HCl in water) to afford arbitrarily assigned cis-(5S,7S)-2,2,2-trifluoro-1-(7-fluoro-5-phenyl-6,7-dihydro-5H-pyrrolo[1,2-b][1,2,4]triazol-2-yl)ethanol (6.3 mg, 9%) as a white solid. $^1$H NMR (400 MHz, CDCl$_3$) δ 7.43-7.36 (m, 3H), 7.25-7.22 (m, 2H), 6.08-5.95 (m, 1H), 5.49-5.45 (m, 1H), 5.16-5.13 (m, 1H), 3.68-3.63 (m, 1H), 3.10-2.88 (m, 2H). LCMS RT=0.768 min, m/z=301.9 [M+H]$^+$.

LCMS (5 to 95% acetonitrile in water+0.03% trifluoroacetic acid over 1.5 mins) retention time 0.768 min, ESI+ found [M+H]=301.9.

Example 5: Method 5

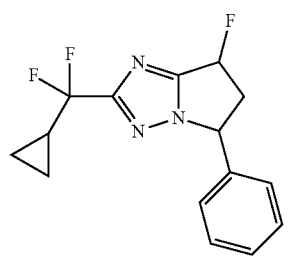 [SMILES: FC1CC(c2ccccc2)n2nc(C(F)(F)C3CC3)nc21]

Cis-(5S,7S)-2-[cyclopropyl(difluoro)methyl]-7-fluoro-1-phenyl-6,7-dihydro-5H-pyrrolo[1,2-b][1,2,4]triazole A mixture of cyclopropyl-(cis-7-fluoro-5-phenyl-6,7-dihydro-5H-pyrrolo[1,2-b][1,2,4]triazol-2-yl)methanone (200 mg, 0.74 mmol) and diethylaminosulfur trifluoride (0.2 mL, 1.47 mmol) was stirred at 50° C. for 72 h under nitrogen atmosphere. The mixture was slowly added into the stirred saturated aqueous sodium bicarbonate (20 mL) and extracted with dichloromethane (3×20 mL). The combined organic layers were washed with brine (20 mL), dried over anhydrous sodium sulfate and concentrated under reduced pressure. The residue was purified by RP-HPLC (acetonitrile 40-70%/0.05% ammonia hydroxide in water) to afford arbitrarily assigned cis-2-[cyclopropyl(difluoro)methyl]-7-fluoro-5-phenyl-6,7-dihydro-5H-pyrrolo[1,2-b][1,2,4]triazole (13 mg, 6%) as a yellow solid. $^1$H NMR (400 MHz, CD$_3$OD) δ 7.43-7.24 (m, 5H), 6.16-6.14 (m, 0.5H), 6.02-6.00 (m, 0.5H), 5.60-5.56 (m, 1H), 3.77-3.69 (m, 1H), 2.81-2.77 (m, 1H), 1.79-1.74 (m, 1H), 0.73-0.69 (m, 4H). LCMS R$_T$=0.900 min, m/z=293.9 [M+H]$^+$.

LCMS (10 to 80% acetonitrile in water+0.03% ammonium bicarbonate over 3.0 mins) retention time 0.900 min, ESI+ found [M+H]=293.9.

Example 6: Method 6

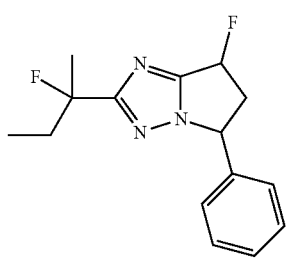 [SMILES: CCC(C)(F)c1nc2n(n1)C(c1ccccc1)CC2F]

Cis-(5S,7S)-2-(1-fluoro-1-methyl-propyl)-7-fluoro-5-phenyl-6,7-dihydro-5H-pyrrolo[1,2-b][1,2,4]triazole

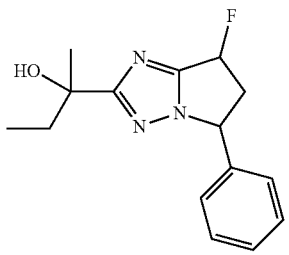 [SMILES: CCC(C)(O)c1nc2n(n1)C(c1ccccc1)CC2F]

Step 1: 2-(cis-7-fluoro-5-phenyl-6,7-dihydro-5H-pyrrolo[1,2-b][1,2,4]triazol-2-yl)butan-2-ol To a solution of 1-[cis-7-fluor-5-phenyl-6,7-dihydro-5H-pyrrolo[1,2-b][1,2,4]triazol-2-yl]propan-1-one (230 mg, 0.89 mmol) in tetrahydrofuran (30 mL) was added methylmagnesium bromide (3.0 N in tetrahydrofuran, 1.18 mL, 3.55 mmol) at −78° C. under nitrogen atmosphere. After addition, the mixture was stirred at −78° C. for 1 h and then quenched by addition of saturated aqueous ammonium chloride (20 mL). The resulting mixture was extracted with ethyl acetate (3×15 mL). The combined organic layers were concentrated under reduce pressure and the residue was purified by RP-HPLC (acetonitrile 27-57%/0.05% hydrochloric acid in water) to afford 2-[cis-7-fluoro-5-phenyl-6,7-dihydro-5H-pyrrolo[1,2-b][1,2,4]triazol-2-yl]butan-2-ol (160 mg, 65%) as a white solid. $^1$H NMR (400 MHz, CD$_3$OD) δ 7.45-7.29 (m, 5H), 6.31-6.28 (m, 0.5H), 6.17-6.14 (m, 0.5H), 5.67-5.62 (m, 1H), 3.87-3.73 (m, 1H), 2.92-2.78 (m, 1H), 1.97-1.82 (m, 2H), 1.56-1.55 (m, 3H), 0.89-0.82 (m, 3H). LCMS R$_T$=0.571 min, m/z=276.1 [M+H]$^+$.

LCMS (5 to 95% acetonitrile in water+0.03% trifluoacetic acid over 1.5 mins) retention time 0.571 min, ESI+ found [M+H]=276.1.

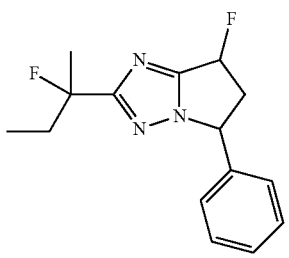 [SMILES: CCC(C)(F)c1nc2n(n1)C(c1ccccc1)CC2F]

Step 2: Cis-2-(1-fluoro-1-methyl-propyl)-7-fluoro-5-phenyl-6,7-dihydro-5H-pyrrolo[1,2-b][1,2,4]triazole To a solution of 2-[cis-7-fluoro-5-phenyl-6,7-dihydro-5H-pyrrolo[1,2-b][1,2,4]triazol-2-yl]butan-2-ol (60 mg, 0.22 mmol) in dichloromethane (10 mL) was added diethylaminosulfur trifluoride (0.14 mL, 1.09 mmol) at 0° C. under nitrogen atmosphere. The mixture was stirred at 25° C. for 2 h, and then quenched by addition of saturated aqueous sodium bicarbonate (10 mL). The resulting mixture was extracted with dichloromethane (3×20 mL). The combined organic layers were washed with brine (20 mL), dried over sodium sulfate and concentrated under reduced pressure. The residue was purified by RP-HPLC (acetonitrile 40-70%/0.05% ammonia hydroxide in water) to afford arbitrarily assigned cis-(5S,7S)-2-(1-fluoro-1-methyl-propyl)-7-fluoro-5-phenyl-6,7-dihydro-5H-pyrrolo[1,2-b][1,2,4]triazole (44.5 mg, 73%) as a white solid. $^1$H NMR (400 MHz, CD$_3$OD) δ 7.52-7.15 (m, 5H), 6.14-6.11 (m, 0.5H), 5.99-5.97 (m, 0.5H), 5.58-5.51 (m, 1H), 3.79-3.65 (m, 1H), 2.81-2.68 (m, 1H), 2.14-2.01 (m, 2H), 1.72-1.66 (m, 3H), 0.90-0.86 (m, 3H). LCMS R$_T$=1.889 min, m/z=277.6 [M+H]$^+$.

LCMS (10 to 80% acetonitrile in water+0.1% ammonia water over 3.0 mins) retention time 1.889 min, ESI+ found [M+H]=277.6.

Examples 7 and 8: Method 7

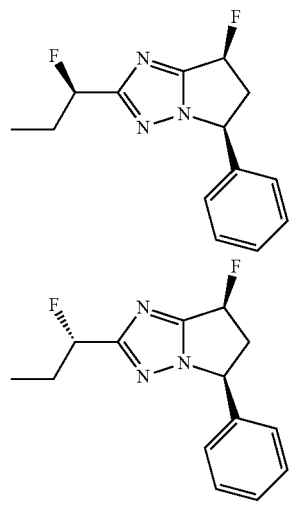

rac-(5S,7S)-7-fluoro-5-phenyl-2-[rac-(1R)-1-fluoropropyl]-6,7-dihydro-5H-pyrrolo[1,2-b][1,2,4]triazole and rac-(5S,7S)-7-fluoro-5-phenyl-2-[rac-(1S)-1-fluoropropyl]-6,7-dihydro-5H-pyrrolo[1,2-b][1,2,4]triazole Cis-(5S,7S)-7-fluoro-2-(1-fluoropropyl)-5-phenyl-6,7-dihydro-5H-pyrrolo[1,2-b][1,2,4]triazole was purified by chiral SFC (Chiralcel OX; 150×21.2 mm, 5 um; 15% methanol with 0.1% Ammonium Hydroxide isocratic elution with Carbon Dioxide) affording arbitrarily assigned diastereomers rac-(5S,7S)-7-fluoro-5-phenyl-2-[rac-(1R)-1-fluoropropyl]-6,7-dihydro-H-pyrrolo[1,2-b][1,2,4]triazole (5 mg, 11%) and rac-(5S,7S)-7-fluoro-5-phenyl-2-[rac-(1S)-1-fluoropropyl]-6,7-dihydro-5H-pyrrolo[1,2-b][1,2,4]triazole (3 mg, 7%) as white solids:

Analytical data for the first eluting diastereomer rac-(5S,7S)-7-fluoro-5-phenyl-2-[rac-(1R)-1-fluoropropyl]-6,7-dihydro-5H-pyrrolo[1,2-b][1,2,4]triazole (arbitrarily assigned 5S, 7S, 1R configuration): SFC R$_T$ (OX, 10% methanol+0.1% ammonium hydroxide isocratic elution with Carbon Dioxide, 2.5 min method): 0.720 min, 100% ee. LCMS R$_T$=4.65 min, m/z=264.2 (M+H)$^+$.

LCMS (5 to 95% acetonitrile in water+0.1% formic acid over 10 mins) retention time 4.65 min, ESI+ found [M+H]=264.2

Analytical data for the fourth eluting diastereomer (arbitrarily assigned 5S, 7S, 1S configuration): SFC $R_T$(OX, 10% methanol+0.1% ammonium hydroxide isocratic elution with Carbon Dioxide, 2.5 min method): 1.338 min, 100% ee. LCMS $R_T$=4.67 min, m/z=264.1 (M+H)$^+$.

LCMS (5 to 95% acetonitrile in water+0.1% formic acid over 10 mins) retention time 4.67 min, ESI+ found [M+H]=264.1

Example 9: Method 8

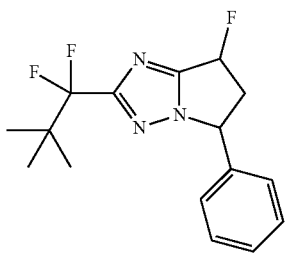 [SMILES: CC(C)(C)C(F)(F)c1nc2n(n1)C(c1ccccc1)CC2F]

Cis-2-(1,1-difluoro-2,2-dimethyl-propyl)-7-fluoro-5-phenyl-6,7-dihydro-5H-pyrrolo[1,2-b][1,2,4]triazole A mixture of diethylaminosulfur trifluoride (3.68 mL, 27.84 mmol) and 1-(cis-7-fluoro-5-phenyl-6,7-dihydro-5H-pyrrolo[1,2-b][1,2,4]triazol-2-yl)-2,2-dimethyl-propan-1-one (80 mg, 0.28 mmol) was stirred at 25° C. for 72 h under nitrogen atmosphere. The mixture was slowly added into saturated aqueous sodium bicarbonate (20 mL) and extracted with dichloromethane (3×30 mL). The combined organic layers were washed with brine (20 mL), dried over sodium sulfate and concentrated under reduced pressure. The residue was purified by RP-HPLC (acetonitrile 50-80%/0.05% ammonia hydroxide in water) to afford arbitrarily assigned cis-2-(1,1-difluoro-2,2-dimethyl-propyl)-7-fluoro-5-phenyl-6,7-dihydro-5H-pyrrolo[1,2-b][1,2,4]triazole (30 mg, 35%) as a white solid. $^1$H NMR (400 MHz, CD$_3$OD) δ 7.40-7.38 (m, 3H), 7.22-7.20 (m, 2H), 6.15-6.14 (m, 0.5H), 6.02-5.99 (m, 0.5H), 5.62-5.58 (m, 1H), 3.77-3.69 (m, 1H), 2.82-2.71 (m, 1H), 1.07 (s, 9H). LCMS $R_T$=2.052 min, m/z=310.1 [M+H]$^+$.

LCMS (10 to 80% acetonitrile in water+0.1% ammonia water over 3.0 mins) retention time 2.052 min, ESI+ found [M+H]=310.1.

Example 10: Method 9

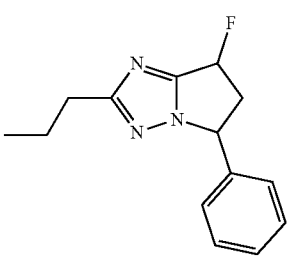 [SMILES: CCCc1nc2n(n1)C(c1ccccc1)CC2F]

Cis-(5S,7S)-7-fluoro-5-phenyl-2-propyl-6,7-dihydro-5H-pyrrolo[1,2-b][1,2,4]triazole

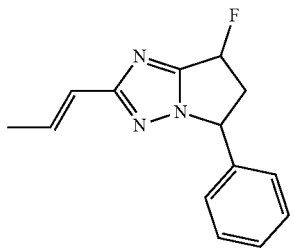 [SMILES: C/C=C/c1nc2n(n1)C(c1ccccc1)CC2F]

Step 1: (E)cis-7-fluoro-5-phenyl-2-(prop-1-en-1-yl)-6,7-dihydro-5H-pyrrolo[1,2-b][1,2,4]triazole To a solution of 1-(cis-7-fluoro-5-phenyl-6,7-dihydro-5H-pyrrolo[1,2-b][1,2,4]triazol-2-yl)propan-1-ol (100 mg, 0.38 mmol) in acetonitrile (3 mL) was added thionyl chloride (228 mg, 1.91 mmol) at 0° C. The resulting mixture was stirred for 15 min at 0° C. and then stirred for 1 h at 35° C. After cooled, the mixture was quenched by addition of water (10 mL), and then extracted with ethyl acetate (2×10 mL). The combined organic layers were dried over sodium sulfate and concentrated under reduced pressure. The residue was purified by preparative TLC (50% ethyl acetate in petroleum ether, $R_f$=0.6) to afford (E)-cis-7-fluoro-5-phenyl-2-(prop-1-en-1-yl)-6,7-dihydro-5H-pyrrolo[1,2-b][1,2,4]triazole (30 mg, 32%) as a light yellow oil. LCMS $R_T$=0.645 min, m/z=244.1 [M+H]$^+$.

LCMS (5 to 95% acetonitrile in water+0.03% trifluoacetic acid over 1.5 mins) retention time 0.645 min, ESI+ found [M+H]=244.1.

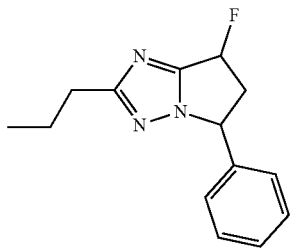 [SMILES: CCCc1nc2n(n1)C(c1ccccc1)CC2F]

Step 2: Cis-7-fluoro-5-phenyl-2-propyl-6,7-dihydro-5H-pyrrolo[1,2-b][1,2,4]triazole A mixture of (E)-cis-7-fluoro-5-phenyl-2-(prop-1-en-1-yl)-6,7-dihydro-5H-pyrrolo [1,2-b][1,2,4]triazole (30 mg, 0.12 mmol) and palladium (10% on carbon, 13 mg, 0.01 mmol) in methanol (5 mL) was hydrogenated (15 psi) at 25° C. for 2 h and then filtered. The filtrate was concentrated under reduced pressure and the residue was purified by RP-HPLC (acetonitrile 25-55%/0.05% ammonia hydroxide in water) to afford arbitrarily assigned cis-7-fluoro-5-phenyl-2-propyl-6,7-dihydro-5H-pyrrolo[1,2-b][1,2,4]triazole (16.0 mg, 53%) as a white solid. $^1$H NMR (400 MHz, CD$_3$OD) δ 7.39-7.36 (m, 3H), 7.27-7.25 (m, 2H), 6.26-6.23 (m, 0.5H), 6.12-6.09 (m, 0.5H), 5.60-5.58 (m, 1H), 3.79-3.70 (m, 1H), 2.83-2.73 (m, 3H), 1.79-1.70 (m, 2H), 0.96-0.92 (m, 3H). LCMS $R_T$=1.698 min, m/z=246.2[M+H]$^+$.

LCMS (10 to 80% acetonitrile in water+0.03% trifluoacetic acid over 2 mins) retention time 1.698 min, ESI+ found [M+H]=246.2.

Example 11: Method 10

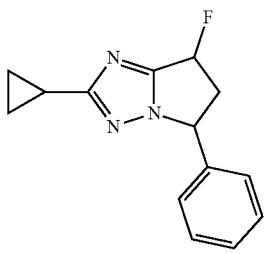 [SMILES: FC1CC(c2ccccc2)n2nc(C3CC3)nc21]

Cis-2-cyclopropyl-7-fluoro-5-phenyl-6,7-dihydro-5H-pyrrolo[1,2-b][1,2,4]triazole A mixture of cis-2-bromo-7-fluoro-5-phenyl-6,7-dihydro-5H-pyrrolo[1,2-b][1,2,4]triazole (35 mg, 0.12 mmol), 1,1'-bis(diphenylphosphino)ferrocene-palladium(II) dichloride dichloromethane complex (10 mg, 0.01 mmol), cyclopropylboronicacid (21 mg, 0.25 mmol) and cesium carbonate (101 mg, 0.31 mmol) in 1,4-dioxane (2 mL) and water (0.35 mL) was heated at 110° C. for 1 h under microwave conditions. After cooled, the mixture was diluted with water (15 mL) and then extracted with ethyl acetate (2×10 mL). The combined organic layers were concentrated under reduced pressure and the residue was purified by RP-HPLC (acetonitrile 40-70%/0.225% formic acid in water) to afford arbitrarily assigned cis-2-cyclopropyl-7-fluoro-5-phenyl-6,7-dihydro-5H-pyrrolo[1,2-b][1,2,4]triazole (3.1 mg, 10%) as a white solid. $^1$H NMR (400 MHz, CD$_3$OD) δ 7.41-7.34 (m, 3H), 7.22-7.20 (m, 2H), 6.05-6.02 (m, 0.5H), 5.90-5.88 (m, 0.5H), 5.46-5.41 (m, 1H), 3.73-3.60 (m, 1H), 2.73-2.62 (m, 1H), 2.03-1.98 (m, 1H), 0.99-0.92 (m, 4H). LCMS R$_T$=0.827 min, m/z=244.0[M+H]$^+$.

LCMS (5 to 95% acetonitrile in water+0.03% trifluoacetic acid over 1.5 mins) retention time 0.827 min, ESI+ found [M+H]=244.0.

Example 12: Method 11

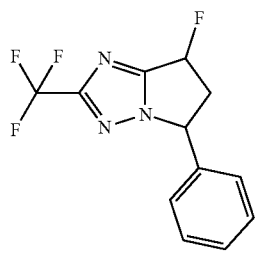 [SMILES: FC1CC(c2ccccc2)n2nc(C(F)(F)F)nc21]

Cis-7-fluoro-5-phenyl-2-(trifluoromethyl)-6,7-dihydro-5H-pyrrolo[1,2-b][1,2,4]triazole

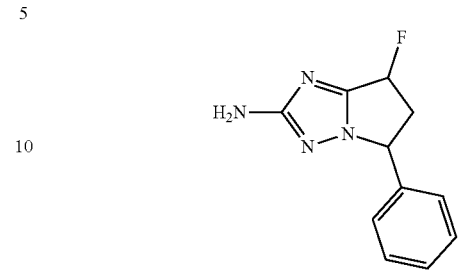

Step 1: cis-7-fluoro-5-phenyl-6,7-dihydro-5H-pyrrolo[1,2-b][1,2,4]triazol-2-amine To a mixture of cis-7-fluoro-5-phenyl-6,7-dihydro-5H-pyrrolo[1,2-b][1,2,4]triazole-2-carboxylic acid (500 mg, 2.02 mmol) in 1,4-dioxane (30 mL) was added anhydrous sodium sulfate (4.0 g), triethylamine (0.85 mL, 6.07 mmol) and azido diphenyl phosphate (1.15 mL, 5.06 mmol) under nitrogen atmosphere. The mixture was stirred at 35° C. for 18 h, and the solution was transferred to a hot solution (95° C.) of 1,4-dioxane (30 mL) and water (10 mL). The mixture was stirred at 95° C. for another 18 h and then concentrated under reduced pressure. The residue was purified by column chromatography (silica gel, 100-200 mesh, 0 to 50% ethyl acetate/ethanol (1:1) in petroleum ether) to afford arbitrarily assigned cis-7-fluoro-5-phenyl-6,7-dihydro-5H-pyrrolo[1,2-b][1,2,4]triazol-2-amine (200 mg, 45%) as a white solid. $^1$H NMR (400 MHz, CD$_3$OD) δ 7.40-7.35 (m, 2H), 7.24-7.04 (m, 3H), 6.00-5.97 (m, 0.5H), 5.85-5.83 (m, 0.5H), 5.35-5.30 (m, 1H), 3.63-3.53 (m, 1H), 2.63-2.52 (m, 1H). LCMS R$_T$=0.617 min, m/z=218.9 [M+H]$^+$.

LCMS (5 to 95% acetonitrile in water+0.03% trifluoacetic acid over 1.5 mins) retention time 0.617 min, ESI+ found [M+H]=218.9.

Example 13: Method 12

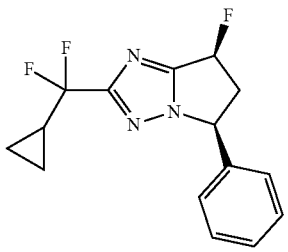

(5S,7S)-2-[cyclopropyl(difluoro)methyl]-7-fluoro-5-phenyl-6,7-dihydro-5H-pyrrolo[1,2-b][1,2,4]triazole A mixture of cyclopropyl-[(5S,7S)-7-fluoro-5-phenyl-6,7-dihydro-5H-pyrrolo[1,2-b][1,2,4]triazol-2-yl]methanone (200 mg, 0.74 mmol) and diethylaminosulfur trifluoride (6.0 mL, 44.10 mmol) was stirred at 50° C. for 72 h under nitrogen atmosphere. The mixture was slowly added into a stirred saturated aqueous sodium bicarbonate (20 mL) and extracted with dichloromethane (3×20 mL). The combined organic layers were washed with brine (20 mL), dried over anhydrous sodium sulfate and concentrated under reduced pressure. The residue was purified by RP-HPLC (acetonitrile 45-75%/0.05% ammonia in water) to afford arbitrarily assigned rac-(5S,7S)-2-[cyclopropyl(difluoro)methyl]-7-fluoro-5-phenyl-6,7-dihydro-5H-pyrrolo[1,2-b][1,2,4]triazole (80 mg, 36%) as a yellow solid. $^1$H NMR (400 MHz, CDCl$_3$) δ 7.42-7.38 (m, 3H), 7.24-7.22 (m, 2H), 6.08-5.92 (m, 1H), 5.48-5.44 (m, 1H), 3.67-3.57 (m, 1H), 2.97-2.87 (m, 1H), 1.81-1.75 (m, 1H), 0.86-0.82 (m, 2H), 0.72-0.70 (m, 2H). LCMS R$_T$=0.921 min, m/z=293.9 [M+H]$^+$.

LCMS (5 to 95% acetonitrile in water+0.03% trifluoacetic acid over 1.5 mins) retention time 0.921 min, ESI+ found [M+H]=293.9.

Example 14: Method 13

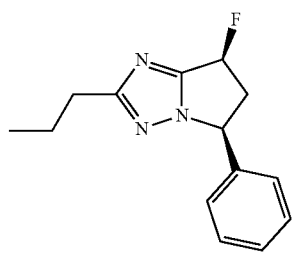 [SMILES: CCCc1nc2n(n1)[C@H](c1ccccc1)C[C@@H]2F]

(5S,7S)-7-fluoro-5-phenyl-2-propyl-6,7-dihydro-5H-pyrrolo[1,2-b][1,2,4]triazole

A mixture of (5S,7S)-2-bromo-7-fluoro-5-phenyl-6,7-dihydro-5H-pyrrolo[1,2-b][1,2,4]triazole (100 mg, 0.35 mmol), bis(di-tert-butyl(4-dimethylaminophenyl) phosphine)dichloro palladium(II) (25 mg, 0.04 mmol), n-propylboronicacid (37 mg, 0.43 mmol) and cesium carbonate (347 mg, 1.06 mmol) in 1,4-dioxane (2 mL) and water (0.35 mL) was heated at 80° C. for 16 h under nitrogen atmosphere. After cooled, the mixture was diluted with water (10 mL) and extracted with dichloromethane (2×20 mL). The combined organic layers were washed with brine (15 mL), dried over sodium sulfate and concentrated under reduced pressure. The residue was purified by RP-HPLC (acetonitrile 43-53%/0.05% ammonia hydroxide in water) to afford arbitrarily assigned (5S,7S)-7-fluoro-5-phenyl-2-propyl-6,7-dihydro-5H-pyrrolo[1,2-b][1,2,4]triazole (6.2 mg, 7%) as a white solid. $^1$H NMR (400 MHz, CD$_3$OD) δ 7.41-7.35 (m, 3H), 7.22-7.19 (m, 2H), 6.09-5.92 (m, 1H), 5.50-5.46 (m, 1H), 3.75-3.62 (m, 1H), 2.75-2.64 (m, 3H), 1.79-1.69 (m, 2H), 0.94 (t, J=7.6 Hz, 3H). LCMS R$_T$=1.689 min, m/z=246.2 [M+H]$^+$.

LCMS (10 to 80% acetonitrile in water+0.1% ammonia water over 3.0 mins) retention time 1.689 min, ESI+ found [M+H]=246.2.

Example 15: Method 14

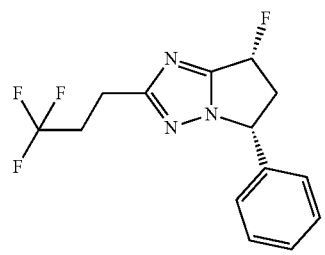 [SMILES: F[C@@H]1C[C@H](c2ccccc2)n2nc(CCC(F)(F)F)nc21]

(5R,7R)-7-fluoro-5-phenyl-2-(3,3,3-trifluoropropyl)-6,7-dihydro-5H-pyrrolo[1,2-b][1,2,4]triazole A mixture of (5R,7R)-2-bromo-7-fluoro-5-phenyl-6,7-dihydro-5H-pyrrolo[1,2-b][1,2,4]triazole (50 mg, 0.18 mmol), RuPhos-Pd-G2 (14 mg, 0.02 mmol), potassium 3,3,3-trifluoropropane-1-trifluoroborate (54 mg, 0.27 mmol), cesium carbonate (173 mg, 0.53 mmol) in toluene (3 mL) and water (0.3 mL) was heated at 100° C. for 24 h under nitrogen atmosphere and then concentrated under reduced pressure. The residue was then diluted with water (15 mL) and extracted with ethyl acetate (3×15 mL). The combined organic layers were washed with brine (20 mL), dried over sodium sulfate and concentrated under reduced pressure. The residue was purified by RP-HPLC (acetonitrile 40-70%/0.05% ammonia hydroxide in water) to afford arbitrarily assigned (5R,7R)-7-fluoro-5-phenyl-2-(3,3,3-trifluoropropyl)-6,7-dihydro-5H-pyrrolo[1,2-b][1,2,4]triazole (23.8 mg, 44%) as a white solid. $^1$H NMR (400 MHz, CDCl$_3$) δ 7.41-7.37 (m, 3H), 7.23-7.21 (m, 2H), 6.04-5.89 (m, 1H), 5.40-5.36 (m, 1H), 3.61-3.55 (m, 1H), 3.06-3.02 (m, 2H), 2.95-2.85 (m, 1H), 2.64-2.59 (m, 2H). LCMS R$_T$=0.892 min, m/z=299.9 [M+H]$^+$.

LCMS (5 to 95% acetonitrile in water+0.03% trifluoacetic acid over 1.5 mins) retention time 0.892 min, ESI+ found [M+H]=299.9.

Example 16: Method 15

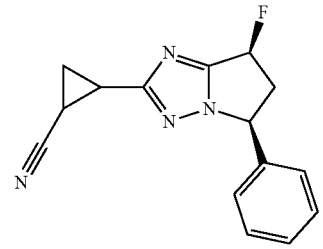 [SMILES: N#CC1CC1c1nc2n(n1)[C@H](c1ccccc1)C[C@@H]2F]

Trans-2-[(5S,7S)-7-fluoro-5-phenyl-6,7-dihydro-5H-pyrrolo[1,2-b][1,2,4]triazol-2-yl]cyclopropanecarbonitrile A mixture of (5S,7S)-2-bromo-7-fluoro-5-phenyl-6,7-dihydro-5H-pyrrolo[1,2-b][1,2,4]triazole (10 0 mg, 0.35 mmol), potassium (2-cyanocyclopropyl)-trifluoroborate (92 mg, 0.53 mmol), CataCXium A-Pd-G2 (24 mg, 0.04 mmol) and cesium fluoride (161 mg, 1.06 mmol) in 1,4-dioxane (3 mL) and water (0.3 mL) was heated at 90° C. for 15 h under nitrogen atmosphere. After cooled, the mixture was diluted with water (20 mL) and extracted with ethyl acetate (3×15 mL). The combined organic layers were concentrated under reduced pressure. The residue was purified by RP-HPLC (acetonitrile 30-60%/0.05% ammonia hydroxide in water) to afford arbitrarily assigned trans-2-[(5S,7S)-7-fluoro-5-phenyl-6,7-dihydro-5H-pyrrolo[1,2-b][1,2,4]triazol-2-yl]cyclopropanecarbonitrile (8 mg, 8%) as a white solid. $^1$H NMR (400 MHz, CDCl$_3$) δ 7.42-7.39 (m, 3H), 7.24-7.22 (m, 2H), 6.00-5.84 (m, 1H), 5.38-5.34 (m, 1H), 3.64-3.56 (m, 1H), 2.92-2.72 (m, 2H), 2.01-1.94 (m, 1H), 1.67-1.62 (m, 2H). LCMS R$_T$=0.822 min, m/z=269.0 [M+H]$^+$.

LCMS (5 to 95% acetonitrile in water+0.03% trifluoroacetic acid over 1.5 mins) retention time 0.822 min, ESI+ found [M+H]=269.0.

Example 17: Method 16

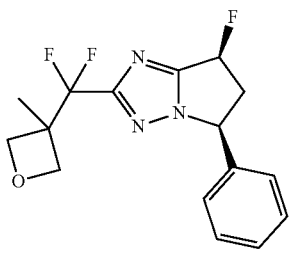 [SMILES: CC1(C(F)(F)c2nc3n(n2)[C@H](c2ccccc2)C[C@@H]3F)COC1]

(5S,7S)-2-[difluoro-(3-methyloxetan-3-yl)methyl]-7-fluoro-5-phenyl-6,7-dihydro-5H-pyrrolo[1,2-b][1,2,4]triazole

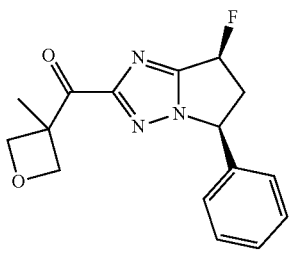 [SMILES: CC1(C(=O)c2nc3n(n2)[C@H](c2ccccc2)C[C@@H]3F)COC1]

Step 1: (5S,7S)-2-[difluoro-(3-methyloxetan-3-yl)methyl]-7-fluoro-5-phenyl-6,7-dihydro-5H-pyrrolo[1,2-b][1,2,4]triazole To a cooled (−78° C.) solution of (5S,7S)-2-bromo-7-fluoro-5-phenyl-6,7-dihydro-5H-pyrrolo[1,2-b][1,2,4]triazole (300 mg, 1.06 mmol) and N-methoxy-N,3-dimethyloxetane-3-carboxamide (338 mg, 2.13 mmol) in tetrahydrofuran (10 mL) was added n-butyllithium (2.5 M in hexanes, 1.28 mL, 3.19 mmol) under nitrogen atmosphere. After addition, the mixture was stirred at −78° C. for 1 h and then quenched by addition of saturated aqueous ammonium chloride (20 mL). The resulting mixture was extracted with ethyl acetate (3×15 mL). The combined organic layers were concentrated under reduce pressure and the residue was purified by RP-HPLC (acetonitrile 30-60%/0.05% ammonia hydroxide in water) to afford (5S,7S)-2-[difluoro-(3-methyloxetan-3-yl)methyl]-7-fluoro-5-phenyl-6,7-dihydro-5H-pyrrolo[1,2-b][1,2,4]triazole (190 mg, 59%) as a pink solid used as is in the next step.

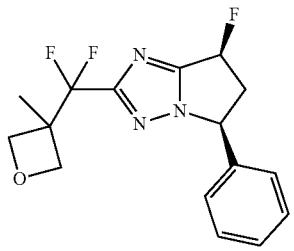 [SMILES: CC1(C(F)(F)c2nc3n(n2)[C@H](c2ccccc2)C[C@@H]3F)COC1]

Step 2: (5S,7S)-2-[difluoro-(3-methyloxetan-3-yl)methyl]-7-fluoro-5-phenyl-6,7-dihydro 5H-pyrrolo[1,2-b][1,2,4]triazole A mixture of (5S,7S)-2-[difluoro-(3-methyloxetan-3-yl)methyl]-7-fluoro-5-phenyl-6,7-dihydro-5H-pyrrolo[1,2-b][1,2,4]triazole (47 mg, 0.16 mmol) in bis(2-methoxyethyl)aminosulphur trifluoride (3.0 mL) was heated at 80° C. for 2 h. After cooled, the mixture was diluted with dichloromethane (5 mL) and then ice water (10 mL). The resulting mixture was extracted with dichloromethane (3×10 mL). The combined organic layers were dried over anhydrous sodium sulfate and concentrated under reduced pressure. The residue was purified by RP-HPLC (acetonitrile 39-59%/10 mM ammonium hydrogen carbonate in water) to afford arbitrarily assigned (5S,7S)-2-[difluoro-(3-methyloxetan-3-yl)methyl]-7-fluoro-5-phenyl-6,7-dihydro-5H-pyrrolo[1,2-b][1,2,4]triazole (15.7 mg, 31%) as a brown oil. $^1$H NMR (400 MHz, CD$_3$OD) δ 7.40-7.36 (m, 3H), 7.21-7.19 (m, 2H), 6.14-6.11 (m, 0.5H), 6.00-5.97 (m, 0.5H), 5.61-5.54 (m, 1H), 5.01-4.98 (m, 2H), 4.42-4.36 (m, 2H), 3.80-3.65 (m, 1H), 2.83-2.70 (m, 1H), 1.42 (s, 3H). LCMS R$_T$=0.735 min, m/z=324.1[M+H]$^+$.

LCMS (5 to 95% acetonitrile in water+0.03% trifluoroacetic acid over 1.5 mins) retention time 0.735 min, ESI+ found [M+H]=324.1.

Example 18: Method 18

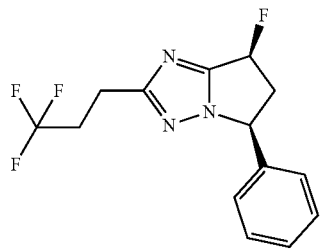 [SMILES: F[C@H]1C[C@@H](c2ccccc2)n2nc(CCC(F)(F)F)nc21]

(5S,7S)-7-fluoro-5-phenyl-2-(3,3,3-trifluoropropyl)-6,7-dihydro-5H-pyrrolo[1,2-b][1,2,4]triazole A mixture of (5S,7S)-2-bromo-7-fluoro-5-phenyl-6,7-dihydro-5H-pyrrolo[1,2-b][1,2,4]triazole (50 mg, 0.18 mmol), RuPhos-Pd-G2 (14 mg, 0.02 mmol), potassium 3,3,3-trifluoropropane-1-trifluoroborate (54 mg, 0.27 mmol), cesium carbonate (173 mg, 0.53 mmol) in toluene (3 mL) and water (0.3 mL) was heated at 100° C. for 24 h under nitrogen atmosphere and then concentrated under reduced pressure. The residue was then diluted with water (15 mL) and extracted with ethyl acetate (3×15 mL). The combined organic layers were washed with brine (20 mL), dried over sodium sulfate and concentrated under reduced pressure. The residue was purified by RP-HPLC (acetonitrile 40-70%/0.05% ammonia hydroxide in water) to afford arbitrarily assigned (5S,7S)-7-fluoro-5-phenyl-2-(3,3,3-trifluoropropyl)-6,7-dihydro-5H-pyrrolo[1,2-b][1,2,4]triazole (19 mg, 34%) as a white solid. $^1$H NMR (400 MHz, CDCl$_3$) δ 7.42-7.36 (m, 3H), 7.23-7.21 (m, 2H), 6.04-5.88 (m, 1H), 5.40-5.36 (m, 1H), 3.63-3.59 (m, 1H), 3.06-3.02 (m, 2H), 2.95-2.85 (m, 1H), 2.64-2.57 (m, 2H). LCMS R$_T$=0.891 min, m/z=299.9 [M+H]$^+$.

LCMS (5 to 95% acetonitrile in water+0.03% trifluoacetic acid over 1.5 mins) retention time 0.891 min, ESI+ found [M+H]=299.9.

Example 19: Method 19

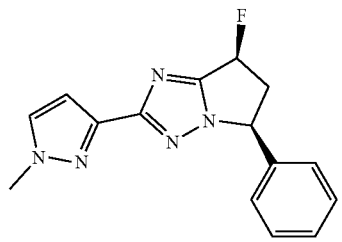 [SMILES: Cn1ccc(-c2nc3n(n2)[C@H](c2ccccc2)C[C@@H]3F)n1]

(5S,7S)-7-fluoro-2-(1-methyl-1H-pyrazol-3-yl)-5-phenyl-6,7-dihydro-5H-pyrrolo[1,2-b][1,2,4]triazole A mixture of (5S,7S)-2-bromo-7-fluoro-5-phenyl-6,7-dihydro-5h-pyrrolo [1,2-b][1,2,4]triazole (25 mg, 0.09 mmol), 1-methyl-3-(4,4,5,5-tetramethyl-1,3,2-dioxaborolan-2-yl)-1h-pyrazole (0.01 mL, 0.18 mmol), 1,1'-bis(diphenylphosphino)ferrocene palladium dichloride (6 mg, 0.01 mmol) and potassium carbonate (37 mg, 0.27 mmol) in 1,2-dimethoxyethane (1 mL) and water (0.2 mL) was heated at 120'C for 0.5 h under microwave conditions and diluted with water (5 mL). The mixture was extracted with ethyl acetate (3×5 mL). The combine organic layers were washed with brine (2×5 mL), dried over sodium sulfate and concentrated under reduced pressure. The residue was purified by RP-HPLC (acetonitrile 30-60%/0.05% ammonia hydroxide in water) to afford arbitrarily assigned (5S,7S)-7-fluoro-2-(1-methyl-1H-pyrazol-3-yl)-5-phenyl-6,7-dihydro-5H-pyrrolo[1,2-b][1,2,4]triazole (6 mg, 24%) as a faint pink solid. $^1$H NMR (400 MHz, CD$_3$OD) δ 7.49 (d, J=2.0 Hz, 1H), 7.46-7.34 (m, 3H), 7.33-7.20 (m, 2H), 6.82 (d, J=2.4 Hz, 1H), 6.25-5.99 (m, 1H), 5.66-5.59 (m, 1H), 4.15 (s, 3H), 3.81-3.71 (m, 1H), 2.85-2.74 (m, 1H). LCMS R$_T$=1.621 min, m/z=284.2 [M+H]$^+$.

LCMS (10 to 80% acetonitrile in water+0.1% ammonia water over 3.0 mins) retention time 1.621 min, ESI+ found [M+H]=284.2.

Example 20: Method 20

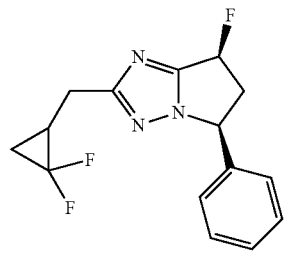 [SMILES: F[C@H]1C[C@@H](c2ccccc2)n2nc(CC3CC3(F)F)nc21]

(5S,7S)-2-[(2,2-difluorocyclopropyl)methyl]-7-fluoro-5-phenyl-6,7-dihydro-5H-pyrrolo[1,2-b][1,2,4]triazole

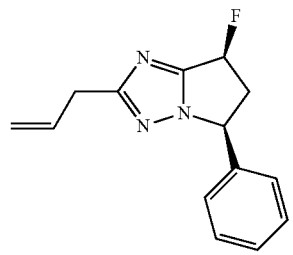 [SMILES: C=CCc1nc2n(n1)[C@H](c1ccccc1)C[C@@H]2F]

Step 1: (5S,7S)-2-allyl-7-fluoro-5-phenyl-6,7-dihydro-5H-pyrrolo[1,2-b][1,2,4]triazole A mixture of (5S,7S)-2-bromo-7-fluoro-5-phenyl-6,7-dihydro-5H-pyrrolo[1,2-b][1,2,4]triazole (150 mg, 0.53 mmol), allylboronic acid pinacolester (179 mg, 1.06 mmol), RuPhos-Pd-G2 (4 1 mg, 0.05 mmol), cesium carbonate (520 mg, 1.60 mmol) in 1,4-dioxane (5 mL) and water (1 mL) was heated at 100° C. for 12 h under nitrogen atmosphere and then concentrated under reduced pressure. The residue was diluted with water (30 mL) and extracted with ethyl acetate (3×15 mL). The combined organic layers were concentrated under reduce pressure. The residue was purified by preparative TLC (35% of ethyl acetate in petroleum ether, R$_f$=0.4) to afford (5S,7S)-2-allyl-7-fluoro-5-phenyl-6,7-dihydro-5H-pyrrolo[1,2-b][1,2,4]triazole (90 mg, 70%) as a colorless oil. LCMS R$_T$=0.733 min, m/z=244.1 [M+H]$^+$.

LCMS (5 to 95% acetonitrile in water+0.03% trifluoacetic acid over 1.5 mins) retention time 0.733 min, ESI+ found [M+H]=244.1.

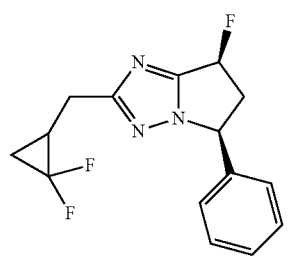 [SMILES: F[C@H]1C[C@@H](c2ccccc2)n2nc(CC3CC3(F)F)nc21]

Step 2: (5S,7S)-2-[(2,2-difluorocyclopropyl)methyl]-7-fluoro-5-phenyl-6,7-dihydro-5H-pyrrolo[1,2-b][1,2,4]triazole To a solution of (5S,7S)-2-allyl-7-fluoro-5-phenyl-6,7-dihydro-5H-pyrrolo[1,2-b][1,2,4]triazole (50 mg, 0.21 mmol) in toluene (1 mL) was added benzyltriethylammonium chloride (6 mg, 0.02 mmol) and [chloro(difluoro)methyl]trimethylsilane (98 mg, 0.62 mmol). The mixture was heated at 110° C. for 4 h under microwave conditions and diluted with water (10 mL). The resulting mixture was extracted with ethyl acetate (3×10 mL). The combined organic layers were concentrated under reduced pressure and the residue was purified by RP-HPLC (acetonitrile 35-65%/0.05% ammonia hydroxide in water) to afford arbitrarily assigned (5S,7S)-2-[(2,2-difluorocyclopropyl)methyl]-7-fluoro-5-phenyl-6,7-dihydro-5H-pyrrolo[1,2-b][1,2,4]triazole (10.7 mg, 17%) as a white solid. $^1$H NMR (400 MHz, CDCl$_3$) δ 7.41-7.36 (m, 3H), 7.24-7.22 (m, 2H), 6.05-5.89 (m, 1H), 5.41-5.37 (m, 1H), 3.63-3.55 (m, 1H), 3.06-3.03 (m, 1H), 2.85-2.81 (m, 2H), 2.01-2.00 (m, 1H), 1.50-1.46 (m, 1H), 1.16-1.11 (m, 1H). LCMS R$_T$=1.775 min, m/z=294.1[M+H]$^+$.

LCMS (10 to 80% acetonitrile in water+0.1% ammonia water over 3.0 mins) retention time: 1.775 min, ESI+ found [M+H]=294.1.

Example 21: Method 21

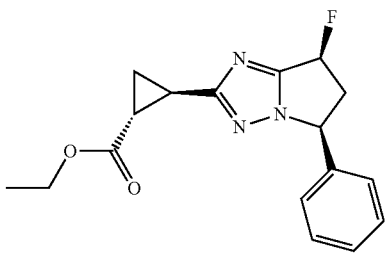 [SMILES: CCOC(=O)[C@@H]1C[C@H]1c1nc2n(n1)[C@H](c1ccccc1)C[C@@H]2F]

ethyl rac-(1R,2R)-2-[(5S,7S)-7-fluoro-5-phenyl-6,7-dihydro-5H-pyrrolo[1,2-b][1,2,4]triazol-2-yl]cyclopropanecarboxylate and To a solution of ethyl diazoacetate (0.85 g, 7.42 mmol) in toluene (20 mL) was added (5S,7S)-7-fluoro-5-phenyl-2-vinyl-6,7-dihydro-5H-pyrrolo[1,2-b][1,2,4]triazole (170 mg, 0.74 mmol). The reaction mixture was heated at 110° C. for 12 h and concentrated under reduced pressure. The residue was first purified by preparative TLC (40% ethyl acetate in petroleum ether, R$_f$=0.3&0.4), then RP-HPLC (acetonitrile 5-55%/0.05% ammonia hydroxide in water) to afford arbitrarily assigned ethyl rac-(1R,2R)-2-[(5S,7S)-7-fluoro-5-phenyl-6,7-dihydro-5H-pyrrolo[1,2-b][1,2,4]triazol-2-yl]cyclopropanecarboxylate (120 mg, 50%) as a colorless oil. $^1$H NMR (400 MHz, CDCl$_3$) δ 7.39-7.36 (m, 3H), 7.23-7.20 (m, 2H), 5.99-5.96 (m, 0.5H), 5.85-5.82 (m, 0.5H), 5.35-5.31 (m, 1H), 4.17-4.11 (m, 2H), 3.58-3.48 (m, 1H), 2.90-2.80 (m, 1H), 2.65-2.63 (m, 1H), 2.22-2.15 (m, 1H), 1.58-1.55 (m, 2H), 1.27-1.23 (m, 3H). LCMS R$_T$=0.890 min, m/z=316.0 [M+H]$^+$.

LCMS (5 to 95% acetonitrile in water+0.03% trifluoacetic acid over 1.5 mins) retention time 0.890 min, ESI+ found [M+H]=316.0.

Arbitrarily assigned ethyl rac-(1R,2S)-2-[(5S,7S)-7-fluoro-5-phenyl-6,7-dihydro-5H-pyrrolo[1,2-b][1,2,4]triazol-2-yl]cyclopropanecarboxylate (30 mg, 13%) as a colorless oil. $^1$H NMR (400 MHz, CD$_3$OD) δ 7.46-7.32 (m, 3H), 7.25-7.17 (m, 2H), 6.10-6.04 (m, 0.5H), 5.96-5.90 (m, 0.5H), 5.54-5.47 (m, 1H), 4.01-3.93 (m, 1H), 3.93-3.87 (m, 1H), 3.75-3.59 (m, 1H), 2.78-2.62 (m, 1H), 2.61-2.53 (m, 1H), 2.18-2.10 (m, 1H), 1.80-1.72 (m, 1H), 1.50-1.41 (m, 1H), 1.13-1.04 (m, 3H). LCMS R$_f$=0.730 min, m/z=316.1 [M+H]$^+$.

LCMS (5 to 95% acetonitrile in water+0.03% trifluoacetic acid over 1.5 mins) retention time 0.730 min, ESI+ found [M+H]=316.1.

Example 22: Method 22

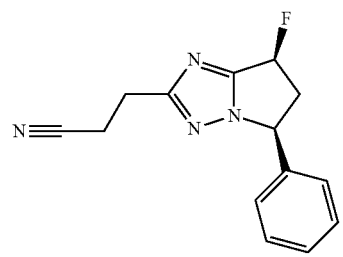 [SMILES: N#CCCc1nc2n(n1)[C@H](c1ccccc1)C[C@@H]2F]

3-((5S,7S)-7-fluoro-5-phenyl-6,7-dihydro-5H-pyrrolo[1,2-b][1,2,4]triazol-2-yl)propanenitrile

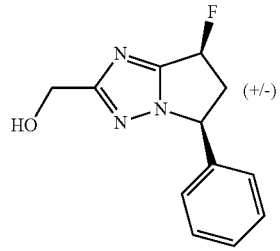 [SMILES: OCc1nc2n(n1)[C@H](c1ccccc1)C[C@@H]2F]

Step 1: rac-(5S,7S)-(7-fluoro-5-phenyl-6,7-dihydro-5H-pyrrolo[1,2-b][1,2,4]triazol-2-yl)methanol To a solution of ethyl [rac-(5S,7S)-7-fluoro-5-phenyl-6,7-dihydro-5H-pyrrolo[1,2-b][1,2,4]triazole-2-carboxylate (520 mg, 1.89 mmol, 1.0 equiv) in ethanol (10 mL) cooled to 0° C. was added lithium borohydride (2 M in tetrahydrofuran, 5.66 mL, 11.33 mmol, 6.0 equiv). The ice bath was removed, and the mixture was stirred 6 h at RT. After this time, the reaction mixture was poured into 5% aqueous citric acid (100 mL). The mixture was extracted with isopropyl acetate (3×50 mL). The combined organics were washed with brine, dried over sodium sulfate, and concentrated to afford rac-(5S,7S)-(7-fluoro-5-phenyl-6,7-dihydro-5H-pyrrolo[1,2-b][1,2,4]triazol-2-yl)methanol as a white solid which was used without further purification (428 mg, 97% yield).

LCMS (5 to 95% acetonitrile in water+0.1% formic acid over 2 mins) retention time 0.88 min, ESI+ found [M+H]=234.

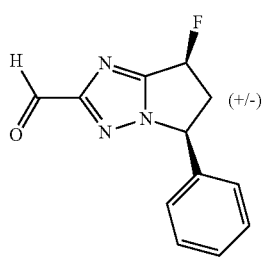 [SMILES: O=Cc1nc2n(n1)[C@H](c1ccccc1)C[C@@H]2F]

Step 2: rac-(5S,7S)-7-fluoro-5-phenyl-6,7-dihydro-5H-pyrrolo[1,2-b][1,2,4]triazole-2-carbaldehyde To a solution of rac-(5S,7S)-(7-fluoro-5-phenyl-6,7-dihydro-5H-pyrrolo[1,2-b][1,2,4]triazol-2-yl)methanol (420 mg, 1.8 mmol, 1.0 equiv) in dichloromethane (8 mL) was added Dess-Martin periodinane (866 mg, 1.98 mmol, 1.1 equiv). The mixture was stirred 2 h at RT. After this time, it was diluted with dichloromethane (75 mL), quenched with 100 mL 1:1 10% aqueous NaHCO₃/20% Na2S2O3 and stirred 30 mins at RT. The layers were separated, and the dichloromethane layer was washed with brine, dried over sodium sulfate and concentrated to afford rac-(5S,7S)-7-fluoro-5-phenyl-6,7-dihydro-5H-pyrrolo[1,2-b][1,2,4]triazole-2-carbaldehyde as a yellow residue which was used in the next step without further purification (410 mg, 98% yield).

LCMS (5 to 95% acetonitrile in water+0.1% formic acid over 2 mins) retention time 1.04 min, ESI+ found [M+H]=232.

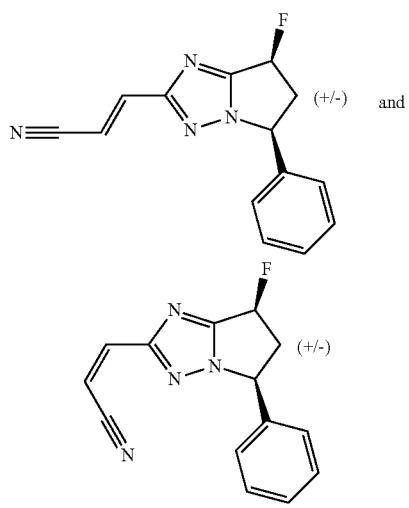

Step 3: (E)-rac-(5S,7S)-3-(7-fluoro-5-phenyl-6,7-dihydro-5H-pyrrolo[1,2-b][1,2,4]triazol-2-yl)prop-2-enenitrile and (Z)-rac-(5S,7S)-3-(7-fluoro-5-phenyl-6,7-dihydro-5H-pyrrolo[1,2-b][1,2,4]triazol-2-yl)prop-2-enenitrile To a solution of diethyl cyanomethylphosphonate (0.324 mL, 354 mg, 2.0 mmol, 1.1 equiv) in tetrahydrofuran (10 mL) was added potassium tert-butoxide (1 M in tetrahydrofuran, 1.9 mL, 1.9 mmol, 1.05 equiv). The resulting mixture was stirred 1 h at RT, then to it was added rac-(5S,7S)-7-fluoro-5-phenyl-6,7-dihydro-5H-pyrrolo[1,2-b][1,2,4]triazole-2-carbaldehyde (420 mg, 1.82 mmol, 1.0 equiv) in tetrahydrofuran (10 mL). The resulting mixture was stirred 16 h at RT. After this time, the reaction was quenched with 5% aqueous citric acid (75 mL) and extracted with isopropyl acetate (3×50 mL). The combined organics were washed with saturated NaHCO₃, water and brine, dried over sodium sulfate and concentrated. The resulting residue was purified by column chromatography (silica gel, 100-200 mesh, 0 to 100% isopropyl acetate in heptane) to afford (E)-rac-(5S,7S)-3-(7-fluoro-5-phenyl-6,7-dihydro-5H-pyrrolo[1,2-b][1,2,4]triazol-2-yl)prop-2-enenitrile (155 mg, 34% yield) and (Z)-rac-(5S,7S)-3-(7-fluoro-5-phenyl-6,7-dihydro-5H-pyrrolo[1,2-b][1,2,4]triazol-2-yl)prop-2-enenitrile (90 mg, 20% yield).

(E) isomer: LCMS (5 to 95% acetonitrile in water+0.1% formic acid over 2 mins) retention time 1.16 min, ESI+ found [M+H]=255.

(Z) isomer: LCMS (5 to 95% acetonitrile in water+0.1% formic acid over 2 mins) retention time 1.11 min, ESI+ found [M+H]=255.

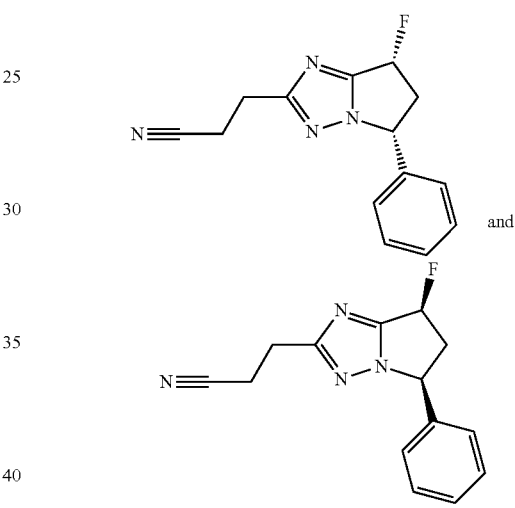

Step 4: 3-((5R,7R)-7-fluoro-5-phenyl-6,7-dihydro-5H-pyrrolo[1,2-b][1,2,4]triazol-2-yl)propanenitrile and 3-((5S,7)-7-fluoro-5-phenyl-6,7-dihydro-5H-pyrrolo[1,2-b][1,2,4]triazol-2-yl)propanenitrile To a solution of (Z)-rac-(5S,7S)-3-(7-fluoro-5-phenyl-6,7-dihydro-5H-pyrrolo[1,2-b][1,2,4]triazol-2-yl)prop-2-enenitrile in tetrahydrofuran (5 mL) and ethanol (5 mL) was added sodium borohydride (80 mg, 2.1 mmol, 6.0 equiv). The mixture was stirred at 50° C. for 3 h. After this time, the mixture was filtered through a plug of silica gel eluting with isopropyl acetate, and concentrated. The residue was purified by column chromatography (silica gel, 100-200 mesh, 0 to 100% isopropyl acetate in heptane) to afford rac-(5S,7S)-3-(7-fluoro-5-phenyl-6,7-dihydro-H-pyrrolo[1,2-b][1,2,4]triazol-2-yl)propanenitrile as a white solid (60 mg, 66% yield). This racemic material was further separated by chiral SFC to afford arbitrarily assigned:

3-((5R,7R)-7-fluoro-5-phenyl-6,7-dihydro-5H-pyrrolo[1,2-b][1,2,4]triazol-2-yl)propanenitrile (Peak 1, SFC analytical retention time=0.73 min, Whelk-01 (S,S), isocratic 15% MeOH+0.1% NH₄OH, 2.5 min method) (19.1 mg, 21%) as a white solid. $^1$H NMR (400 MHz, DMSO-d6) δ 7.45-7.30 (m, 3H), 7.26-7.15 (m, 2H), 6.14 (ddd, J=57.0, 7.1, 1.7 Hz, 1H), 5.66-5.52 (m, 1H), 3.77-3.59 (m, 1H), 3.06-2.95 (m, 2H), 2.94-2.81 (m, 2H), 2.70-2.56 (m, 1H). LC-MS $R_T$=3.78 min, m/z=257.1 (M+H)$^+$.

LCMS (5 to 95% acetonitrile in water+0.1% formic add over 10 mins) retention time 3.78 min, ESI+ found [M+H]=257.1.

3-((5S,7S)-7-fluoro-5-phenyl-6,7-dihydro-5H-pyrrolo[,2-b][1,2,4]triazol-2-yl)propanenitrile (Peak 2, SFC analytical retention time=0.86 min, Whelk-01 (S,S), isocratic 15% MeOH+0.1% NH$_4$OH, 2.5 min method) (21.0 mg, 23%) as a white solid. $^1$H NMR (400 MHz, DMSO-d6) δ 7.47-7.29 (m, 3H), 7.26-7.13 (m, 2H), 6.14 (ddd, J=57.0, 7.1, 1.7 Hz, 1H), 5.59 (ddd, J=8.3, 7.1, 2.8 Hz, 1H), 3.79-3.57 (m, 1H), 3.06-2.94 (m, 2H), 2.93-2.81 (m, 2H), 2.73-2.54 (m, 1H). LC-MS $R_T$=3.78 min, m/z=257.1 (M+H)$^+$.

LCMS (5 to 95% acetonitrile in water+0.1% formic add over 10 mins) retention time 3.78 min, ESI+ found [M+H]=257.1.

SFC condition (prep): Column: Whelk 0-1 (S,S) 150×21.2 mm I.D., 5 um Mobile phase: A: CO2 B:methanol, Isocratic 20% methanol for 25 mins, Flow rate: 80 mL/min, column temp 40° C.

Example 23: Method 23

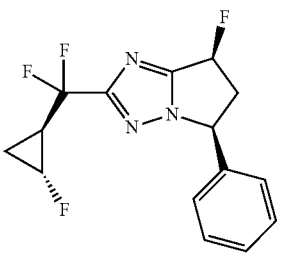 [SMILES: F[C@@H]1C[C@H]1C(F)(F)c1nc2n(n1)[C@H](c1ccccc1)C[C@@H]2F]

(5S,7S)-2-[difluoro-(rac-(1R,2R)-2-fluorocyclopropyl)methyl])-7-fluoro-5-phenyl-6,7-dihydro-5H-pyrrolo[1,2-b][1,2,4]triazole A mixture of (trans-2-fluorocyclopropyl)-[(5S,7S)-7-fluoro-5-phenyl-6,7-dihydro-5H-pyrrolo[1,2-b][1,2,4]triazol-2-yl]methanone (44 mg, 0.15 mmol) in diethylaminosulfur trifluoride (2.0 g, 12.41 mmol) was heated at 50° C. for 24 h and then slowly added into saturated aqueous sodium bicarbonate (20 mL). The resulting mixture was extracted with dichloromethane (3×30 mL). The combined organic layers were washed with brine (20 mL), dried over sodium sulfate and concentrated under reduced pressure. The residue was purified by RP-HPLC (acetonitrile 40-70%/ 0.05% ammonia hydroxide in water) to afford the crude product, which was further purified by preparative TLC (40% ethyl acetate in petroleum ether, $R_f$=0.5) to afford arbitrarily assigned (5S,7S)-2-[difluoro-(rac-(1R,2R)-2-fluorocyclopropyl)methyl]-7-fluoro-5-phenyl-6,7-dihydro-5H-pyrrolo[1,2-b][1,2,4]triazole (7.2 mg, 15%) as a white solid. $^1$H NMR (400 MHz, CDCl$_3$) δ 7.44-7.39 (m, 3H), 7.26-7.24 (m, 2H), 6.10-6.08 (m, 1H), 5.50-5.45 (m, 1H), 4.92-4.75 (m, 1H), 3.69-3.58 (m, 1H), 3.00-2.90 (m, 1H), 2.31-2.25 (m, 1H), 1.43-1.36 (m, 1H), 1.24-1.19 (m, 1H). LCMS $R_T$=1.931 min, m/z=312.1 [M+H]$^+$.

LCMS (10 to 80% acetonitrile in water+0.05% ammonia hydroxide over 3 mins) retention time 1.931 min, ESI+ found [M+H]=312.1.

Example 24: Method 24

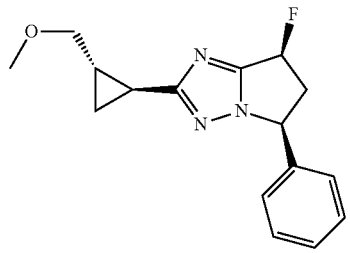 [SMILES: COC[C@H]1C[C@@H]1c1nc2n(n1)[C@H](c1ccccc1)C[C@@H]2F]

(S,7S)-7-fluoro-5-phenyl-2-[rac-(1R,2R)-2-(methoxymethyl)cyclopropyl]-6,7-dihydro-5H-pyrrolo[1,2-b][1,2,4]triazole

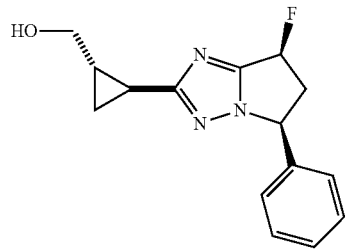

Step 1: (trans-2-((5S,7S)-7-fluoro-5-phenyl-6,7-dihydro-5H-pyrrolo[1,2-b][1,2,4]triazol-2-yl)cyclopropyl)methanol To a cooled solution of ethyl rac-(1R,2R)-2-[(5S,7S)-7-fluoro-5-phenyl-6,7-dihydro-5H-pyrrolo[1,2-b][1,2,4]triazol-2-yl]cyclopropanecarboxylate (60 mg, 0.19 mmol) in tetrahydrofuran (2 mL) was added lithiumaluminum hydride (14 mg, 0.38 mmol) at 0° C. After addition, the mixture was stirred at 0° C. for 1 h and quenched by addition of water (0.05 mL). The resulting mixture was diluted with ethyl acetate (10 mL). The separated organic layer was dried over sodium sulfate and concentrated under reduced pressure. The residue was purified by preparative TLC (50% ethyl acetate in petroleum ether, $R_f$=0.4) to afford arbitrarily assigned rac-(1R,2R)-2-[(5S,7S)-7-fluoro-5-phenyl-6,7-dihydro-5H-pyrrolo [1,2-b][1,2,4]triazol-2-yl]cyclopropylmethanol (45 mg, 87%) as a white solid. $^1$H NMR (400 MHz, CD$_3$OD) δ 7.45-7.33 (m, 3H), 7.27-7.20 (m, 2H), 6.07-6.05 (m, 0.5H), 5.93-5.90 (m, 0.5H), 5.50-5.43 (m, 1H), 3.76-3.55 (m, 2H), 3.52-3.44 (m, 1H), 2.78-2.63 (m, 1H), 1.99-1.94 (m, 1H), 1.70-1.58 (m, 1H), 1.18-1.12 (m, 1H), 1.02-0.94 (m, 1H). LCMS $R_T$=0.654 min, m/z=274.1 [M+H]$^+$.

LCMS (5 to 95% acetonitrile in water+0.03% trifluoacetic acid over 1.5 mins) retention time 0.654 min, ESI+ found [M+H]=274.1.

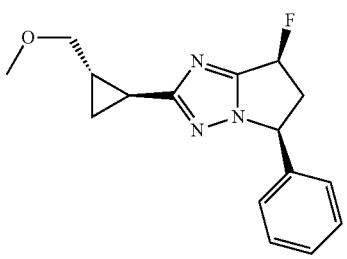 [SMILES: COC[C@H]1C[C@@H]1c1nc2n(n1)[C@H](c1ccccc1)C[C@@H]2F]

Step 2: (5,7S)-7-fluoro-5-phenyl-2-[rac-(1R,2R)-2-(methoxymethyl)cyclopropyl]-6,7-dihydro-5H-pyrrolo[1,2-b][1,2,4]triazole To a cooled solution of rac-(1R,2R)-2-[(5S,7S)-7-fluoro-5-phenyl-6,7-dihydro-5H-pyrrolo[1,2-b][1,2,4]triazol-2-yl]cyclopropylmethanol (45 mg, 0.16 mmol) in tetrahydrofuran (2 mL) was added sodium hydride (60%, 13 mg, 0.33 mmol) at 0° C. The mixture was stirred at 0° C. for 2 min, then iodomethane (47 mg, 0.33 mmol) was added. After addition, the mixture was stirred at 0° C. for 1 h and quenched by addition of water (5 mL). The resulting mixture was extracted with ethyl acetate (2×5 mL). The combined organic layers were dried over sodium sulfate and concentrated under reduced pressure. The residue was purified by RP-HPLC (acetonitrile 24-54%/0.05% ammonia hydroxide in water) to afford arbitrarily assigned (5S,7S)-7-fluoro-5-phenyl-2-[rac-(1R,2R)-2-(methoxymethyl)cyclopropyl]-6,7-dihydro-5H-pyrrolo[1,2-b][1,2,4]triazole (9.9 mg, 21%) as a white solid. $^1$H NMR (400 MHz, CD$_3$OD) δ 7.40-7.29 (m, 3H), 7.20-7.17 (m, 2H), 6.03-6.01 (m, 0.5H), 5.89-5.86 (m, 0.5H), 5.45-5.39 (m, 1H), 3.71-3.56 (m, 1H), 3.47-3.41 (m, 1H), 3.30 (s, 3H), 3.30-3.24 (m, 1H), 2.72-2.59 (m, 1H), 1.96-1.91 (m, 1H), 1.66-1.54 (m, 1H), 1.18-1.08 (m, 1H), 0.98-0.90 (m, 1H). LCMS R$_T$=0.724 min, m/z=288.2 [M+H]$^+$.

LCMS (5 to 95% acetonitrile in water+0.03% trifluoacetic acid over 1.5 mins) retention time 0.724 min, ESI+ found [M+H]=288.2.

Example 25: Method 25

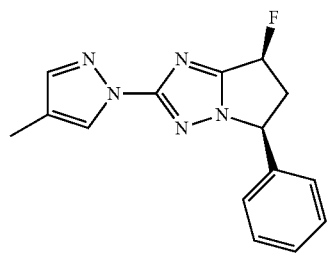 [SMILES: Cc1cnn(-c2nc3n(n2)[C@H](c2ccccc2)C[C@@H]3F)c1]

(5S,7S)-7-fluoro-2-(4-methyl-1H-pyrazol-1-yl)-5-phenyl-6,7-dihydro-5H-pyrrolo[1,2-b][1,2,4]triazole A mixture of (5S,7S)-2-bromo-7-fluoro-5-phenyl-6,7-dihydro-5H-pyrrolo[1,2-b][1,2,4]triazole (100 mg, 0.35 mmol), copper(I) iodide (14 mg, 0.07 mmol), (1S,2S)—N$^1$,N$^2$-dimethylcyclohexane-1,2-diamine (50 mg, 0.35 mmol), cesium carbonate (346 mg, 1.06 mmol) and 4-methylpyrazole (291 mg, 3.54 mmol) in 1,4-dioxane (2 mL) was heated at 140° C. for 3 min a sealed tube under microwave conditions. After filtration, the filtrate was concentrated under reduced pressure. The residue was purified by RP-HPLC (acetonitrile 25-50%/0.05% ammonia hydroxide in water) to afford arbitrarily assigned (5S,7S)-7-fluoro-2-(4-methylpyrazol-1-yl)-5-phenyl-6,7-dihydro-5H-pyrrolo[1,2-b][1,2,4]triazole (8 mg, 8%) as a yellow solid. $^1$H NMR (400 MHz, CD$_3$OD) δ 8.05 (s, 1H), 7.57 (s, 1H), 7.44-7.29 (m, 5H), 6.18-6.02 (m, 1H), 5.62-5.56 (m, 1H), 3.78-3.85 (m, 1H), 2.80-2.69 (m, 1H), 2.14 (s, 3H). LCMS R$_T$=0.710 min, m/z=283.9 [M+H]j.

LCMS (5 to 95% acetonitrile in water+0.03% trifluoacetic acid over 1.5 mins) retention time 0.710 min, ESI+ found [M+H]=283.9.

Example 26: Method 26

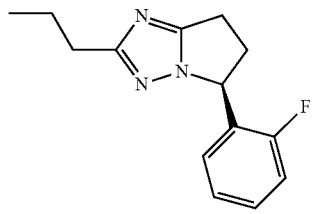 [SMILES: CCCc1nc2n(n1)[C@H](c1ccccc1F)CC2]

(S)-5-(2-fluorophenyl)-2-propyl-6,7-dihydro-5H-pyrrolo[1,2-b][1,2,4]triazole

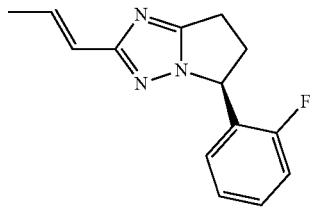 [SMILES: C/C=C/c1nc2n(n1)[C@H](c1ccccc1F)CC2]

Step 1: (S,E)-5-(2-fluorophenyl)-2-(prop-1-en-1-yl)-6,7-dihydro-5H-pyrrolo[1,2-b][1,2,4]triazole A mixture of (S)-2-bromo-5-(2-fluorophenyl)-6,7-dihydro-5H-pyrrolo[1,2-b][1,2,4]triazole (20 mg, 0.07 mmol), 1,1'-bis(diphenylphosphino)ferrocene palladium dichloride (5 mg, 0.01 mmol), 4,4,5,5-tetramethyl-2-[(1E)-prop-1-en-1-yl]-1,3,2-dioxaborolane (24 mg, 0.14 mmol) and cesium carbonate (70 mg, 0.21 mmol) in 1,4-dioxane (2 mL) and water (0.4 mL) was heated at 100° C. for 16 h under nitrogen atmosphere and concentrated under reduced pressure. The aqueous residue was diluted with water (15 mL) and extracted with ethyl acetate (3×15 mL). The combined organic layers were dried over sodium sulfate and concentrated under reduced pressure to afford crude (S)-5-(2-fluorophenyl)-2-[(E)-prop-1-enyl]-6,7-dihydro-5H-pyrrolo[1,2-b][1,2,4]triazole (40 mg, crude, 100%) as a dark oil. LCMS R$_T$=0.603 min, m/z=244.1 [M+H]$^+$.

LCMS (5 to 95% acetonitrile in water+0.03% trifluoacetic acid over 1.5 mins) retention time 0.603 min, ESI+ found [M+H]=244.1.

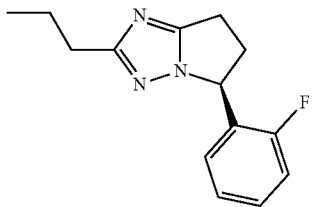 [SMILES: CCCc1nc2n(n1)[C@H](c1ccccc1F)CC2]

Step 2: (S)-5-(2-fluorophenyl)-2-propyl-6,7-dihydro-5H-pyrrolo[1,2-b][1,2,4]triazole A mixture of (S)-5-(2-fluorophenyl)-2-[(E)-prop-1-enyl]-6,7-dihydro-5H-pyrrolo [1,2-b][1,2,4]triazole (40 mg, 0.16 mmol) and palladium (10% on carbon, 175 mg, 0.16 mmol) in methanol (5 mL) was hydrogenated (15 psi) for 16 h at 30° C. and then filtered. The filtrate was concentrated under reduced pressure and the residue was purified by RP-HPLC (acetonitrile 40-70%/0.05% ammonia hydroxide in water) to afford arbitrarily assigned (S)-5-(2-fluorophenyl)-2-propyl-6,7-dihydro-5H-pyrrolo[1,2-b][1,2,4]triazole (11.6 mg, 41%) as a white solid. $^1$H NMR (400 MHz, CD$_3$OD) δ 7.42-7.36 (m, 1H), 7.21-7.07 (m, 3H), 5.69-5.66 (m, 1H), 3.29-3.22 (m, 1H), 3.08-3.00 (m, 2H), 2.67-2.58 (m, 3H), 1.78-1.68 (m, 2H), 0.94 (t, J=7.2 Hz, 3H). LCMS R$_T$=1.588 min, m/z=246.1[M+H]$^+$.

LCMS (10 to 80% acetonitrile in water+0.05% ammonia hydroxide over 3 mins) retention time 1.588 min, ESI+ found [M+H]=246.1.

Example 27 and 32: Method 27

(5S,7S)-7-fluoro-5-phenyl-2-[(S)-1-fluoro-1-methyl-propyl]-6,7-dihydro-5H-pyrrolo[1,2-b][1,2,4]triazole and (5S,7S)-7-fluoro-5-phenyl-2-[(R)-1-fluoro-1-methyl-propyl]-6,7-dihydro-5H-pyrrolo[1,2-b][1,2,4]triazole

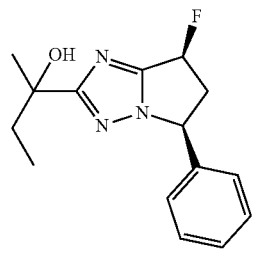 [SMILES: CCC(C)(O)c1nc2n(n1)[C@H](c1ccccc1)C[C@@H]2F]

Step 1: 2-((5S,7S)-7-fluoro-5-phenyl-6,7-dihydro-5H-pyrrolo[1,2-b][1,2,4]triazol-2-yl)butan-2-ol To a solution of 1-[(5S,7S)-7-fluoro-5-phenyl-6,7-dihydro-5H-pyrrolo[1,2-b][1,2,4]triazol-2-yl]propan-1-one (89 mg, 0.34 mmol) in tetrahydrofuran (5 mL) was added methylmagnesium bromide (3.0 M in diethyl ether, 0.46 mL, 1.37 mmol) dropwise at 0° C. under nitrogen atmosphere. After addition, the resulting mixture was stirred at 0° C. for 1 h and quenched by addition of saturated aqueous ammonium chloride (10 mL). The mixture was extracted with ethyl acetate (3×10 mL). The combined organic layers were concentrated under reduce pressure and the residue was purified by preparative TLC (50% ethyl acetate in petroleum ether, R$_f$=0.6) to afford 2-((5S,7S)-7-fluoro-5-phenyl-6,7-dihydro-5H-pyrrolo[1,2-b][1,2,4]triazol-2-yl)butan-2-ol (60 mg, 64%) as a yellow oil. LCMS R$_T$=0.579 min, m/z=276.1 (M+H)$^+$ LCMS (5 to 95% acetonitrile in water+0.03% trifluoacetic acid over 1.5 mins) retention time 0.579 min, ESI+ found [M+H]=276.1.

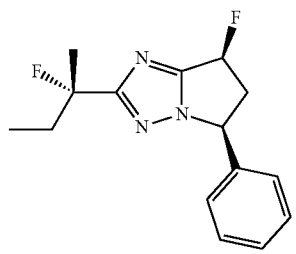

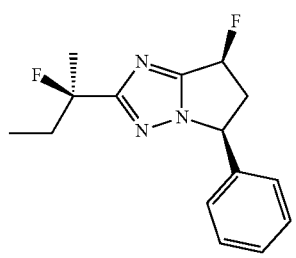

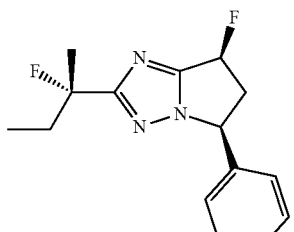

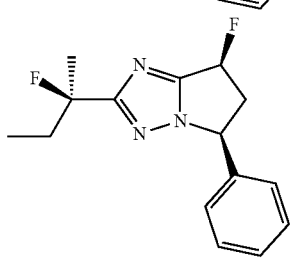

Step 2

(5S,7S)-7-fluoro-5-phenyl-2-[(S)-1-fluoro-1-methyl-propyl]-6,7-dihydro-5H-pyrrolo[1,2-b][1,2,4]triazole and (5S,7S)-7-fluoro-5-phenyl-2-[(R)-1-fluoro-1-methyl-propyl]-6,7-dihydro-5H-pyrrolo[1,2-b][1,2,4]triazole To a solution of 2-[(5S,7S)-7-fluoro-5-phenyl-6,7-dihydro-5H-pyrrolo[1,2-b][1,2,4]triazol-2-yl]butan-2-ol (60 mg, 0.22 mmol) in dichloromethane (10 mL) was added diethylaminosulfur trifluoride (0.14 mL, 1.09 mmol) at 0° C. under nitrogen atmosphere. The mixture was stirred at 25° C. for 2 h and then quenched by addition of saturated aqueous sodium bicarbonate (10 mL). The resulting mixture was extracted with dichloromethane (3×20 mL). The combined organic layers were concentrated under reduce pressure and the residue was purified by preparative TLC (50% ethyl acetate in petroleum ether, $R_f$=0.3) to afford crude (5S,7S)-7-fluoro-2-(1-fluoro-1-methyl-propyl)-5-phenyl-6,7-dihydro-5H-pyrrolo[1,2-b][1,2,4]triazole (80 mg, 128%) as a white solid. The racemic material (80 mg) was further purified by chiral SFC to afford arbitrarily assigned:

(5S,7S)-7-fluoro-5-phenyl-2-[(S)-1-fluoro-1-methyl-propyl]-6,7-dihydro-5H-pyrrolo[1,2-b][1,2,4]triazole (Peak 1, Retention time=2.008 min) (26 mg, 32%) as a white solid. $^1$H NMR (400 MHz, CD$_3$OD) δ 7.42-7.35 (m, 3H), 7.23-7.22 (m, 2H), 6.13-5.97 (m, 1H), 5.57-5.52 (m, 1H), 3.79-3.69 (m, 1H), 2.80-2.69 (m, 1H), 2.13-2.02 (m, 2H), 1.69 (d, J=22.0 Hz, 3H), 0.88 (t, J=7.6 Hz, 3H). LCMS $R_T$=0.732 min, m/z=278.0 [M+H]$^+$.

LCMS (5 to 95% acetonitrile in water+0.03% trifluoroacetic acid over 1.5 mins) retention time 0.732 min, ESI+ found [M+H]=278.0.

(5S,7S)-7-fluoro-5-phenyl-2-[(R)-1-fluoro-1-methyl-propyl]-6,7-dihydro-5H-pyrrolo[1,2-b][1,2,4]triazole (Peak 2, Retention time=2.589 min) (24 mg, 29%) as a white solid. $^1$H NMR (400 MHz, CD$_3$OD) δ 7.43-7.35 (m, 3H), 7.23-7.21 (m, 2H), 6.14-5.97 (m, 1H), 5.57-5.52 (m, 1H), 3.79-3.65 (m, 1H), 2.80-2.69 (m, 1H), 2.13-2.02 (m, 2H), 1.69 (d, J=21.6 Hz, 3H), 0.88 (t, J=7.6 Hz, 3H). LCMS $R_T$=0.857 min, m/z=278.0 [M+H]$^+$ LCMS (5 to 95% acetonitrile in water+0.03% trifluoroacetic acid over 1.5 mins) retention time 0.857 min, ESI+ found [M+H]=278.0.

SFC condition: Column: ChiralPak IC-3 150×4.6 mm I.D., 3 um Gradient: from 5% to 40% of IPA (0.05% DEA) in CO2 Flow rate: 2.5 mL/min. Column temperature: 40° C.

Example 28: Method 28

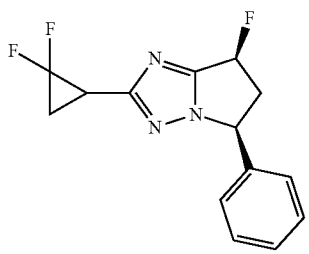 [SMILES: F[C@H]1C[C@@H](c2ccccc2)n2nc(C3CC3(F)F)nc21]

(5S,7S)-2-(2,2-difluorocyclopropyl)-7-fluoro-5-phenyl-6,7-dihydro-5H-pyrrolo[1,2-b][1,2,4]triazole

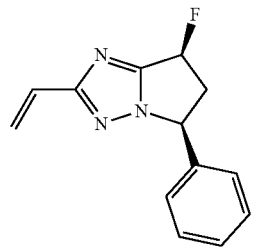 [SMILES: C=Cc1nc2n(n1)[C@H](c1ccccc1)C[C@@H]2F]

Step 1: (5S,7S)-7-fluoro-5-phenyl-2-vinyl-6,7-dihydro-5H-pyrrolo[1,2-b][1,2,4]triazole A mixture of (5S,7S)-2-bromo-7-fluoro-5-phenyl-6,7-dihydro-5H-pyrrolo[1,2-b][1,2,4]triazole (150 mg, 0.53 mmol), potassium vinyl trifluoroborate (142 mg, 1.06 mmol), 1,1'-bis(diphenylphosphino)ferrocene palladium dichloride (78 mg, 0.11 mmol) and cesium carbonate (520 mg, 1.60 mmol) in 1,4-dioxane (30 mL) and water (3 mL) was heated at 100° C. for 16 h under nitrogen atmosphere. After cooled, the mixture was diluted with water (30 mL) and extracted with ethyl acetate (3×15 mL). The combined organic layers were dried over anhydrous sodium sulfate and concentrated under reduced pressure. The residue was purified by column chromatography (silica gel, 100-200 mesh, 0 to 30% ethyl acetate in petroleum ether) to afford (5S,7S)-7-fluoro-5-phenyl-2-vinyl-6,7-dihydro-5H-pyrrolo[1,2-b][1,2,4]triazole (100 mg, 82%) as a white solid. LCMS $R_T$=0.606 min, m/z=230.2 [M+H]$^+$.

LCMS (5 to 95% acetonitrile in water+0.03% trifluoroacetic acid over 1.5 mins) retention time 0.606 min, ESI+ found [M+H]=230.2.

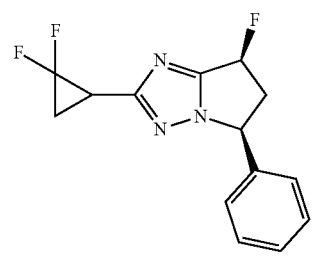 [SMILES: F[C@H]1C[C@@H](c2ccccc2)n2nc(C3CC3(F)F)nc21]

Step 2: (5S,7S)-2-(2,2-difluorocyclopropyl)-7-fluoro-5-phenyl-6,7-dihydro-5H-pyrrolo[1,2-b][1,2,4]triazole A mixture of (5S,7S)-7-fluoro-5-phenyl-2-vinyl-6,7-dihydro-5H-pyrrolo[1,2-b][1,2,4]triazole (50 mg, 0.22 mmol), [chloro(difluoro)methyl]-trimethylsilane (10 mg, 0.65 mmol) and tetrabutylammonium chloride (6 mg, 0.02 mmol) in toluene (1 mL) was heated at 110° C. for 4 h under microwave conditions and then concentrated under reduced pressure. The residue was purified by RP-HPLC (acetonitrile 40-70%/0.05% ammonium bicarbonate in water) to afford arbitrarily assigned (5S,7S)-2-(2,2-difluorocyclopropyl)-7-fluoro-5-phenyl-6,7-dihydro-5H-pyrrolo[1,2-b][1,2,4]triazole (28.3 mg, 46%) as a pale yellow solid. $^1$H NMR (400 MHz, CDCl$_3$) δ 7.42-7.38 (m, 3H), 7.23-7.21 (m, 2H), 6.06-5.89 (m, 1H), 5.42-5.38 (m, 1H), 3.62-3.55 (m, 1H), 2.93-2.85 (m, 2H), 2.18-2.10 (m, 1H), 1.88-1.84 (m, 1H). LCMS R$_T$=0.826 min, m/z=279.9 [M+H]$^+$.

LCMS (5 to 95% acetonitrile in water+0.03% trifluoacetic acid over 1.5 mins) retention time 0.826 min, ESI+ found [M+H]=279.9.

Example 29: Method 29

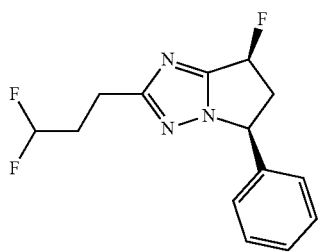 [SMILES: FC(F)CCc1nc2n(n1)[C@H](c1ccccc1)C[C@@H]2F]

(5S,7S)-2-(3,3-difluoropropyl)-7-fluoro-5-phenyl-6,7-dihydro-5H-pyrrolo[1,2-b][1,2,4]triazole

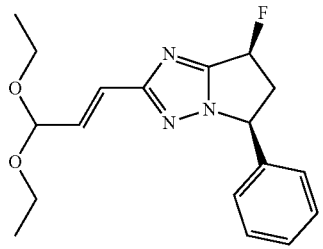 [SMILES: CCOC(/C=C/c1nc2n(n1)[C@H](c1ccccc1)C[C@@H]2F)OCC]

Step 1: (5S,7S)-2-[(E)-3,3-diethoxyprop-1-enyl]-7-fluoro-5-phenyl-6,7-dihydro-5H-pyrrolo[1,2-b][1,2,4]triazole A mixture of (5S,7S)-2-bromo-7-fluoro-5-phenyl-6,7-dihydro-5H-pyrrolo[1,2-b][1,2,4]triazole (100 mg, 0.35 mmol) and 2-[(E)-3,3-diethoxyprop-1-enyl]-4,4,5,5-tetramethyl-1,3,2-dioxaborolane (182 mg, 0.71 mmol), 1,1'-bis(diphenylphosphino)ferrocene palladium dichloride (52 mg, 0.07 mmol) and cesium carbonate (347 mg, 1.06 mmol) in 1,4-dioxane (2 mL) and water (0.2 mL) was heated at 90'C for 16 h under a nitrogen atmosphere. The solid was removed by filtration and the filtrate was concentrated under reduced pressure to afford crude (5S,7S)-2-[(E)-3,3-diethoxyprop-1-enyl]-7-fluoro-5-phenyl-6,7-dihydro-5H-pyrrolo[1,2-b][1,2,4]triazole (100 mg, 85%) as a yellow oil. The crude product was used in next step without further purification. LCMS R$_T$=0.694 min, m/z=332.2 [M+H]$^+$.

LCMS (5 to 95% acetonitrile in water+0.03% trifluoacetic acid over 1.5 mins) retention time 0.694 min, ESI+ found [M+H]=332.2.

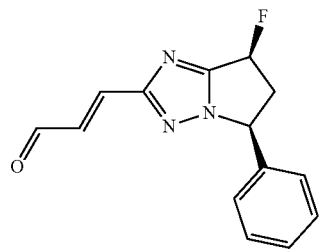 [SMILES: O=C/C=C/c1nc2n(n1)[C@H](c1ccccc1)C[C@@H]2F]

Step 2: (E)-3-[(5S,7S)-7-fluoro-5-phenyl-6,7-dihydro-5H-pyrrolo[1,2-b][1,2,4]triazol-2-yl]prop-2-enal A mixture of (5S,7S)-2-[(E)-3,3-diethoxyprop-1-enyl]-7-fluoro-5-phenyl-6,7-dihydro-5H-pyrrolo[1,2-b][1,2,4]triazole (100 mg, 0.30 mmol) and hydrochloric acid (12 M, 0.25 mL, 3.02 mmol) in acetonitrile (5 mL) was stirred at 25° C. for 1 h and then adjusted to pH=8 by addition of aqueous sodium bicarbonate. The resulting mixture was extracted with ethyl acetate (3×20 mL). The combined organic layers were concentrated under reduced pressure to afford (E)-3-[(5S,7S)-7-fluoro-5-phenyl-6,7-dihydro-5H-pyrrolo[1,2-b][1,2,4]triazol-2-yl]prop-2-enal (70 mg, 90%) as a brown solid. LCMS R$_T$=0.595 min, m/z=258.1 [M+H]$^+$.

LCMS (5 to 95% acetonitrile in water+0.03% trifluoacetic acid over 1.5 mins) retention time 0.595 min, ESI+ found [M+H]=258.1.

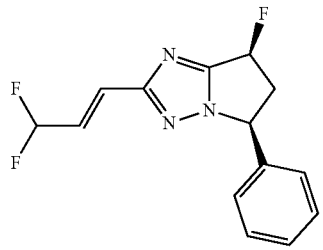 [SMILES: FC(F)/C=C/c1nc2n(n1)[C@H](c1ccccc1)C[C@@H]2F]

Step 3: (5S,7S)-2-[(E)-3,3-difluroprop-1-enyl]-7-fluoro-5-phenyl-6,7-dihydro-5H-pyrrolo[1,2-b][1,2,4]triazole To a solution of (E)-3-[(5S,7S)-7-fluoro-5-phenyl-6,7-dihydro-5H-pyrrolo[1,2-b][1,2,4]triazol-2-yl]prop-2-enal (60 mg, 0.23 mmol) in dichloromethane (3 mL) was slowly added diethylaminosulfur trifluoride (150 mg, 0.93 mmol) at 0° C. The reaction mixture was stirred at 0° C. for 2 h and then quenched by slow addition of saturated aqueous sodium bicarbonate (10 mL). The mixture was extracted with dichloromethane (3×20 mL). The combined organic layers were washed with brine (20 mL), dried over anhydrous sodium sulfate and concentrated under reduced pressure. The residue was purified by preparative TLC (30% ethyl acetate in petroleum ether, R$_f$=0.3) to afford (5S,7S)-2-[(E)-3,3-difluoroprop-1-enyl]-7-fluoro-5-phenyl-6,7-dihydro-5H-pyrrolo[1,2-b][1,2,4]triazole (50 mg, 77%) as a white solid. LCMS R$_T$=0.666 min, m/z=280.1 [M+H]$^+$.

LCMS (5 to 95% acetonitrile in water+0.03% trifluoacetic acid over 1.5 mins) retention time 0.666 min, ESI+ found [M+H]=280.1.

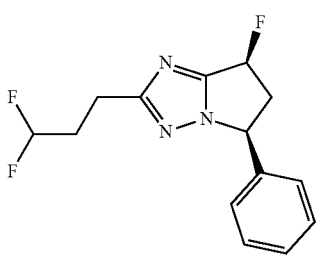 [SMILES: FC(F)CCc1nc2n(n1)[C@H](c1ccccc1)C[C@@H]2F]

Step 4: (5S,7S)-2-(3,3-difluoropropyl)-7-fluoro-5-phenyl-6,7-dihydro-5H-pyrrolo[1,2-b][1,2,4]triazole A mixture of (5S,7S)-2-[(E)-3,3-difluoroprop-1-enyl]-7-fluoro-5-phenyl-6,7-dihydro-5H-pyrrolo[1,2-b][1,2,4]triazole (50 mg, 0.18 mmol) and palladium (10% on carbon, 25 mg) in methanol (5 mL) was hydrogenated (15 psi) at 25° C. for 1 h and then filtered. The filtrate was concentrated under reduced pressure and the residue was purified by RP-HPLC (acetonitrile 35-65%/0.05% ammonia hydroxide in water) to afford arbitrarily assigned (5S,7S)-2-(3,3-difluoropropyl)-7-fluoro-5-phenyl-6,7-dihydro-5H-pyrrolo [1,2-b][1,2,4]triazole (20 mg, 38%) as a white solid. $^1$H NMR (400 MHz, CD$_3$OD) δ 7.43-7.32 (m, 3H), 7.23-7.22 (m, 2H), 6.11-5.83 (m, 2H), 5.50-5.48 (m, 1H), 3.74-3.64 (m, 1H), 2.92-2.88 (m, 2H), 2.71-2.69 (m, 1H), 2.28-2.23 (m, 2H). LCMS R$_T$=0.843 min, m/z=281.9 [M+H]$^+$.

LCMS (5 to 95% acetonitrile in water+0.03% trifluoroacetic acid over 1.5 mins) retention time 0.587 min, ESI+ found [M+H]=281.9.

Example 30: Method 30

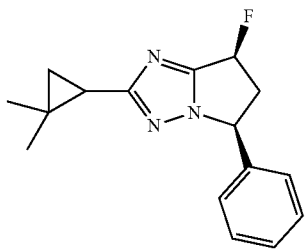 [SMILES: CC1(C)CC1c1nc2n(n1)[C@H](c1ccccc1)C[C@@H]2F]

(5S,7S)-2-(2,2-dimethylcyclopropyl)-7-fluoro-5-phenyl-6,7-dihydro-H-pyrrolo[1,2-b][1,2,4]triazole

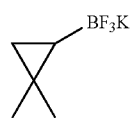

Step 1: potassium (2,2-dimethylcyclopropyl)-trifluoroborate

To a solution of 2-(2,2-dimethylcyclopropyl)-4,4,5,5-tetramethyl-1,3,2-dioxaborolane (200 mg, 1.02 mmol) in methanol (4 mL) was added a solution of potassium bifluoride (558 mg, 7.14 mmol) in water (0.8 mL). The mixture was stirred at 25° C. for 16 h and then concentrated under reduced pressure. The residue was extracted with acetonitrile (3×10 mL). The combined organic layers were concentrated and the residue was triturated with petroleum ether (10 mL). The resulting solid was collected by filtration to afford crude potassium (2,2-dimethylcyclopropyl)-trifluoroborate (60 mg, 33%) as a white solid. $^1$H NMR (400 MHz, DMSO-d$_6$) δ 0.95 (s, 3H), 0.93 (s, 3H), −0.10-−0.12 (m, 2H), −0.85-−0.90 (m, 1H).

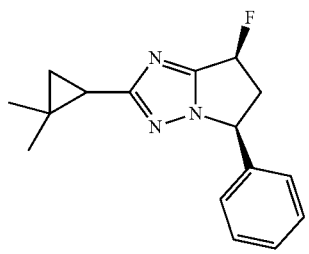 [SMILES: CC1(C)CC1c1nc2n(n1)[C@H](c1ccccc1)C[C@@H]2F]

Step 2: (5S,7S)-2-(2,2-dimethylcyclopropyl)-7-fluoro-1-phenyl-6,7-dihydro-5H-pyrrolo[1,2-b][1,2,4]triazole A mixture of (5S,7S)-2-bromo-7-fluoro-5-phenyl-6,7-dihydro-5H-pyrrolo[1,2-b][1,2,4]triazole (50 mg, 0.18 mmol), RuPhos-Pd-G2 (14 mg, 0.02 mmol), potassium (2,2-dimethylcyclopropyl)-trifluoroborate (47 mg, 0.27 mmol), cesium carbonate (173 mg, 0.53 mmol) in toluene (2 mL) and water (0.2 mL) was heated at 100° C. for 24 h under nitrogen atmosphere and concentrated under reduced pressure. The residue was diluted with water (15 mL) and extracted with ethyl acetate (3×15 mL). The combined organic layers were concentrated under reduced pressure. The residue was purified by RP-HPLC (acetonitrile 45-75%/0.05% ammonia hydroxide in water) to afford arbitrarily assigned (5S,7S)-2-(2,2-dimethylcyclopropyl)-7-fluoro-5-phenyl-6,7-dihydro-5H-pyrrolo[1,2-b][1,2,4]triazole (26.2 mg, 54%) as a white solid. $^1$H NMR (400 MHz, CDCl$_3$) δ 7.38-7.35 (m, 3H), 7.20-7.18 (m, 2H), 6.01-5.85 (m, 1H), 5.37-5.35 (m, 1H), 3.58-3.51 (m, 1H), 2.85-2.79 (m, 1H), 1.97-1.94 (m, 1H), 1.20 (s, 3H), 1.18-1.15 (m, 1H), 1.03 (d, J=8.4 Hz, 3H), 0.90-0.88 (m, 1H). LCMS R$_T$=0.889 min, m/z=272.0 [M+H]$^+$.

LCMS (5 to 95% acetonitrile in water+0.03% trifluoroacetic acid over 1.5 mins) retention time 0.889 min, ESI+ found [M+H]=272.0

Example 31: Method 31

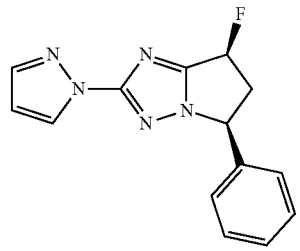 [SMILES: F[C@H]1C[C@@H](c2ccccc2)n2nc(-n3cccn3)nc21]

(5S,7S)-7-fluoro-5-phenyl-2-(1H-pyrazol-1-yl)-6,7-dihydro-5H-pyrrolo[1,2-b][1,2,4]triazole A mixture of (5S,7S)-2-bromo-7-fluoro-5-phenyl-6,7-dihydro-5H-pyrrolo[1,2-b][1,2,4]triazole (100 mg, 0.35 mmol), copper(I) iodide (13 mg, 0.07 mmol), (1S,2S)—N$^1$,N$^2$-dimethylcyclohexane-1,2-diamine (50 mg, 0.35 mmol), cesium carbonate (346 mg, 1.06 mmol) and pyrazole (241 mg, 3.54 mmol) in 1,4-dioxane (2 mL) was heated at 140° C. for 3 min a sealed tube under microwave conditions and then concentrated under reduced pressure. The residue was first purified by RP-HPLC (acetonitrile 31-51%/0.05% ammonia hydroxide in water), then SFC to afford arbitrarily assigned (5S,7S)-7-fluoro-5-phenyl-2-pyrazol-1-yl-6,7-dihydro-5H-pyrrolo[1,2-b][1,2,4]triazole (Retention time=4.814 min) (15 mg, 16%) as a white solid. $^1$H NMR (400 MHz, CD$_3$OD) δ 8.30 (d, J=2.4 Hz, 1H), 7.75 (s, 1H), 7.44-7.30 (m, 5H), 6.55-6.54 (m, 1H), 6.20-6.03 (m, 1H), 5.62-5.58 (m, 1H), 3.80-3.66 (m, 1H), 2.82-2.70 (m, 1H). LCMS R$_T$=0.809 min, m/z=269.9 [M+H]$^+$.

LCMS (5 to 95% acetonitrile in water+0.03% trifluoacetic acid over 1.5 mins) retention time 0.809 min, ESI+ found [M+H]=269.9.

SFC condition: Column: OD (250 mm*30 mm, 5 um), Mobile phase: A: CO$_2$ B:ethanol (0.1% NH$_3$H$_2$O) Gradient: from 5% to 40% of B in 5 min and hold 40% for 2.5 min, then 5% of B for 2.5 min. Flow rate: 60 mL/min Column temp. 35° C.

Example 33: Method 32

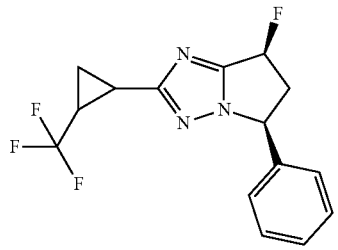 [SMILES: F[C@H]1C[C@@H](c2ccccc2)n2nc(C3CC3C(F)(F)F)nc21]

(5S,7S)-7-fluoro-5-phenyl-2-(2-(trifluoromethyl)cyclopropyl)-6,7-dihydro-5H-pyrrolo[1,2-b][1,2,4]triazole A mixture of (5S,7S)-2-bromo-7-fluoro-5-phenyl-6,7-dihydro-5H-pyrrolo[1,2-b][1,2,4]triazole (200 mg, 0.71 mmol), dibutoxy-[2-(trifluoromethyl)cyclopropyl]borane (226 mg, 0.85 mmol), (2-dicyclohexylphosphino-2',6'-diisopropoxy-1,1'-biphenyl) [2-(2'-amino-1,1'-biphenyl)]palladium(ii) methanesulfonate (59 mg, 0.07 mmol) and cesium carbonate (693 mg, 2.13 mmol) in 1,4-dioxane (3 mL) and water (0.5 mL) was heated at 100° C. for 1.5 h under microwave conditions. The reaction was diluted with water (5 mL) and extracted with ethyl acetate (3×15 mL). The combined organic layers were washed with brine (2×15 mL), dried over sodium sulfate and concentrated under reduced pressure. The residue was first purified by preparative TLC (35% ethyl acetate in petroleum ether, R$_f$=0.7), then RP-HPLC (acetonitrile 40-70%/0.05% ammonia hydroxide in water) to afford arbitrarily assigned (5S,7S)-7-fluoro-5-phenyl-2-[2-(trifluoromethyl)cyclopropyl]-6,7-dihydro-5H-pyrrolo[1,2-b][1,2,4]triazole (5.6 mg, 3%) as a white solid. $^1$H NMR (400 MHz, CD$_3$OD) δ 7.42-7.37 (m, 3H), 7.24-7.22 (m, 2H), 6.08-6.05 (m, 0.5H), 5.93-5.91 (m, 0.5H), 5.49-5.46 (m, 1H), 3.70-3.62 (m, 1H), 2.76-2.65 (m, 1H), 2.47-2.43 (m, 1H), 2.23-2.21 (m, 1H), 1.44-1.39 (m, 2H). LCMS R$_T$=0.804 min, m/z=312.1[M+H]$^+$.

LCMS (5 to 95% acetonitrile in water+0.03% trifluoacetic acid over 1.5 mins) retention time: 0.804 min, ESI+ found [M+H]=312.1.

Examples 34 and 35: Method 33

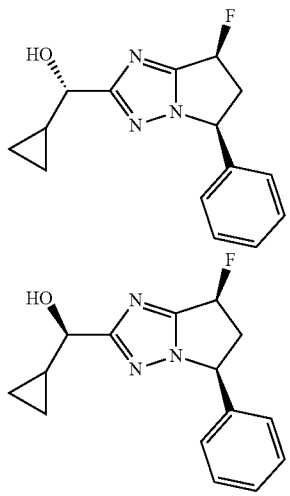

(S)-cyclopropyl[(5S,7S)-7-fluoro-5-phenyl-6,7-dihydro-5H-pyrrolo[1,2-b][1,2,4]triazol-2-yl]methanol and (R)-cyclopropyl-[(5S,7S)-7-fluoro-5-phenyl-6,7-dihydro-5H-pyrrolo[1,2-b][1,2,4]triazol-2-yl]methanol To a solution of cyclopropyl-[(5S,7S)-7-fluoro-5-phenyl-6,7-dihydro-5H-pyrrolo [1,2-b][1,2,4]triazol-2-yl]methanone (70 mg, 0.26 mmol) in methanol (4 mL) was added sodium borohydride (49 mg, 1.29 mmol) at 0° C. The mixture was stirred at 0° C. for 2 h and quenched by addition of saturated aqueous ammonium chloride (20 mL). The resulting mixture was extracted with ethyl acetate (3×15 mL). The combined organic layers were concentrated under reduce pressure and the residue was purified by preparative TLC (petroleum ether: ethyl acetate=1:1) to afford arbitrarily assigned cyclopropyl-[(5S,7S)-7-fluoro-5-phenyl-6,7-dihydro-5H-pyrrolo[1,2-b][1,2,4]triazol-2-yl]methanol (58 mg, 82%) as a white solid. LCMS R$_T$=0.588 min, m/z=274.2 [M+H]$^+$.

LCMS (5 to 95% acetonitrile in water+0.03% trifluoacetic acid over 1.5 mins) retention time 0.588 min, ESI+ found [M+H]=274.2.

The racemic material (58 mg, 0.21 mmol) was further separated by chiral SFC to afford arbitrarily assigned:

(S)-cyclopropyl-[(5S,7S)-7-fluoro-5-phenyl-6,7-dihydro-5H-pyrrolo[1,2-b][1,2,4]triazol-2-yl]methanol (Peak 1, retention time=3.277 min) (15.1 mg, 26%) as a white solid. $^1$H NMR (400 MHz, CDCl$_3$) δ 7.42-7.36 (m, 3H), 7.24-7.22 (m, 2H), 6.06-5.91 (m, 1H), 5.44-5.39 (m, 1H), 4.27-4.24 (m, 1H), 3.63-3.55 (m, 1H), 2.94-2.83 (m, 1H), 2.54-2.52 (m, 1H), 1.43-1.38 (m, 1H), 0.64-0.58 (m, 2H), 0.50-0.48 (m, 2H). LCMS RT=1.345 min, m/z=274.1 [M+H]$^+$.

LCMS (10 to 80% acetonitrile in water+0.03% trifluoacetic acid over 3 mins) retention time 1.345 min, ESI+ found [M+H]=274.1.

(R)-cyclopropyl-[(5S,7S)-7-fluoro-5-phenyl-6,7-dihydro-5H-pyrrolo[1,2-b][1,2,4]triazol-2-yl]methanol (Peak 2, retention time=4.193 min) (31.5 mg, 54%) as a white solid. $^1$H NMR (400 MHz, CDCl$_3$) δ 7.42-7.37 (m, 3H), 7.24-7.22 (m, 2H), 6.07-5.91 (m, 1H), 5.43-5.40 (m, 1H), 4.24-4.22 (m, 1H), 3.65-3.55 (m, 1H), 2.93-2.83 (m, 1H), 2.60-2.59 (m, 1H), 1.41-1.36 (m, 1H), 0.64-0.47 (m, 4H). LCMS R$_T$=1.325 min, m/z=274.1 [M+H]$^+$.

LCMS (10 to 80% acetonitrile in water+0.03% trifluoacetic acid over 3 mins) retention time 1.325 min, ESI+ found [M+H]=274.1.

SFC condition: Column: Lux Cellulose-2 150×4.6 mm I.D., 3 um, Mobile phase: A: CO$_2$ B: Ethanol (0.05% DEA) Gradient: from 5% to 40% of B in 5 min and hold 40% for 2.5 min, then 5% of B for 2.5 min Flow rate: 2.5 mL/min Column temp. 40° C.

Example 36: Method 34

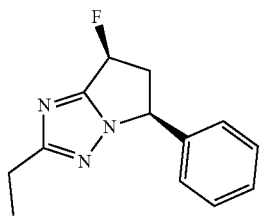 [SMILES: CCc1nc2n(n1)[C@H](c1ccccc1)C[C@@H]2F]

(5S,7S)-2-ethyl-7-fluoro-5-phenyl-6,7-dihydro-5H-pyrrolo[1,2-b][1,2,4]triazole

To a 2-dram vial equipped with a pressure relief cap was charged with (5S,7S)-2-bromo-7-fluoro-5-phenyl-6,7-dihydro-5H-pyrrolo[1,2-b][1,2,4]triazole (50 mg, 0.18 mmol), potassium ethyltrifluoroborate (5 equiv., 0.89 mmol), palladium(II) acetate (0.2 equiv., 0.04 mmol), butyldi-1-adamantylphosphine (0.3 equiv., 0.05 mmol), and cesium carbonate (4 equiv., 0.71 mmol) and the vial was purged with nitrogen for 2 minutes. Toluene (5 mL) and water (0.5 mL) were added and the reaction was stirred at 110'C for 72 h. The reaction mixture was filtered through a plug of CELITE® and concentrated in vacuo. The crude mixture was diluted with ethyl acetate (15 mL) and washed with water (2×15 mL), brine (15 mL) and dried using a Sep-Pak (sodium sulfate). The organic layer was evaporated to dryness and purified via prep-HPLC 20-60% ACN (0.1% NH$_4$OH in water for aqueous modifier) to afford (5S,7S)-2-ethyl-7-fluoro-5-phenyl-6,7-dihydro-5H-pyrrolo[1,2-b][1,2,4]triazole (9.3 mg, 23%).

1H NMR (400 MHz, DMSO-d6) δ 7.52-7.23 (m, 3H), 7.31-7.05 (m, 2H), 6.09 (ddd, J=57.2, 7.1, 1.7 Hz, 1H), 5.65-5.41 (m, 1H), 3.82-3.48 (m, 1H), 2.70-2.53 (m, 3H), 1.20 (t, J=7.6 Hz, 3H). LCMS RT=4.07 min, m/z=232.1 [M+H]$^+$.

LCMS (2 to 98% acetonitrile in water+0.1% formic acid over 10 mins) retention time 4.07 min, ESI+ found=232.1 [M+H]$^+$.

Example 37: Method 34

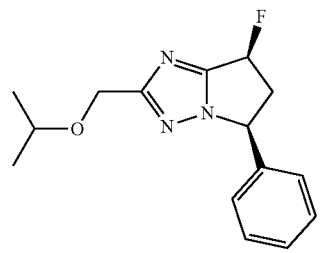 [SMILES: CC(C)OCc1nc2n(n1)[C@H](c1ccccc1)C[C@@H]2F]

(5S,7S)-7-fluoro-2-(isopropoxymethyl)-5-phenyl-6,7-dihydro-5H-pyrrolo[1,2-b][1,2,4]triazole (4.5 mg, 9% yield)

1H NMR (400 MHz, DMSO-d6) δ 7.44-7.32 (m, 3H), 7.24-7.17 (m, 2H), 6.14 (ddd, J=57.0, 7.1, 1.7 Hz, 1H), 5.63-5.54 (m, 1H), 4.42 (s, 2H), 3.76-3.58 (m, 2H), 2.70-2.56 (m, 1H), 1.09 (d, J=6.1 Hz, 6H). LC-MS R$_T$=4.43 min, m/z=276.1 (M+H)$^+$.

LCMS (2 to 98% acetonitrile in water+0.1% formic acid over 10 mins) retention time 4.43 min, ESI+ found=276.1 [M+H]$^+$.

Example 38: Method 34

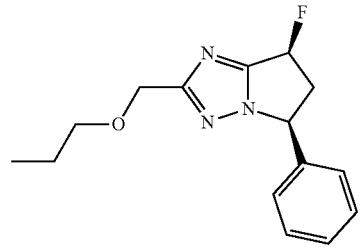 [SMILES: CCCOCc1nc2n(n1)[C@H](c1ccccc1)C[C@@H]2F]

(5S,7S)-2-(2-ethoxyethyl)-7-fluoro-5-phenyl-6,7-dihydro-5H-pyrrolo[1,2-b][1,2,4]triazole (2.1 mg, 4%)
LCMS (2 to 98% acetonitrile in water+0.1% formic acid over 10 mins) retention time 4.24 min, ESI+ found=276.1 [M+H]$^+$.

Example 39: Method 35

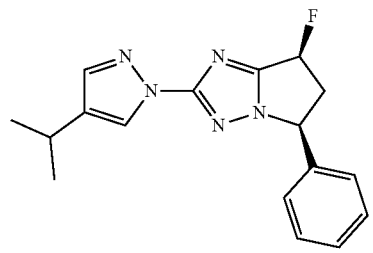 [SMILES: CC(C)c1cnn(-c2nc3n(n2)[C@H](c2ccccc2)C[C@@H]3F)c1]

(5S,7S)-7-fluoro-2-(4-isopropylpyrazol-1-yl)-5-phenyl-6,7-dihydro-5H-pyrrolo[1,2-b][1,2,4]triazole A microwave vial equipped with a stir bar was charged with (5S,7S)-2-bromo-7-fluoro-5-phenyl-6,7-dihydro-5H-pyrrolo[1,2-b][1,2,4]triazole (50 mg, 0.18 mmol), 4-isopropyl-1H-pyrazole hydrochloride (10 equiv., 1.77 mmol), cesium carbonate (5 equiv., 0.89 mmol), cuprous iodide (1.2 equiv., 0.21 mmol), trans-N,N'-dimethylcyclohexane-1,2-diamine (8 equiv., 1.42 mmol) and 1,4-dioxane (1.7 mL) degassed with nitrogen was added to the reaction. The microwave vial was sealed and heated to 140° C. while stirring for 20 min. The mixture was then diluted with ethyl acetate (5 mL), washed with water (2×5 mL), the organic layer was dried using a Sep-Pak (sodium, sulfate) and was then evaporated to dryness. The crude mixture was purified via prep-HPLC 30-70% ACN (0.1% formic acid in water for aqueous modifier) to afford (5S,7S)-7-fluoro-2-(4-isopropylpyrazol-1-yl)-5-phenyl-6,7-dihydro-5H-pyrrolo[1,2-b][1,2,4]triazole (3.8 mg, 6%).

$^1$H NMR (400 MHz, DMSO-d6) δ 8.11 (s, 1H), 7.69 (s, 1H), 7.47-7.35 (m, 3H), 7.32-7.23 (m, 2H), 6.23 (ddd, J=56.8, 7.2, 1.8 Hz, 1H), 5.66 (td, J=8.0, 2.9 Hz, 1H), 3.87-3.58 (m, 1H), 2.85 (hept, J=13.9, 6.9 Hz, 1H), 2.72-2.56 (m, 1H), 1.20 (d, J=6.8 Hz, 6H). LCMS $R_T$=5.44 min, m/z=312.1 [M+H]$^+$.

LCMS (2 to 98% acetonitrile in water+0.1% formic acid over 10 mins) retention time 5.44 min, ESI+ found=312.1 [M+H]$^+$.

Example 40: Method 36

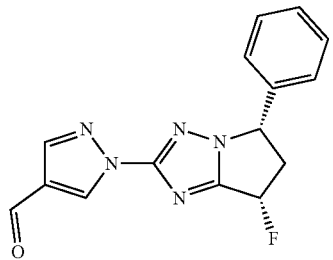 [SMILES: O=Cc1cnn(-c2nc3n(n2)[C@H](c2ccccc2)C[C@@H]3F)c1]

1-[(5S,7S)-7-fluoro-5-phenyl-6,7-dihydro-5H-pyrrolo[1,2-b][1,2,4]triazol-2-yl]pyrazole-4-carbaldehyde A microwave vial equipped with a stir bar was charged with (5S,7S)-2-bromo-7-fluoro-5-phenyl-6,7-dihydro-5H-pyrrolo[1,2-b][1,2,4]triazole (50 mg, 0.18 mmol), 1H-pyrazole-4-carbaldehyde (10 equiv., 1.77 mmol), cesium carbonate (3 equiv., 0.53 mmol), cuprous iodide (1.2 equiv., 0.21 mmol), trans-n,n'-dimethylcyclohexane-1,2-diamine (8 equiv., 1.42 mmol) and 1,4-dioxane (1.7 mL) degassed with nitrogen was added to the reaction. The microwave vial was sealed and heated to 140° C. while stirring for 20 min. The mixture was diluted with ethyl acetate (5 mL), washed with water (2×5 mL). The organic layer was dried using a Sep-Pak (sodium sulfate) and evaporated to dryness. The crude mixture was purified via prep-HPLC 5-50% ACN (0.1% formic acid in water for aqueous modifier) to afford 1-[(5S,7S)-7-fluoro-5-phenyl-6,7-dihydro-5H-pyrrolo[1,2-b][1,2,4]triazol-2-yl]pyrazole-4-carbaldehyde (15 mg, 28%).

$^1$H NMR (400 MHz, DMSO-d6) δ 9.93 (s, 1H), 9.14 (d, J=0.6 Hz, 1H), 8.27 (d, J=0.6 Hz, 1H), 7.56-7.36 (m, 3H), 7.35-7.20 (m, 2H), 6.28 (ddd, J=56.6, 7.2, 1.9 Hz, 1H), 5.72 (td, J=8.0, 3.1 Hz, 1H), 3.86-3.63 (m, 1H), 2.84-2.52 (m, 1H). LC-MS $R_T$=4.20 min, m/z=298.1 (M+H)$^+$.

LCMS (2 to 98% acetonitrile in water+0.1% formic acid over 10 mins) retention time 4.20 min, ESI+ found=298.1 [M+H]$^+$.

Example 41: Method 36

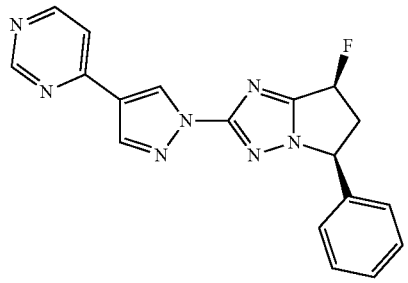 [SMILES: F[C@H]1C[C@@H](c2ccccc2)n2nc(-n3cc(-c4ccncn4)cn3)nc21]

(5S,7S)-7-fluoro-5-phenyl-2-(4-pyrimidin-4-ylpyrazol-1-yl)-6,7-dihydro-5H-pyrrolo[1,2-b][1,2,4]triazole The title compound was prepared analogously by replacing 1H-pyrazole-4-carbaldehyde with 2-4-(pyrimidin-4-yl)pyrazole. (CASRN 28648-87-5).

$^1$H NMR (400 MHz, DMSO-d$_6$) δ 9.19 (s, 1H), 9.14 (d, J=1.5 Hz, 1H), 8.78 (d, J=5.3 Hz, 1H), 8.47 (s, 1H), 7.99 (dd, J=5.3, 1.5 Hz, 1H), 7.49-7.35 (m, 3H), 7.35-7.28 (m, 2H), 6.28 (ddd, J=56.7, 7.2, 2.0 Hz, 1H), 5.72 (td, J=8.0, 3.1 Hz, 1H), 3.83-3.65 (m, 1H), 2.77-2.60 (m, 1H). LC-MS RT=4.52 min, m/z=348.2 (M+H)$^+$.

LCMS (2 to 98% acetonitrile in water+0.1% formic acid over 10 mins) retention time 4.52 min, ESI+ found=348.2 [M+H]$^+$.

Example 42: Method 37

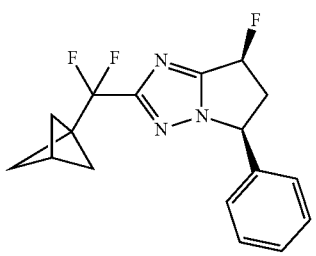 [SMILES: F[C@H]1C[C@@H](c2ccccc2)n2nc(C(F)(F)C34CC(C3)C4)nc21]

(5S,7S)-2-[1-bicyclo[1.1.1]pentanyl(difluoro)methyl]-7-fluoro-5-phenyl-6,7-dihydro-5H-pyrrolo[1,2-b][1,2,4]triazole Diethylaminosulfur trifluoride (0.150 mL, 1.08 mmol) was added to a solution of 3-bicyclo[1.1.1]pentanyl-[(5S,7S)-7-fluoro-5-phenyl-6,7-dihydro-5H-pyrrolo[1,2-b][1,2,4]triazol-2-yl]methanone (40 mg, 0.135 mmol) in dichloromethane (2.7 mL) at rt. After 36 h, additional diethylaminosulfur trifluoride (0.150 mL, 1.08 mmol) was added. After 12 h the reaction was poured into a separatory funnel containing saturated aqueous sodium bicarbonate. The aqueous layer was extracted with dichloromethane (3×20 mL). The combined organic layers were dried with sodium sulfate, concentrated and the crude residue was purified by reverse phase HPLC to give (5S,7S)-2-[3-bicyclo[1.1.1]pentanyl(difluoro)methyl]-7-fluoro-5-phenyl-6,7-dihydro-5H-pyrrolo[1,2-b][1,2,4]triazole (14.6 mg, 0.046 mmol, 34% Yield). $^1$H NMR (400 MHz, DMSO-d$_6$) δ 7.48-7.32 (m, 3H), 7.25-7.15 (m, 2H), 6.20 (ddd, J=56.5, 7.1, 1.8 Hz, 1H), 5.69 (ddd, J=9.1, 6.9, 2.9 Hz, 1H), 3.82-3.63 (m, 1H), 2.76-2.59 (m, 1H), 2.57 (s, 1H), 1.91 (s, 6H). LRMS $R_T$=5.80 min, m/z=320.1 [M+H]$^+$.

Prep HPLC Information: Column: Gemini-NX C18 5 μm, (50×30 mm), Mobile Phase: 0.1% Ammonium Hydroxide in Water (A)/Acetonitrile (B), Elution Program, Gradient: 30% to 70% B, Flow Rate: 60 mL/min, Column Temperature: 25° C., Wavelength: 220 nm Example 43: Method 39

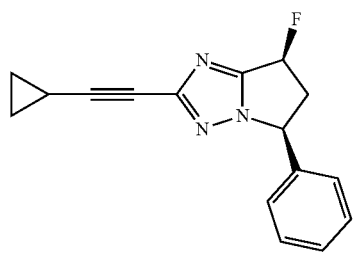 [SMILES: F[C@H]1C[C@@H](c2ccccc2)n2nc(C#CC3CC3)nc21]

(5S,7S)-2-(2-cyclopropylethynyl)-7-fluoro-5-phenyl-6,7-dihydro-5H-pyrrolo[1,2-b][1,2,4]triazole Copper(I) iodide (1.7 mg, 0.0088 mmol) was added to a degassed solution of (5S,7S)-2-bromo-7-fluoro-5-phenyl-6,7-dihydro-5H-pyrrolo[1,2-b][1,2,4]triazole (50 mg, 0.177 mmol), [1,1'-bis(diphenylphosphino)ferrocene]dichloropalladium(II) (13.2 mg, 0.0177 mmol) and cyclopropylacetylene (0.150 mL, 1.77 mmol) in triethylamine (0.90 mL) and THF (0.90 mL). The reaction was sealed with a yellow cap and was heated at 60'C for 24 h. After cooling to rt, the reaction was filtered through a plug of celite using isopropyl acetate. The filtrate was concentrated and the crude residue was purified by reverse phase HPLC to give (5S,7S)-2-(2-cyclopropylethynyl)-7-fluoro-5-phenyl-6,7-dihydro-5H-pyrrolo[1,2-b][1,2,4]triazole (4.4 mg, 0.016 mmol, 9.2% Yield). $^1$H NMR (400 MHz, DMSO-d$_6$) δ 7.46-7.31 (m, 3H), 7.25-7.14 (m, 2H), 6.24-6.01 (m, 1H), 5.59 (ddd, J=8.3, 6.9, 3.0 Hz, 1H), 3.77-3.57 (m, 1H), 2.72-2.54 (m, 1H), 1.57 (tt, J=8.2, 5.0 Hz, 1H), 0.95-0.87 (m, 2H), 0.80-0.72 (m, 2H). LRMS $R_T$=5.00 min, m/z=268.1 [M+H]$^+$.

Prep HPLC Information: Column: Gemini-NX C18 5 μm, (50×30 mm), Mobile Phase: 0.1% Ammonium Hydroxide in Water (A)/Acetonitrile (B), Elution Program, Gradient: 20% to 60% B, Flow Rate: 60 mL/min, Column Temperature: 25° C., Wavelength: 254 nm Example 44: Method 40

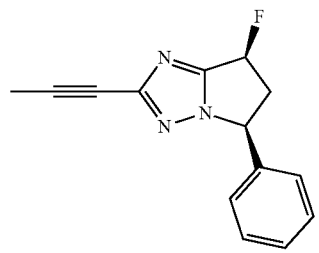 [SMILES: CC#Cc1nc2n(n1)[C@H](c1ccccc1)C[C@@H]2F]

(5S,7S)-7-fluoro-5-phenyl-2-prop-1-ynyl-6,7-dihydro-5H-pyrrolo[1,2-b][1,2,4]triazole Potassium propynyltrifluoroborate (40 mg, 0.27 mmol), (5S,7S)-2-bromo-7-fluoro-5-phenyl-6,7-dihydro-5H-pyrrolo[1,2-b][1,2,4]triazole (50 mg, 0.177 mmol), cesium carbonate (0.173 g, 0.53 mmol), and [1,1'-bis(diphenylphosphino)ferrocene]dichloropalladium(I) (13.2 mg, 0.0177 mmol) were dissolved in THF (1.5 mL) and water (0.15 mL). The reaction was degassed with nitrogen for 5 minutes. Then, the reaction was heated at 80'C for 1 h. After cooling to rt, the reaction was filtered through a plug of celite using isopropyl acetate. The filtrate was evaporated and the crude residue was purified by reverse phase HPLC to give (5S,7S)-7-fluoro-5-phenyl-2-prop-1-ynyl-6,7-dihydro-5H-pyrrolo[1,2-b][1,2,4]triazole (30.0 mg, 0.124 mmol, 70% Yield). $^1$H NMR (400 MHz, DMSO-d$_6$) δ 7.47-7.30 (m, 3H), 7.23-7.12 (m, 2H), 6.24-6.03 (m, 1H), 5.65-5.54 (m, 1H), 3.78-3.56 (m, 1H), 2.63 (ddt, J=27.0, 15.2, 2.2 Hz, 1H), 2.05 (s, 3H). LRMS $R_T$=4.50 min, m/z=242.1 [M+H]$^+$.

Prep HPLC Information: Column: Gemini-NX C18 5 μm, (50×30 mm), Mobile Phase: 0.1% Formic Acid in Water (A)/Acetonitrile (B), Elution Program Gradient: 20% to 60% B, Flow Rate: 60 mL/min, Column Temperature: 25° C., Wavelength: 230 nm Example 45 and 46: Method 41

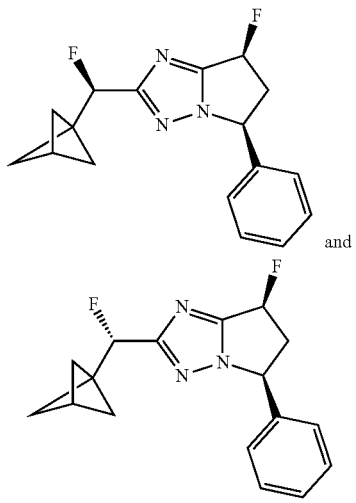

(5S,7S)-2-((R)-bicyclo[1.1.1]pentan-1-ylfluoromethyl)-7-fluoro-5-phenyl-6,7-dihydro-5H-pyrrolo[1,2-b][1,2,4]triazole and (5S,7S)-2-((S)-bicyclo[1.1.1]pentan-1-ylfluoromethyl)-7-fluoro-5-phenyl-6,7-dihydro-5H-pyrrolo[1,2-b][1,2,4]triazole Sodium borohydride (0.133 g, 3.36 mmol) was added to a solution of 3-bicyclo[1.1.1]pentanyl-[(5S,7S)-7-fluoro-5-phenyl-6,7-dihydro-5H-pyrrolo[1,2-b][1,2,4]triazol-2-yl]methanone (0.100 g, 0.336 mmol) in ethanol (3.4 mL) at rt. After 20 minutes, the reaction was diluted with dichloromethane and water. Saturated aqueous ammonium chloride was added and the aqueous layer was extracted with dichloromethane (3×30 mL). The combined organic layers were dried with sodium sulfate, concentrated and the crude residue was submitted to the next step without further purification.

Diethylaminosulfur trifluoride (0.24 mL, 1.68 mmol) was added to a solution of the crude residue in dichloromethane (3.4 mL) at rt. After 20 minutes the reaction was quenched with saturated aqueous sodium bicarbonate. The aqueous layer was extracted with dichloromethane (3×30 mL). The combined organic layers were dried with sodium sulfate, concentrated and the crude residue was purified by SFC to give arbitrarily assigned (5S,7S)-2-((R)-bicyclo[1.1.1]pentan-1-ylfluoromethyl)-7-fluoro-5-phenyl-6,7-dihydro-5H-pyrrolo[1,2-b][1,2,4]triazole (1.49 mg, 0.005 mmol, 1.4% Yield) and (5S,7S)-2-((S)-bicyclo[1.1.1]pentan-1-ylfluoromethyl)-7-fluoro-5-phenyl-6,7-dihydro-5H-pyrrolo[1,2-b][1,2,4]triazole (1.96 mg, 0.0065 mmol, 1.9% Yield) over 2 steps. LRMS $R_T$=4.90 min, m/z=302.1 [M+H]$^+$ and LRMS $R_T$=4.82 min, m/z=302.1 [M+H]$^+$ respectively.

Prep SFC Information: Column: Chiralcel OX 5 µm, (250×21.2 mm), Mobile Phase: Carbon Dioxide (A)/0.1% Ammonium Hydroxide in Isopropanol (B), Elution Program Isocratic: 12% B, Flow Rate: 70 mL/min, Column Temperature: 25° C., Wavelength: 211 nm Prep SFC Information: Column: Chiralcel OX 5 µm, (250×21.2 mm), Mobile Phase: Carbon Dioxide (A)/0.1% Ammonium Hydroxide in Isopropanol (B), Elution Program Isocratic: 12% B, Flow Rate: 70 mL/min, Column Temperature: 25° C., Wavelength: 211 nm.

Example 47: Method 42

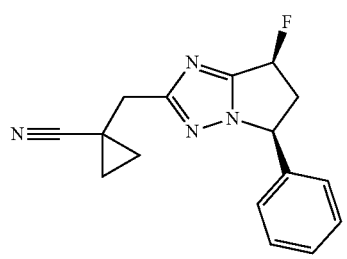 [SMILES: N#CC1(Cc2nc3n(n2)[C@H](c2ccccc2)C[C@@H]3F)CC1]

1-[[(5S,7S)-7-fluoro-5-phenyl-6,7-dihydro-5H-pyrrolo[1,2-b][1,2,4]triazol-2-yl]methyl]cyclopropanecarbonitrile Step 1: rac-(5S,7S)-2-(bromomethyl)-7-fluoro-5-phenyl-6,7-dihydro-5H-pyrrolo[1,2-b][1,2,4]triazole

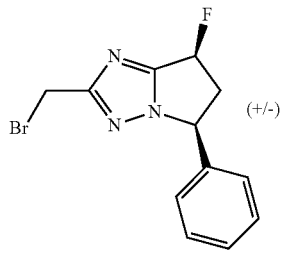 [SMILES: F[C@H]1C[C@@H](c2ccccc2)n2nc(CBr)nc21]

To a solution of (7-fluoro-5-phenyl-6,7-dihydro-5H-pyrrolo[1,2-b][1,2,4]triazol-2-yl)methanol (350 mg, 1.5 mmol, 1.0 equiv) in dichloromethane (10 mL) was added polymer-bound triphenylphosphine (2000 mg, 6.0 mmol, 4.0 equiv, ~3 mmol/g) followed by carbon tetrabromide (746 mg, 2.25 mmol, 1.5 equiv). The mixture was shaken 2 h at 230 rpm. After this time, the mixture was filtered through Celite and concentrated to afford rac-(5S,7S)-2-(bromomethyl)-7-fluoro-5-phenyl-6,7-dihydro-5H-pyrrolo[1,2-b][1,2,4]triazole (370 mg, 83% yield) which was used without further purification.

LCMS (5 to 95% acetonitrile in water+0.1% formic acid over 2 mins) retention time 1.15 min, ESI+ found [M+H]=296.

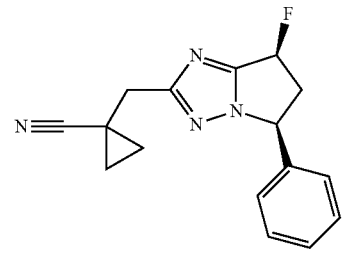 [SMILES: N#CC1(Cc2nc3n(n2)[C@H](c2ccccc2)C[C@@H]3F)CC1]

Step 2: 1-[[(5S,7S)-7-fluoro-5-phenyl-6,7-dihydro-5H-pyrrolo[1,2-b][1,2,4]triazol-2-yl]methyl]cyclopropanecarbonitrile A solution of lithium bis(trimethylsilyl)amide (1 M in tetrahydrofuran, 2.5 mL, 2.0 equiv) was diluted with tetrahydrofuran (5 mL) and cooled to 0° C. To it was slowly added cyclopropanecarbonitrile (0.184 mL, 1678 mg, 2.5 mmol, 2.0 equiv). The resulting mixture was stirred 10 mins at 0° C., then to it was added a solution of 2-(bromomethyl)-7-fluoro-5-phenyl-6,7-dihydro-5H-pyrrolo[1,2-b][1,2,4]triazole (370 mg, 1.25 mmol, 1.0 equiv) in tetrahydrofuran (5 mL). The resulting mixture was stirred 1 h at 0° C. After this time, the reaction was quenched with 5% aqueous citric acid (75 mL), then extracted with isopropyl acetate (3×50 mL). The combined organics were washed with water and brine, dried over sodium sulfate and concentrated. The residue was purified by column chromatography (silica gel, 100-200 mesh, 0 to 100% isopropyl acetate in heptane) to afford rac-(5S,7S)-1-[(7-fluoro-5-phenyl-6,7-dihydro-5H-pyrrolo [1,2-b][1,2,4]triazol-2-yl)methyl]cyclopropanecarbonitrile (40 mg, 11% yield) as a white solid.

This racemic material was further separated by chiral SFC to give arbitrarily assigned:

1-[[(5R,7R)-7-fluoro-5-phenyl-6,7-dihydro-5H-pyrrolo[1,2-b][1,2,4]triazol-2-yl]methyl]cyclopropanecarbonitrile (Peak 1, SFC analytical retention time=0.58 min, Chiralpak AD, isocratic 10% MeOH+0.1% NH₄OH, 2.5 min method) (5.5 mg, 2%) as a white solid. 1H NMR (400 MHz, DMSO-d6) δ 7.46-7.29 (m, 3H), 7.24-7.13 (m, 2H), 6.16 (ddd, J=57.0, 7.1, 1.7 Hz, 1H), 5.62 (ddd, J=8.8, 7.2, 2.7 Hz, 1H), 3.79-3.58 (m, 1H), 2.92 (s, 2H), 2.70-2.54 (m, 1H), 1.28-1.23 (m, 2H), 1.11-1.03 (m, 2H) LC-MS $R_T$=4.27 min, m/z=283.1 (M+H)⁺.

LCMS (5 to 95% acetonitrile in water+0.1% formic acid over 10 mins) retention time 4.27 min, ESI+ found [M+H]=283.1.

1-[[(5S,7S)-7-fluoro-5-phenyl-6,7-dihydro-5H-pyrrolo[1,2-b][1,2,4]triazol-2-yl]methyl]cyclopropanecarbonitrile (Peak 2, SFC analytical retention time=0.68 min, Chiralpak AD, isocratic 10% MeOH+0.1% NH₄OH, 2.5 min method) (6.5 mg, 2%) as a white solid. ¹H NMR (400 MHz, DMSO-d6) δ 7.44-7.30 (m, 3H), 7.24-7.16 (m, 2H), 6.16 (ddd, J=57.0, 7.1, 1.6 Hz, 1H), 5.62 (ddd, J=8.6, 8.0, 2.7 Hz, 1H), 3.79-3.57 (m, 1H), 2.92 (s, 2H), 2.70-2.54 (m, 1H), 1.30-1.20 (m, 2H), 1.13-1.02 (m, 2H). LC-MS $R_T$=4.27 min, m/z=283.1 (M+H)⁺.

LCMS (5 to 95% acetonitrile in water+0.1% formic acid over 10 mins) retention time 4.27 min, ESI+ found [M+H]=283.1.

SFC condition (prep): Column: Chiralpak AD 250×21.2 mm I.D., Sum Mobile phase: A: CO2 B:methanol, Isocratic 15% methanol for 25 mins, Flow rate: 70 mL/min, column temp 40° C.

Example 48: Method 43

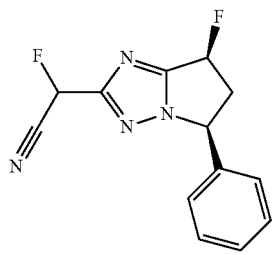 [SMILES: N#CC(F)c1nc2n(n1)[C@H](c1ccccc1)C[C@@H]2F]

2-fluoro-2-[(5S,7S)-7-fluoro-5-phenyl-6,7-dihydro-5H-pyrrolo[1,2-b][1,2,4]triazol-2-yl]acetonitrile To a solution of 2-[(5S,7S)-7-fluoro-5-phenyl-6,7-dihydro-5H-pyrrolo[1,2-b][1,2,4]triazol-2-yl]acetonitrile (250 mg, 1.0 mmol, 1.0 equiv) in tetrahydrofuran (5 mL) cooled to −78° C. was added lithium bis(trimethylsilyl)amide (1 M in tetrahydrofuran, 2.58 mL, 2.5 equiv). The resulting mixture was stirred 30 mins at −78° C., then to it was added N-fluorobenzenesulfonimide (814 mg, 2.58 mmol, 2.5 equiv). The cooling bath was removed, and the mixture was allowed to slowly warm to RT over 1 h. After this time the reaction was quenched with 5% aqueous citric acid and extracted with isopropyl acetate (3×50 mL). The combined organics were washed with water and brine, dried over sodium sulfate and concentrated. The residue was purified by column chromatography (silica gel, 100-200 mesh, 0 to 50% isopropyl acetate in heptane) to afford 2-fluoro-2-[(5S, 7S)-7-fluoro-5-phenyl-6,7-dihydro-5H-pyrrolo[1,2-b][1,2,4]triazol-2-yl]acetonitrile (16 mg, 6% yield) as a white solid. 1H NMR (400 MHz, Methanol-d4) δ 7.47-7.32 (m, 3H), 7.31-7.19 (m, 2H), 6.58 (d, J=45.7 Hz, 1H), 6.10 (ddd, J=56.2, 7.3, 2.0 Hz, 1H), 5.68-5.55 (m, 1H), 3.83-3.64 (m, 1H), 2.80 (dddd, J=26.6, 15.3, 3.3, 2.0 Hz, 1H). LC-MS $R_T$=1.17 min, m/z=261 (M+H)⁺.

LCMS (5 to 95% acetonitrile in water+0.1% formic acid over 2 mins) retention time 1.17 min, ESI+ found [M+H]=261.

Example 49: Method 44

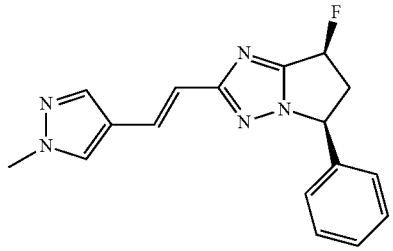 [SMILES: Cn1cc(/C=C/c2nc3n(n2)[C@H](c2ccccc2)C[C@@H]3F)cn1]

(5S,7S)-7-fluoro-2-[(E)-2-(1-methylpyrazol-4-yl) vinyl]-5-phenyl-6,7-dihydro-5H-pyrrolo[1,2-b][1,2,4]triazole A mixture of (5S,7S)-2-bromo-7-fluoro-5-phenyl-6,7-dihydro-5H-pyrrolo[1,2-b][1,2,4]triazole (100 mg, 0.35 mmol), 1-methyl-4-vinyl-1H-pyrazole (134 mg, 1.24 mmol), 2,6-di-tert-butyl-4-methylphenol (8 mg, 0.04 mmol), 1,1'-bis(diphenylphosphino)ferrocene-palladium(ii) dichloride dichloromethane complex (59 mg, 0.07 mmol) and triethylamine (0.59 mL, 4.25 mmol) in N,N-dimethylacetamide (2 mL) was heated at 110° C. for 18 h. The reaction mixture was diluted with 100 ml EtOAc, washed with water, filtered over celite, and the organic layer was washed with brine. The crude product was purified by column chromatography, flushed with 0-10% MeOH in DCM and further purified by prep-HPLC (Gemini-NX C18 50×30 mm, Sum, 20-60% of 0.1% Formic Acid in Water Acetonitrile) to afford final product (6 mg, 5%) as a white solid. ¹H NMR (400 MHz, DMSO-d₆) δ 7.96 (s, 1H), 7.76 (s, 1H), 7.46-7.29 (m, 4H), 7.27-7.19 (m, 2H), 6.77 (d, J=16.3 Hz, 1H), 6.14 (ddd, J=57.1, 7.1, 1.8 Hz, 1H), 5.58 (ddd, J=8.3, 7.0, 2.8 Hz, 1H), 3.82 (s, 3H), 3.77-3.59 (m, 1H), 2.71-2.50 (m, 1H). LC-MS $R_T$=4.24 min, m/z=310.1 (M+H)⁺.

LCMS (5 to 95% acetonitrile in water+0.1% formic acid over 10 mins) retention time 4.24 min, ESI+ found [M+H]=310.1

Example 50: Method 45

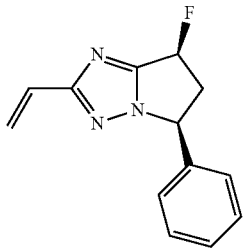 [SMILES: C=Cc1nc2n(n1)[C@H](c1ccccc1)C[C@@H]2F]

(5S,7S)-7-fluoro-5-phenyl-2-vinyl-6,7-dihydro-5H-pyrrolo[1,2-b][1,2,4]triazole

A mixture of (5S,7S)-2-bromo-7-fluoro-5-phenyl-6,7-dihydro-5H-pyrrolo[1,2-b][1,2,4]triazole (200 mg, 0.71 mmol), potassium vinyl trifluoroborate (130 mg, 0.92 mmol), 1,1'-bis(diphenylphosphino)ferrocene palladium dichloride (59 mg, 0.07 mmol) and cesium carbonate (693 mg, 2.13 mmol) in 1,4-dioxane (5 mL) and water (0.5 mL) was heated at 90° C. for 16 h under nitrogen atmosphere. After cooling, the mixture was diluted with water (30 mL) and extracted with ethyl acetate (3×15 mL). The combined organic layers were dried over anhydrous sodium sulfate and concentrated under reduced pressure. The residue was purified by column chromatography (silica gel, 100-200 mesh, 0 to 100% ethyl acetate in petroleum ether) to afford (5S,7S)-7-fluoro-5-phenyl-2-vinyl-6,7-dihydro-5H-pyrrolo[1,2-b][1,2,4]triazole (133 mg, 82%) as a white solid. $^1$H NMR (400 MHz, DMSO-d$_6$) δ 7.45-7.31 (m, 3H), 7.26-7.18 (m, 2H), 6.65 (dd, J=17.5, 11.0 Hz, 1H), 6.21 (dd, J=7.1, 1.8 Hz, 0H), 6.13 (dd, J=17.5, 1.8 Hz, 1H), 6.07 (dd, J=7.1, 1.8 Hz, 0H), 5.59 (ddd, J=8.4, 6.9, 2.9 Hz, 1H), 5.51 (dd, J=11.0, 1.9 Hz, 1H), 3.68 (dddd, J=26.0, 15.4, 8.4, 7.1 Hz, 1H), 2.63 (dddd, J=26.4, 15.2, 3.0, 1.8 Hz, 1H). LC-MS R$_T$=4.23 min, m/z=230.1 (M+H)$^+$.

LCMS (5 to 95% acetonitrile in water+0.1% formic acid over 10 mins) retention time 4.23 min, ESI+ found [M+H]=230.1

Example 51: Method 46

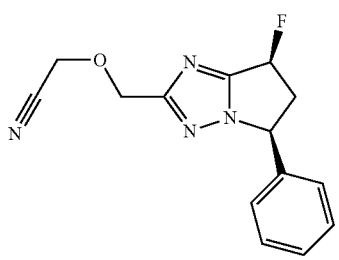 [SMILES: N#CCOCc1nc2n(n1)[C@H](c1ccccc1)C[C@@H]2F]

2-[(7-fluoro-5-phenyl-6,7-dihydro-5H-pyrrolo[1,2-b][1,2,4]triazol-2-yl)methoxy]acetonitrile Step 1: rac-(5S,7S)-(7-fluoro-5-phenyl-6,7-dihydro-5H-pyrrolo[1,2-b][1,2,4]triazol-2-yl)methanol

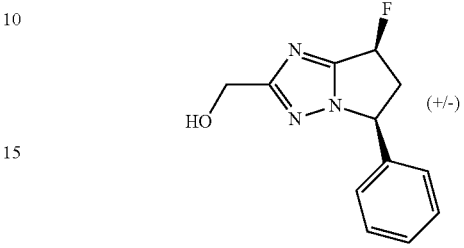

To a solution of ethyl [rac-(5S,7S)-7-fluoro-5-phenyl-6,7-dihydro-5H-pyrrolo[1,2-b][1,2,4]triazole-2-carboxylate (1000 mg, 3.63 mmol, 1.0 equiv) in THF (25 mL) cooled to 0° C. was added lithium borohydride (2 M in tetrahydrofuran, 1.91 mL, 3.81 mmol, 1.05 equiv). The ice bath was removed, and the mixture was stirred 3 h at RT. After this time, the reaction mixture was poured into 5% aqueous citric acid (100 mL). The mixture was extracted with isopropyl acetate (3×50 mL). The combined organics were washed with brine, dried over sodium sulfate, and concentrated to afford rac-(5S,7S)-(7-fluoro-5-phenyl-6,7-dihydro-5H-pyrrolo[1,2-b][1,2,4]triazol-2-yl)methanol as a white solid which was used without further purification (805 mg, 95% yield). LC-MS R$_T$=0.88 min, m/z=234.1 (M+H)$^+$.

LCMS (5 to 95% acetonitrile in water+0.1% formic acid over 2 mins) retention time 0.88 min, ESI+ found [M+H]=234.1

Step 2: 2-[(7-fluoro-5-phenyl-6,7-dihydro-5H-pyrrolo[1,2-b][1,2,4]triazol-2-yl)methoxy]acetonitrile To a solution of rac-(5S,7S)-(7-fluoro-5-phenyl-6,7-dihydro-5H-pyrrolo[1,2-b][1,2,4]triazol-2-yl)methanol (60 mg, 0.26 mmol) in tetrahydrofuran (1 mL) was added NaH 60% (13 mg, 0.33 mmol). The resulting mixture was stirred half hour at RT, to this reaction mixture was added bromoacetonitrile (0.025 mL, 0.36 mmol) in tetrahydrofuran (0.5 mL). The resulting mixture was stirred 3h at RT. After this time, the reaction was quenched with water and extracted with isopropyl acetate (3×50 mL). The combined organics were washed with brine, dried over sodium sulfate and concentrated. The resulting residue was purified by prep-HPLC (Gemini-NX C18 50×30 mm, 5 um, 10-60% of 0.1% Formic Acid in Water Acetonitrile) to afford final product (41 mg, 58%) as a white solid. $^1$H NMR (400 MHz, DMSO-d$_6$) δ 7.45-7.31 (m, 3H), 7.26-7.18 (m, 2H), 6.16 (ddd, J=56.8, 7.1, 1.8 Hz, 1H), 5.61 (ddd, J=8.4, 6.9, 2.9 Hz, 1H), 4.60 (s, 2H), 4.53 (s, 2H), 3.69 (dddd, J=26.0, 15.4, 8.5, 7.1 Hz, 1H), 2.65 (dddd, J=26.5, 15.2, 3.0, 1.8 Hz, 1H). LC-MS R$_T$=3.96 min, m/z=273.1 (M+H)$^+$.

LCMS (5 to 95% acetonitrile in water+0.1% formic acid over 10 mins) retention time 3.96 min, ESI+ found [M+H]=273.1

Example 52: Method 45

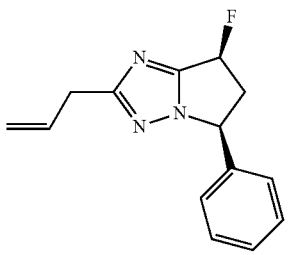 [SMILES: C=CCc1nc2n(n1)[C@H](c1ccccc1)C[C@@H]2F]

(5S,7S)-2-allyl-7-fluoro-5-phenyl-6,7-dihydro-5H-pyrrolo[1,2-b][1,2,4]triazole (7 mg, 8% Yield). $^1$H NMR (400 MHz, DMSO-d$_6$) δ 7.45-7.30 (m, 3H), 7.24-7.16 (m, 2H), 6.11 (ddd, J=57.1, 7.1, 1.6 Hz, 1H), 6.01-5.90 (m, 1H), 5.55 (ddd, J=8.3, 7.2, 2.8 Hz, 1H), 5.20-5.01 (m, 2H), 3.65 (dddd, J=26.4, 15.4, 8.4, 7.1 Hz, 1H), 3.44 (dt, J=6.7, 1.5 Hz, 2H), 2.60 (dddd, J=26.3, 15.3, 2.8, 1.7 Hz, 1H). LC-MS R$_T$=4.32 Min, m/z=244.1 (M+H)$^+$ LCMS (5 to 95% acetonitrile in water+0.1% formic acid over 10 mins) retention time 4.32 min, ESI+ found [M+H]=244.1

Example 53: Method 47

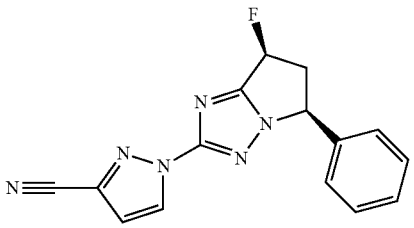 [SMILES: N#Cc1ccn(-c2nc3n(n2)[C@H](c2ccccc2)C[C@@H]3F)n1]

1-[(5S,7S)-7-fluoro-5-phenyl-6,7-dihydro-5H-pyrrolo[1,2-b][1,2,4]triazol-2-yl]pyrazole-3-carbonitrile A mixture of (5S,7S)-2-bromo-7-fluoro-5-phenyl-6,7-dihydro-5H-pyrrolo[1,2-b][1,2,4]triazole (15 mg, 0.053 mmol), copper(I) iodide (2 mg, 0.011 mmol), (1S,2S)—N$^1$,N$^2$-dimethylcyclohexane-1,2-diamine (8 mg, 0.053 mmol), cesium carbonate (52 mg, 0.16 mmol) and 1H-pyrazole-3-carbonitrile (52 mg, 0.53 mmol) in 1,4-dioxane (0.5 mL) was heated at 140° C. for 3 h a sealed tube under microwave. After cooled, the mixture was diluted with water (30 mL) and extracted with ethyl acetate (3×15 mL). The combined organic layers were dried over anhydrous sodium sulfate and concentrated under reduced pressure. The residue was purified by prep-HPLC (Gemini-NX C18 50×30 mm, 5 um, 20-60% of 0.1% Formic Acid in Water Acetonitrile) to afford final product (4 mg, 26%) as a white solid. $^1$H NMR (400 MHz, DMSO-d$_6$) $^1$H NMR (400 MHz, DMSO-d$_6$) δ 8.69 (d, J=2.7 Hz, 1H), 7.51-7.30 (m, 3H), 7.38-7.17 (m, 3H), 6.23 (dddd, J=56.6, 38.4, 7.2, 2.0 Hz, 1H), 5.68 (dtd, J=31.1, 7.9, 3.1 Hz, 1H), 3.89-3.55 (m, 1H), 2.80-2.52 (m, 1H). LC-MS R$_T$=4.81 min, m/z=295.1 (M+H)$^+$.

LCMS (5 to 95% acetonitrile in water+0.1% formic acid over 10 mins) retention time 4.81 min, ESI+ found [M+H]=295.1

Example 54: Method 47

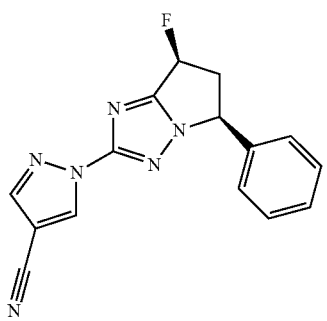 [SMILES: N#Cc1cnn(-c2nc3n(n2)[C@H](c2ccccc2)C[C@@H]3F)c1]

1-[(5S,7S)-7-fluoro-5-phenyl-6,7-dihydro-5H-pyrrolo[1,2-b][1,2,4]triazol-2-yl]pyrazole-4-carbonitrile (8 mg, 15% yield). $^1$H NMR (400 MHz, DMSO-d$_6$) δ 9.27 (s, 1H), 8.39 (s, 1H), 7.52-7.36 (m, 3H), 7.40-7.26 (m, 2H), 6.27 (ddd, J=56.5, 7.3, 2.0 Hz, 1H), 5.72 (td, J=8.0, 3.1 Hz, 1H), 3.73 (dddd, J=24.9, 15.4, 8.5, 7.3 Hz, 1H), 2.76-2.58 (m, 1H). LC-MS R$_T$=4.52 min, m/z=295.1 (M+H)$^+$ LCMS (5 to 95% acetonitrile in water+0.1% formic acid over 10 mins) retention time 4.52 min, ESI+ found [M+H]=295.1

Example 55: Method 44

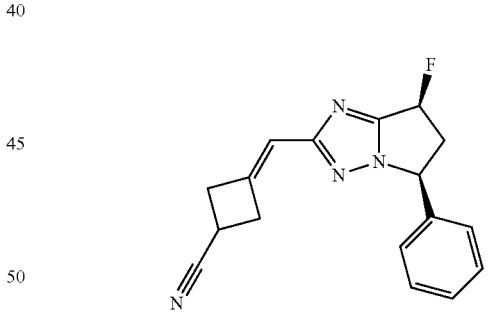

3-[[rac-(5S,7S)-7-fluoro-5-phenyl-6,7-dihydro-5H-pyrrolo[1,2-b][1,2,4]triazol-2-yl]methylene]cyclobutanecarbonitrile (21 mg, 10% yield). $^1$H NMR (400 MHz, DMSO-d6) δ 7.64-7.51 (m, OH), 7.48-7.30 (m, 3H), 7.19 (dd, J=7.8, 1.7 Hz, 2H), 6.25-6.02 (m, 2H), 5.63-5.51 (m, 1H), 3.66 (dddd, J=26.6, 15.5, 8.5, 7.1 Hz, 1H), 3.55-3.43 (m, 2H), 3.30-3.10 (m, 3H), 2.73-2.53 (m, 1H). LC-MS R$_T$=4.57 min, m/z=295.1 (M+H)$^+$.

LCMS (5 to 95% acetonitrile in water+0.1% formic acid over 10 mins) retention time 4.57 min, ESI+ found [M+H]=295.1

Example 56: Method 47

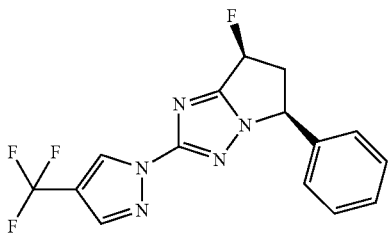 [SMILES: F[C@H]1C[C@@H](c2ccccc2)n2nc(-n3cc(C(F)(F)F)cn3)nc21]

(5S,7S)-7-fluoro-5-phenyl-2-[4-(trifluoromethyl)pyrazol-1-yl]-6,7-dihydro-5H-pyrrolo[1,2-b][1,2,4]triazole (14 mg, 19% yield). $^1$H NMR (400 MHz, DMSO-d$_6$) δ 9.07 (s, 1H), 8.28 (s, 1H), 7.42 (ddt, J=14.6, 7.7, 6.2 Hz, 3H), 7.35-7.25 (m, 2H), 6.40-6.16 (m, 1H), 5.73 (td, J=7.9, 3.1 Hz, 1H), 3.83-3.62 (m, 1H), 2.77-2.58 (m, 1H). LC-MS R$_T$=5.39 min, m/z=338.1 (M+H)$^+$.

LCMS (5 to 95% acetonitrile in water+0.1% formic acid over 10 mins) retention time 5.39 min, ESI+ found [M+H]=338.1

Example 57: Method 47

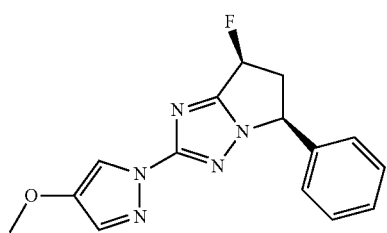 [SMILES: COc1cnn(-c2nc3n(n2)[C@H](c2ccccc2)C[C@@H]3F)c1]

(5S,7S)-7-fluoro-2-(4-methoxypyrazol-1-yl)-5-phenyl-6,7-dihydro-5H-pyrrolo[1,2-b][1,2,4]triazole (20 mg, 30% yield). $^1$H NMR (400 MHz, DMSO-d$_6$) δ 8.05 (s, 1H), 7.60 (s, 1H), 7.42 (q, J=6.2 Hz, 3H), 7.31-7.12 (m, 2H), 6.22 (ddd, J=56.9, 7.3, 1.9 Hz, 1H), 5.65 (td, J=8.0, 3.0 Hz, 1H), 3.72-3.56 (m, 1H), 2.64 (ddt, J=26.7, 15.1, 2.4 Hz, 1H). LC-MS R$_T$=4.47 min, m/z=300.1 (M+H)$^+$.

LCMS (5 to 95% acetonitrile in water+0.1% formic acid over 10 mins) retention time 4.47 min, ESI+ found [M+H]=300.1

Example 58: Method 47

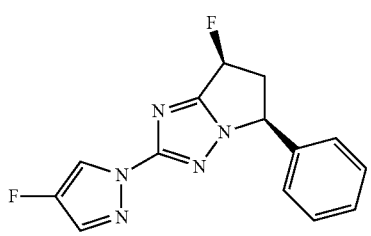 [SMILES: Fc1cnn(-c2nc3n(n2)[C@H](c2ccccc2)C[C@@H]3F)c1]

(5S,7S)-7-fluoro-2-(4-fluoropyrazol-1-yl)-5-phenyl-6,7-dihydro-5H-pyrrolo[1,2-b][1,2,4]triazole (29 mg, 47% yield). $^1$H NMR (400 MHz, DMSO-d6) δ 8.53 (dd, J=4.6, 0.8 Hz, 1H), 7.91 (dd, J=4.2, 0.8 Hz, 1H), 7.48-7.25 (m, 5H), 6.24 (ddd, J=56.7, 7.3, 1.9 Hz, 1H), 5.68 (td, J=8.0, 3.0 Hz, 1H), 3.71 (dddd, J=25.1, 15.4, 8.3, 7.2 Hz, 1H), 2.80-2.55 (m, 1H). LC-MS R$_T$=4.62 min, m/z=288.1 (M+H)$^+$.

LCMS (5 to 95% acetonitrile in water+0.1% formic acid over 10 mins) retention time 4.62 min, ESI+ found [M+H]=288.1

Example 59: Method 47

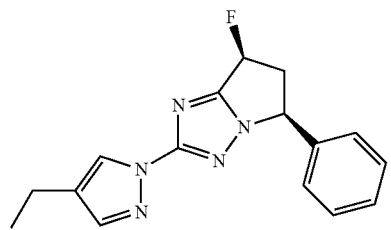 [SMILES: CCc1cnn(-c2nc3n(n2)[C@H](c2ccccc2)C[C@@H]3F)c1]

(5S,7S)-2-(4-ethylpyrazol-1-yl)-7-fluoro-5-phenyl-6,7-dihydro-5H-pyrrolo[1,2-b][1,2,4]triazole (21 mg, 33% yield). $^1$H NMR (400 MHz, DMSO-d$_6$) δ 8.12 (d, J=1.0 Hz, 1H), 7.64 (s, 1H), 7.47-7.34 (m, 3H), 7.38-7.21 (m, 2H), 6.23 (ddd, J=56.8, 7.2, 1.9 Hz, 1H), 5.66 (td, J=8.0, 2.9 Hz, 1H), 3.70 (dddd, J=25.3, 15.4, 8.4, 7.2 Hz, 1H), 2.64 (dddd, J=26.7, 15.2, 3.0, 1.9 Hz, 1H), 2.50-2.42 (m, 2H), 1.17 (t, J=7.5 Hz, 3H). LC-MS R$_T$=5.03 min, m/z=298.1 (M+H)$^+$.

LCMS (5 to 95% acetonitrile in water+0.1% formic acid over 10 mins) retention time 5.03 min, ESI+ found [M+H]=298.1

Example 60: Method 47

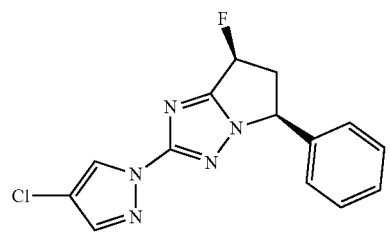 [SMILES: F[C@H]1C[C@@H](c2ccccc2)n2nc(-n3cc(Cl)cn3)nc21]

(5S,7S)-2-(4-chloropyrazol-1-yl)-7-fluoro-phenyl-6,7-dihydro-5H-pyrrolo[1,2-b][1,2,4]triazole (14 mg, 22% yield). $^1$H NMR (400 MHz, DMSO-d$_6$) δ 8.63 (s, 1H), 7.93 (s, 1H), 7.51-7.35 (m, 3H), 7.33-7.25 (m, 2H), 6.25 (ddd, J=56.7, 7.3, 1.9 Hz, 1H), 5.69 (td, J=7.9, 3.1 Hz, 1H), 3.72 (dddd, J=25.1, 15.4, 8.4, 7.2 Hz, 1H), 2.74-2.58 (m, 1H). LC-MS R$_T$=5.04 min, m/z=304.0 (M+H)$^+$.

LCMS (5 to 95% acetonitrile in water+0.1% formic acid over 10 mins) retention time 5.04 min, ESI+ found [M+H]=304.0

Example 61: Method 48

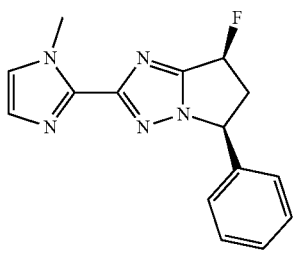 [SMILES: Cn1ccnc1-c1nc2n(n1)[C@H](c1ccccc1)C[C@@H]2F]

(5S,7S)-7-fluoro-2-(1-methylimidazol-2-yl)-5-phenyl-6,7-dihydro-5H-pyrrolo[1,2-b][1,2,4]triazole A mixture of (5S,7S)-2-bromo-7-fluoro-5-phenyl-6,7-dihydro-5H-pyrrolo[1,2-b][1,2,4]triazole (60 mg, 0.21 mmol), 1-methyl-2-(tributylstannyl)-1H-imidazole (250 mg, 0.64 mmol), bis(triphenylphosphine)palladium(ii) dichloride (15 mg, 0.021 mmol) in N,N-dimethylacetamide (1.5 mL) was heated at 100° C. for overnight. The reaction mixture was diluted with 100 ml EtOAc, washed with water, filtered over CELITE®, layer were separated, and the organic layer was washed with brine. The crude product was further purified by prep-HPLC (Gemini-NX C18 50×30 mm, 5 um, 5-50% of 0.1% Ammonium Hydroxide in Water Acetonitrile) to afford product (17 mg, 29%) as a white solid. $^1$H NMR (500 MHz, DMSO-d6) δ 7.46-7.40 (m, 2H), 7.40-7.32 (m, 1H), 7.31 (s, 1H), 7.29-7.24 (m, 2H), 6.99 (s, 1H), 6.24 (ddd, J=56.8, 7.1, 1.6 Hz, 1H), 5.71 (td, J=8.6, 2.7 Hz, 1H), 3.74 (dddd, J=26.3, 15.4, 8.3, 7.2 Hz, 1H), 3.34 (s, 2H), 2.75-2.63 (m, 1H). LC-MS $R_T$=2.78 min, m/z=284.1 (M+H)$^+$.

LCMS (5 to 95% acetonitrile in water+0.1% formic acid over 10 mins) retention time 2.78 min, ESI+ found [M+H]=284.1

Example 62: Method 47

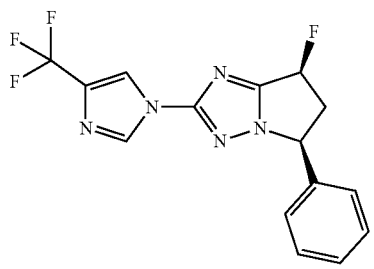 [SMILES: F[C@H]1C[C@@H](c2ccccc2)n2nc(-n3cnc(C(F)(F)F)c3)nc21]

(5S,7S)-7-fluoro-5-phenyl-2-[4-(trifluoromethyl) Imidazol-1-yl]-6,7-dihydro-5H-pyrrolo[1,2-b][1,2,4] triazole (30 mg, 72% yield). $^1$H NMR (400 MHz, DMSO-d6) δ 8.56-8.51 (m, 1H), 8.41 (p, J=1.3 Hz, 1H), 7.48-7.34 (m, 3H), 7.39-7.27 (m, 2H), 6.27 (ddd, J=56.5, 7.3, 2.0 Hz, 1H), 5.71 (td, J=7.9, 3.1 Hz, 1H), 3.74 (dddd, J=24.9, 15.5, 8.4, 7.3 Hz, 1H), 2.75-2.58 (m, 1H). LC-MS $R_T$=5.39 min, m/z=338.1 (M+H)

LCMS (5 to 95% acetonitrile in water+0.1% formic acid over 10 mins) retention time 5.39 min, ESI+ found [M+H]=338.1

Example 63: Method 49

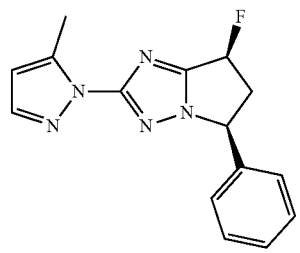 [SMILES: Cc1ccnn1-c1nc2n(n1)[C@H](c1ccccc1)C[C@@H]2F]

(5S,7S)-7-fluoro-2-(5-methylpyrazol-1-yl)-5-phenyl-6,7-dihydro-5H-pyrrolo[1,2-b][1,2,4]triazole

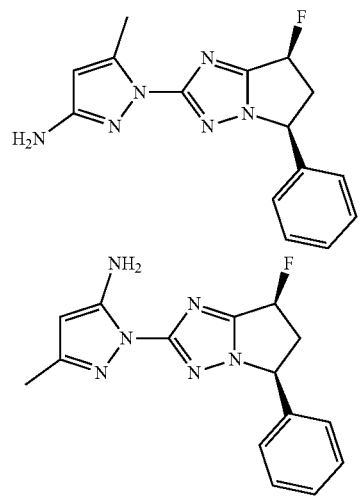

Step 1: 1-(5S,7S)-7-fluoro-5-phenyl-6,7-dihydro-5H-pyrrolo[1,2-b][1,2,4]triazol-2-yl-5-methyl-1H-pyrazol-3-amine and 1-((5S,7S)-7-fluoro-5-phenyl-6,7-dihydro-5H-pyrrolo[1,2-b][1,2,4]triazol-2-yl)-3-methyl-1H-pyrazol-5-amine A mixture of (5S,7S)-2-bromo-7-fluoro-5-phenyl-6,7-dihydro-5H-pyrrolo[1,2-b][1,2,4]triazole (120 mg, 0.43 mmol), copper(I) iodide (97 mg, 0.51 mmol), (1S,2S)—N$^1$, N$^2$-dimethylcyclohexane-1,2-diamine (484 mg, 3.40 mmol), cesium carbonate (416 mg, 1.28 mmol) and 3-amino-5-methylpyrazole (426 mg, 4.25 mmol) in 1,4-dioxane (2 mL) was heated at 140° C. for 3 h a sealed tube under microwave. After cooled, the mixture was diluted with water (30 mL) and extracted with ethyl acetate (3×15 mL). The combined organic layers were dried over anhydrous sodium sulfate and concentrated under reduced pressure. The residue was purified by achiral SFC to afford two peaks:

1-((5S,7S)-7-fluoro-5-phenyl-6,7-dihydro-5H-pyrrolo[1,22-b][1,2,4]triazol-2-yl)-5-methyl-1H-pyrazol-3-amine (Peak 1, 9 mg, 7%) as a white solid. $^1$H NMR (500 MHz, DMSO-d6) δ 7.42 (dd, J=8.0, 6.6 Hz, 2H), 7.40-7.34 (m, 1H), 7.27-7.22 (m, 2H), 6.20 (ddd, J=57.0, 7.1, 1.6 Hz, 1H), 5.63 (td, J=8.0, 2.7 Hz, 1H), 5.54 (s, 1H), 4.95 (s, 2H), 3.74-3.60 (m, 1H), 2.61 (ddt, J=26.4, 15.1, 1.9 Hz, 1H), 2.36 (s, 3H). LC-MS $R_T$=3.89 min, m/z=299.1 (M+H)$^+$.

LCMS (5 to 95% acetonitrile in water+0.1% formic acid over 10 mins) retention time 3.89 min, ESI+ found [M+H]=299.1.

1-((5S,7S)-7-fluoro-5-phenyl-6,7-dihydro-5H-pyrrolo[1,2-b][1,2,4]triazol-2-yl)-3-methyl-1H-pyrazol-5-amine (Peak 2, 12 mg, 10%) as a white solid. $^1$H NMR (500 MHz, DMSO-d6) δ 7.46-7.40 (m, 2H), 7.40-7.36 (m, 1H), 7.30-7.24 (m, 2H), 6.28 (dd, J=7.1, 1.7 Hz, 1H), 6.17 (d, J=5.8 Hz, 3H), 5.64 (td, J=8.1, 2.8 Hz, 1H), 5.21 (s, 1H), 3.77-3.62 (m, 1H), 2.70-2.57 (m, 1H), 2.02 (s, 3H). LC-MS $R_T$=3.94 min, m/z=299.1 (M+H)$^+$.

LCMS (5 to 95% acetonitrile in water+0.1% formic acid over 10 mins) retention time 3.94 min, ESI+ found [M+H]=299.1.

SFC condition (prep): Column: PIC 200 Achiral 150×30 mm, Sum Mobile phase: A: CO2 B: 0.1% Ammonium Hydroxide in Methanol, Isocratic 20% 0.1% Ammonium Hydroxide in Methanol for 5 mins X4 cycle, Flow rate: 150 mL/min, column temp 40° C.

Step 2: (5S,7S)-7-fluoro-2-(5-methylpyrazol-1-yl)-5-phenyl-6,7-dihydro-5H-pyrrolo[1,2-b][1,2,4]triazole

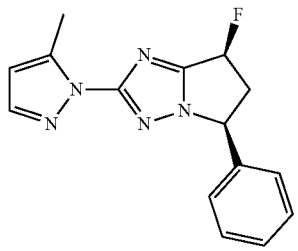 [SMILES: Cc1ccnn1-c1nc2n(n1)[C@H](c1ccccc1)C[C@@H]2F]

To a solution of 1-((5S,7S)-7-fluoro-5-phenyl-6,7-dihydro-5H-pyrrolo[1,2-b][1,2,4]triazol-2-yl)-3-methyl-1H-pyrazol-5-amine (9 mg, 0.030 mmol) in tetrahydrofuran (0.5 mL) was added isoamyl nitrite (11 mg, 0.012 mmol). The resulting mixture was heated at 70° C. for 4h. After cooled, the mixture was diluted with water (30 mL) and extracted with ethyl acetate (3×15 mL). The combined organic layers were dried over anhydrous sodium sulfate and concentrated under reduced pressure. The resulting residue was purified by prep-HPLC (Gemini-NX C18 50×30 mm, 5 um, 20-60% of 0.1% Ammonium Hydroxide in Water Acetonitrile) to afford final product (2.7 mg, 31%) as a white solid. $^1$H NMR (400 MHz, DMSO-d6) δ 7.60 (d, J=1.6 Hz, 1H), 7.48-7.33 (m, 3H), 7.31-7.24 (m, 2H), 6.42-6.12 (m, 2H), 5.72 (td, J=7.9, 2.9 Hz, 1H), 3.72 (dddd, J=25.7, 15.4, 8.4, 7.2 Hz, 1H), 2.74-2.56 (m, 1H), 2.42 (s, 3H). LC-MS $R_T$=4.61 min, m/z=284.1 (M+H)$^+$.

LCMS (5 to 95% acetonitrile in water+0.1% formic acid over 10 mins) retention time 4.61 min, ESI+ found [M+H]=284.1

Example 64: Method 49

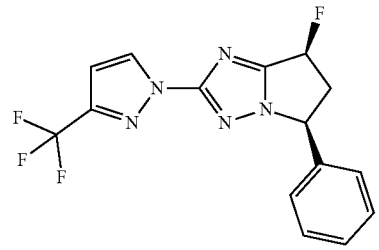 [SMILES: F[C@H]1C[C@@H](c2ccccc2)n2nc(-n3ccc(C(F)(F)F)n3)nc21]

(5S,7S)-7-fluoro-5-phenyl-2-[3-(trifluoromethyl)pyrazol-1-yl]-6,7-dihydro-5H-pyrrolo[1,2-b][1,2,4]triazole (20 mg, 58% yield). $^1$H NMR (400 MHz, DMSO-d6) δ 8.63 (dq, J=2.2, 1.0 Hz, 1H), 7.53-7.36 (m, 3H), 7.35-7.25 (m, 2H), 7.06 (d, J=2.6 Hz, 1H), 6.28 (ddd, J=56.7, 7.2, 2.0 Hz, 1H), 5.71 (td, J=8.1, 3.2 Hz, 1H), 3.74 (dddd, J=24.8, 15.5, 8.4, 7.3 Hz, 1H), 2.78-2.60 (m, 1H). LC-MS $R_T$=5.64 min, m/z=338.1 (M+H)$^+$.

LCMS (5 to 95% acetonitrile in water+0.1% formic add over 10 mins) retention time 5.64 min, ESI+ found [M+H]=338.1

Example 65: Method 47

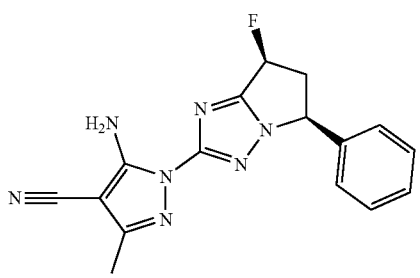 [SMILES: Cc1nn(-c2nc3n(n2)[C@H](c2ccccc2)C[C@@H]3F)c(N)c1C#N]

5-amino-1-[(5S,7S)-7-fluoro-5-phenyl-6,7-dihydro-5H-pyrrolo[1,2-b][1,2,4]triazol-2-yl]-3-methyl-pyrazole-4-carbonitrile (27 mg, 10% yield). $^1$H NMR (500 MHz, DMSO-d6) δ 7.50 (s, 2H), 7.45-7.36 (m, 3H), 7.30-7.27 (m, 2H), 6.33-6.14 (m, 1H), 5.90 (s, OH), 5.67 (td, J=8.0, 3.0 Hz, 1H), 3.78-3.62 (m, 1H), 2.72-2.59 (m, 1H), 2.14 (s, 3H). LC-MS $R_T$=1.13 min, m/z=324.0 (M+H)$^+$.

LCMS (5 to 95% acetonitrile in water+0.1% formic acid over 2 mins) retention time 1.13 min, ESI+ found [M+H]=324.0

Example 66: Method 47

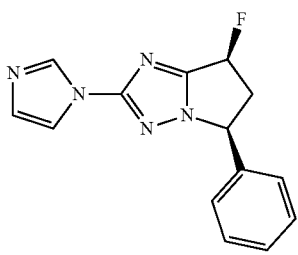 [SMILES: F[C@H]1C[C@@H](c2ccccc2)n2nc(-n3ccnc3)nc21]

(5S,7S)-7-fluoro-2-imidazol-1-yl-5-phenyl-6,7-dihydro-5H-pyrrolo[1,2-b][1,2,4]triazole (42 mg, 51% yield). $^1$H NMR (400 MHz, DMSO-d$_6$) δ 8.30 (t, J=1.1 Hz, 1H), 7.72 (q, J=1.3 Hz, 1H), 7.48-7.32 (m, 3H), 7.36-7.17 (m, 2H), 7.15-7.08 (m, 1H), 6.24 (ddd, J=56.6, 7.2, 1.9 Hz, 1H), 5.68 (td, J=8.0, 3.1 Hz, 1H), 3.72 (dddd, J=25.0, 15.4, 8.4, 7.2 Hz, 1H), 2.64 (dddd, J=26.9, 15.1, 3.1, 2.0 Hz, 1H). LC-MS R$_T$=3.30 min, m/z=270.1 (M+H)$^+$.

LCMS (5 to 95% acetonitrile in water+0.1% formic acid over 10 mins) retention time 3.30 min, ESI+ found [M+H]=270.1

Example 67: Method 47

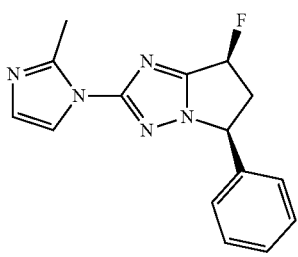 [SMILES: Cc1nccn1-c1nc2n(n1)[C@H](c1ccccc1)C[C@@H]2F]

(5S,7S)-7-fluoro-2-(2-methylimidazol-1-yl)-5-phenyl-6,7-dihydro-5H-pyrrolo[1,2-b][1,2,4]triazole (10 mg, 12% yield). $^1$H NMR (400 MHz, DMSO-d$_6$) δ 7.54 (d, J=1.5 Hz, 1H), 7.48-7.31 (m, 3H), 7.32-7.23 (m, 2H), 6.91 (d, J=1.6 Hz, 1H), 6.25 (ddd, J=56.6, 7.2, 1.9 Hz, 1H), 5.71 (td, J=8.0, 3.0 Hz, 1H), 3.71 (dddd, J=25.6, 15.4, 8.4, 7.1 Hz, 1H), 2.72-2.55 (m, 1H), 2.55-2.50 (m, 3H). LC-MS R$_T$=2.95 min, m/z=284.1 (M+H)$^+$.

LCMS (5 to 95% acetonitrile in water+0.1% formic acid over 10 mins) retention time 2.95 min, ESI+ found [M+H]=284.1

Example 68: Method 47

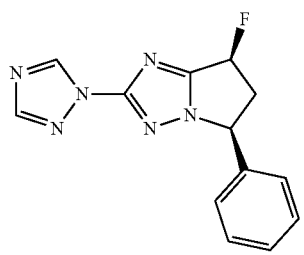 [SMILES: F[C@H]1C[C@@H](c2ccccc2)n2nc(-n3cncn3)nc21]

(5S,7S)-7-fluoro-5-phenyl-2-(1,2,4-triazol-1-yl)-6,7-dihydro-5H-pyrrolo[1,2-b][1,2,4]triazole (2 mg, 3% yield).
LC-MS R$_T$=4.01 min, m/z=271.1 (M+H)$^+$.
LCMS (5 to 95% acetonitrile in water+0.1% formic acid over 10 mins) retention time 4.01 min, ESI+ found [M+H]=271.1

Example 69: Method 47

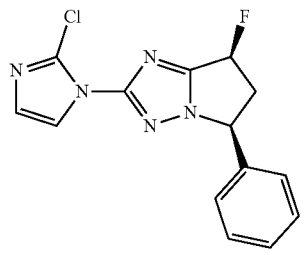 [SMILES: F[C@H]1C[C@@H](c2ccccc2)n2nc(-n3ccnc3Cl)nc21]

(5S,7S)-2-(2-chloroimidazol-1-yl)-7-fluoro-5-phenyl-6,7-dihydro-5H-pyrrolo[1,2-b][1,2,4]triazole (2 mg, 3% yield). $^1$H NMR (400 MHz, DMSO-d$_6$) δ 7.73 (d, J=1.7 Hz, 1H), 7.51-7.34 (m, 4H), 7.32-7.24 (m, 2H), 7.09 (d, J=1.7 Hz, 1H), 6.42-6.18 (m, 1H), 5.75 (ddd, J=8.3, 7.2, 3.0 Hz, 1H), 3.73 (dddd, J=25.6, 15.4, 8.5, 7.2 Hz, 1H), 2.75-2.55 (m, 1H). LC-MS R$_T$=4.50 min, m/z=304.1 (M+H)$^+$.

LCMS (5 to 95% acetonitrile in water+0.1% formic acid over 10 mins) retention time 4.50 min, ESI+ found [M+H]=304.1

Example 70: Method 47

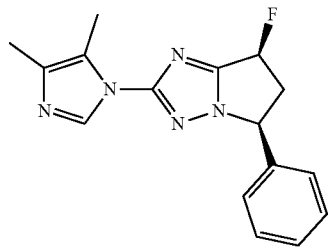 [SMILES: Cc1ncn(-c2nc3n(n2)[C@H](c2ccccc2)C[C@@H]3F)c1C]

(5S,7S)-2-(4,5-dimethylimidazol-1-yl)-7-fluoro-5-phenyl-6,7-dihydro-5H-pyrrolo[1,2-b][1,2,4]triazole (53 mg, 63% yield). $^1$H NMR (400 MHz, DMSO-d6) δ 7.97 (s, 1H), 7.47-7.33 (m, 3H), 7.30-7.23 (m, 2H), 6.24 (ddd, J=56.6, 7.2, 1.9 Hz, 1H), 5.70 (td, J=7.9, 2.9 Hz, 1H), 3.70 (dddd, J=25.7, 15.4, 8.4, 7.2 Hz, 1H), 2.63 (dddd, J=26.6, 15.2, 3.0, 1.9 Hz, 1H), 2.29 (d, J=0.9 Hz, 3H), 2.08 (d, J=0.9 Hz, 3H). LC-MS $R_T$=3.21 min, m/z=298.2 (M+H)$^+$.

LCMS (5 to 95% acetonitrile in water+0.1% formic acid over 10 mins) retention time 3.21 min, ESI+ found [M+H]=298.2

Example 71: Method 47

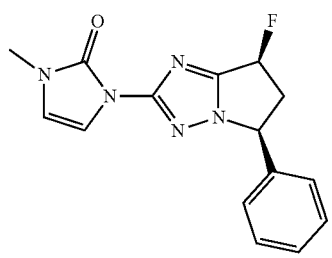 [SMILES: Cn1ccn(-c2nc3n(n2)[C@H](c2ccccc2)C[C@@H]3F)c1=O]

1-[(5S,7S)-7-fluoro-5-phenyl-6,7-dihydro-5H-pyrrolo[1,2-b][1,2,4]triazol-2-yl]-3-methyl-imidazol-2-one (29 mg, 46% yield). $^1$H NMR (400 MHz, DMSO-d6) δ 7.47-7.33 (m, 3H), 7.37-7.21 (m, 2H), 6.87 (d, J=3.2 Hz, 1H), 6.71 (d, J=3.2 Hz, 1H), 6.19 (ddd, J=56.9, 7.2, 1.8 Hz, 1H), 5.64 (td, J=8.0, 2.9 Hz, 1H), 3.68 (dddd, J=25.7, 15.3, 8.4, 7.1 Hz, 1H), 3.15 (s, 3H), 2.61 (dddd, J=26.6, 15.3, 3.0, 1.8 Hz, 1H). LC-MS $R_T$=3.78 min, m/z=300.1 (M+H)$^+$.

LCMS (5 to 95% acetonitrile in water+0.1% formic acid over 10 mins) retention time 3.78 min, ESI+ found [M+H]=300.1

Example 72: Method 47

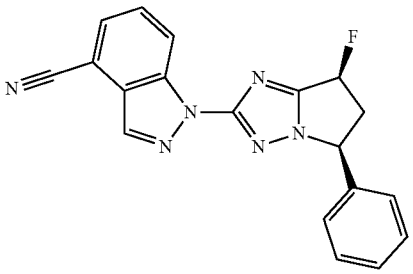 [SMILES: N#Cc1cccc2c1cnn2-c1nc2n(n1)[C@H](c1ccccc1)C[C@@H]2F]

1-[(5S,7S)-7-fluoro-5-phenyl-6,7-dihydro-5H-pyrrolo[1,2-b][1,2,4]triazol-2-yl]indazole-4-carbonitrile (43 mg, 59% yield). $^1$H NMR (500 MHz, DMSO-d6) δ 8.68 (d, J=0.8 Hz, 1H), 8.60 (d, J=8.7 Hz, 1H), 7.97-7.92 (m, 1H), 7.77 (dd, J=8.6, 7.3 Hz, 1H), 7.48-7.42 (m, 2H), 7.42-7.37 (m, 1H), 7.37-7.31 (m, 2H), 6.32 (ddd, J=56.7, 7.2, 1.8 Hz, 1H), 5.77 (td, J=8.0, 2.9 Hz, 1H), 3.84-3.69 (m, 1H), 2.76-2.65 (m, 1H). LC-MS $R_T$=5.54 min, m/z=345.1 (M+H)$^+$.

LCMS (5 to 95% acetonitrile in water+0.1% formic acid over 10 mins) retention time 5.54 min, ESI+ found [M+H]=345.1

Example 73: Method 47

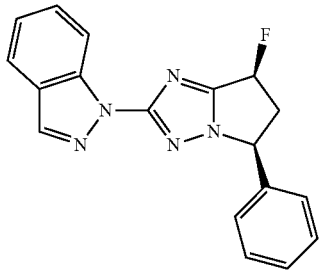

1-[rac-(5S,7S)-7-fluoro-5-phenyl-6,7-dihydro-5H-pyrrolo[1,2-b][1,2,4]triazol-2-yl]indazole (20 mg, 29% yield). $^1$H NMR (500 MHz, DMSO-d6) δ 8.43 (d, J=0.7 Hz, 1H), 8.27 (dd, J=8.5, 0.8 Hz, 1H), 7.91 (d, J=8.0 Hz, 1H), 7.58 (ddd, J=8.3, 7.0, 1.0 Hz, 1H), 7.48-7.42 (m, 2H), 7.42-7.36 (m, 1H), 7.36-7.30 (m, 3H), 6.31 (ddd, J=56.9, 7.1, 1.7 Hz, 1H), 5.74 (td, J=8.0, 2.8 Hz, 1H), 3.83-3.68 (m, 1H), 2.75-2.62 (m, 1H). LC-MS $R_T$=5.47 min, m/z=320.1 (M+H)$^+$.

LCMS (5 to 95% acetonitrile in water+0.1% formic acid over 10 mins) retention time 5.47 min, ESI+ found [M+H]=320.1

Example 74: Method 49

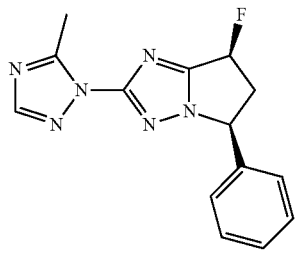 [SMILES: Cc1ncnn1-c1nc2n(n1)[C@H](c1ccccc1)C[C@@H]2F]

(5S,7S)-7-fluoro-2-(5-methyl-1,2,4-triazol-1-yl)-5-phenyl-6,7-dihydro-5H-pyrrolo[1,2-b][1,2,4]triazole Step 1. (13 mg, 85% yield). $^1$H NMR (500 MHz, DMSO-d6) δ 7.46-7.32 (m, 3H), 7.30-7.25 (m, 2H), 7.01 (s, 2H), 6.29-5.66 (m, 1H), 3.83-3.61 (m, 1H), 2.71-2.59 (m, 1H), 2.08 (s, 3H). LC-MS $R_T$=3.66 min, m/z=300.1 (M+H)$^+$.

LCMS (5 to 95% acetonitrile in water+0.1% formic add over 10 mins) retention time 3.66 min, ESI+ found [M+H]=300.1

Step 2

(3 mg, 22% yield). LC-MS $R_T$=4.03 min, m/z=285.1 (M+H)$^+$.

LCMS (5 to 95% acetonitrile in water+0.1% formic acid over 10 mins) retention time 4.03 min, ESI+ found [M+H]=285.1

Example 75: Method 47

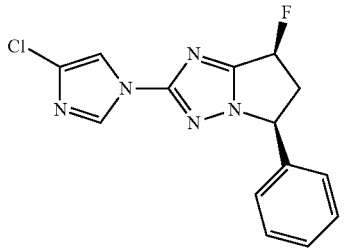 [SMILES: F[C@H]1C[C@@H](c2ccccc2)n2nc(-n3cnc(Cl)c3)nc21]

(5S,7S)-2-(4-chloroimidazol-1-yl)-7-fluoro-5-phenyl-6,7-dihydro-5H-pyrrolo[1,2-b][1,2,4]triazole (17 mg, 23% yield). $^1$H NMR (400 MHz, DMSO-d6) δ 8.32 (d, J=1.5 Hz, 1H), 7.87 (d, J=1.5 Hz, 1H), 7.50-7.34 (m, 3H), 7.33-7.25 (m, 2H), 6.25 (ddd, J=56.7, 7.2, 2.0 Hz, 1H), 5.68 (td, J=7.9, 3.1 Hz, 1H), 3.72 (dddd, J=24.8, 15.4, 8.4, 7.3 Hz, 1H), 2.64 (dddd, J=27.0, 15.1, 3.1, 1.9 Hz, 1H). LC-MS $R_T$=4.99 min, m/z=304.1 (M+H)$^+$.

LCMS (5 to 95% acetonitrile in water+0.1% formic acid over 10 mins) retention time 4.99 min, ESI+ found [M+H]=304.1

Example 76: Method 47

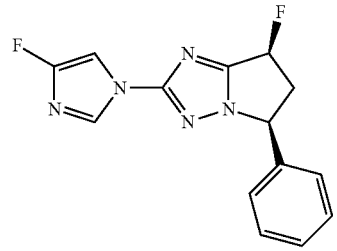 [SMILES: Fc1cn(-c2nc3n(n2)[C@H](c2ccccc2)C[C@@H]3F)cn1]

(5S,7S)-7-fluoro-2-(4-fluoroimidazol-1-yl)-5-phenyl-6,7-dihydro-5H-pyrrolo[1,2-b][1,2,4]triazole (25 mg, 35% yield). $^1$H NMR (400 MHz, DMSO-d6) δ 8.11 (t, J=1.7 Hz, 1H), 7.50 (dd, J=8.1, 1.7 Hz, 1H), 7.47-7.35 (m, 3H), 7.33-7.25 (m, 2H), 6.24 (ddd, J=56.5, 7.3, 2.0 Hz, 1H), 5.68 (td, J=8.0, 3.1 Hz, 1H), 3.72 (dddd, J=24.9, 15.4, 8.4, 7.3 Hz, 1H), 2.64 (dddd, J=27.0, 15.1, 3.1, 2.0 Hz, 1H). LC-MS $R_T$=4.84 min, m/z=288.1 (M+H)$^+$.

LCMS (5 to 95% acetonitrile in water+0.1% formic acid over 10 mins) retention time 4.84 min, ESI+ found [M+H]=288.1

Example 77: Method 50

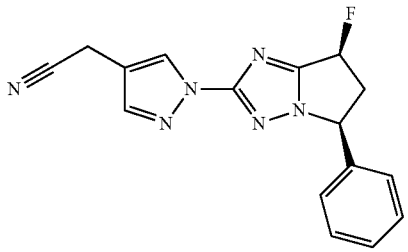 [SMILES: N#CCc1cnn(-c2nc3n(n2)[C@H](c2ccccc2)C[C@@H]3F)c1]

2-[1-[(5S,7S)-7-fluoro-5-phenyl-6,7-dihydro-5H-pyrrolo[1,2-b][1,2,4]triazol-2-yl]pyrazol-4-yl]acetonitrile

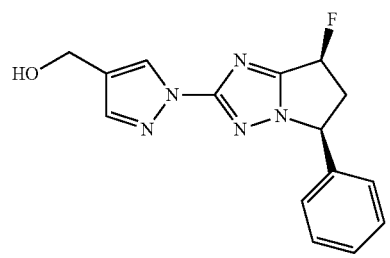 [SMILES: OCc1cnn(-c2nc3n(n2)[C@H](c2ccccc2)C[C@@H]3F)c1]

Step 1: (1-((5S,7S)-7-fluoro-5-phenyl-6,7-dihydro-5H-pyrrolo[1,2-b][1,2,4]triazol-2-yl)-1H-pyrazol-4-yl)methanol A mixture of (5S,7S)-2-bromo-7-fluoro-5-phenyl-6,7-dihydro-5H-pyrrolo[1,2-b][1,2,4]triazole (300 mg, 1.06 mmol), copper(I) iodide (1064 mg, 10.63 mmol), (1S,2S)—N$^1$,N$^2$-dimethylcyclohexane-1,2-diamine (1210 mg, 8.51 mmol), cesium carbonate (1039 mg, 3.19 mmol) and (1H-pyrazol-4-yl)methanol (1064 mg, 10.63 mmol) in 1,4-dioxane (2.5 mL) was heated at 140° C. for 3h a sealed tube under microwave. After cooled, the mixture was diluted with water (30 mL) and extracted with ethyl acetate (3×15 mL). The combined organic layers were dried over anhydrous sodium sulfate and concentrated under reduced pressure. The residue was purified by column chromatography (silica gel, 100-200 mesh, 0 to 15% MeOH in isopropyl acetate) to afford final product (169 mg, 53%) as a white solid. LC-MS $R_T$=0.92 min, m/z=300.1 (M+H)$^+$.

LCMS (5 to 95% acetonitrile in water+0.1% formic acid over 2 mins) retention time 0.92 min, ESI+ found [M+H]=300.1

Step 2: 2-[1-[(5S,7S)-7-fluoro-5-phenyl-6,7-dihydro-5H-pyrrolo[1,2-b][1,2,4]triazol-2-yl]pyrazol-4-yl]acetonitrile To a solution of (1-((5S,7S)-7-fluoro-5-phenyl-6,7-dihydro-5H-pyrrolo[1,2-b][1,2,4]triazol-2-yl)-1H-pyrazol-4-yl)methanol (50 mg, 0.17 mmol) in DCM (1 mL) cooled to 0° C. was added trimethylamine (0.09 mL, 0.67 mmol), then added methanesulfonyl chloride (0.017 mL, 0.22 mmol). The resulting mixture was warmed to RT, and was stirred 3h at RT. After this time, the reaction was quenched with water and extracted with isopropyl acetate (3×50 mL). The combined organics were washed with brine, dried over sodium sulfate and concentrated. The resulting residue was dissolved in DMF (1 mL), and sodium cyanide (16 mg, 0.33 mmol) was added. The mixture was stirred at 50° C. for 3 h. The reaction was quenched with water and extracted with isopropyl acetate (3×50 mL). The combined organics were washed with brine, dried over sodium sulfate and concentrated. The residue was purified by column chromatography (silica gel, 100-200 mesh, 0 to 100% isopropyl acetate in heptane) to afford final product (7 mg, 14%) as a white solid. $^1$H NMR (400 MHz, DMSO-d$_6$) δ 8.36 (q, J=0.9 Hz, 1H), 7.79 (d, J=0.7 Hz, 1H), 7.48-7.33 (m, 3H), 7.33-7.25 (m, 2H), 6.24 (ddd, J=56.7, 7.2, 1.9 Hz, 1H), 5.68 (td, J=8.0, 3.0 Hz, 1H), 3.97-3.86 (m, 2H), 3.83-3.56 (m, 1H), 2.65 (dddd, J=26.9, 15.2, 3.1, 1.9 Hz, 1H). LC-MS $R_T$=4.42 min, m/z=309.1 (M+H)$^+$.

LCMS (5 to 95% acetonitrile in water+0.1% formic acid over 10 mins) retention time 4.42 min, ESI+ found [M+H]=309.1

Example 78: Method 47

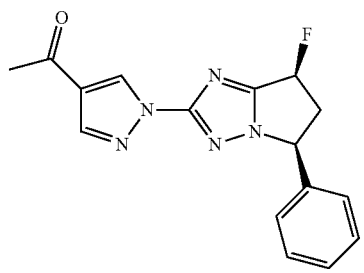 [SMILES: CC(=O)c1cnn(-c2nc3n(n2)[C@H](c2ccccc2)C[C@@H]3F)c1]

1-[1-[rac-(5S,7S)-7-fluoro-5-phenyl-6,7-dihydro-5H-pyrrolo[1,2-b][1,2,4]triazol-2-yl]pyrazol-4-yl]ethanone (13 mg, 17% yield). $^1$H NMR (400 MHz, DMSO-d$_6$) δ 9.04 (s, 1H), 8.18 (s, 1H), 7.48-7.37 (m, 3H), 7.34-7.26 (m, 2H), 6.43-6.16 (m, 1H), 5.71 (td, J=7.9, 3.1 Hz, 1H), 3.83-3.63 (m, 1H), 2.76-2.63 (m, 1H), 2.47 (s, 3H). LC-MS $R_T$=4.56 min, m/z=312.1 (M+H)$^+$.

LCMS (5 to 95% acetonitrile in water+0.1% formic acid over 10 mins) retention time 4.56 min, ESI+ found [M+H]=312.1

Example 79: Method 47

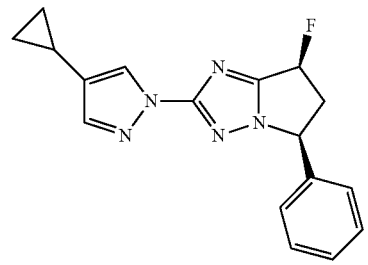 [SMILES: F[C@H]1C[C@@H](c2ccccc2)n2nc(-n3cc(C4CC4)cn3)nc21]

(5S,7S)-2-(4-cyclopropylpyrazol-1-yl)-7-fluoro-5-phenyl-6,7-dihydro-5H-pyrrolo[1,2-b][1,2,4]triazole (28 mg, 36% yield). $^1$H NMR (400 MHz, DMSO-d6) δ 8.09 (d, J=0.7 Hz, 1H), 7.59 (d, J=0.8 Hz, 1H), 7.47-7.35 (m, 3H), 7.37-7.24 (m, 2H), 6.22 (ddd, J=56.8, 7.2, 1.9 Hz, 1H), 5.65 (td, J=8.0, 3.0 Hz, 1H), 3.70 (dddd, J=25.3, 15.4, 8.4, 7.2 Hz, 1H), 2.63 (dddd, J=26.8, 15.2, 3.0, 1.9 Hz, 1H), 1.76 (tt, J=8.4, 5.1 Hz, 1H), 0.91-0.77 (m, 2H), 0.67-0.55 (m, 2H). LC-MS $R_T$=5.40 min, m/z=310.2 (M+H)$^+$.

LCMS (5 to 95% acetonitrile in water+0.1% formic acid over 10 mins) retention time 5.40 min, ESI+ found [M+H]=310.2

Example 80: Method 47

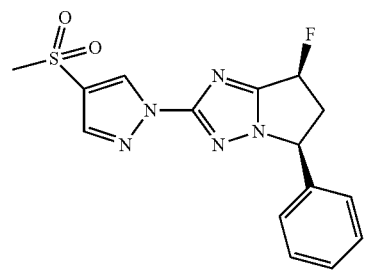 [SMILES: CS(=O)(=O)c1cnn(-c2nc3n(n2)[C@H](c2ccccc2)C[C@@H]3F)c1]

(5S,7S)-7-fluoro-2-(4-methylsulfonylpyrazol-1-yl)-5-phenyl-6,7-dihydro-5H-pyrrolo[1,2-b][1,2,4]triazole (4 mg, 4% yield). $^1$H NMR (400 MHz, DMSO-d6) δ 8.98 (s, 1H), 8.23 (s, 1H), 7.48-7.34 (m, 3H), 7.34-7.26 (m, 2H), 6.28 (ddd, J=56.5, 7.3, 1.9 Hz, 1H), 5.73 (td, J=7.9, 3.1 Hz, 1H), 3.83-3.64 (m, 1H), 2.76-2.60 (m, 1H). LC-MS $R_T$=4.45 min, m/z=348.1 (M+H)$^+$.

LCMS (5 to 95% acetonitrile in water+0.1% formic acid over 10 mins) retention time 4.45 min, ESI+ found [M+H]=348.1

Example 81: Method 47

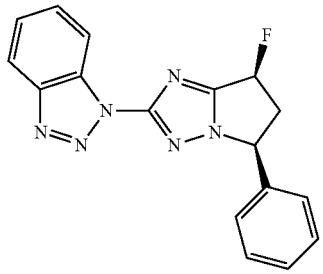

1-[(5S,7S)-7-fluoro-5-phenyl-6,7-dihydro-5H-pyrrolo[1,2-b][1,2,4]triazol-2-yl]benzotriazole (11 mg, 15% yield). $^1$H NMR (400 MHz, DMSO-d$_6$) δ 8.26-8.13 (m, 2H), 7.75 (ddd, J=8.3, 7.1, 1.1 Hz, 1H), 7.57 (ddd, J=8.2, 7.0, 1.1 Hz, 1H), 7.54-7.33 (m, 6H), 6.36 (ddd, J=56.5, 7.2, 2.0 Hz, 1H), 5.82 (td, J=7.9, 3.0 Hz, 1H), 3.80 (dddd, J=25.1, 15.4, 8.4, 7.2 Hz, 1H), 2.82-2.66 (m, 1H). LC-MS R$_T$=5.29 min, m/z=321.1 (M+H)$^+$.

LCMS (5 to 95% acetonitrile in water+0.1% formic acid over 10 mins) retention time 5.29 min, ESI+ found [M+H]=321.1

Example 82: Method 47

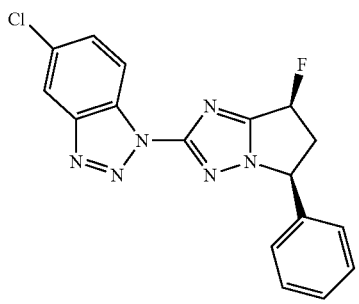 [SMILES: F[C@H]1C[C@@H](c2ccccc2)n2nc(-n3nnc4cc(Cl)ccc43)nc21]

5-chloro-1-[rac-(5S,7S)-7-fluoro-5-phenyl-6,7-dihydro-5H-pyrrolo[1,2-b][1,2,4]triazol-2-yl]benzotriazole (10 mg, 10% yield). $^1$H NMR (400 MHz, DMSO-d6) δ 8.48-8.09 (m, 2H), 7.70 (ddd, J=66.7, 8.8, 1.9 Hz, 1H), 7.51-7.33 (m, 5H), 6.50-6.23 (m, 1H), 5.91-5.74 (m, 1H), 3.79 (dddd, J=25.3, 15.4, 8.2, 7.1 Hz, 1H), 2.85-2.63 (m, 1H). LC-MS R$_T$=5.81 min, m/z=355.1 (M+H)$^+$.

LCMS (5 to 95% acetonitrile in water+0.1% formic acid over 10 mins) retention time 5.81 min, ESI+ found [M+H]=355.1

Example 83: Method 47

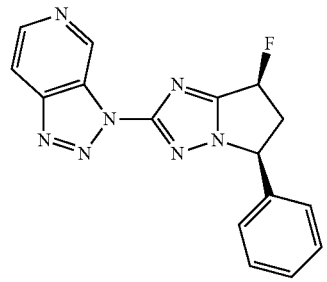 [SMILES: F[C@H]1C[C@@H](c2ccccc2)n2nc(-n3nnc4ccncc43)nc21]

3-[(5S,7S)-7-fluoro-5-phenyl-6,7-dihydro-5H-pyrrolo[1,2-b][1,2,4]triazol-2-yl]triazolo[4,5-c]pyridine (2 mg, 2% yield). LC-MS R$_T$=4.27 min, m/z=322.2 (M+H)$^+$.

LCMS (5 to 95% acetonitrile in water+0.1% formic acid over 10 mins) retention time 4.27 min, ESI+ found [M+H]=322.2

Example 84: Method 47

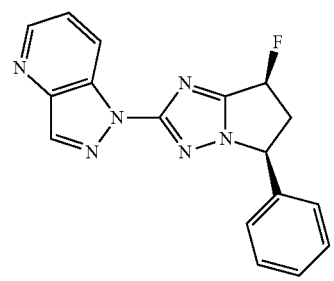 [SMILES: F[C@H]1C[C@@H](c2ccccc2)n2nc(-n3ncc4ncccc43)nc21]

1-[(5S,7S)-7-fluoro-5-phenyl-6,7-dihydro-5H-pyrrolo[1,2-b][1,2,4]triazol-2-yl]pyrazolo[4,3-b]pyridine (33 mg, 36% yield). $^1$H NMR (500 MHz, DMSO-d6) δ 8.70 (dd, J=4.4, 1.3 Hz, 1H), 8.67 (d, J=0.7 Hz, 1H), 8.61 (dd, J=8.5, 0.9 Hz, 1H), 7.61 (dd, J=8.6, 4.4 Hz, 1H), 7.45 (dd, J=7.9, 6.6 Hz, 2H), 7.42-7.36 (m, 1H), 7.36-7.31 (m, 2H), 6.31 (ddd, J=56.8, 7.2, 1.7 Hz, 1H), 5.75 (td, J=8.0, 2.9 Hz, 1H), 3.76 (ddt, J=25.3, 15.4, 7.4 Hz, 1H), 2.69 (ddt, J=26.7, 15.1, 2.0 Hz, 1H). LC-MS R$_T$=4.51 min, m/z=321.2 (M+H)$^+$.

LCMS (5 to 95% acetonitrile in water+0.1% formic add over 10 mins) retention time 4.51 min, ESI+ found [M+H]=321.2

Example 85: Method 47

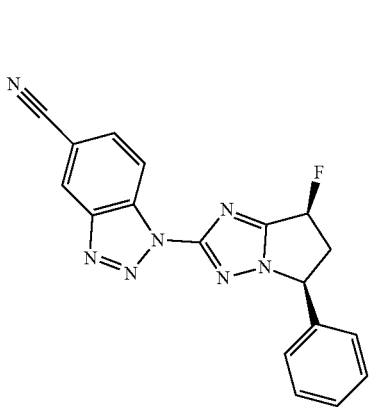 [SMILES: N#Cc1ccc2c(c1)nnn2-c1nc2n(n1)[C@H](c1ccccc1)C[C@@H]2F]

1-[rac-(5S,7S)-7-fluoro-5-phenyl-6,7-dihydro-5H-pyrrolo[1,2-b][1,2,4]triazol-2-yl]benzotriazole-5-carbonitrile (2 mg, 2% yield). LC-MS $R_T$=5.49 min, m/z=346.1 (M+H)$^+$.

LCMS (5 to 95% acetonitrile in water+0.1% formic acid over 10 mins) retention time 5.49 min, ESI+ found [M+H]=346.1

Example 86: Method 47

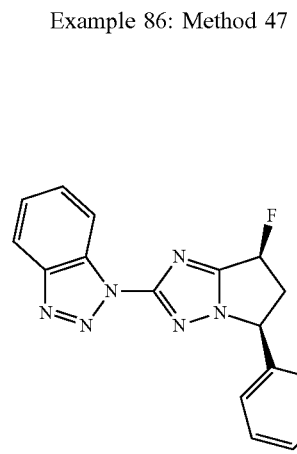

1-(rac-(5S,7S)-7-fluoro-5-phenyl-6,7-dihydro-5H-pyrrolo[1,2-b][1,2,4]triazol-2-yl]-4,5,6,7-tetrahydrobenzotriazole (2 mg, 2% yield). LC-MS $R_T$=5.16 min, m/z=325.2 (M+H)$^+$.

LCMS (5 to 95% acetonitrile in water+0.1% formic acid over 10 mins) retention time 5.16 min, ESI+ found [M+H]=325.2

Example 87: Method 47

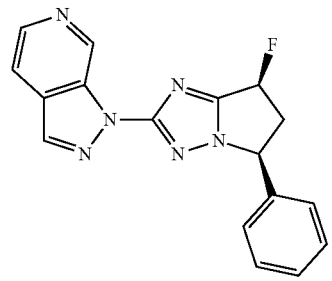 [SMILES: F[C@H]1C[C@@H](c2ccccc2)n2nc(-n3ncc4ccncc43)nc21]

1-[rac-(5S,7S)-7-fluoro-5-phenyl-6,7-dihydro-5H-pyrrolo[1,2-b][1,2,4]triazol-2-yl]pyrazolo[3,4-c]pyridine (34 mg, 38% yield). $^1$H NMR (400 MHz, DMSO-d$_6$) δ 9.63 (d, J=1.1 Hz, 1H), 8.58 (d, J=0.8 Hz, 1H), 8.46 (d, J=5.5 Hz, 1H), 7.93 (dd, J=5.5, 1.3 Hz, 1H), 7.50-7.31 (m, 5H), 6.33 (ddd, J=56.7, 7.2, 1.9 Hz, 1H), 5.77 (td, J=8.0, 3.0 Hz, 1H), 3.77 (dddd, J=25.3, 15.4, 8.3, 7.1 Hz, 1H), 2.71 (dddd, J=26.7, 15.1, 3.0, 1.9 Hz, 1H). LC-MS $R_T$=4.02 min, m/z=321.2 (M+H)$^+$.

LCMS (5 to 95% acetonitrile in water+0.1% formic acid over 10 mins) retention time 4.02 min, ESI+ found [M+H]=321.2

Example 88: Method 47

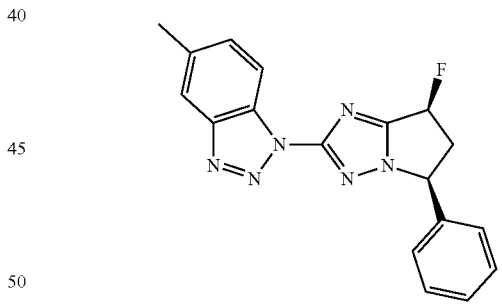

5-methyl-1-[rac-(5S,7S)-7-fluoro-5-phenyl-6,7-dihydro-5H-pyrrolo[1,2-b][1,2,4]triazol-2-yl]benzotriazole (16 mg, 17% yield). H NMR (400 MHz, DMSO-d$_6$) δ 8.08 (dd, J=10.3, 8.4 Hz, 1H), 7.99 (dq, J=9.6, 1.2 Hz, 1H), 7.65-7.32 (m, 6H), 6.36 (ddt, J=56.5, 7.3, 2.0 Hz, 1H), 5.87-5.77 (m, 1H), 3.79 (dddd, J=25.0, 15.5, 8.4, 7.2, 1.3 Hz, 1H), 2.82-2.66 (m, 1H), 2.55 (d, J=0.9 Hz, 3H). LC-MS $R_T$=5.78 min, m/z=335.2 (M+H)$^+$.

LCMS (5 to 95% acetonitrile in water+0.1% formic acid over 10 mins) retention time 5.78 min, ESI+ found [M+H]=335.2

Example 89: Method 47

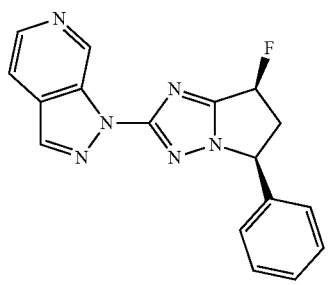 [SMILES: F[C@H]1C[C@@H](c2ccccc2)n2nc(-n3ncc4ccncc43)nc21]

1-[(5S,7S)-7-fluoro-5-phenyl-6,7-dihydro-5H-pyrrolo[1,2-b][1,2,4]triazol-2-yl]pyrazolo[4,3-c]pyridine (46 mg, 50% yield). $^1$H NMR (400 MHz, DMSO-d6) δ 9.23 (d, J=1.2 Hz, 1H), 8.65 (d, J=0.9 Hz, 1H), 8.58 (d, J=5.9 Hz, 1H), 8.15 (dt, J=6.0, 1.1 Hz, 1H), 7.51-7.36 (m, 3H), 7.36-7.29 (m, 2H), 6.32 (ddd, J=56.7, 7.2, 1.9 Hz, 1H), 5.76 (td, J=7.9, 3.0 Hz, 1H), 3.76 (dddd, J=25.3, 15.4, 8.4, 7.2 Hz, 1H), 2.84-2.58 (m, 1H). LC-MS $R_T$=3.13 min, m/z=321.2 (M+H)$^+$.

LCMS (5 to 95% acetonitrile in water+0.1% formic acid over 10 mins) retention time 3.13 min, ESI+ found [M+H]=321.2

Example 90: Method 47

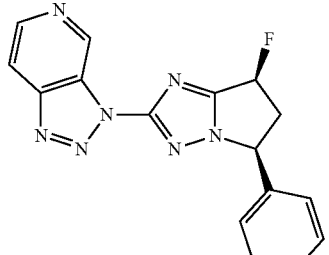

1-[(5S,7S)-7-fluoro-5-phenyl-6,7-dihydro-5H-pyrrolo[1,2-b][1,2,4]triazol-2-yl]triazolo[4,5-c]pyridine (3 mg, 2% yield). LC-MS $R_T$=4.36 min, m/z=322.1 (M+H)$^+$.

LCMS (5 to 95% acetonitrile in water+0.1% formic acid over 10 mins) retention time 4.36 min, ESI+ found [M+H]=322.1

Example 91: Method 47

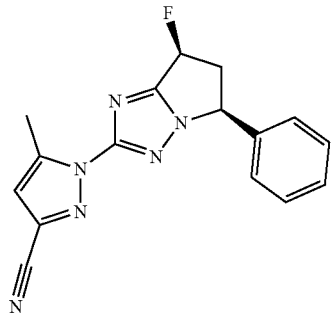 [SMILES: Cc1cc(C#N)nn1-c1nc2n(n1)[C@H](c1ccccc1)C[C@@H]2F]

1-[(5S,7S)-7-fluoro-5-phenyl-6,7-dihydro-5H-pyrrolo[1,2-b][1,2,4]triazol-2-yl]-5-methyl-pyrazole-3-carbonitrile (7 mg, 5% yield). $^1$H NMR (500 MHz, DMSO-d6) δ 7.47-7.41 (m, 2H), 7.41-7.35 (m, 1H), 7.32-7.26 (m, 2H), 7.03 (d, J=0.8 Hz, 1H), 6.30 (ddd, J=56.4, 7.2, 1.9 Hz, 1H), 5.76 (td, J=8.1, 3.0 Hz, 1H), 3.82-3.66 (m, 1H), 2.75-2.63 (m, 1H), 2.47 (d, J=0.6 Hz, 3H). LC-MS $R_T$=5.05 min, m/z=309.1 (M+H)$^+$.

LCMS (5 to 95% acetonitrile in water+0.1% formic acid over 10 mins) retention time 5.05 min, ESI+ found [M+H]=309.1

Example 92: Method 49

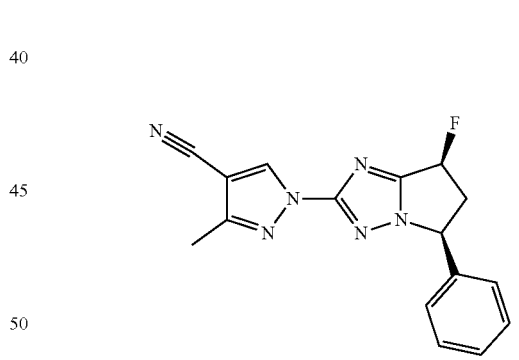

1-[(5S,7S)-7-fluoro-5-phenyl-6,7-dihydro-5H-pyrrolo[1,2-b][1,2,4]triazol-2-yl]-3-methyl-pyrazole-4-carbonitrile (10 mg, 35% yield). $^1$H NMR (400 MHz, DMSO-d6) δ 9.14 (s, 1H), 7.48-7.34 (m, 3H), 7.33-7.25 (m, 2H), 6.26 (ddd, J=56.5, 7.2, 2.0 Hz, 1H), 5.69 (td, J=8.0, 3.1 Hz, 1H), 3.72 (dddd, J=24.9, 15.5, 8.3, 7.2 Hz, 1H), 2.67 (dddd, J=27.0, 15.2, 3.1, 2.0 Hz, 1H), 2.36 (s, 3H). LC-MS $R_T$=4.99 min, m/z=309.1 (M+H)$^+$.

LCMS (5 to 95% acetonitrile in water+0.1% formic acid over 10 mins) retention time 4.99 min, ESI+ found [M+H]=309.1

Example 93: Method 49

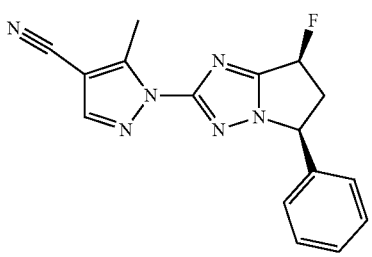 [SMILES: Cc1c(C#N)cnn1-c1nc2n(n1)[C@H](c1ccccc1)C[C@@H]2F]

1-[(5S,7S)-7-fluoro-5-phenyl-6,7-dihydro-5H-pyr-rolo[1,2-b][1,2,4]triazol-2-yl]-5-methyl-pyrazole-4-carbonitrile (8 mg, 29% yield). $^1$H NMR (400 MHz, DMSO-d6) δ 8.25 (s, 1H), 7.48-7.34 (m, 3H), 7.33-7.21 (m, 2H), 6.29 (ddd, J=56.4, 7.2, 2.0 Hz, 1H), 5.75 (ddd, J=8.3, 7.2, 3.1 Hz, 1H), 3.73 (dddd, J=25.2, 15.4, 8.4, 7.2 Hz, 1H), 2.76-2.61 (m, 1H), 2.59 (s, 3H). LC-MS $R_T$=4.91 min, m/z=309.1 (M+H)$^+$.

LCMS (5 to 95% acetonitrile in water+0.1% formic acid over 10 mins) retention time 4.91 min, ESI+ found [M+H]=309.1

Example 94: Method 34

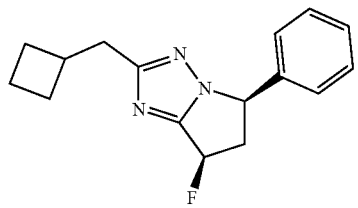 [SMILES: F[C@@H]1C[C@H](c2ccccc2)n2nc(CC3CCC3)nc21]

(5S,7S)-2-(cyclobutylmethyl)-7-fluoro-5-phenyl-6,7-dihydro-5H-pyrrolo[1,2-b][1,2,4]triazole (16.9 mg, 63% yield). 1H NMR (400 MHz, DMSO-d6) δ 7.50-7.29 (m, 3H), 7.25-7.10 (m, 2H), 6.09 (ddd, J=57.1, 7.1, 1.7 Hz, 1H), 5.54 (ddd, J=8.4, 7.1, 2.8 Hz, 1H), 4.09 (d, J=5.4 Hz, 1H), 3.64 (dddd, J=26.7, 15.3, 8.4, 7.0 Hz, 1H), 3.17 (d, J=4.0 Hz, 1H), 2.78-2.55 (m, 3H), 2.05-1.96 (m, 1H), 1.88-1.62 (m, 3H), 1.06 (t, J=6.4 Hz, 1H). LC-MS $R_T$=5.08 min, m/z=272.1 (M+H)$^+$.

LCMS (5 to 95% acetonitrile in water+0.1% formic acid over 10 mins) retention time 4.91 min, ESI+ found [M+H]=309.1

Example 95 and 96: Method 51

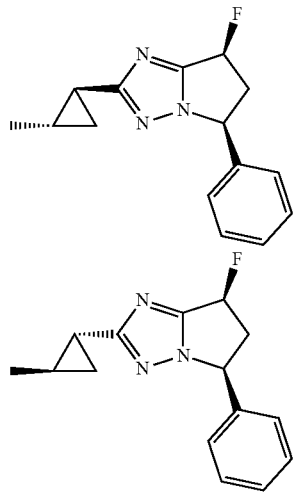

(5S,7S)-7-fluoro-5-phenyl-2-[(1S,2S)-2-methylcyclopropyl]-6,7-dihydro-5H-pyrrolo[1,2-b][1,2,4]triazole and (5S,7S)-7-fluoro-5-phenyl-2-[(1R,2R)-2-methylcyclopropyl]-6,7-dihydro-5H-pyrrolo[1,2-b][1,2,4]triazole Step 1: 4,4,5,5-tetramethyl-2-[(1R,2R)-2-methylcyclopropyl]-1,3,2-dioxaborolane To a solution of diethylzinc (23.8 mL, 23.8 mmol, 1 M in toluene) in dichloromethane (10 mL) was added a solution of trifluoroacetic acid (2714 mg, 23.8 mmol) in dichloromethane (2 mL), followed by a solution of diiodomethane (1.92 mL, 23.8 mmol) in dichloromethane (2 mL). After stirring for 1 h at 0° C., the mixture was added a solution of 4,4,5,5-tetramethyl-2-[(1E)-prop-1-en-1-yl]-1,3,2-dioxaborolane (1000 mg, 11.9 mmol) in dichloromethane (2 mL). The reaction mixture was stirred for 16 h at 25° C. and quenched by addition of saturated aqueous ammonium chloride (50 mL). The mixture was extracted with petroleum ether (3×50 mL). The combined organic layers were washed with brine (50 mL), dried over sodium sulfate and concentrated under reduced pressure to afford crude 4,4,5,5-tetramethyl-2-[trans-2-methylcyclopropyl]-1,3,2-dioxaborolane (2000 mg, 92%) as a yellow oil. $^1$H NMR (400 MHz, CDCl$_3$) δ 1.25 (s, 12H), 1.12-1.11 (m, 3H), 1.02-0.94 (m, 1H), 0.75-0.66 (m, 1H), 0.44-0.35 (m, 1H), −0.39--0.44 (m, 1H).

Step 2: potassium trifluoro-[trans-2-methylcyclopropyl]boranuide

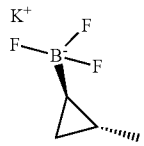

To a solution of 4,4,5,5-tetramethyl-2-[trans-2-methylcyclopropyl]-1,3,2-dioxaborolane (1000 mg, 5.49 mmol) in methanol (10 mL) was added a solution of potassium bifluoride (3002 mg, 38.45 mmol) in water (1 mL). The mixture was stirred at 25° C. for 16 h and concentrated under reduced pressure. The residue was diluted with acetonitrile (5 mL) and filtered. The solid was washed with petroleum ether (20 mL) to give crude potassium trifluoro-[trans-2-methylcyclopropyl]boranuide (500 mg, 56%) as a white powder. $^1$H NMR (400 MHz, DMSO-$d_6$) δ 0.91 (d, J=6.0 Hz, 3H), 0.30-0.22 (m, 1H), 0.00--0.03 (m, 1H), -0.38-- 0.40 (m, 1H), -1.01--1.12 (m, 1H).

Step 3: (5S,7S)-7-fluoro-5-phenyl-2-[(1S,2S)-2-methylcyclopropyl]-6,7-dihydro-5H-pyrrolo[1,2-b][1,2,4]triazole and (5S,7S)-7-fluoro-5-phenyl-2-[(1R,2R)-2-methylcyclopropyl]-6,7-dihydro-5H-pyrrolo[1,2-b][1,2,4]triazole A mixture of (5S,7S)-2-bromo-7-fluoro-5-phenyl-6,7-dihydro-5H-pyrrolo[1,2-b][1,2,4]triazole (100 mg, 0.35 mmol), cesium carbonate (346 mg, 1.06 mmol), potassium trifluoro-[trans-2-methylcyclopropyl]boranuide (248 mg, 1.53 mmol) and (2-dicyclohexylphosphino-2',6'-diisopropoxy-1,1'-biphenyl)[2-(2'-amino-1,1'-biphenyl)]palladium(ii) methanesulfonate (30 mg, 0.04 mmol) in 1,4-dioxane (1 mL) and water (0.20 mL) was stirred at 110° C. for 3 h under microwave and then concentrated under reduced pressure. The residue was first purified by preparative TLC (20% ethyl acetate in petroleum ether, $R_f$=0.4), and then by RP-HPLC (acetonitrile 39-29/0.05% HCl in water) to afford (5S,7S)-7-fluoro-2-[trans-2-methylcyclopropyl]-5-phenyl-6,7-dihydro-5H-pyrrolo[1,2-b][1,2,4]triazole (15 mg, 16%) as a white solid. LCMS $R_T$=3.594 min, m/z=258.3 [M+H]$^+$.

LCMS (10 to 80% acetonitrile in water+0.03% trifluoacetic acid over 7 mins) retention time 3.594 min, ESI+ found [M+H]=258.3.

The material combined from several parallel batches (100 mg) was further separated by chiral SFC to give arbitrarily assigned.

(5S,7S)-7-fluoro-2-[(1S,2S)-2-methylcyclopropyl]-5-phenyl-6,7-dihydro-5H-pyrrolo [1,2-b][1,2,4]triazole (Peak 1, retention time=3.129 min) (23.8 mg, 24%) as a white solid. $^1$H NMR (400 MHz, CD$_3$OD) δ 7.44-7.30 (m, 3H), 7.22-7.20 (m, 2H), 6.06-5.87 (m, 1H), 5.47-5.42 (m, 1H), 3.73-3.58 (m, 1H), 2.75-2.60 (m, 1H), 1.73-1.68 (m, 1H), 1.32-1.24 (m, 1H), 1.16 (d, J=6.0 Hz, 3H), 1.15-1.09 (m, 1H), 0.82-0.74 (m, 1H). LCMS $R_T$=0.858 min, m/z=258.0 [M+H]$^+$.

LCMS (5 to 95% acetonitrile in water+0.03% trifluoacetic acid over 1.5 mins) retention time 0.858 min, ESI+ found [M+H]=258.0.

(5S,7S)-7-fluoro-2-[(1R,2R)-2-methylcyclopropyl]-5-phenyl-6,7-dihydro-5H-pyrrolo[1,2-b][1,2,4]triazole (Peak 2, retention time=3.907 min) (28.2 mg, 27%) as a white solid. $^1$H NMR (400 MHz, CD$_3$OD) δ 7.47-7.30 (m, 3H), 7.25-7.17 (m, 2H), 6.07-5.86 (m, 1H), 5.46-5.42 (m, 1H), 3.74-3.60 (m, 1H), 2.75-2.59 (m, 1H), 1.73-1.68 (m, 1H), 1.34-1.29 (m, 1H), 1.16 (d, J=6.0 Hz, 3H), 1.12-1.08 (m, 1H), 0.79-0.74 (m, 1H). LCMS $R_T$=0.851 min, m/z=258.0 [M+H]$^+$.

LCMS (5 to 95% acetonitrile in water+0.03% trifluoacetic acid over 1.5 mins) retention time 0.858 min, ESI+ found [M+H]=258.0.

SFC condition: Column: Chiralpak AD—250×30 mm I.D., 5 um; Mobile phase: A: CO$_2$ B: IPA (0.05% DEA); Gradient: from 25% to 25% of B in 3.5 min and hold 40% for 2.5 min, then 5% of B for 1.5 min; Flow rate: 50m/min; Column temp: 40° C.

Example 97: Method 52

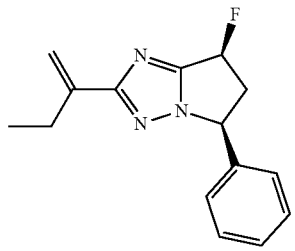 [SMILES: C=C(CC)c1nc2n(n1)[C@H](c1ccccc1)C[C@@H]2F]

(5S,7S)-7-fluoro-2-(1-methylenepropyl)-5-phenyl-6,7-dihydro-5H-pyrrolo[1,2-b][1,2,4]triazole Step 1: potassium trifluoro-(1-methylcyclopropyl)boranuide

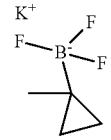

To a solution of 4,4,5,5-tetramethyl-2-(1-methylcyclopropyl)-1,3,2-dioxaborolane (500 mg, 2.75 mmol) in methanol (5 mL) was added a solution of potassium bifluoride (1501 mg, 19.22 mmol) in water (0.5 mL). The mixture was stirred at 25° C. for 16 h and concentrated under reduced pressure. The residue was diluted with acetonitrile (5 mL) and filtered. The solid was washed with petroleum ether (20 mL) to give crude potassium trifluoro-(1-methylcyclopropyl)boranuide (300 mg, 67%) as a white powder. $^1$H NMR (400 MHz, DMSO-d6) δ 0.74 (s, 3H), 0.03-0.03 (m, 2H), -0.42--0.44 (m, 2H).

Step 2: (5S,7S)-7-fluoro-2-(1-methylenepropyl)-5-phenyl-6,7-dihydro-5H-pyrrolo[1,2-b][1,2,4]triazole

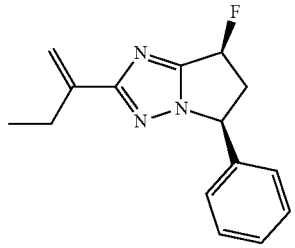 [SMILES: C=C(CC)c1nc2n(n1)[C@H](c1ccccc1)C[C@@H]2F]

A mixture of (5S,7S)-2-bromo-7-fluoro-5-phenyl-6,7-dihydro-5H-pyrrolo[1,2-b][1,2,4]triazole (150 mg, 0.53 mmol), cesium carbonate (520 mg, 1.60 mmol), potassium trifluoro-(1-methylcyclopropyl)boranuide (290 mg, 1.79 mmol) and (2-dicyclohexylphosphino-2',6'-diisopropoxy-1, 1'-biphenyl)[2-(2'-amino-1,1'-biphenyl)]palladium(ii) methanesulfonate (44 mg, 0.05 mmol) in 1,4-dioxane (1 mL) and water (0.20 mL) was stirred at 110° C. for 3 h under microwave and concentrated under reduced pressure. The residue was first purified by preparative TLC (20% ethyl acetate in petroleum ether, $R_f$=0.4), then by RP-HPLC (acetonitrile 40-70/0.05% HCl in water) to afford (5S,7S)-7-fluoro-2-(1-methylenepropyl)-5-phenyl-6,7-dihydro-5H-pyrrolo[1,2-b][1,2,4]triazole (1.6 mg, 1%) as a white solid. $^1$H NMR (400 MHz, CD$_3$OD) δ 7.44-7.33 (m, 3H), 7.26-7.22 (m, 2H), 6.15-6.11 (m, 1H), 6.00-5.98 (m, 1H), 5.58-5.50 (m, 1H), 5.32 (s, 1H), 3.79-3.64 (m, 1H), 2.80-2.67 (m, 1H), 2.51 (q, J=7.6 Hz, 2H), 1.13 (t, J=7.6 Hz, 3H). LCMS $R_T$=0.890 min, m/z=257.9 [M+H]$^+$.

LCMS (10 to 80% acetonitrile in water+0.03% trifluoacetic acid over 2 mins) retention time 0.890 min, ESI+ found [M+H]=257.9.

Example 98: Method 53

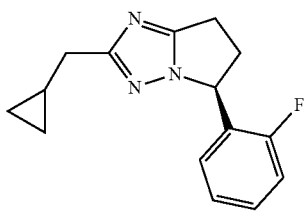 [SMILES: Fc1ccccc1[C@@H]1CCc2nc(CC3CC3)nn21]

(5)-2-(cyclopropylmethyl)-5-(2-fluorophenyl)-6,7-dihydro-5H-pyrrolo[1,2-b][1,2,4]triazole Step 1: cyclopropyl-[(5S)-5-(2-fluorophenyl)-6,7-dihydro-5H-pyrrolo[1,2-b][1,2,4]triazol-2-yl]methanol

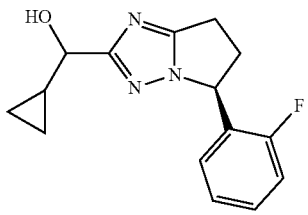 [SMILES: OC(c1nc2n(n1)[C@H](c1ccccc1F)CC2)C1CC1]

To a solution of cyclopropyl-[(5S)-5-(2-fluorophenyl)-6,7-dihydro-5H-pyrrolo[1,2-b][1,2,4]triazol-2-yl]methanone (117 mg, 0.43 mmol) in methanol (2 mL) was added sodium borohydride (81 mg, 2.16 mmol) at 0° C. The mixture was stirred at 0° C. for 2 h and quenched by addition of saturated aqueous ammonium chloride (10 mL). The resulting mixture was extracted with ethyl acetate (2×15 mL). The combined organic layers were dried over sodium sulfate and concentrated under reduced pressure to afford crude cyclopropyl-[(5S)-5-(2-fluorophenyl)-6,7-dihydro-5H-pyrrolo[1,2-b][1,2,4]triazol-2-yl]methanol (116 mg, 98%) as a white solid. $^1$H NMR (400 MHz, CDCl$_3$) δ 7.34-7.27 (m, 1H), 7.13-7.05 (m, 2H), 6.93-6.87 (m, 1H), 5.67-5.61 (m, 1H), 4.13-4.05 (m, 1H), 3.29-3.18 (m, 1H), 3.11-2.93 (m, 2H), 2.65-2.55 (m, 1H), 1.41-1.32 (m, 1H), 0.65-0.36 (m, 4H).

Step 2: (5S)-2-(cyclopropylmethyl)-5-(2-fluorophenyl)-6,7-dihydro-5H-pyrrolo[1,2-b][1,2,4]triazole

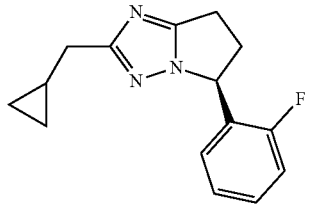 [SMILES: Fc1ccccc1[C@@H]1CCc2nc(CC3CC3)nn21]

To a solution of cyclopropyl-[(5S)-5-(2-fluorophenyl)-6,7-dihydro-5H-pyrrolo[1,2-b][1,2,4]triazol-2-yl]methanol (96 mg, 0.35 mmol) in trifluoroacetic acid (2 mL, 26.93 mmol) was added triethylsilane (2 mL, 10.54 mmol). The mixture was stirred at 50° C. for 24 h and then concentrated under reduced pressure. The residue was added saturated aqueous sodium bicarbonate (20 mL) and extracted with ethyl acetate (3×50 mL). The combined organic layers were dried over sodium sulfate and concentrated under reduced pressure. The residue was purified by column chromatography (silica gel, 100-200 mesh, 0 to 50% ethyl acetate in petroleum ether) to afford (5S)-2-(cyclopropylmethyl)-5-(2-fluorophenyl)-6,7-dihydro-5H-pyrrolo[1,2-b][1,2,4]triazole (15 mg, 16.4%) as colorless oil. $^1$H NMR (400 MHz, CD$_3$OD) δ 7.43-7.36 (m, 1H), 7.22-7.12 (m, 2H), 7.12-7.06 (m, 1H), 5.72-5.65 (m, 1H), 3.30-3.22 (m, 1H), 3.14-2.97 (m, 2H), 2.68-2.59 (m, 1H), 2.59-2.55 (m, 2H), 1.14-1.03 (m, 1H), 0.52-0.46 (m, 2H), 0.23-0.18 (m, 2H). LC-MS $R_T$=0.659 min, m/z=258.1 [M+H]$^+$.

LCMS (5 to 95% acetonitrile in water+0.03% trifluoroacetic acid over 1.5 mins) retention time 0.659 min, ESI+ found [M+H]=258.1

Example 99: Method 54

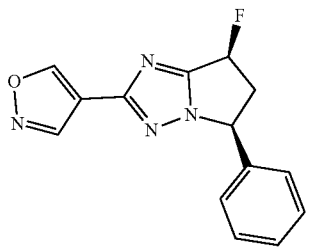 [SMILES: F[C@H]1C[C@@H](c2ccccc2)n2nc(-c3cnoc3)nc21]

4-[(5S,7S)-7-fluoro-5-phenyl-6,7-dihydro-5H-pyrrolo[1,2-b][1,2,4]triazol-2-yl]isoxazole Step 1: Potassium Trifluoro(isoxazol-4-yl)boranuide

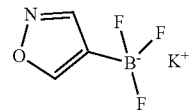

To a solution of isoxazole-4-boronic acid (300 mg, 2.66 mmol) in methanol (5 mL) was added a solution of potassium bifluoride (1036 mg, 13.27 mmol) in water (0.30 mL). The mixture was stirred at 25° C. for 16 h and concentrated under reduced pressure. The residue was diluted acetonitrile (5 mL). The resulting solid was collected by filtration and washed with petroleum ether (20 mL) to give crude potassium trifluoro(isoxazol-4-yl)boranuide (400 mg, 86%) as a yellow solid. $^1$H NMR (400 MHz, DMSO-d$_6$) δ 8.20 (s, 1H), 8.08 (s, 1H).

Step 2: 4-[(5S,7S)-7-fluoro-5-phenyl-6,7-dihydro-5H-pyrrolo[1,2-b][1,2,4]triazol-2-yl]isoxazole

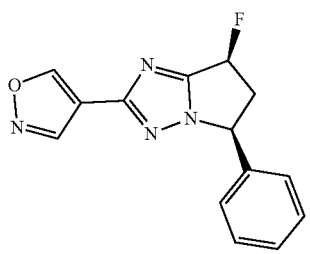 [SMILES: F[C@H]1C[C@@H](c2ccccc2)n2nc(-c3cnoc3)nc21]

A mixture of (5S,7S)-2-bromo-7-fluoro-5-phenyl-6,7-dihydro-5H-pyrrolo[1,2-b][1,2,4]triazole (80 mg, 0.28 mmol), (2-dicyclohexylphosphino-2',6'-diisopropoxy-1,1'-biphenyl)[2-(2'-amino-1,1'-biphenyl)]palladium(ii) methanesulfonate (47 mg, 0.06 mmol), potassium trifluoro(isoxazol-4-yl)boranuide (151 mg, 0.86 mmol) and sodium carbonate (90 mg, 0.85 mmol) in ethanol (3 mL) was stirred at 80° C. for 1 h under microwave conditions and then concentrated under reduced pressure. The residue was purified by RP-HPLC (acetonitrile 35-55%/10 mM ammonium bicarbonate in water) to afford 4-[(5S,7S)-7-fluoro-5-phenyl-6,7-dihydro-5H-pyrrolo[1,2-b][1,2,4]triazol-2-yl]isoxazole (3.4 mg, 4%) as a white solid. $^1$H NMR (400 MHz, CD$_3$OD) δ 9.20 (s, 1H), 8.82 (s, 1H), 7.44-7.37 (m, 3H), 7.29-7.28 (m, 2H), 6.19-6.01 (m, 1H), 5.61-5.56 (m, 1H), 3.82-3.68 (m, 1H), 2.85-2.72 (m, 1H) LCMS R$_T$=0.828 min, m/z=270.9 [M+H]$^+$.

LCMS (10 to 80% acetonitrile in water+0.03% trifluoacetic acid over 7 mins) retention time 0.828 min, ESI+ found [M+H]=270.9.

Example 100: Method 55

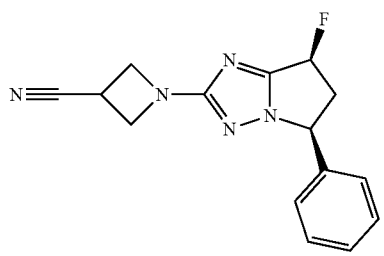 [SMILES: N#CC1CN(c2nc3n(n2)[C@H](c2ccccc2)C[C@@H]3F)C1]

1-[(5S,7S)-7-fluoro-5-phenyl-6,7-dihydro-5H-pyrrolo[1,2-b][1,2,4]triazol-2-yl]azetidine-3-carbonitrile A mixture of (5S,7S)-2-bromo-7-fluoro-5-phenyl-6,7-dihydro-5H-pyrrolo[1,2-b][1,2,4]triazole (200 mg, 0.71 mmol), [2-(2-aminophenyl)phenyl]palladium; dicyclohexyl-[2-(2,4,6-triisopropylphenyl)phenyl]phosphane; methanesulfonate (60 mg, 0.07 mmol), cesiumcarbonate (693 mg, 2.13 mmol) and azetidine-3-carbonitrile hydrochloride (168 mg, 1.42 mmol) was stirred at 90° C. for 16 h under nitrogen atmosphere. The mixture was quenched by addition of saturated aqueous ammonium chloride (10 mL) and extracted with ethyl acetate (3×10 mL). The combined organics were dried over sodium sulfate and concentrated under reduced pressure. The residue was purified by RP-HPLC (acetonitrile 30-60%/0.05% ammonia hydroxide in water) to afford 1-[(5S,7S)-7-fluoro-5-phenyl-6,7-dihydro-5H-pyrrolo[1,2-b][1,2,4]triazol-2-yl]azetidine-3-carbonitrile (15.3 mg, 8%) as a red solid. $^1$H NMR (400 MHz, CDCl$_3$) δ 7.42-7.35 (m, 3H), 7.23-7.21 (m, 2H), 5.98-5.81 (m, 1H), 5.30-5.29 (m, 1H), 4.35-4.22 (m, 4H), 3.63-3.51 (m, 2H), 2.81-2.70 (m, 1H). LCMS R$_T$=1.852 min, m/z=283.9 [M+H]$^+$.

LCMS (10 to 80% acetonitrile in water+0.03% trifluoacetic acid over 7 mins) retention time 1.852 min, ESI+ found [M+H]=283.9.

Example 101: Method 56

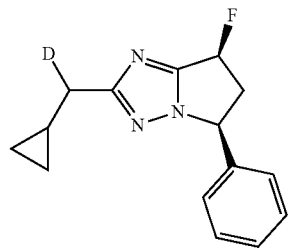 [SMILES: [2H]C(c1nc2n(n1)[C@H](c1ccccc1)C[C@@H]2F)C1CC1]

(5S,7S)-2-[cyclopropyl(deuterio)methyl]-7-fluoro-5-phenyl-6,7-dihydro-5H-pyrrolo[1,2-b][1,2,4]triazole Step 1: cyclopropyl-deuterio-[(5S,7S)-7-fluoro-5-phenyl-6,7-dihydro-5H-pyrrolo[1,2-b][1,2,4]triazol-2-yl]methanol

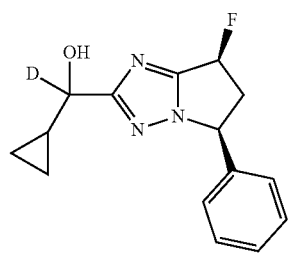

To a solution of cyclopropyl-[(5S,7S)-7-fluoro-5-phenyl-6,7-dihydro-5H-pyrrolo[1,2-b][1,2,4]triazol-2-yl]methanone (300 mg, 1.11 mmol) in methanol (10 mL) was added sodium tetradeuterioborate (93 mg, 2.21 mmol). The mixture was stirred for 1 h and quenched by addition of water (20 mL). The solution was extracted with ethyl acetate (3×20 mL). The combined organics were washed with brine (2×15 mL), dried over sodium sulfate and concentrated under reduced pressure to give crude cyclopropyl-deuterio-

[(5S,7S)-7-fluoro-5-phenyl-6,7-dihydro-5H-pyrrolo[1,2-b][1,2,4]triazol-2-yl]methanol (265 mg, 87%) as a white solid.

Step 2: (5S,7S)-2-[cyclopropyl(deuterio)methyl]-7-fluoro-5-phenyl-6,7-dihydro-5H-pyrrolo[1,2-b][1,2,4]triazole

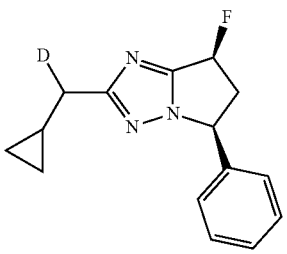 [SMILES: [2H]C(c1nc2n(n1)[C@H](c1ccccc1)C[C@@H]2F)C1CC1]

To a solution of cyclopropyl-deuterio-[(5S,7S)-7-fluoro-5-phenyl-6,7-dihydro-5H-pyrrolo[1,2-b][1,2,4]triazol-2-yl]methanol (265 mg, 0.97 mmol) in trifluoroacetic acid (2.0 mL, 26.93 mmol) was added triethylsilane (2.0 mL, 12.50 mmol). The mixture was stirred at 50° C. for 12 h and concentrated under reduced pressure. The residue was diluted with saturated aqueous sodium bicarbonate (10 mL) and extracted with ethyl acetate (10 mL). The separated organic layer was dried over sodium sulfate and concentrated under reduced pressure. The residue was purified by RP-HPLC (acetonitrile 40-70%/0.05% ammonia hydroxide in water) to afford (5S,7S)-2-[cyclopropyl(deuterio)methyl]-7-fluoro-5-phenyl-6,7-dihydro-5H-pyrrolo[1,2-b][1,2,4]triazole (111.4 mg, 44%) as a white solid. $^1$H NMR (400 MHz, CDCl$_3$) $^1$H NMR (400 MHz, CDCl$_3$) δ 7.40-7.35 (m, 3H), 7.23-7.21 (m, 2H), 6.05-6.03 (m, 0.5H), 5.91-5.88 (m, 0.5H), 5.40-5.37 (m, 1H), 3.60-3.54 (m, 1H), 2.89-2.79 (m, 1H), 2.68-2.63 (m, 1H), 1.16-1.13 (m, 1H), 0.56-0.50 (m, 2H), 0.26-0.23 (m, 2H). LCMS R$_T$=1.712 min, m/z=259.2 [M+H]$^+$.

LCMS (10 to 80% acetonitrile in water+0.1% ammonia water over 3.0 mins) retention time 1.712 min, ESI+ found [M+H]=259.2.

Example 102: Method 57

2-[rac-(5S,7S)-7-fluoro-5-phenyl-6,7-dihydro-5H-pyrrolo[1,2-b][1,2,4]triazol-2-yl]acetonitrile Step 1: [cis-7-fluoro-5-phenyl-6,7-dihydro-5H-pyrrolo[1,2-b][1,2,4]triazol-2-yl]methanol

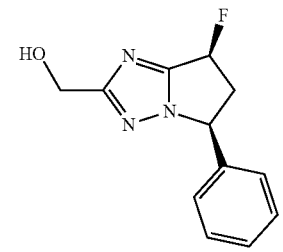 [SMILES: OCc1nc2n(n1)[C@H](c1ccccc1)C[C@@H]2F]

To a solution of cis-7-fluoro-N-methoxy-N-methyl-5-phenyl-6,7-dihydro-5H-pyrrolo[1,2-b][1,2,4]triazole-2-carboxamide (3.00 g, 103.3 mmol) in methanol (70 mL) at 0° C. was added sodium borohydride (1.95 g, 51.7 mmol). The mixture was stirred at 0° C. for 2 h and quenched by addition of water (100 mL). The resulting mixture extracted with ethyl acetate (2×100 mL). The combined organic layers were dried over sodium sulfate and concentrated under reduced pressure to give crude [cis-7-fluoro-5-phenyl-6,7-dihydro-5H-pyrrolo[1,2-b][1,2,4]triazol-2-yl]methanol (2.0 g, 83%) as a white solid.

Step 2: [cis-7-fluoro-5-phenyl-6,7-dihydro-5H-pyrrolo[1,2-b][1,2,4]triazol-2-yl]methyl 4-methylbenzenesulfonate

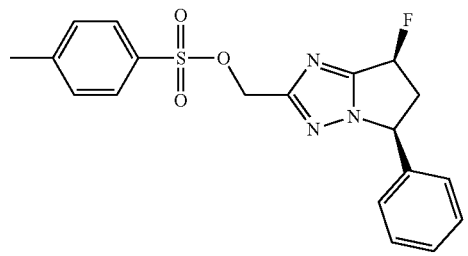 [SMILES: Cc1ccc(S(=O)(=O)OCc2nc3n(n2)[C@H](c2ccccc2)C[C@@H]3F)cc1]

To a solution of [cis-7-fluoro-5-phenyl-6,7-dihydro-5H-pyrrolo[1,2-b][1,2,4]triazol-2-yl]methanol (2.0 g, 8.57 mmol) in tetrahydrofuran (24 mL) was added sodium hydride (60% in mineral oil, 515 mg, 12.86 mmol) and then p-toluenesulfonic acid (1500 mg, 8.57 mmol). The reaction was stirred at 25° C. for 12 h and quenched by addition of water (15 mL). The resulting mixture extracted with ethyl acetate (3×25 mL). The combined organic layers were dried over sodium sulfate and concentrated under reduced pressure. The residue was purified by column chromatography (silica gel, 100-200 mesh, 0 to 40% ethyl acetate in petroleum ether) to afford [cis-7-fluoro-5-phenyl-6,7-dihydro-5H-pyrrolo[1,2-b][1,2,4]triazol-2-yl]methyl 4-methylbenzene sulfonate (1.8 g, 54%) as colorless oil.

Step 3: 2-[rac-(5S,7S)-7-fluoro-5-phenyl-6,7-dihydro-5H-pyrrolo[1,2-b][1,2,4]triazol-2-yl]acetonitrile

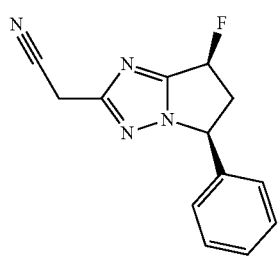

To a solution of [cis-7-fluoro-5-phenyl-6,7-dihydro-5H-pyrrolo[1,2-b][1,2,4]triazol-2-yl]methyl 4-methylbenzenesulfonate (700 mg, 1.81 mmol) in dimethyl sulfoxide (20 mL) was added sodium cyanide (620 mg, 12.65 mmol). The mixture was stirred at 90° C. for 2 h and cooled to 20° C. The mixture was diluted with water (50 mL) and extracted with ethyl acetate (2×20 mL). The combined organic layers were washed with brine (20 mL), dried over sodium sulfate and concentrated under reduced pressure. The residue was purified by preparative TLC (50% ethyl acetate in petroleum ether, $R_f$=0.6) to afford crude 2-[rac-(5S,7S)-7-fluoro-5-phenyl-6,7-dihydro-5H-pyrrolo[1,2-b][1,2,4]triazol-2-yl]acetonitrile (360 mg, 82%, 80% purity). A portion of this crude was further purified by RP-HPLC (30-60% acetonitrile in water (0.05% ammonia hydroxide v/v)) to give 2-[rac-(5S,7S)-7-fluoro-5-phenyl-6,7-dihydro-5H-pyrrolo[1,2-b][1,2,4]triazol-2-yl]acetonitrile (26.9 mg, 53%) as colorless oil. $^1$H NMR (400 MHz, CD$_3$OD) δ 7.43-7.36 (m, 3H), 7.26-7.23 (m, 2H), 6.13-6.10 (m, 0.5H), 5.99-5.96 (m, 0.5H), 5.56-5.51 (m, 1H), 3.74-3.67 (m, 1H), 3.33-3.32 (m, 2H), 2.81-2.70 (m, 1H). LCMS $R_T$=0.870 min, m/z=243.2 [M+H]$^+$.

LCMS (5 to 95% acetonitrile in water+0.03% trifluoacetic acid over 2.0 mins) retention time 0.870 min, ESI+ found [M+H]=243.2.

Example 103: Method 58

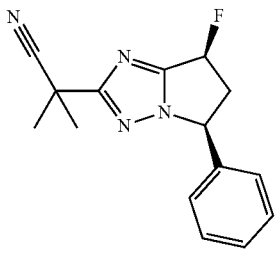 [SMILES: CC(C)(C#N)c1nc2n(n1)[C@H](c1ccccc1)C[C@@H]2F]

2-[rac-(5S,7S)-7-fluoro-5-phenyl-6,7-dihydro-5H-pyrrolo[1,2-b][1,2,4]triazol-2-yl]-2-methyl-propanenitrile To a solution of 2-[cis-7-fluoro-5-phenyl-6,7-dihydro-5H-pyrrolo[1,2-b][1,2,4]triazol-2-yl]acetonitrile (80 mg, 0.33 mmol) in N,N-dimethylformamide (2 mL) was added sodium hydride (60% in mineral oil, 30 mg, 0.74 mmol) at 0° C., followed by iodomethane (0.09 mL, 1.49 mmol). The mixture was stirred at 25° C. for 1 h and quenched by addition of water (10 mL). The mixture was extracted with ethyl acetate (3×5 mL). The combined organic layers were dried over sodium sulfate and concentrated under reduced pressure. The residue was purified by preparative TLC (30% ethyl acetate in petroleum ether, $R_f$=0.7) to afford 2-[rac-(5S,7S)-7-fluoro-5-phenyl-6,7-dihydro-5H-pyrrolo[1,2-b][1,2,4]triazol-2-yl]-2-methyl-propanenitrile (11 mg, 11%) as a white solid. $^1$H NMR (400 MHz, CD$_3$OD) δ 7.42-7.36 (m, 3H), 7.26-7.23 (m, 2H), 6.13-6.10 (m, 0.5H), 5.99-5.96 (m, 0.5H), 5.55-5.51 (m, 1H), 3.74-3.65 (m, 1H), 2.81-2.73 (m, 1H), 1.76 (s, 6H). LCMS $R_T$=0.999 min, m/z=271.2 [M+H]$^+$.

LCMS (10 to 80% acetonitrile in water+0.03% trifluoacetic acid over 2.0 mins) retention time 0.999 min, ESI+ found [M+H]=271.2.

Example 104: Method 59

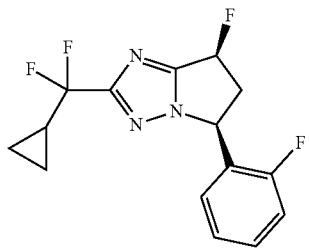 [SMILES: Fc1ccccc1[C@@H]1C[C@H](F)c2nc(C(F)(F)C3CC3)nn21]

(5S,7S)-2-[cyclopropyl(difluoro)methyl]-7-fluoro-5-(2-fluorophenyl)-6,7-dihydro-5H-pyrrolo[1,2-b][1,2,4]triazole Step 1: cyclopropyl-[(5S,7S)-7-fluoro-5-(2-fluorophenyl)-6,7-dihydro-5H-pyrrolo[1,2-b][1,2,4]triazol-2-yl]methanone

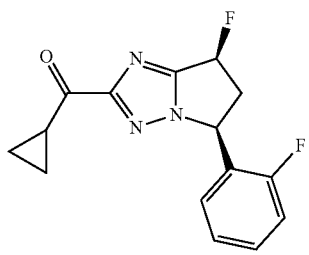 [SMILES: O=C(c1nc2n(n1)[C@H](c1ccccc1F)C[C@@H]2F)C1CC1]

To a solution of (5S,7S)-2-bromo-7-fluoro-5-(2-fluorophenyl)-6,7-dihydro-5H-pyrrolo[1,2-b][1,2,4]triazole (500 mg, 1.67 mmol) and N-methoxy-N-methyl-cyclopropanecarboxamide (430 mg, 3.33 mmol) in tetrahydrofuran (10 mL) was added isopropylmagnesium chloride (2.0 M in tetrahydrofuran, 4.2 mL, 8.4 mmol) at 0° C. under nitrogen atmosphere. The reaction mixture was stirred at 0'C for 2 h and then quenched by addition of water (10 mL). The mixture was extracted with ether acetate (3×10 mL). The combined organic layers were dried over sodium sulfate and concentrated under reduced pressure to afford crude cyclopropyl-[(5S,7S)-7-fluoro-5-(2-fluorophenyl)-6,7-dihydro-5H-pyrrolo[1,2-b][1,2,4]triazol-2-yl]methanone (350 mg, 72%) as green oil.

Step 2: (5S,7S)-2-(2-cyclopropyl-1,3-dithiolan-2-yl)-7-fluoro-5-(2-fluorophenyl)-6,7-dihydro-5H-pyrrolo[1,2-b][1,2,4]triazole

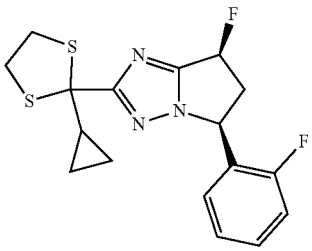 [SMILES: Fc1ccccc1[C@@H]1C[C@H](F)c2nc(C3(C4CC4)SCCS3)nn21]

To s solution of cyclopropyl-[(5S,7S)-7-fluoro-5-(2-fluorophenyl)-6,7-dihydro-5H-pyrrolo[1,2-b][1,2,4]triazol-2-yl]methanone (250 mg, 0.86 mmol) in dichloromethane (10 mL) was added 1,2-ethanedithiol (0.30 mL, 3.46 mmol) and boron trifluoride diethyl etherate (0.12 mL, 0.95 mmol) at 0° C. The reaction mixture was stirred at 0° C. for 4 h and then poured into water (10 mL). The resulting mixture was extracted with dichloromethane (2×15 mL). The combined organic layers were dried over sodium sulfate and concentrated under reduced pressure. The residue was purified by column chromatography (silica gel, 100-200 mesh, 0 to 30% ethyl acetate in petroleum ether) to afford 2-(2-cyclopropyl-1,3-dithiolan-2-yl)-7-fluoro-5-(2-fluorophenyl)-6,7-dihydro-5H-pyrrolo[1,2-b][1,2,4]triazole (250 mg, 79%) as a green solid.

Step 3: (5S,7S)-2-[cyclopropyl(difluoro)methyl]-7-fluoro-5(2-fluorophenyl-6,7-dihydro-5H-pyrrolo[1,2-b][1,2,4]triazole

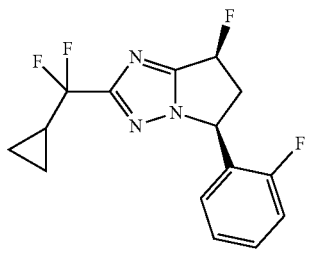 [SMILES: Fc1ccccc1[C@@H]1C[C@H](F)c2nc(C(F)(F)C3CC3)nn21]

To a solution of 1-bromo-2,5-pyrrolidinedione (134 mg, 0.75 mmol) in dichloromethane (2 mL) was added diethylaminosulfur trifluoride (0.2 mL, 1.37 mmol) at 0° C. The reaction mixture was stirred at 0° C. for 30 min and then (5S,7S)-2-(2-cyclopropyl-1,3-dithiolan-2-yl)-7-fluoro-5-(2-fluorophenyl)-6,7-dihydro-5H-pyrrolo[1,2-b][1,2,4]triazole (250 mg, 0.68 mmol) in dichloromethane (0.50 mL) was added to the reaction mixture. The resulting mixture was stirred at 0° C. for 1 h and then quenched by addition of saturated aqueous sodium bicarbonate (2 mL). The resulting mixture was extracted with dichloromethane (2×5 mL). The combined organic layers were dried over anhydrous sodium sulfate and concentrated under reduced pressure. The residue was purified by RP-HPLC (acetonitrile 57-87/0.2% formic acid in water) to afford (5S,7S)-2-[cyclopropyl(difluoro)methyl]-7-fluoro-5-(2-fluorophenyl)-6,7-dihydro-5H-pyrrolo[1,2-b][1,2,4]triazole (60.9 mg, 28%) as a white solid. $^1$H NMR (400 MHz, CD$_3$OD) δ 7.45-7.42 (m, 1H), 7.24-7.21 (m, 2H), 7.11-7.08 (m, 1H), 6.18-6.02 (m, 1H), 5.88-5.75 (m, 1H), 3.83-3.73 (m, 1H), 2.88-2.80 (m, 1H), 1.81-1.75 (m, 1H), 0.75-0.70 (m, 4H). LCMS R$_T$=0.809 min, m/z=312.1 [M+H]$^+$.

LCMS (5 to 95% acetonitrile in water+0.03% trifluoacetic acid over 1.5 mins) retention time 0.809 min, ESI+ found [M+H]=312.1.

Example 105: Method 60

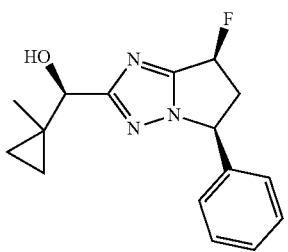 [SMILES: CC1([C@@H](O)c2nc3n(n2)[C@H](c2ccccc2)C[C@@H]3F)CC1]

(R)-(1-methylcyclopropyl)-[(5S,7S)-7-fluoro-5-phenyl-6,7-dihydro-5H-pyrrolo[1,2-b][1,2,4]triazol-2-yl]methanol Step 1: N-methoxy-N,1-dimethylcyclopropanecarboxamide

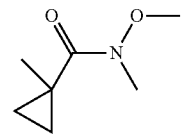

A mixture of 1-methylcyclopropanecarboxylic acid (1.0 g, 9.99 mmol), N,N-diisopropylethylamine (3.2 g, 24.97 mmol), 2-(7-azabenzotriazol-1-yl)-N,N,N',N'-tetramethyluronium hexafluorophosphate (5.7 g, 14.98 mmol) and N,O-dimethylhydroxylamine hydrochloride (2.0 g, 19.98 mmol) in N,N-dimethylformamide (20 mL) was stirred at 25° C. for 16 h and then quenched by addition of saturated ammonium chloride (30 mL). The resulting mixture was extracted with ethyl acetate (3×20 mL). The organic layers were dried over sodium sulfate and concentrated under reduced pressure. The residue was purified by column chromatography (silica gel, 100-200 mesh, 0 to 10% ethyl acetate in petroleum ether) to afford N-methoxy-N,1-dimethyl-cyclopropanecarboxamide (740 mg, 52%) as colorless oil. $^1$H NMR (400 MHz, CDCl$_3$) δ 3.71 (s, 3H), 3.22 (s, 3H), 1.35 (s, 3H), 1.04-1.01 (m, 2H), 0.56-0.53 (m, 2H). LCMS R$_T$=0.354 min, m/z=144.2 [M+H]J.

LCMS (5 to 95% acetonitrile in water+0.03% trifluoacetic acid over 1.5 mins) retention time 0.354 min, ESI+ found [M+H]=144.2.

Step 2: ((5S,7S)-7-fluoro-5-phenyl-6,7-dihydro-5H-pyrrolo[1,2-b][1,2,4]triazol-2-yl)(1-methylcyclopropyl)methanone

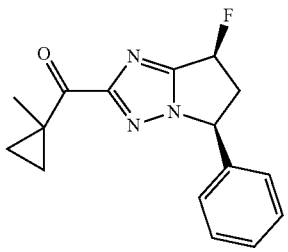 [SMILES: CC1(C(=O)c2nc3n(n2)[C@H](c2ccccc2)C[C@@H]3F)CC1]

To a solution of N-methoxy-N,1-dimethyl-cyclopropanecarboxamide (198 mg, 1.38 mmol) and (5S,7S)-2-bromo-7-fluoro-5-phenyl-6,7-dihydro-5H-pyrrolo[1,2-b][1,2,4]triazole (300 mg, 1.06 mmol) in tetrahydrofuran (2 mL) was added isopropylmagnesium chloride (2.0 M in tetrahydrofuran, 1.6 mL, 3.20 mmol) at 0° C. under nitrogen atmosphere. The mixture was stirred at 0° C. for 2 h and quenched by addition of saturated aqueous ammonium chloride (10 mL). The resulting mixture was extracted with ethyl acetate (3×10 mL). The combined organic layers were dried over sodium sulfate and concentrated under reduced pressure to afford crude [(5S,7S)-7-fluoro-5-phenyl-6,7-dihydro-5H-pyrrolo[1,2-b][1,2,4]triazol-2-yl]-(1-methyl cyclopropyl)methanone (290 mg, 96%) as a brown solid, used as is in the next step. LCMS $R_T$=0.675 min, m/z=286.2 [M+H]$^+$.

LCMS (5 to 95% acetonitrile in water+0.03% trifluoacetic acid over 1.5 mins) retention time 0.675 min, ESI+ found [M+H]=286.2.

Step 3: (R)-(1-methylcyclopropyl)-[(5S,7S)-7-fluoro-5-phenyl-6,7-dihydro-5H-pyrrolo[1,2-b][1,2,4]triazol-2-yl]methanol To a solution of [(5S,7S)-7-fluoro-5-phenyl-6,7-dihydro-5H-pyrrolo[1,2-b][1,2,4]triazol-2-yl]-(1-methylcyclopropyl)methanone (290 mg, 1.02 mmol) in methanol (10 mL) was added sodium borohydride (38 mg, 1.02 mmol) at 25° C. The mixture was stirred at 25° C. for 2 h and quenched by addition of saturated aqueous ammonium chloride (10 mL). The mixture was extracted with ethyl acetate (3×10 mL). The combined organic layers were dried over sodium sulfate and concentrated under reduced pressure. The residue was purified by RP-HPLC (acetonitrile 32-62%/0.05% ammonia hydroxide in water) to afford [(5S,7S)-7-fluoro-5-phenyl-6,7-dihydro-5H-pyrrolo[1,2-b][1,2,4]triazol-2-yl]-(1-methylcyclopropyl)methanol (60 mg, 21%) as a white solid. LCMS $R_T$=1.512 min, m/z=288.2 [M+H]$^+$.

LCMS (10 to 80% acetonitrile in water+0.1% ammonia water over 3.0 mins) retention time 1.512 min, ESI+ found [M+H]=288.2.

This material (60 mg) was further separated by chiral SFC to give arbitrarily assigned:

(R)-[(5S,7S)-7-fluoro-5-phenyl-6,7-dihydro-5H-pyrrolo[1,2-b][1,2,4]triazol-2-yl]-(1-methyl cyclopropyl)methanol (Peak 2, retention time=4.322 min) (29.7 mg, 49%) as a white solid. $^1$H NMR (400 MHz, CDCl$_3$) δ 7.42-7.36 (m, 3H), 7.21-7.19 (m, 2H), 6.07-5.90 (m, 1H), 5.45-5.41 (m, 1H), 4.30-4.28 (m, 1H), 3.68-3.53 (m, 1H), 2.91-2.76 (m, 2H), 1.07 (s, 3H), 0.82-0.78 (m, 1H), 0.64-0.60 (m, 1H), 0.44-0.37 (m, 2H). LCMS $R_T$=0.918 min, m/z=288.2 [M+H]$^+$.

LCMS (10 to 80% acetonitrile in water+0.03% trifluoacetic acid over 2 mins) retention time 0.918 min, ESI+ found [M+H]=288.2.

SFC condition: Column: Chiralpak AD-3 150×4.6 mm I.D., 3 um Mobile phase: A: CO2 B:methanol (0.05% DEA) Gradient: from 5% to 40% of B in 5 min and hold 40% for 2.5 min, then 5% of B for 2.5 min, Flow rate: 2.5 ml/min, Column temp: 40° C.

(S)-[(5S,7S)-7-fluoro-5-phenyl-6,7-dihydro-5H-pyrrolo[1,2-b][1,2,4]triazol-2-yl]-(1-methyl cyclopropyl)methanol (Peak 1, retention time=3.549 min) (27.4 mg, 42%) as a white solid. $^1$H NMR (400 MHz, CDCl$_3$) δ 7.42-7.36 (m, 3H), 7.21-7.19 (m, 2H), 6.07-5.90 (m, 1H), 5.45-5.41 (m, 1H), 4.31 (d, J=4.0 Hz, 1H), 3.68-3.53 (m, 1H), 2.91-2.82 (m, 1H), 2.68 (d, J=8.0 Hz, 1H), 1.07 (s, 3H), 0.82-0.78 (m, 1H), 0.64-0.60 (m, 1H), 0.44-0.42 (m, 2H). LCMS $R_T$=0.918 min, m/z=288.2 [M+H]$^+$.

LCMS (10 to 80% acetonitrile in water+0.03% trifluoacetic acid over 2 mins) retention time 0.918 min, ESI+ found [M+H]=288.2.

Example 106: Method 61

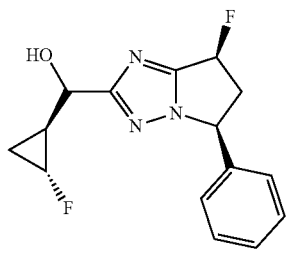 [SMILES: OC(c1nc2n(n1)[C@H](c1ccccc1)C[C@@H]2F)[C@@H]1C[C@H]1F]

[(1R,2S)-2-fluorocyclopropyl]-[(5S,7S)-7-fluoro-5-phenyl-6,7-dihydro-5H-pyrrolo[1,2-b][1,2,4]triazol-2-yl]methanol To a solution of [(1R,2S)-2-fluorocyclopropyl]-[(5S,7S)-7-fluoro-5-phenyl-6,7-dihydro-5H-pyrrolo[1,2-b][1,2,4]triazol-2-yl]methanone (110 mg, 0.38 mmol) in methanol (5 mL) was added sodium borohydride (144 mg, 3.80 mmol) at 0° C. The mixture was stirred at 25° C. for 2 h and quenched by addition of saturated aqueous ammonium chloride (10 mL). The resulting mixture was extracted with ethyl acetate (3×10 mL). The combined organic layers were dried over sodium sulfate and concentrated under reduced pressure. The residue was purified by RP-HPLC (acetonitrile 30-60/0.05% ammonia hydroxide in water) to afford [(1R,2S)-2-fluorocyclopropyl]-[(5S,7S)-7-fluoro-5-phenyl-6,7-dihydro-5H-pyrrolo[1,2-b][1,2,4]triazol-2-yl]methanol (35 mg, 31%) as a white solid. $^1$H NMR (400 MHz, CDCl$_3$) δ 7.45-7.35 (m, 3H), 7.24-7.21 (m, 2H), 6.10-5.86 (m, 1H), 5.50-5.41 (m, 1H), 4.81-4.44 (m, 2H), 3.71-3.51 (m, 1H), 2.98-2.81 (m, 1H), 2.73-2.57 (m, 1H), 1.99-1.62 (m, 1H), 1.19-1.06 (m, 1H), 0.91-0.84 (m, 1H). LCMS $R_T$=0.766 min, m/z=292.0 [M+H]$^+$.

LCMS (5 to 95% acetonitrile in water+0.03% trifluoacetic acid over 1.5 mins) retention time 0.766 min, ESI+ found [M+H]=292.0.

Example 107 and 109: Method 62

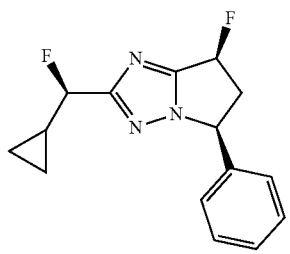

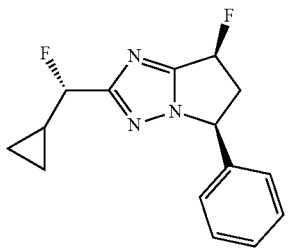

(5S,7S)-2-[(R)-cyclopropyl(fluoro)methyl]-7-fluoro-5-phenyl-6,7-dihydro-5H-pyrrolo[1,2-b][1,2,4]triazole and (5S,7S)-2-[(S)-cyclopropyl(fluoro)methyl]-7-fluoro-5-phenyl-6,7-dihydro-5H-pyrrolo[1,2-b][1,2,4]triazole To a cooled 0° C. solution of cyclopropyl-[(5S,7S)-7-fluoro-5-phenyl-6,7-dihydro-5H-pyrrolo[1,2-b][1,2,4]triazol-2-yl]methanol (180 mg, 0.66 mmol) in dichloromethane (5 mL) was added diethylaminosulfur trifluoride (0.18 mL, 1.32 mmol). The mixture was stirred at 0° C. for 0.5 h and quenched by addition of ice water (20 mL). The mixture was extracted with dichloromethane (3×10 mL). The combined organic layers were dried over sodium sulfate and concentrated under reduced pressure. The residue was purified by column chromatography (silica gel, 100-200 mesh, 0 to 25% ethyl acetate in petroleum ether) to afford (5S,7S)-2-[cyclopropyl(fluoro)methyl]-7-fluoro-5-phenyl-6,7-dihydro-5H-pyrrolo[1,2-b][1,2,4]triazole (100 mg, 55%) as a light yellow solid. This material was further purified by chiral SFC to give arbitrarily assigned:

(5S,7S)-2-[(S)-cyclopropyl(fluoro)methyl]-7-fluoro-5-phenyl-6,7-dihydro-5H-pyrrolo[1,2-b][1,2,4]triazole (Peak 1, retention time=2.921 min) (30 mg, 30%) as a white solid. $^1$H NMR (400 MHz, CDCl$_3$) δ 7.42-7.37 (m, 3H), 7.27-7.23 (m, 2H), 6.08-5.92 (m, 1H), 5.46-5.42 (m, 1H), 4.91-4.76 (m, 1H), 3.69-3.54 (m, 1H), 2.96-2.84 (m, 1H), 1.70-1.67 (m, 1H), 0.79-0.75 (m, 1H), 0.70-0.62 (m, 2H), 0.52-0.45 (m, 1H). LCMS: $R_T$=1.018 min, m/z=276.2 [M+H]$^+$.

LCMS (10 to 80% acetonitrile in water+0.03% trifluoacetic acid over 2.0 mins) retention time 1.018 min, ESI+ found [M+H]=276.2.

(5S,7S)-2-[(R)-cyclopropyl(fluoro)methyl]-7-fluoro-5-phenyl-6,7-dihydro-5H-pyrrolo[1,2-b][1,2,4]triazole (peak 2, retention time=3.924 min) (44.8 mg, 45%) as a white solid. $^1$H NMR (400 MHz, CDCl$_3$) δ 7.39-7.34 (m, 3H), 7.23-7.20 (m, 2H), 6.05-5.88 (m, 1H), 5.41-5.37 (m, 1H), 4.86-4.71 (m, 1H), 3.60-3.52 (m, 1H), 2.92-2.81 (m, 1H), 1.65-1.61 (m, 1H), 0.75-0.70 (m, 1H), 0.62-0.57 (m, 2H), 0.45-0.39 (m, 1H). $R_T$=0.764 min, m/z=276.1 [M+H]$^+$.

LCMS (5 to 95% acetonitrile in water+0.03% trifluoacetic acid over 1.5 mins) retention time 0.764 min, ESI+ found [M+H]=276.1.

SFC condition: Column: Chiralpak AD-3 150×4.6 mm I.D., 3 um Mobile phase: A: CO$_2$ B:ethanol (0.05% DEA) Gradient: from 5% to 40% of B in 5 min and hold 40% for 2.5 min, then 5% of B for 2.5 min Flow rate: 2.5 mL/min, Column temp: 35° C.

Example 108: Method 63

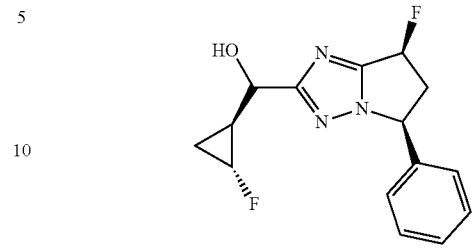

[(1S,2R)-2-fluorocyclopropyl]-[(5S,7S)-7-fluoro-5-phenyl-6,7-dihydro-5H-pyrrolo[1,2-b][1,2,4]triazol-2-yl]methanol To a solution of [(1S,2R)-2-fluorocyclopropyl]-[(5S,7S)-7-fluoro-5-phenyl-6,7-dihydro-5H-pyrrolo[1,2-b][1,2,4]triazol-2-yl]methanone (300 mg, 1.0 mmol) in methanol (10 mL) was added sodium borohydride (196 mg, 5.2 mmol) at 25° C. The mixture was stirred at 25° C. for 2 h and quenched by addition of saturated aqueous ammonium chloride (10 mL). The resulting mixture was extracted with ethyl acetate (3×10 mL). The combined organic layers were dried over sodium sulfate and concentrated under reduced pressure. The residue was purified by RP-HPLC (acetonitrile 25-50/0.05% ammonia hydroxide in water) to afford [(1S,2R)-2-fluorocyclopropyl]-[(5S,7S)-7-fluoro-5-phenyl-6,7-dihydro-5H-pyrrolo[1,2-b][1,2,4]triazol-2-yl]methanol (240 mg, 79%) as a white solid. $^1$H NMR (400 MHz, CDCl$_3$) δ 7.43-7.33 (m, 3H), 7.25-7.20 (m, 2H), 6.02-5.90 (m, 1H), 5.46-5.34 (m, 1H), 4.79-4.44 (m, 2H), 3.63-3.56 (m, 1H), 2.93-2.82 (m, 1H), 1.86-1.83 (m, 1H), 1.19-1.04 (m, 1H), 0.92-0.78 (m, 1H). LCMS $R_T$=0.769 min, m/z=292.0 [M+H]$^+$.

LCMS (5 to 95% acetonitrile in water+0.03% trifluoacetic acid over 1.5 mins) retention time 0.769 min, ESI+ found [M+H]=292.0.

Example 110 and 111: Method 64

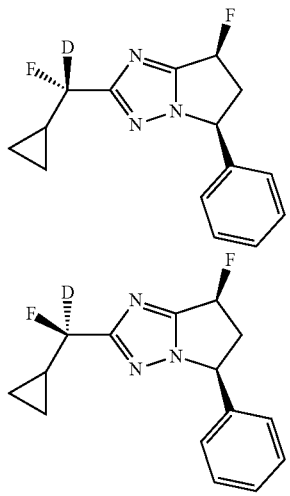

(5S,7S)-7-fluoro-5-phenyl-2-[(S)-cyclopropyl-deuterio-fluoro-methyl]-6,7-dihydro-5H-pyrrolo[1,2-b][1,2,4]triazole and (5S,7S)-7-fluoro-5-phenyl-2-[(R)-cyclopropyl-deutero-fluoro-methyl]-6,7-dihydro-5H-pyrrolo[1,2-b][1,2,4]triazole To a cooled (0° C.) solution of cyclopropyl-deuterio-[(5S,7S)-7-fluoro-5-phenyl-6,7-dihydro-5H-pyrrolo[1,2-b][1,2,4]triazol-2-yl]methanol (0.15 g, 0.55 mmol) in dichloromethane (2 mL) was added diethylaminosulfur trifluoride (0.29 mL, 2.19 mmol). The mixture was stirred at 0° C. for 1 h and poured into ice-water (10 mL). The mixture was extracted with ethyl acetate (3×10 mL). The combined organic layers were washed with brine (2×10 mL), dried over sodium sulfate and concentrated under reduced pressure. The residue was purified by column chromatography (silica gel, 100-200 mesh, 0 to 16% ethyl acetate in petroleum ether) to afford (5S,7S)-2-(cyclopropyl-deuterio-fluoro-methyl)-7-fluoro-5-phenyl-6,7-dihydro-5H-pyrrolo[1,2-b][1,2,4]triazole (70 mg, 45%) as a white solid. The material was further purified by chiral SFC to afford arbitrarily assigned:

(5S,7)-7-fluoro-5-phenyl-2-[(S)-cyclopropyl-deuterio-fluoro-methyl]-6,7-dihydro-5H-pyrrolo[1,2-b][1,2,4]triazole (Peak 1, retention time=3.021 min) (14.9 mg, 21%) as a white solid. $^1$H NMR (400 MHz, DMSO-$d_6$) δ 7.44-7.36 (m, 3H), 7.24-7.21 (m, 2H), 6.25-6.24 (m, 0.5H), 6.11-6.09 (m, 0.5H), 5.65-5.62 (m, 1H), 3.77-3.64 (m, 1H), 2.75-2.62 (m, 1H), 1.61-1.58 (m, 1H), 0.74-0.67 (m, 1H), 0.60-0.54 (m, 2H), 0.40-0.37 (m, 1H). LCMS $R_T$=0.761 min, m/z=277.1 [M+H]$^+$.

LCMS (5 to 95% acetonitrile in water+0.03% trifluoacetic acid over 1.5 mins) retention time 0.761 min, ESI+ found [M+H]=277.1.

(5S,7S)-7-fluoro-5-phenyl-2-[(R)-cyclopropyl-deuterio-fluoro-methyl]-6,7-dihydro-5H-pyrrolo[1,2-b][1,2,4]triazole (Peak 2, retention time=4.052 min) (15.2 mg, 21%) as a white solid. $^1$H NMR (400 MHz, CD$_3$OD) δ 7.44-7.37 (m, 3H), 7.24-7.22 (m, 2H), 6.14-6.12 (m, 0.5H), 5.99-5.97 (m, 0.5H), 5.55-5.51 (m, 1H), 3.77-3.67 (m, 1H), 2.80-2.69 (m, 1H), 1.59-1.52 (m, 1H), 0.74-0.72 (m, 1H), 0.61-0.56 (m, 2H), 0.39-0.33 (m, 1H). LCMS $R_T$=0.762 min, m/z=277.2 [M+H]$^+$.

LCMS (5 to 95% acetonitrile in water+0.03% trifluoacetic acid over 1.5 mins) retention time 0.762 min, ESI+ found [M+H]=277.2.

SFC condition: Column: AD-3_EtOH (DEA)_5_40_2.5M, Mobile phase: A: CO$_2$ B: Ethanol (0.05% DEA) Gradient: from 5% to 40% of B in 5.5 min and hold 40% for 3 min, then 5% of B for 1.5 min Flow rate: 2.5 mL/min Column temp. 40° C.

Example 112: Method 65

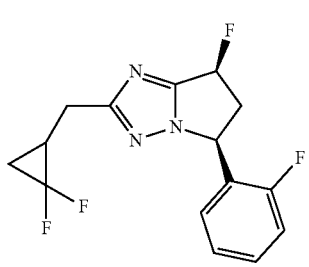 [SMILES: Fc1ccccc1[C@@H]1C[C@H](F)c2nc(CC3CC3(F)F)nn21]

(5S,7S)-2-[(2,2-difluorocyclopropyl)methyl]-7-fluoro-5-(2-fluorophenyl)-6,7-dihydro-5H-pyrrolo[1,2-b][1,2,4]triazole Step 1: (5S,7S)-2-allyl-7-fluoro-5-(2-fluorophenyl)-6,7-dihydro-5H-pyrrolo[1,2-b][1,2,4]triazole

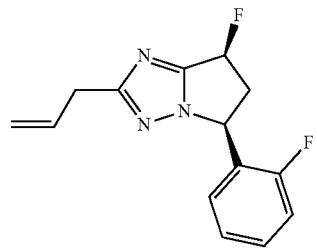 [SMILES: C=CCc1nc2n(n1)[C@H](c1ccccc1F)C[C@@H]2F]

A mixture of (5S,7S)-2-bromo-7-fluoro-5-(2-fluorophenyl)-6,7-dihydro-5H-pyrrolo[1,2-b][1,2,4]triazole (1000 mg, 3.33 mmol), cesium carbonate (3257 mg, 10 mmol), Ruphos-Pd-G2 (259 mg, 0.33 mmol) and allylboronic acid pinacolester (1119 mg, 6.66 mmol) in 1,4-dioxane (10 mL) and water (2.5 mL) was stirred at 100° C. for 12 h under nitrogen atmosphere. The mixture was filtered and the filtrate was concentrated under reduced pressure. The residue was diluted with water (20 mL) and extracted with ethyl acetate (3×20 mL). The combined organic layers were dried over anhydrous sodium sulfate and concentrated under reduced pressure. The residue was purified by preparative TLC (35% ethyl acetate in petroleum ether, R=0.4) to afford (5S,7S)-2-allyl-7-fluoro-5-(2-fluorophenyl)-6,7-dihydro-5H-pyrrolo[1,2-b][1,2,4]triazole (400 mg, 46%) as colorless oil, used as is in the next step.

Step 2: (5S,7S)-2-[(2,2-difluorocyclopropyl)methyl]-7-fluoro-5-(2-fluorophenyl)-6,7-dihydro-5H-pyrrolo[1,2-b][1,2,4]triazole A mixture of (5S,7S)-2-allyl-7-fluoro-5-(2-fluorophenyl)-6,7-dihydro-5H-pyrrolo[1,2-b][1,2,4]triazole (300 mg, 1.15 mmol), tetrabutylammonium bromide (37 mg, 0.11 mmol) and [chloro(difluoro)methyl]-trimethyl-silane (364 mg, 2.30 mmol) in toluene (20 mL) was stirred at 110° C. for 4 h under microwave conditions. The reaction mixture was concentrated to dryness under reduced pressure. The residue was purified by RP-HPLC (acetonitrile 48-68/0.2% formic acid in water) to afford (5S,7S)-2-[(2,2-difluorocyclopropyl)methyl]-7-fluoro-5-(2-fluorophenyl)-6,7-dihydro-5H-pyrrolo[1,2-b][1,2,4]triazole (27.9 mg, 8%) as a white solid. $^1$H NMR (400 MHz, CD$_3$OD) δ 7.47-7.37 (m, 1H), 7.23-7.17 (m, 2H), 7.07-7.02 (m, 1H), 6.15-5.95 (m, 1H), 5.83-5.74 (m, 1H), 3.84-3.66 (m, 1H), 3.05-2.94 (m, 1H), 2.88-2.69 (m, 2H), 2.09-1.94 (m, 1H), 1.54-1.51 (m, 1H), 1.25-1.11 (m, 1H). LCMS $R_T$=0.769 min, m/z=312.1 [M+H]$^+$.

LCMS (5 to 95% acetonitrile in water+0.03% ammonium bicarbonate over 1.5 mins) retention time 0.769 min, ESI+ found [M+H]=312.1.

Example 113: Method 66

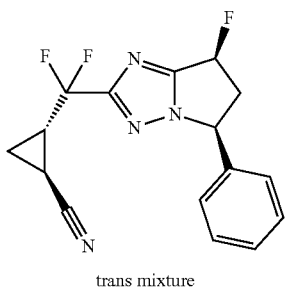 [SMILES: N#C[C@H]1C[C@@H]1C(F)(F)c1nc2n(n1)[C@H](c1ccccc1)C[C@@H]2F]

trans mixture rac-(1S,2S)-2-[difluoro-[(5S,7S)-7-fluoro-5-phenyl-6,7-dihydro-5H-pyrrolo[1,2-b][1,2,4]triazol-2-yl]methyl]cyclopropanecarbonitrile A mixture of diethylaminosulfur trifluoride (0.2 mL, 1.52 mmol) and trans-2-[(5S,7S)-7-fluoro-5-phenyl-6,7-dihydro-5H-pyrrolo[1,2-b][1,2,4]triazole-2-carbonyl]cyclopropanecarbonitrile (45 mg, 0.15 mmol) was stirred at 0° C. for 16 h under nitrogen atmosphere and quenched by addition of saturated aqueous sodium bicarbonate (20 mL). The mixture was extracted with dichloromethane (3×15 mL). The combined organic layers were washed with brine (15 mL), dried over sodium sulfate and concentrated under reduced pressure. The residue was purified by RP-HPLC (acetonitrile 35-65%/0.05% HCl in water) to give rac-(1S,2S)-2-[difluoro-[(5S,7S)-7-fluoro-5-phenyl-6,7-dihydro-5H-pyrrolo[1,2-b][1,2,4]triazol-2-yl]methyl]cyclopropane carbonitrile (16 mg, 30%) as a light yellow solid. $^1$H NMR (400 MHz, CD$_3$OD) δ 7.44-7.38 (m, 3H), 7.27-7.26 (m, 2H), 6.18-6.15 (m, 0.5H), 6.04-6.01 (m, 0.5H), 5.63-5.60 (m, 1H), 3.80-3.70 (m, 1H), 2.86-2.76 (m, 1H), 2.59-2.57 (m, 1H), 2.08-2.03 (m, 1H), 1.49-1.45 (m, 2H). LCMS R$_T$=1.785 min, m/z=319.1[M+H]$^+$.

LCMS (10 to 80% acetonitrile in water+0.03% ammonium bicarbonate over 3.0 mins) retention time 1.785 min, ESI+ found [M+H]=319.1.

Examples 115 and 114: Method 67

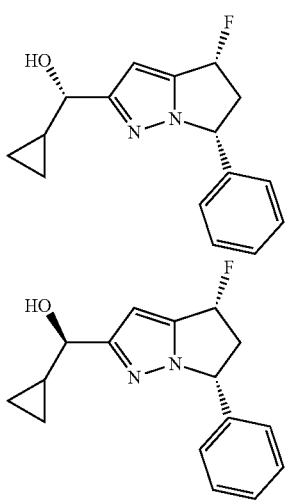

(S)-cyclopropyl-[(4R,6R)-4-fluoro-6-phenyl-5,6-dihydro-4H-pyrrolo[1,2-b]pyrazol-2-yl]methanol and (R)-cyclopropyl-[(4R,6R)-4-fluoro-6-phenyl-5,6-dihydro-4H-pyrrolo[1,2-b]pyrazol-2-yl]methanol To a mixture of arbitrarily assigned cyclopropyl-[(4R,6R)-4-fluoro-6-phenyl-5,6-dihydro-4H-pyrrolo[1,2-b]pyrazol-2-yl]methanone (100 mg, 0.37 mmol) in methanol (15 mL) was added sodium borohydride (21 mg, 0.55 mmol). The mixture was stirred at 25° C. for 2 h and quenched by addition of saturated aqueous ammonium chloride (10 mL). The resulting mixture extracted with ethyl acetate (3×10 mL). The combined organic layers were dried over sodium sulfate and concentrated under reduced pressure. The residue was separated by chiral SFC to afford arbitrarily assigned:

(S)-cyclopropyl-[(4R,6R)-4-fluoro-6-phenyl-5,6-dihydro-4H-pyrrolo[1,2-b]pyrazol-2-yl]methanol (Peak 1, retention time=3.806 min) (38.0 mg, 37%) as a white solid. $^1$H NMR (400 MHz, CDCl$_3$) δ 7.37-7.31 (m, 3H), 7.19-7.17 (m, 2H), 6.45 (d, J=2.4 Hz, 1H), 6.04 (d, J=5.2 Hz, 0.5H), 5.91-5.89 (m, 0.5H), 5.41-5.39 (m, 1H), 4.15-4.12 (m, 1H), 3.50-3.41 (m, 1H), 2.81-2.71 (m, 1H), 2.39 (d, J=3.6 Hz, 1H), 1.29-1.27 (m, 1H), 0.63-0.58 (m, 2H), 0.47-0.39 (m, 2H). LCMS R$_T$=0.808 min, m/z=272.9 [M+H]$^+$.

LCMS (5 to 95% acetonitrile in water+0.03% trifluoacetic acid over 1.5 mins) retention time 0.808 min, ESI+ found [M+H]=272.9.

(R)-cyclopropyl-[(4R,6R)-4-fluoro-6-phenyl-5,6-dihydro-4H-pyrrolo[1,2-b]pyrazol-2-yl]methanol (Peak 2, retention time=4.181 min) (36.0 mg, 35%) as a white solid. $^1$H NMR (400 MHz, CDCl$_3$) δ 7.37-7.31 (m, 3H), 7.19-7.17 (m, 2H), 6.45 (d, J=2.4 Hz, 1H), 6.04 (d, J=5.2 Hz, 0.5H), 5.91-5.89 (m, 0.5H), 5.40-5.39 (m, 1H), 4.15-4.11 (m, 1H), 3.51-3.41 (m, 1H), 2.80-2.71 (m, 1H), 2.43 (d, J=3.6 Hz, 1H), 1.29-1.27 (m, 1H), 0.63-0.56 (m, 2H), 0.48-0.38 (m, 2H). LCMS R$_T$=0.816 min, m/z=273.0 [M+H]$^+$.

LCMS (5 to 95% acetonitrile in water+0.03% trifluoacetic acid over 1.5 mins) retention time 0.816 min, ESI+ found [M+H]=273.0.

SFC condition: Column: DAICEL CHIRALPAK IC (250 mm*30 mm, 5um), Mobile phase: A: CO$_2$ B: Ethanol (0.05% DEA) Gradient: from 5% to 40% of B in 5 min and hold 40% for 3.0 min, then 5% of B for 1.5 min Flow rate: 2.5 mL/min Column temp. 40° C.

Example 116: Method 68

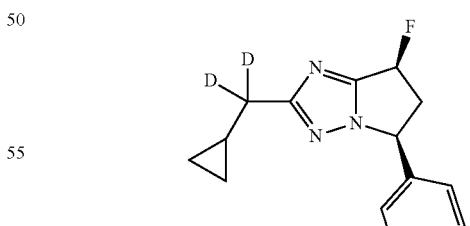

(5S,7S)-2-[cyclopropyl(dideuterio)methyl]-7-fluoro-5-phenyl-6,7-dihydro-5H-pyrrolo(1,2-b][1,2,4]triazole A mixture of cyclopropyl-deuterio-[(5S,7S)-7-fluoro-5-phenyl-6,7-dihydro-5H-pyrrolo[1,2-b][1,2,4]triazol-2-yl]

methanol (100 mg, 0.36 mmol), triethylsilane-d (0.4 mL, 2.48 mmol) and trifluoroacetic acid-d (0.4 mL, 5.34 mmol) was stirred at 50° C. for 16 h and concentrated under reduced pressure. The residue was diluted saturated aqueous sodium bicarbonate (10 mL) and extracted with ethyl acetate (3×10 mL). The combined organic layers were dried over sodium sulfate and concentrated under reduced pressure. The residue was purified by RP-HPLC (acetonitrile 45-75/0.05% ammonia hydroxide in water) to afford (5S,7S)-2-[cyclopropyl(dideuterio)methyl]-7-fluoro-5-phenyl-6,7-dihydro-5H-pyrrolo[1,2-b][1,2,4]triazole (22 mg, 21%) as a white solid. $^1$H NMR (400 MHz, CD$_3$OD) δ 7.44-7.33 (m, 3H), 7.24-7.22 (m, 2H), 6.15-5.92 (m, 1H), 5.55-5.44 (m, 1H), 3.78-3.61 (m, 1H), 2.80-2.64 (m, 1H), 1.15-1.03 (m, 1H), 0.53-0.45 (m, 2H), 0.26-0.17 (m, 2H). LCMS R$_T$=0.995 min, m/z=260.2 [M+H]$^+$.

LCMS (10 to 80% acetonitrile in water+0.1% ammonia water over 3.0 mins) retention time 0.995 min, ESI+ found [M+H]=260.2.

Example 117: Method 69

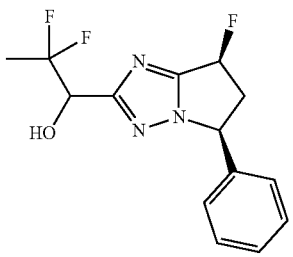 [SMILES: CC(F)(F)C(O)c1nc2n(n1)[C@H](c1ccccc1)C[C@@H]2F]

2,2-difluoro-1-[(5S,7S)-7-fluoro-5-phenyl-6,7-dihydro-5H-pyrrolo[1,2-b][1,2,4]triazol-2-yl]propan-1-ol Step 1:
2,2-difluoro-N-methoxy-N-methyl-propanamide

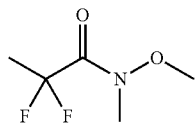

A mixture of 2,2-difluoropropanoic acid (2.00 g, 18.17 mmol), N,O-dimethyl hydroxylamine hydrochloride (3.54 g, 36.34 mmol), N,N-diisopropylethylamine (7.05 g, 54.52 mmol), (1-[Bis(dimethylamino)methylene]-1H-1,2,3-triazolo[4,5-b]pyridinium 3-oxid hexafluorophosphate (7.25 g, 19.08 mmol) in N,N-dimethylformamide (50 mL) was stirred at 20° C. for 2 h. The mixture was diluted with water (60 mL) and extracted with dichloromethane (3×50 mL). The combined organic layers were washed with water (2×20 mL), dried over sodium sulfate and concentrated under reduced pressure to give the crude 2,2-difluoro-N-methoxy-N-methyl-propanamide (1.50 g, 54%) as light yellow oil. $^1$H NMR (400 MHz, CDCl$_3$) δ 3.78-3.69 (m, 3H), 3.28-3.18 (m, 2H), 2.81-2.72 (m, 1H), 1.88-1.74 (m, 3H).

Step 2: 2,2-difluoro-1-[(5S,7S)-7-fluoro-5-phenyl-6,7-dihydro-5H-pyrrolo[1,2-b][1,2,4]triazol-2-yl]propane-1,1-diol

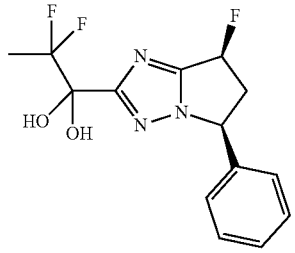 [SMILES: CC(F)(F)C(O)(O)c1nc2n(n1)[C@H](c1ccccc1)C[C@@H]2F]

To the cooled (0° C.) mixture of (5S,7S)-2-bromo-7-fluoro-5-phenyl-6,7-dihydro-5H-pyrrolo[1,2-b][1,2,4]triazole (100 mg, 0.35 mmol), 2,2-difluoro-N-methoxy-N-methyl-propanamide (54 mg, 0.35 mmol) in tetrahydrofuran (2 mL) was added isopropylmagnesium chloride (2.0 M in tetrahydrofuran, 0.18 mL, 0.35 mmol) at 0° C. under nitrogen atmosphere. The mixture was stirred at 0° C. for 1 h and quenched by addition of water (10 mL). The resulting solution was extracted with ether acetate (3×10 mL). The combined organic layers were dried over sodium sulfate and concentrated under reduced pressure. The residue was purified by preparative TLC (50% ethyl acetate in petroleum ether, R$_f$=0.4) to afford 2,2-difluoro-1-[(5S,7S)-7-fluoro-5-phenyl-6,7-dihydro-5H-pyrrolo[1,2-b][1,2,4]triazol-2-yl] propane-1,1-diol (30 mg, 27%) as light brown oil. LCMS R$_T$=0.549 min, m/z=314.1 [M+H]$^+$.

LCMS (5 to 95% acetonitrile in water+0.03% trifluoacetic acid over 2.0 mins) retention time 0.549 min, ESI+ found [M+H]=314.1.

Step 3: 2,2-difluoro-[(5S,7S)-7-fluoro-5-phenyl-6,7-dihydro-5H-pyrrolo[1,2-b][1,2,4]triazol-2-yl]propan-1-ol

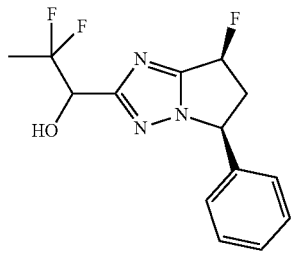 [SMILES: CC(F)(F)C(O)c1nc2n(n1)[C@H](c1ccccc1)C[C@@H]2F]

To a solution of 2,2-difluoro-1[(5S,7S)-7-fluoro-5-phenyl-6,7-dihydro-5H-pyrrolo[1,2-b][1,2,4]triazol-2-yl]propane-1,1-diol (30 mg, 0.10 mmol) in methanol (3 mL) was added sodium borohydride (4 mg, 0.10 mmol) at 0° C. The mixture was stirred at 0° C. for 1 h and quenched by addition of water (3 mL). The solid was removed by filtration and the filtrate was concentrated under reduced pressure. The residue was purified by RP-HPLC (40%-70% acetonitrile in water (0.05% ammonia hydroxide v/v)) to afford 2,2-difluoro-1-[(5S,7S)-7-fluoro-5-phenyl-6,7-dihydro-5H-pyrrolo

[1,2-b][1,2,4]triazol-2-yl]propan-1-ol (12.3 mg, 43%) as a white solid. ¹H NMR (400 MHz, CDCl₃) δ 7.40-7.36 (m, 3H), 7.23-7.15 (m, 2H), 6.06-5.90 (m, 1H), 5.49-5.37 (m, 1H), 5.00-4.84 (m, 1H), 3.69-3.52 (m, 1H), 3.30-3.13 (m, 1H), 3.00-2.81 (m, 1H), 1.77-1.66 (m, 3H). LCMS $R_T$=0.722 min, m/z=298.1 [M+H]⁺.

LCMS (5 to 95% acetonitrile in water+0.03% trifluoacetic acid over 1.5 mins) retention time 0.722 min, ESI+ found [M+H]=298.1.

Example 108: Method 70

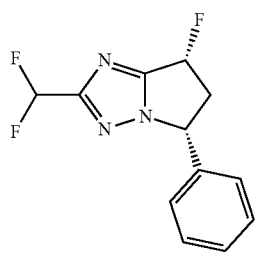 [SMILES: FC(F)c1nc2n(n1)[C@@H](c1ccccc1)C[C@H]2F]

(5R,7R)-2-(difluoromethyl)-7-fluoro-5-phenyl-6,7-dihydro-5H-pyrrolo[1,2-b][1,2,4]triazole Step 1

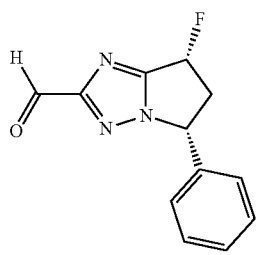 [SMILES: O=Cc1nc2n(n1)[C@@H](c1ccccc1)C[C@H]2F]

cis-7-fluoro-5-phenyl-6,7-dihydro-5H-pyrrolo[1,2-b][1,2,4]triazole-2-carbaldehyde To a mixture of ethyl cis-7-fluoro-5-phenyl-6,7-dihydro-5H-pyrrolo[1,2-b][1,2,4]triazole-2-carboxylate (1000 mg, 3.63 mmol) in dichloromethane (50 mL) was added diisobutylaluminum hydride (1.0 M in toluene, 9.08 mL, 9.08 mmol) dropwise at −70° C. The reaction mixture was stirred at −70° C. for 2 h and then quenched by addition of sodium sulfate decahydrate (10.0 g). The solid was removed by filtration and the filtrate was concentrated under reduced pressure to afford crude cis-7-fluoro-5-phenyl-6,7-dihydro-5H-pyrrolo[1,2-b][1,2,4]triazole-2-carbaldehyde (1200 mg, 100%) as colorless oil.

Step 2

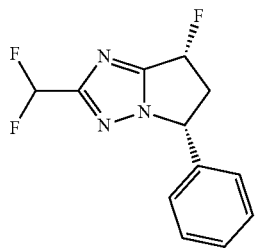 [SMILES: FC(F)c1nc2n(n1)[C@@H](c1ccccc1)C[C@H]2F]

(5R,7R)-2-(difluoromethyl)-7-fluoro-5-phenyl-6,7-dihydro-5H-pyrrolo[1,2-b][1,2,4]triazole To a solution of cis-7-fluoro-5-phenyl-6,7-dihydro-5H-pyrrolo[1,2-b][1,2,4]triazole-2-carbaldehyde (140 mg, 0.61 mmol) in dichloromethane (10 mL) was added diethylaminosulfur trifluoride (0.4 mL, 3.03 mmol) at 0° C. The reaction was stirred at 0° C. for 1 h and quenched by addition of saturated aqueous sodium bicarbonate (20 mL). The mixture was extracted with dichloromethane (3×20 mL). The combined organic layers were washed with brine (20 mL), dried over sodium sulfate and concentrated under reduced pressure. The residue was purified by column chromatography (silica gel, 100-200 mesh, 0 to 50% ethyl acetate in petroleum ether) to afford cis-2-(difluoromethyl)-7-fluoro-5-phenyl-6,7-dihydro-5H-pyrrolo[1,2-b][1,2,4]triazole (90 mg, 59%) as a colorless oil, which was separated by chiral SFC to afford arbitrarily assigned:

(5R,7R)-2-(difluoromethyl)-7-fluoro-5-phenyl-6,7-dihydro-5H-pyrrolo[1,2-b][1,2,4]triazole (Peak 2, Retention time=2.621 min) (28 mg, 30%) as a white solid. ¹H NMR (400 MHz, CDCl₃) δ 7.43-7.39 (m, 3H), 7.27-7.24 (m, 2H), 6.69 (t, J=53.6 Hz, 1H), 6.11-5.95 (m, 1H), 5.49-5.45 (m, 1H), 3.70-3.60 (m, 1H), 3.01-2.90 (m, 1H). LCMS $R_T$=1.649 min, m/z=254.1 [M+H]⁺.

LCMS (10 to 80% acetonitrile in water+0.03% ammonium bicarbonate over 3.0 mins) retention time 1.649 min, ESI+ found [M+H]=254.1.

SFC condition: Column: DAICEL CHIRAL OD (250 mm×30 mm, 5 um) Mobile phase: A: CO2 B:Ethanol (0.1% NH₃.H₂O) Gradient: from 15% to 15% of B Flow rate: 50 mL/min Column temperature: 40° C.

Peak 1 was also collected as: (5S,7S)-2-(difluoromethyl)-7-fluoro-S-phenyl-6,7-dihydro-5H-pyrrolo[1,2-b][1,2,4]triazole (Peak 1, Retention time=2.222 min) (26 mg, 29%) as a white solid. ¹H NMR (400 MHz, CDCl₃) δ 7.44-7.40 (m, 3H), 7.27-7.25 (m, 2H), 6.83-6.56 (m, 1H), 6.11-5.95 (m, 1H), 5.49-5.46 (m, 1H), 3.70-3.60 (m, 1H), 3.01-2.91 (m, 1H). LCMS $R_T$=1.661 min, m/z=254.1 (M+H)⁺.

LCMS (10 to 80% acetonitrile in water+0.03% ammonium bicarbonate over 3.0 mins) retention time 1.661 min, ESI+ found [M+H]=254.1.

RIP1 Kinase Inhibition Assays (Biochemical Assay)

The compounds of the present invention were tested for their capacity to inhibit RIP1K activity as described below.

Enzyme Assay:

The ability of the receptor interacting protein kinase (RIPK1) to catalyze the hydrolysis of adenosine-5'-triphosphate (ATP) is monitored using the Transcreener ADP (adenosine-5'-diphosphate) assay (BellBrook Labs). Purified human RIP1 kinase domain (2-375) (50 nM) derived from a baculovirus-infected insect cell expression system is incubated with test compounds for 2 hours in 50 mM Hepes buffer (pH 7.5) containing 30 mM MgCl$_2$, 1 mM dithiothreitol, 50 uM ATP, 0.002% Brij-35, and 0.5% dimethyl sulfoxide (DMSO). Reactions are quenched by the addition of 1× Bell Brooks Stop buffer B (20 mM Hepes (ph7.5), 40 mM ethylenediaminetetraacetic acid and 0.02% Brij-35) containing an additional 12 mM EDTA and 55 ug/mL ADP2 antibody and 4 nM ADP-AlexaFluor® 633 tracer. The tracer bound to the antibody is displaced by the ADP generated during the RIP1K reaction, which causes a decrease in fluorescence polarization that is measured by laser excitation at 633 nm with a FP microplate reader M1000. Fractional activity was plotted against test article concentration. Using Genedata Screener software (Genedata; Basel, Switzerland), the data were fit to the tight-binding apparent inhibition constant ($K_i^{app}$) Morrison equation [Williams, J. W. and Morrison, J. F. (1979) The kinetics of reversible tight-binding inhibition. *Methods Enzymol* 63: 437-67]. The following equation was used to calculate fractional activity and $K_i^{app}$:

Fractional activity =

$$\frac{v_i}{v_o} = 1 - \frac{([E]_T + [I]_T K_i^{app}) - \sqrt{([E]_T + [I]_T + K_i^{app})^2 - 4[E]_T[I]_T}}{2[E]_T}$$

where $[E]_T$ and $[I]_T$ are the total concentrations of active enzyme and test article, respectively.

Exemplary compounds of the present invention are provided in Table 1 along with their physiochemical characterization and in vitro RIP1 kinase inhibitory activity data. "Method" in the first column of each table refers to the synthetic method(s) used to prepare each compound as shown in the Examples above. In certain examples, chiral column retention times (min) are provided for certain stereoisomers. Unless otherwise specified, the stereochemistry shown in each structure represents relative configuration of a single stereoisomer, and absolute configuration (i.e., "R" and/or "S") is arbitrarily assigned. In some embodiments, where the Method is described to include the separation of stereoisomers, a single stereoisomer of a compound of Table 1 is provided.

TABLE 1

| Ki (μM) METHOD | Ex No. | Structure | Stereo | $^1$H NMR | MS (m/z) R.T. |
|---|---|---|---|---|---|
| 0.406 Method 1 | 1 | Cis-7-fluoro-5-phenyl-6,7-dihydro-5H-pyrrolo[1,2-b][1,2,4]triazol-2-yl]propan-1-ol | Mixture of Diastereomers | $^1$H NMR (400 MHz, CD$_3$OD) δ 7.40-7.33 (m, 3H), 7.25-7.22 (m, 2H), 6.16-6.13 (m, 0.5H), 6.02-5.98 (m, 0.5H), 5.56-5.52 (m, 1H), 4.65 4.61 (m, 1H), 3.75-3.67 (m, 1H), 2.81-2.74 (m, 1H), 1.93-1.82 (m, 2H), 0.94-0.89 (m, 3H) | 262.0 0.762 min |
| 0.041 Method 2 | 2 | Cis-2-(1,1-difluoropropyl)-7-fluoro-5-phenyl-6,7-dihydro-5H-pyrrolo[1,2-b][1,2,4]triazole | Mixture of Diastereomers | $^1$H NMR (400 MHz, CD$_3$OD) δ 7.41-7.23 (m, 5H), 6.16-6.00 (m, 1H), 5.58 (s, 1H), 3.78-3.69 (m, 1H), 2.80-2.77 (m, 1H), 2.31-2.25 (m, 2H), 1.02 (t, J = 7.6 Hz, 3H) | 281.9 0.859 min |

TABLE 1-continued

| Ki (μM) METHOD | Ex No. | Structure | Stereo | ¹H NMR | MS (m/z) R.T. |
|---|---|---|---|---|---|
| 0.051 Method 3 | 3 | Cis-7-fluoro-2-(1-fluoropropyl)-5-phenyl-6,7-dihydro-5H-pyrrolo[1,2-b][1,2,4]triazole | Mixture of Diastereomers | ¹H NMR (400 MHz, CD₃OD) δ 7.40-7.21 (m, 5H), 6.14-5.98 (m, 1H), 5.56-5.34 (m, 2H), 3.77-3.67 (m, 1H), 2.81-2.70 (m, 1H), 2.13-2.03 (m, 2H), 0.38 (t, J = 7.6 Hz, 3H). | 263.9 0.820 min |
| 0.470 Method 4 | 4 | Cis-2,2,2-trifluoro-1-(7-fluoro-5-phenyl-6,7-dihydro-5H-pyrrolo[1,2-b][1,2,4]triazol-2-yl)ethanol | Mixture of Diastereomers | ¹H NMR (400 MHz, CDCl₃) δ 7.43-7.36 (m, 3H), 7.25-7.22 (m, 2H), 6.08-5.95 (m, 1H), 5.49-5.45 (m, 1H), 5.16-5.13 (m, 1H), 3.68-3.63 (m, 1H), 3.10-2.88 (m, 2H) | 301.9 0.768 min |
| 0.027 Method 5 | 5 | Cis-2-[cyclopropyl(difluoro)methyl]-7-fluoro-5-phenyl-6,7-dihydro-5H-pyrrolo[1,2-b][1,2,4]triazole | Mixture of Diastereomers | ¹H NMR (400 MHz, CD₃OD) δ 7.43-7.24 (m, 5H), 6.16-6.14 (m, 0.5H), 6.02-6.00 (m, 0.5H), 5.60-5.56 (m, 1H), 3.77-3.69 (m, 1H), 2.81-2.77 (m, 1H), 1.79-1.74 (m, 1H), 0.73-0.69 (m, 4H) | 293.9 0.900 min |
| 0.069 Method 6 | 6 | Cis-7-fluoro-2-(1-fluoro-1-methyl-propyl)-5-phenyl-6,7-dihydro-5H-pyrrolo[1,2-b][1,2,4]triazole | Mixture of Diastereomers | ¹H NMR (400 MHz, CD₃OD) δ 7.52-7.15 (m, 5H), 6.14-6.11 (m, 0.5H), 5.99-5.97 (m, 0.5H), 5.58-5.51 (m, 1H), 3.79-3.65 (m, 1H), 2.81-2.68 (m, 1H), 2.14-2.01 (m, 2H), 1.72-1.66 (m, 3H), 0.90-0.86 (m, 3H) | 277.6 1.889 min |

TABLE 1-continued

| Ki (µM) METHOD | Ex No. | Structure | Stereo | ¹H NMR | MS (m/z) R.T. |
|---|---|---|---|---|---|
| 0.004 Method 7 | 7 | rac-(5S,7S)-7-fluoro-5-phenyl-2-[rac-(1R)-1-fluoropropyl]-6,7-dihydro-5H-pyrrolo[1,2-b][1,2,4]triazole | Single Unknown Stereoisomer | NO NMR | 264.2 4.65 min |
| 0.014 Method 7 | 8 | rac-(5S,7S)-7-fluoro-2-((S)-1-fluoropropyl)-5-phenyl-6,7-dihydro-5H-pyrrolo[1,2-b][1,2,4]triazole | Single Unknown Stereoisomer | NO NMR | 264.1 4.67 min |
| 0.068 Method 8 | 9 | Cis-2-(1,1-difluoro-2,2-dimethyl-propyl)-7-fluoro-5-phenyl-6,7-dihydro-5H-pyrrolo[1,2-b][1,2,4]triazole | Mixture of Enantiomers | ¹H NMR (400 MHz, CD₃OD) δ 7.40-7.38 (m, 3H), 7.22-7.20 (m, 2H), 6.15-6.14 (m, 0.5H), 6.02-5.99 (m, 0.5H), 5.62-5.58 (m, 1H), 3.77-3.69 (m, 1H), 2.82-2.71 (m, 1H), 1.07 (s, 9H) | 310.1 2.052 min |
| 0.078 Method 9 | 10 | Cis-7-fluoro-5-phenyl-2-propyl-6,7-dihydro-5H-pyrrolo[1,2-b][1,2,4]triazole | Mixture of Enantiomers | ¹H NMR (400 MHz, CD₃OD) δ 7.39-7.36 (m, 3H), 7.27-7.25 (m, 2H), 6.26-6.23 (m, 0.5H), 6.12-6.09 (m, 0.5H), 5.60-5.58 (m, 1H), 3.79-3.70 (m, 1H), 2.83-2.73 (m, 3H), 1.79-1.70 (m, 2H), 0.96-0.92 (m, 3H) | 246.2 1.698 min |

TABLE 1-continued

| Ki (μM) METHOD | Ex No. | Structure | Stereo | ¹H NMR | MS (m/z) R.T. |
|---|---|---|---|---|---|
| 0.320 Method 10 | 11 | 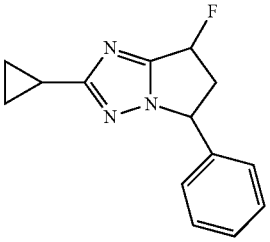<br>Cis-2-cyclopropyl-7-fluoro-5-phenyl-6,7-dihydro-5H-pyrrolo[1,2-b][1,2,4]triazole | Mixture of Enantiomers | ¹H NMR (400 MHz, CD₃OD) δ 7.41-7.34 (m, 3H), 7.22-7.20 (m, 2H), 6.05-6.02 (m, 0.5H), 5.90-5.88 (m, 0.5H), 5.46-5.41 (m, 1H), 3.73-3.60 (m, 1H), 2.73-2.62 (m, 1H), 2.03-1.98 (m, 1H), 0.99-0.92 (m, 4H) | 244.0 0.827 min |
| 0.130 Method 11 | 12 | 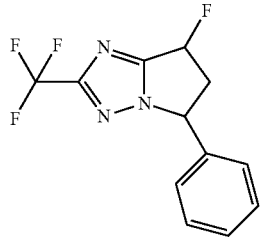<br>Cis-7-fluoro-5-phenyl-2-(trifluoromethyl)-6,7-dihydro-5H-pyrrolo[1,2-b][1,2,4]triazole | Mixture of Enantiomers | ¹H NMR (400 MHz, CD₃OD) δ 7.44-7.38 (m, 3H), 7.27-7.24 (m, 2H), 6.18-6.15 (m, 0.5H), 6.04-6.02 (m, 0.5H), 5.65-5.59 (m, 1H), 3.81-3.70 (m, 1H), 2.88-2.76 (m, 1H) | 271.9 0.923 min |
| 0.003 Method 12 | 13 | 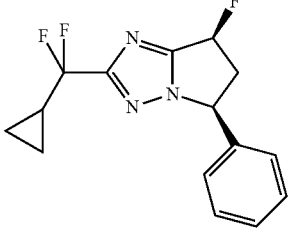<br>rac-(5S,7S)-2-[cyclopropyl(difluoro)methyl]-7-fluoro-5-phenyl-6,7-dihydro-5H-pyrrolo[1,2-b][1,2,4]triazole | Single Unknown Stereoisomer | ¹H NMR (400 MHz, CDCl₃) δ 7.42-7.38 (m, 3H), 7.24-7.22 (m, 2H), 6.08-5.92 (m, 1H), 5.48-5.44 (m, 1H), 3.67-3.57 {m, 1H), 2.97-2.87 (m, 1H), 1.81-1.75 (m, 1H), 0.86-0.82 (m, 2H), 0.72-0.70 (m, 2H) | 293.9 0.921 min |
| 0.028 Method 13 | 14 | 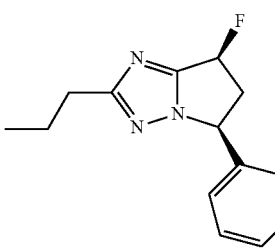<br>rac-(5S,7S)-7-fluoro-5-phenyl-2-propyl-6,7-dihydro-5H-pyrrolo[1,2-b][1,2,4]triazole | Single Unknown Stereoisomer | ¹H NMR (400 MHz, CD₃OD) δ 7.41-7.35 (m, 3H), 7.22-7.19 (m, 2H), 6.09-5.92 (m, 1H), 5.50-5.46 (m, 1H), 3.75-3.62 (m, 1H), 2.75-2.64 (m, 3H), 1.79-1.69 (m, 2H), 0.94 (t, J = 7.6 Hz, 3H) | 246.2 1.689 min |

TABLE 1-continued

| Ki (μM) METHOD | Ex No. | Structure | Stereo | ¹H NMR | MS (m/z) R.T. |
|---|---|---|---|---|---|
| 1.1 Method 14 | 15 | rac-(5R,7R)-7-fluoro-5-phenyl-2-(3,3,3-trifluoropropyl)-6,7-dihydro-5H-pyrrolo[1,2-b][1,2,4]triazole | Single Unknown Stereoisomer | ¹H NMR (400 MHz, CDCl$_3$) δ 7.41-7.37 (m, 3H), 7.23-7.21 (m, 2H), 6.04-5.89 (m, 1H), 5.40-5.36 (m, 1H), 3.61-3.55 (m, 1H), 3.06-3.02 (m, 2H), 2.95-2.85 (m, 1H), 2.64-2.59 (m, 2H) | 299.9 0.892 min |
| 0.051 Method 15 | 16 | Trans-2-[(5S,7S)-7-fluoro-5-phenyl-6,7-dihydro-5H-pyrrolo[1,2-b][1,2,4]triazol-2-yl]cyclopropane-carbonitrile | Mixture of Diastereomers | ¹H NMR (400 MHz, CDCl$_3$) δ 7.42-7.39 (m, 3H), 7.24-7.22 (m, 2H), 6.00-5.84 (m, 1H), 5.38-5.34 (m, 1H), 3.64-3.56 (m, 1H), 2.92-2.72 (m, 2H), 2.01-1.94 (m, 1H), 1.67-1.62 (m, 2H) | 269.0 0.822 min |
| 0.034 Method 16 | 17 | rac-(5S,7S)-2-[difluoro-(3-methyloxetan-3-yl)methyl]-7-fluoro-5-phenyl-6,7-dihydro-5H-pyrrolo[1,2-b][1,2,4]triazole | Single Unknown Stereoisomer | ¹H NMR (400 MHz, CD$_3$OD) δ 7.40-7.36 (m, 3H), 7.21-7.19 (m, 2H), 6.14-6.11 (m, 0.5H), 6.00-5.97 (m, 0.5H), 5.61-5.54 (m, 1H), 5.01-4.98 (m, 2H), 4.42-4.36 (m, 2H), 3.80-3.65 (m, 1H), 2.83-2.70 (m, 1H), 1.42 (s, 3H) | 324.1 0.735 min |
| 0.012 Method 18 | 18 | rac-(5S,7S)-7-fluoro-5-phenyl-2-(3,3,3-trifluoropropyl)-6,7-dihydro-5H-pyrrolo[1,2-b][1,2,4]triazole | Single Unknown Stereoisomer | ¹H NMR (400 MHz, CDCl$_3$) δ 7.42-7.36 (m, 3H), 7.23-7.21 (m, 2H), 6.04-5.88 (m, 1H), 5.40-5.36 (m, 1H), 3.63-3.59 (m, 1H), 3.06-3.02 (m, 2H), 2.95-2.85 (m, 1H), 2.64-2.57 (m, 2H) | 299.9 0.891 min |

TABLE 1-continued

| Ki (μM) METHOD | Ex No. | Structure | Stereo | ¹H NMR | MS (m/z) R.T. |
|---|---|---|---|---|---|
| 1.1 Method 19 | 19 | 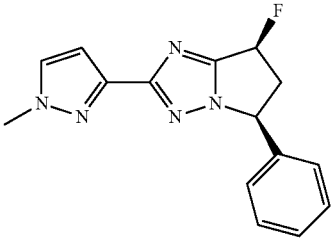<br>rac-(5S,7S)-7-fluoro-2-(1-methylpyrazol-3-yl)-5-phenyl-6,7-dihydro-5H-pyrrolo[1,2-b][1,2,4]triazole | Single Unknown Stereoisomer | ¹H NMR (400 MHz, CD₃OD) δ 7.49 (d, J = 2.0 Hz, 1H), 7.46-7.34 (m, 3H), 7.33-7.20 (m, 2H), 6.82 (d, J = 2.4 Hz, 1H), 6.25-5.99 (m, 1H), 5.66-5.59 (m, 1H), 4.15 (s, 3H), 3.81-3.71 (m, 1H), 2.85-2.74 (m, 1H) | 284.2 1.621 min |
| 0.004 Method 20 | 20 | 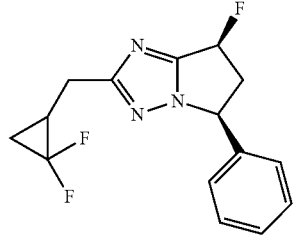<br>rac-(5S,7S)-2-[(2,2-difluorocyclopropyl)methyl]-7-fluoro-5-phenyl-6,7-dihydro-5H-pyrrolo[1,2-b][1,2,4]triazole | Mixture of Diastereomers | ¹H NMR (400 MHz, CDCl₃) δ 7.41-7.36 (m, 3H), 7.24-7.22 (m, 2H), 6.05-5.89 (m, 1H), 5.41-5.37 (m, 1H), 3.63-3.55 (m, 1H), 3.06-3.03 (m, 1H), 2.85-2.81 (m, 2H), 2.01-2.00 (m, 1H), 1.50-1.46 (m, 1H), 1.16-1.11 (m, 1H) | 294.1 1.775 min |
| 0.100 Method 21 | 21 | 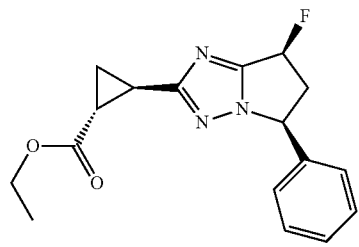<br>ethyl rac-(1R,2R)-2-[rac-(5S,7S)-7-fluoro-5-phenyl-6,7-dihydro-5H-pyrrolo[1,2-b][1,2,4]triazol-2-yl]cyclopropanecarboxylate | Mixture of Diastereomers | ¹H NMR (400 MHz, CDCl₃) δ 7.39-7.36 (m, 3H), 7.23-7.20 (m, 2H), 5.99-5.96 (m, 0.5H), 5.85-5.82 (m, 0.5H), 5.35-5.31 (m, 1H), 4.17-4.11 (m, 2H), 3.58-3.48 (m, 1H), 2.90-2.80 (m, 1H), 2.65-2.63 (m, 1H), 2.22-2.15 (m, 1H), 1.58-1.55 (m, 2H), 1.27-1.23 (m, 3H) | 316.0 0.890 min |
| 0.011 Method 22 | 22 | 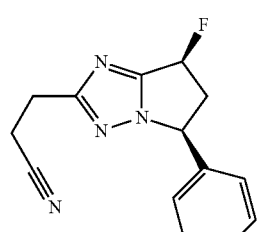<br>3-[rac-(5S,7S)-7-fluoro-5-phenyl-6,7-dihydro-5H-pyrrolo[1,2-b][1,2,4]triazol-2-yl]propanenitrile | Single Unknown Stereoisomer | ¹H NMR (400 MHz, DMSO-d6) δ 7.47-7.29 (m, 3H), 7.26-7.13 (m, 2H), 6.14 (ddd, J = 57.0, 7.1, 1.7 Hz, 1H), 5.59 (ddd, J = 8.3, 7.1, 2.8 Hz, 1H), 3.79-3.57 (m, 1H), 3.06-2.94 (m, 2H), 2.93-2.81 (m, 2H), 2.73-2.54 (m, 1H). LC-MS R$_T$ = 3.78 min, m/z = 257.1 (M + H)⁺. | 257.1 3.78 min |

TABLE 1-continued

| Ki (μM) METHOD | Ex No. | Structure | Stereo | ¹H NMR | MS (m/z) R.T. |
|---|---|---|---|---|---|
| 0.004 Method 23 | 23 | rac-(5S,7S)-2-[difluoro-[rac-(1R,2R)-2-fluorocyclopropyl]methyl]-7-fluoro-5-phenyl-6,7-dihydro-5H-pyrrolo[1,2-b][1,2,4]triazole | Mixture of Diastereomers | ¹H NMR (400 MHz, CDCl₃) δ 7.44-7.39 (m, 3H), 7.26-7.24 (m, 2H), 6.10-6.08 (m, 1H), 5.50-5.45 (m, 1H), 4.92-4.75 (m, 1H), 3.69-3.58 (m, 1H), 3.00-2.90 (m, 1H), 2.31-2.25 (m, 1H), 1.43-1.36 (m, 1H), 1.24-1.19 (m, 1H) | 312.1 1.931 min |
| 0.910 Method 24 | 24 | rac-(5S,7S)-7-fluoro-5-phenyl-2-[rac-(1R,2R)-2-(methoxymethyl)cyclopropyl]-6,7-dihydro-5H-pyrrolo[1,2-b][1,2,4]triazole | Mixture of Diastereomers | ¹H NMR (400 MHz, CD₃OD) δ 7.40-7.2.9 (m, 3H), 7.20-7.17 (m, 2H), 6.03-6.01 (m, 0.5H), 5.89-5.86 (m, 0.5H), 5.45-5.39 (m, 1H), 3.71-3.56 (m, 1H), 3.47-3.41 (m, 1H), 3.30 (s, 3H), 3.30-3.24 (m, 1H), 2.72-2.59 (m, 1H), 1.96-1.91 (m, 1H), 1.66-1.54 (m, 1H), 1.18-1.08 (m, 1H), 0.98-0.90 (m, 1H) | 288.2 0.724 min |
| 0.017 Method 25 | 25 | rac-(5S,7S)-7-fluoro-2-(4-methylpyrazol-1-yl)-5-phenyl-6,7-dihydro-5H-pyrrolo[1,2-b][1,2,4]triazole | Single Unknown Stereoisomer | ¹H NMR (400 MHz, CD₃OD) δ 8.05 (s, 1H), 7.57 (s, 1H), 7.44-7.29 (m, 5H), 6.18-6.02 (m, 1H), 5.62-5.56 (m, 1H), 3.78-3.85 (m, 1H), 2.80-2.69 (m, 1H), 2.14 (s, 3H) | 283.9 0.710 min |
| 0.114 Method 26 | 26 | rac-(5S)-5-(2-fluorophenyl)-2-propyl-6,7-dihydro-5H-pyrrolo[1,2-b][1,2,4]triazole | Single Unknown Stereoisomer | ¹H NMR (400 MHz, CD₃OD) δ 7.42-7.36 (m, 1H), 7.21-7.07 (m, 3H), 5.69-5.66 (m, 1H), 3.29-3.22 (m, 1H), 3.08-3.00 (m, 2H), 2.67-2.58 (m, 3H), 1.78-1.68 (m, 2H), 0.94 (t, J = 7.2 Hz, 3H) | 246.1 1.588 min |

TABLE 1-continued

| Ki (μM) METHOD | Ex No. | Structure | Stereo | $^1$H NMR | MS (m/z) R.T. |
|---|---|---|---|---|---|
| 0.033 Method 27 | 27 | rac-(5S,7S)-7-fluoro-2-((S)-2-fluorobutan-2-yl)-5-phenyl-6,7-dihydro-5H-pyrrolo[1,2-b][1,2,4]triazole | Single Unknown Stereoisomer | $^1$H NMR (400 MHz, CD$_3$OD) δ 7.42-7.35 (m, 3H), 7.23-7.22 (m, 2H), 6.13-5.97 (m, 1H), 5.57-5.52 (m, 1H), 3.79-3.69 (m, 1H), 2.80-2.69 (m, 1H), 2.13-2.02 (m, 2H), 1.69 (d, J = 22.0 Hz, 3H), 0.88 (t, J = 7.6 Hz, 3H) | 278.0 0.732 min |
| 0.070 Method 28 | 28 | rac-(5S,7S)-2-(2,2-difluorocyclopropyl)-7-fluoro-5-phenyl-6,7-dihydro-5H-pyrrolo[1,2-b][1,2,4]triazole | Mixture of Diastereomers | $^1$H NMR (400 MHz, CDCl$_3$) δ 7.42-7.38 (m, 3H), 7.23-7.21 (m, 2H), 6.06-5.89 (m, 1H), 5.42-5.38 (m, 1H), 3.62-3.55 (m, 1H), 2.93-2.85 (m, 2H), 2.18-2.10 (m, 1H), 1.88-1.84 (m, 1H) | 279.9 0.826 min |
| 0.022 Method 29 | 29 | rac-(5S,7S)-2-(3,3-difluoropropyl)-7-fluoro-5-phenyl-6,7-dihydro-5H-pyrrolo[1,2-b][1,2,4]triazole | Single Unknown Stereoisomer | $^1$H NMR (400 MHz, CD$_3$OD) δ 7.43-7.32 (m, 3H), 7.23-7.22 (m, 2H), 6.11-5.83 (m, 2H), 5.50-5.48 (m, 1H), 3.74-3.64 (m, 1H), 2.92-2.88 (m, 2H), 2.71-2.69 (m, 1H), 2.28-2.23 (m, 2H). | 281.9 0.843 min |
| 0.081 Method 30 | 30 | rac-(5S,7S)-2-(2,2-dimethylcyclopropyl)-7-fluoro-5-phenyl-6,7-dihydro-5H-pyrrolo[1,2-b][1,2,4]triazole | Mixture of Diastereomers | $^1$H NMR (400 MHz, CDCl$_3$) δ 7.38-7.35 (m, 3H), 7.20-7.18 (m, 2H), 6.01-5.85 (m, 1H), 5.37-5.35 (m, 1H), 3.58-3.51 (m, 1H), 2.85-2.79 (m, 1H), 1.97-1.94 (m, 1H), 1.20 (s, 3H), 1.18-1.15 (m, 1H), 1.03 (d, J = 8.4 Hz, 3H), 0.90-0.88 (m, 1H) | 272.0 0.889 min |

TABLE 1-continued

| Ki (μM) METHOD | Ex No. | Structure | Stereo | ¹H NMR | MS (m/z) R.T. |
|---|---|---|---|---|---|
| 0.160 Method 31 | 31 | rac-(5S,7S)-7-fluoro-5-phenyl-2-pyrazol-1-yl-6,7-dihydro-5H-pyrrolo[1,2-b][1,2,4]triazole | Single Unknown Stereoisomer | ¹H NMR (400 MHz, CD₃OD) δ 8.30 (d, J = 2.4 Hz, 1H), 7.75 (s, 1H), 7.44-7.30 (m, 5H), 6.55-6.54 (m, 1H), 6.20-6.03 (m, 1H), 5.62-5.58 (m, 1H), 3.80-3.66 (m, 1H), 2.82-2.70 (m, 1H) | 269.9 0.809 min |
| 0.018 Method 27 | 32 | rac-(5S,7S)-7-fluoro-2-((R)-2-fluorobutan-2-yl)-5-phenyl-6,7-dihydro-5H-pyrrolo[1,2-b][1,2,4]triazole | Single Unknown Stereoisomer | ¹H NMR (400 MHz, CD₃OD) δ 7.43-7.35 (m, 3H), 7.23-7.21 (m, 2H), 6.14-5.97 (m, 1H), 5.57-5.52 (m, 1H), 3.79-3.65 (m, 1H), 2.80-2.69 (m, 1H), 2.13-2.02 (m, 2H), 1.69 (d, J = 21.6 Hz, 3H), 0.88 (t, J = 7.6 Hz, 3H) | 278.0 0.857 min |
| 0.034 Method 32 | 33 | rac-(5S,7S)-7-fluoro-5-phenyl-2-[2-(trifluoromethyl)cyclopropyl]-6,7-dihydro-5H-pyrrolo[1,2-b][1,2,4]triazole | Mixture of Diastereomers | ¹H NMR (400 MHz, CD₃OD) δ 7.42-7.37 (m, 3H), 7.24-7.22 (m, 2H), 6.08-6.05 (m, 0.5H), 5.93-5.91 (m, 0.5H), 5.49-5.46 (m, 1H), 3.70-3.62 (m, 1H), 2.76-2.65 (m, 1H), 2.47-2.43 (m, 1H), 2.23-2.21 (m, 1H), 1.44-1.39 (m, 2H) | 312.1 0.804 min |
| 0.904 Method 33 | 34 | rac-(S)-cyclopropyl-[rac-(5S,7S)-7-fluoro-5-phenyl-6,7-dihydro-5H-pyrrolo[1,2-b][1,2,4]triazol-2-yl]methanol | Single Unknown Stereoisomer | ¹H NMR (400 MHz, CDCl₃) δ 7.42-7.36 (m, 3H), 7.24-7.22 (m, 2H), 6.06-5.91 (m, 1H), 5.44-5.39 (m, 1H), 4.27-4.24 (m, 1H), 3.63-3.55 (m, 1H), 2.94-2.83 (m, 1H), 2.54-2.52 (m, 1H), 1.43-1.38 (m, 1H), 0.64-0.58 (m, 2H), 0.50-0.48 (m, 2H) | 274.1 1.345 min |

TABLE 1-continued

| Ki (μM) METHOD | Ex No. | Structure | Stereo | ¹H NMR | MS (m/z) R.T. |
|---|---|---|---|---|---|
| 0.083 Method 33 | 35 | rac-(R)-cyclopropyl-[rac-(5S,7S)-7-fluoro-5-phenyl-6,7-dihydro-5H-pyrrolo[1,2-b][1,2,4]triazol-2-yl]methanol | Single Unknown Stereoisomer | ¹H NMR (400 MHz, CDCl₃) δ 7.42-7.37 (m, 3H), 7.24-7.22 (m, 2H), 6.07-5.91 (m, 1H), 5.43-5.40 (m, 1H), 4.24-4.22 (m, 1H), 3.65-3.55 (m, 1H), 2.93-2.83 (m, 1H), 2.60-2.59 (m, 1H), 1.41-1.36 (m, 1H), 0.64-0.47 (m, 4H) | 274.1 1.325 min |
| 0.049 Method 34 | 36 | (5S,7S)-2-ethyl-7-fluoro-5-phenyl-6,7-dihydro-5H-pyrrolo[1,2-b][1,2,4]triazole | Single Known Stereoisomer | 1H NMR (400 MHz, DMSO-d6) δ 7.52-7.23 (m, 3H), 7.31-7.05 (m, 2H), 6.09 (ddd, J = 57.2, 7.1, 1.7 Hz, 1H), 5.65-5.41 (m, 1H), 3.82-3.48 (m, 1H), 2.70-2.53 (m, 3H), 1.20 (t, J = 7.6 Hz, 3H). | 232.1 4.07 min |
| 3 Method 34 | 37 | (5S,7S)-7-fluoro-2-(isopropoxymethyl)-5-phenyl-6,7-dihydro-5H-pyrrolo[1,2-b][1,2,4]triazole | Single Known Stereoisomer | 1H NMR (400 MHz, DMSO-d6) δ 7.44-7.32 (m, 3H), 7.24-7.17 (m, 2H), 6.14 (ddd, J = 57.0, 7.1, 1.7 Hz, 1H), 5.63-5.54 (m, 1H), 4.42 (s, 2H), 3.76-3.58 (m, 2H), 2.70-2.56 (m, 1H), 1.09 (d, J = 6.1 Hz, 6H). | 276.1 4.43 min |
| 0.49 Method 34 | 38 | (5S,7S)-2-(2-ethoxyethyl)-7-fluoro-5-phenyl-6,7-dihydro-5H-pyrrolo[1,2-b][1,2,4]triazole | Single Known Stereoisomer | No NMR | 276.1 4.24 min |

TABLE 1-continued

| Ki (μM) METHOD | Ex No. | Structure | Stereo | ¹H NMR | MS (m/z) R.T. |
|---|---|---|---|---|---|
| 0.03 Method 35 | 39 | (5S,7S)-7-fluoro-2-(4-isopropylpyrazol-1-yl)-5-phenyl-6,7-dihydro-5H-pyrrolo[1,2-b][1,2,4]triazole | Single Unknown Stereoisomer | 1H NMR (400 MHz, DMSO-d6) δ 8.11 (s, 1H), 7.69 (s, 1H), 7.47-7.35 (m, 3H), 7.32-7.23 (m, 2H), 6.23 (ddd, J = 56.8, 7.2, 1.8 Hz, 1H), 5.66 (td, J = 8.0, 2.9 Hz, 1H), 3.87-3.58 (m, 1H), 2.85 (hept, J = 13.9, 6.9 Hz, 1H), 2.72-2.56 (m, 1H), 1.20 (d, J = 6.8 Hz, 6H). | 312.1 5.44 min |
| 0.052 Method 36 | 40 | 1-[(5S,7S)-7-fluoro-5-phenyl-6,7-dihydro-5H-pyrrolo[1,2-b][1,2,4]triazol-2-carbaldehyde | Single Known Stereoisomer | ¹H NMR (400 MHz, DMSO-d6) δ 9.93 (s, 1H), 9.14 (d, J = 0.6 Hz, 1H), 8.27 (d, J = 0.6 Hz, 1H), 7.56-7.36 (m, 3H), 7.35-7.20 (m, 2H), 6.28 (ddd, J = 56.6, 7.2, 1.9 Hz, 1H), 5.72 (td, J = 8.0, 3.1 Hz, 1H), 3.86-3.63 (m, 1H), 2.84-2.52 (m, 1H). LC-MS R$_T$ = 4.20 min, m/z = 298.1 (M + H)⁺. | 298.1 4.20 min |
| 0.26 Method 36 | 41 | (5S,7S)-7-fluoro-5-phenyl-2-(4-pyrimidin-4-ylpyrazol-1-yl)-6,7-dihydro-5H-pyrrolo[1,2-b][1,2,4]triazole | Single Unknown Stereoisomer | 1H NMR (400 MHz, DMSO-d6) δ 9.19 (s, 1H), 9.14 (d, J = 1.5 Hz, 1H), 8.78 (d, J = 5.3 Hz, 1H), 8.47 (s, 1H), 7.99 (dd, J = 5.3, 1.5 Hz, 1H), 7.49-7.35 (m, 3H), 7.35-7.28 (m, 2H), 6.28 (ddd, J = 56.7, 7.2, 2.0 Hz, 1H), 5.72 (td, J = 8.0, 3.1 Hz, 1H), 3.83-3.65 (m, 1H), 2.77-2.60 (m, 1H). | 348.2 4.52 min |
| 0.006 Method 37 | 42 | rac-(5S,7S)-2-[1-bicyclo[1.1.1]pentanyl(difluoro)methyl]-7-fluoro-5-phenyl-6,7-dihydro-5H-pyrrolo[1,2-b][1,2,4]triazole | Single Known Stereoisomer | ¹H NMR (400 MHz, DMSO-d₆) δ 7.48-7.32 (m, 3H), 7.25-7.15 (m, 2H), 6.20 (ddd, J = 56.5, 7.1, 1.8 Hz, 1H), 5.69 (ddd, J = 9.1, 6.9, 2.9 Hz, 1H), 3.82-3.63 (m, 1H), 2.76-2.59 (m, 1H), 2.57 (s, 1H), 1.91 (s, 6H). | 320.1 5.80 min |

TABLE 1-continued

| Ki (μM) METHOD | Ex No. | Structure | Stereo | ¹H NMR | MS (m/z) R.T. |
|---|---|---|---|---|---|
| 0.45 Method 39 | 43 | rac-(5S,7S)-2-(2-cyclopropylethynyl)-7-fluoro-5-phenyl-6,7-dihydro-5H-pyrrolo[1,2-b][1,2,4]triazole | Single Known Stereoisomer | ¹H NMR (400 MHz, DMSO-d₆) δ 7.46-7.31 (m, 3H), 7.25-7.14 (m, 2H), 6.24-6.01 (m, 1H), 5.59 (ddd, J = 8.3, 6.9, 3.0 Hz, 1H), 3.77-3.57 (m, 1H), 2.72-2.54 (m, 1H), 1.57 (tt, J = 8.2, 5.0 Hz, 1H), 0.95-0.87 (m, 2H), 0.80-0.72 (m, 2H). | 268.1 5.00 min |
| 0.89 Method 40 | 44 | rac-(5S,7S)-7-fluoro-5-phenyl-2-prop-1-ynyl-6,7-dihydro-5H-pyrrolo[1,2-b][1,2,4]triazole | Single Known Stereoisomer | ¹H NMR (400 MHz, DMSO-d₆) δ 7.47-7.30 (m, 3H), 7.23-7.12 (m, 2H), 6.24-6.03 (m, 1H), 5.65-5.54 (m, 1H), 3.78-3.56 (m, 1H), 2.63 (ddt, J = 27.0, 15.2, 2.2 Hz, 1H), 2.05 (s, 3H). | 242.1 4.50 min |
| 0.23 Method 41 | 45 | (5S,7S)-2-((R)-bicyclo[1.1.1]pentan-1-ylfluoromethyl)-7-fluoro-5-phenyl-6,7-dihydro-5H-pyrrolo[1,2-b][1,2,4]triazole | Single Unknown Stereoisomer | No NMR | 302.1 4.90 min |

| Ki (μM) METHOD | Ex No. | Structure | Stereo | ¹H NMR | MS (m/z) R.T. |
|---|---|---|---|---|---|
| 0.84 Method 41 | 46 | 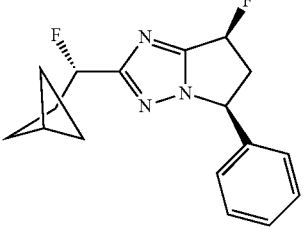<br>(5S,7S)-2-((S)-bicyclo[1.1.1]pentan-1-ylfluoromethyl)-7-fluoro-5-phenyl-6,7-dihydro-5H-pyrrolo[1,2-b][1,2,4]triazole | Single Unknown Stereoisomer | N/A | 302.1 4.82 min |
| 0.095 Method 42 | 47 | 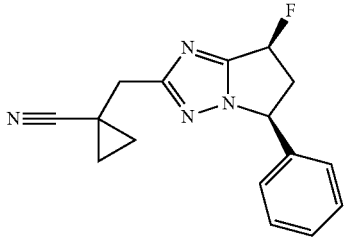<br>1-[[(5S,7S)-7-fluoro-5-phenyl-6,7-dihydro-5H-pyrrolo[1,2-b][1,2,4]triazol-2-yl]methyl]cyclopropane-carbonitrile | Single Unknown Stereoisomer | ¹H NMR (400 MHz, DMSO-d6) δ 7.44-7.30 (m, 3H), 7.24-7.16 (m, 2H), 6.16 (ddd, J = 57.0, 7.1, 1.6 Hz, 1H), 5.62 (ddd, J = 8.6, 8.0, 2.7 Hz, 1H), 3.79-3.57 (m, 1H), 2.92 (s, 2H), 2.70-2.54 (m, 1H), 1.30-1.20 (m, 2H), 1.13-1.02 (m, 2H). | 283.1 4.27 min |
| 0.91 Method 43 | 48 | 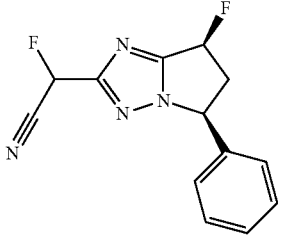<br>2-fluoro-2-[(5S,7S)-7-fluoro-5-phenyl-6,7-dihydro-5H-pyrrolo[1,2-b][1,2,4]triazol-2-yl]acetonitrile | Mixture of Diastereomers | 1H NMR (400 MHz, Methanol-d4) δ 7.47-7.32 (m, 3H), 7.31-7.19 (m, 2H), 6.58 (d, J = 45.7 Hz, 1H), 6.10 (ddd, J = 56.2, 7.3, 2.0 Hz, 1H), 5.68-5.55 (m, 1H), 3.83-3.64 (m, 1H), 2.80 (dddd, J = 26.6, 15.3, 3.3, 2.0 Hz, 1H). | 261 1.17 min (2 min method) |
| 1.2 Method 44 | 49 | 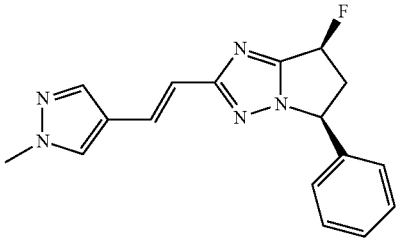<br>(5S,7S)-7-fluoro-2-[(E)-2-(1-methylpyrazol-4-yl)vinyl]-5-phenyl-6,7-dihydro-5H-pyrrolo[1,2-b][1,2,4]triazole | Single Unknown Stereoisomer | ¹H NMR (400 MHz, DMSO-d₆) δ 7.96 (s, 1H), 7.76 (s, 1H), 7.46-7.29 (m, 4H), 7.27-7.19 (m, 2H), 6.77 (d, J = 16.3 Hz, 1H), 6.14 (ddd, J = 57.1, 7.1, 1.8 Hz, 1H), 5.58 (ddd, J = 8.3, 7.0, 2.8 Hz, 1H), 3.82 (s, 3H), 3.77-3.59 (m, 1H), 2.71-2.50 (m, 1H). | 310.1 4.24 min |

TABLE 1-continued

| Ki (μM) METHOD | Ex No. | Structure | Stereo | ¹H NMR | MS (m/z) R.T. |
|---|---|---|---|---|---|
| 0.22 Method 45 | 50 | 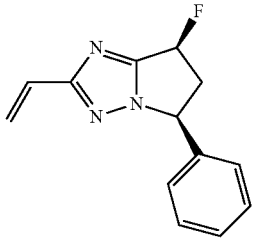<br>(5S,7S)-7-fluoro-5-phenyl-2-vinyl-6,7-dihydro-5H-pyrrolo[1,2-b][1,2,4]triazole | Single Unknown Stereoisomer | ¹H NMR (400 MHz, DMSO-d₆) δ 7.45-7.31 (m, 3H), 7.26-7.18 (m, 2H), 6.65 (dd, J = 17.5, 11.0 Hz, 1H), 6.21 (dd, J = 7.1, 1.8 Hz, 0H), 6.13 (dd, J = 17.5, 1.8 Hz, 1H), 5.59 (ddd, J = 8.4, 6.9, 2.9 Hz, 1H), 5.51 (dd, J = 11.0,1.9 Hz, 1H), 3.68 (dddd, J = 26.0, 15.4, 8.4, 7.1 Hz, 1H), 2.63 (dddd, J = 26.4, 15.2, 3.0, 1.8 Hz, 1H). | 230.1 4.23 min |
| 0.12 Method 46 | 51 | 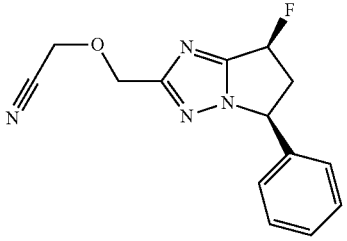<br>2-[(7-fluoro-5-phenyl-6,7-dihydro-5H-pyrrolo[1,2-b][1,2,4]triazol-2-yl)methoxy]acetonitrile | Mixture of Enantiomers | ¹H NMR (400 MHz, DMSO-d₆) δ 7.45-7.31 (m, 3H), 7.26-7.18 (m, 2H), 6.16 (ddd, J = 56.8, 7.1, 1.8 Hz, 1H), 5.61 (ddd, J = 8.4, 6.9, 2.9 Hz, 1H), 4.60 (s, 2H), 4.53 (s, 2H), 3.69 (dddd, J = 26.0, 15.4, 8.5, 7.1 Hz, 1H), 2.65 (dddd, J = 26.5, 15.2, 3.0, 1.8 Hz, 1H). | 273.1 3.96 min |
| 0.1 Method 45 | 52 | 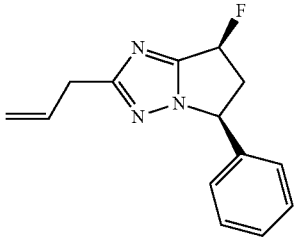<br>(5S,7S)-2-allyl-7-fluoro-5-phenyl-6,7-dihydro-5H-pyrrolo[1,2-b][1,2,4]triazole | Single Unknown Stereoisomer | ¹H NMR (400 MHz, DMSO-d₆) δ 7.45-7.30 (m, 3H), 7.24-7.16 (m, 2H), 6.11 (ddd, J = 57.1, 7.1, 1.6 Hz, 1H), 6.01-5.90 (m, 1H), 5.55 (ddd, J = 8.3, 7.2, 2.8 Hz, 1H), 5.20-5.01 (m, 2H), 3.65 (dddd, J = 26.4, 15.4, 8.4, 7.1 Hz, 1H), 3.44 (dt, J = 6.7, 1.5 Hz, 2H), 2.60 (dddd, J = 26.3, 15.3, 2.8, 1.7 Hz, 1H). | 244.1 4.32 min |
| 0.28 Method 47 | 53 | 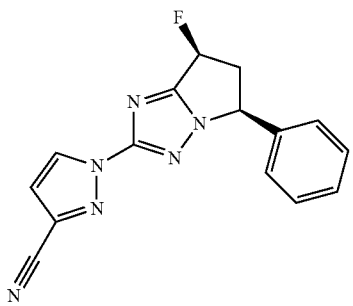<br>1-[(5S,7S)-7-fluoro-5-phenyl-6,7-dihydro-5H-pyrrolo[1,2-b][1,2,4]triazol-2-yl]pyrazole-3-carbonitrile | Single Unknown Stereoisomer | ¹H NMR (400 MHz, DMSO-d₆) δ 8.69 (d, J = 2.7 Hz, 1H), 7.51-7.30 (m, 3H), 7.38-7.17 (m, 3H), 6.23 (dddd, J = 56.6, 38.4, 7.2, 2.0 Hz, 1H), 5.68 (dtd, J = 31.1, 7.9, 3.1 Hz, 1H), 3.89-3.55 (m, 1H), 2.80-2.52 (m, 1H). | 295.1 4.81 min |

TABLE 1-continued

| Ki (μM) METHOD | Ex No. | Structure | Stereo | ¹H NMR | MS (m/z) R.T. |
|---|---|---|---|---|---|
| 0.041 Method 47 | 54 | 1-[(5S,7S)-7-fluoro-5-phenyl-6,7-dihydro-5H-pyrrolo[1,2-b][1,2,4]triazol-2-yl]pyrazole-4-carbonitrile | Single Unknown Stereoisomer | ¹H NMR (400 MHz, DMSO-d₆) δ 9.27 (s, 1H), 839 (s, 1H), 7.52-7.36 (m, 3H), 7.40-7.26 (m, 2H), 6.27 (ddd, J = 56.5, 7.3, 2.0 Hz, 1H), 5.72 (td, J = 8.0, 3.1 Hz, 1H), 3.73 (dddd, J = 24.9, 15.4, 3.5, 7.3 Hz, 1H), 2.76-2.58 (m, 1H). | 295.1 4.52 min |
| 0.13 Method 44 | 55 | 3-[[rac-(5S,7S)-7-fluoro-5-phenyl-6,7-dihydro-5H-pyrrolo[1,2-b][1,2,4]triazol-2-yl]methylene]cyclobutane-carbonitrile | Single Unknown Stereoisomer | ¹H NMR (400 MHz, DMSO-d6) δ 7.64-7.51 (m, 0H), 7.48-7.30 (m, 3H), 7.19 (dd, J = 7.8, 1.7 Hz, 2H), 6.25-6.02 (m, 2H), 5.63-5.51 (m, 1H), 3.66 (dddd, J = 26.6, 15.5, 8.5, 7.1 Hz, 1H), 3.55-3.43 (m, 2H), 3.30-3.10 (m, 3H), 2.73-2.53 (m, 1H). | 295.1 4.57 min |
| <0.005 Method 47 | 56 | (5S,7S)-7-fluoro-5-phenyl-2-[4-(trifluoromethyl)pyrazol-1-yl]-6,7-dihydro-5H-pyrrolo[1,2-b][1,2,4]triazole | Single Unknown Stereoisomer | ¹H NMR (400 MHz, DMSO-d₆) δ 9.07 (s, 1H), 8.28 (s, 1H), 7.42 (ddt, J = 14.6, 7.7, 6.2 Hz, 3H), 7.35-7.25 (m, 2H), 6.40-6.16 (m, 1H), 5.73 (td, J = 7.9, 3.1 Hz, 1H), 3.83-3.62 (m, 1H), 2.77-2.58 (m, 1H), | 338.1 5.39 min |

TABLE 1-continued

| Ki (μM) METHOD | Ex No. | Structure | Stereo | ¹H NMR | MS (m/z) R.T. |
|---|---|---|---|---|---|
| 0.13 Method 47 | 57 | 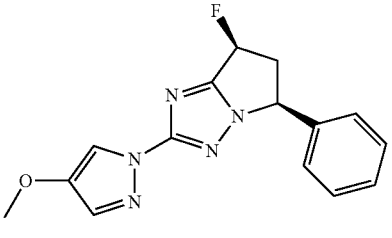<br>(5S,7S)-7-fluoro-2-(4-methoxypyrazol-1-yl)-5-phenyl-6,7-dihydro-5H-pyrrolo[1,2-b][1,2,4]triazole | Single Unknown Stereoisomer | ¹H NMR (400 MHz, DMSO-$d_6$) δ 8.05 (s, 1H), 7.60 (s, 1H), 7.42 (q, J = 6.2 Hz, 3H), 7.31-7.12 (m, 2H), 6.22 (ddd, J = 56.9, 7.3, 1.9 Hz, 1H), 5.65 (td, J = 8.0, 3.0 Hz, 1H), 3.72-3.56 (m, 1H), 2.64 (ddt, J = 26.7, 15.1, 2.4 Hz, 1H). | 300.1 4.47 min |
| 0.009 Method 47 | 58 | 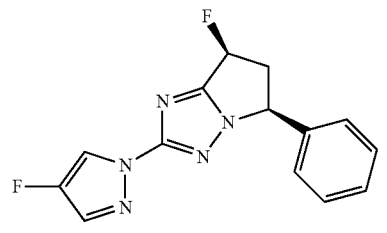<br>(5S,7S)-7-fluoro-2-(4-fluoropyrazol-1-yl)-5-phenyl-6,7-dihydro-5H-pyrrolo[1,2-b][1,2,4]triazole | Single Unknown Stereoisomer | ¹H NMR (400 MHz, DMSO-d6) δ 8.53 (dd, J = 4.6, 0.8 Hz, 1H), 7.91 (dd, J = 4.2, 0.8 Hz, 1H), 7.48-7.2.5 (m, 5H), 6.24 (ddd, J = 56.7, 7.3, 1.9 Hz, 1H), 5.68 (td, J = 8.0, 3.0 Hz, 1H), 3.71 (dddd, J = 25.1, 15.4, 8.3, 7.2 Hz, 1H), 2.80-2.55 (m, 1H). | 288.1 4.62 min |
| 0.011 Method 47 | 59 | 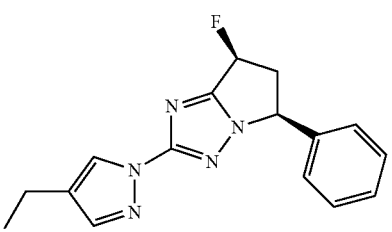<br>(5S,7S)-2-(4-ethylpyrazol-1-yl)-7-fluoro-5-phenyl-6,7-dihydro-5H-pyrrolo[1,2-b][1,2,4]triazole | Single Unknown Stereoisomer | ¹H NMR (400 MHz, DMSO-$d_6$) δ 8.12 (d, J = 1.0 Hz, 1H), 7.64 (s, 1H), 7.47-7.34 (m, 3H), 7.38-7.21 (m, 2H), 6.23 (ddd, J = 56.8, 7.2, 1.9 Hz, 1H), 5.66 (td, J = 8.0, 2.9 Hz, 1H), 3.70 (dddd, J = 25.3, 15.4, 8.4, 7.2 Hz, 1H), 2.64 (dddd, J = 26.7, 15.2, 3.0, 1.9 Hz, 1H), 2.50-2.42 (m, 2H), 1.17 (t, J = 7.5 Hz, 3H). | 298.1 5.03 min |
| 0.0045 Method 47 | 60 | 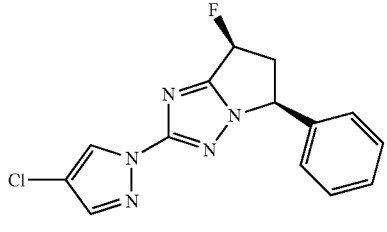<br>(5S,7S)-2-(4-chloropyrazol-1-yl)-7-fluoro-5-phenyl-6,7-dihydro-5H-pyrrolo[1,2-b][1,2,4]triazole | Single Unknown Stereoisomer | ¹H NMR (400 MHz, DMSO-$d_6$) δ 8.63 (s, 1H), 7.93 (s, 1H), 7.51-7.35 (m, 3H), 7.33-7.25 (m, 2H), 6.25 (ddd, J = 56.7, 7.3, 1.9 Hz, 1H), 5.69 (td, J = 7.9, 3.1 Hz, 1H), 3.72 (dddd, J = 25.1, 15.4, 8.4, 7.2 Hz, 1H), 2.74-2.58 (m, 1H). | 304.0 5.04 min |

TABLE 1-continued

| Ki (μM) METHOD | Ex No. | Structure | Stereo | ¹H NMR | MS (m/z) R.T. |
|---|---|---|---|---|---|
| 0.82 Method 48 | 61 | (5S,7S)-7-fluoro-2-(1-methylimidazol-2-yl)-5-phenyl-6,7-dihydro-5H-pyrrolo[1,2-b][1,2,4]triazole | Single Unknown Stereoisomer | ¹H NMR (500 MHz, DMSO-d6) δ 7.46-7.40 (m, 2H), 7.40-7.32 (m, 1H), 7.31 (s, 1H), 7.29-7.24 (m, 2H), 6.99 (s, 1H), 6.24 (ddd, J = 56.8, 7.1, 1.6 Hz, 1H), 5.71 (td, J = 8.6, 2.7 Hz, 1H), 3.74 (dddd, J = 26.3, 15.4, 8.3, 7.2 Hz, 1H), 3.34 (s, 2H), 2.75-2.63 (m, 1H). | 284.1 2.78 min |
| 0.16 Method 47 | 62 | (5S,7S)-7-fluoro-5-phenyl-2-[4-(trifluoromethyl)imidazol-1-yl]-6,7-dihydro-5H-pyrrolo[1,2-b][1,2,4]triazole | Single Unknown Stereoisomer | ¹H NMR (400 MHz, DMSO-d6) δ 8.56-8.51 (m, 1H), 8.41 (p, J = 1.3 Hz, 1H), 7.48-7.34 (m, 3H), 7.39-7.27 (m, 2H), 6.27 (ddd, J = 56.5, 7.3, 2.0 Hz, 1H), 5.71 (td, J = 7.9, 3.1 Hz, 1H), 3.74 (dddd, J = 24.9, 15.5, 8.4, 7.3 Hz, 1H), 2.75-2.58 (m, 1H). | 338.1 5.39 min |
| 0.092 Method 49 | 63 | (5S,7S)-7-fluoro-2-(5-methylpyrazol-1-yl)-5-phenyl-6,7-dihydro-5H-pyrrolo[1,2-b][1,2,4]triazole | Single Unknown Stereoisomer | ¹H NMR (400 MHz, DMSO-d6) δ 7.60 (d, J = 1.6 Hz, 1H), 7.48-7.33 (m, 3H), 7.31-7.24 (m, 2H), 6.42-6.12 (m, 2H), 5.72 (td, J = 7.9, 2.9 Hz, 1H), 3.72 (dddd, J = 25.7, 15.4, 8.4, 7.2 Hz, 1H), 2.74-2.56 (m, 1H), 2.42 (s, 3H) | 284.1 4.61 min |
| 0.61 Method 49 | 64 | (5S,7S)-7-fluoro-5-phenyl-2-[3-(trifluoromethyl)pyrazol-1-yl]-6,7-dihydro-5H-pyrrolo[1,2-b][1,2,4]triazole | Single Unknown Stereoisomer | ¹H NMR (400 MHz, DMSO-d6) δ 8.63 (dq, J = 2.2, 1.0 Hz, 1H), 7.53-7.36 (m, 3H), 7.35-7.25 (m, 2H), 7.06 (d, J = 2.6 Hz, 1H), 6.28 (ddd, J = 56.7, 7.2, 2.0 Hz, 1H), 5.71 (td, J = 8.1, 3.2 Hz, 1H), 3.74 (dddd, J = 24.8, 15.5, 8.4, 7.3 Hz, 1H), 2.78-2.60 (m, 1H). | 338.1 5.64 min |

TABLE 1-continued

| Ki (μM) METHOD | Ex No. | Structure | Stereo | ¹H NMR | MS (m/z) R.T. |
|---|---|---|---|---|---|
| 0.72 Method 47 | 65 | 5-amino-1-[(5S,7S)-7-fluoro-5-phenyl-6,7-dihydro-5H-pyrrolo[1,2-b][1,2,4]triazol-2-yl]-3-methyl-pyrazole-4-carbonitrile | Single Unknown Stereoisomer | ¹H NMR (500 MHz, DMSO-d6) δ 7.50 (s, 2H), 7.45-7.35 (m, 3H), 7.30-7.27 (m, 2H), 6.33-6.14 (m, 1H), 5.90 (s, 0H), 5.67 (td, J = 8.0, 3.0 Hz, 1H), 3.78-3.62 (m, 1H), 2.72-2.59 (m, 1H), 2.14 (s, 3H). | 324.0 1.13 min (2 mins LC_MS method) |
| 0.89 Method 47 | 66 | (5S,7S)-7-fluoro-2-imidazol-1-yl-5-phenyl-6,7-dihydro-5H-pyrrolo[1,2-b][1,2,4]triazole | Single Unknown Stereoisomer | ¹H NMR (400 MHz, DMSO-d$_6$) δ 8.30 (t, J = 1.1 Hz, 1H), 7.72 (q, J = 1.3 Hz, 1H), 7.48-7.32 (m, 3H), 7.36-7.17 (m, 2H), 7.15-7.08 (m, 1H), 6.24 (ddd, J = 56.6, 7.2, 1.9 Hz, 1H), 5.68 (td, J = 8.0, 3.1 Hz, 1H), 3.72 (dddd, J = 25.0, 15.4, 8.4, 7.2 Hz, 1H), 2.64 (dddd, J = 26.9, 15.1, 3.1, 2.0 Hz, 1H). | 270.1 3.30 min |
| 0.89 Method 47 | 67 | (5S,7S)-7-fluoro-2-(2-methylimidazol-1-yl)-5-phenyl-6,7-dihydro-5H-pyrrolo[1,2-b][1,2,4]triazole | Single Unknown Stereoisomer | ¹H NMR (400 MHz, DMSO-d$_6$) δ 7.54 (d, J = 1.5 Hz, 1H), 7.48-7.31 (m, 3H), 7.32-7.23 (m, 2H), 6.91 (d, J = 1.6 Hz, 1H), 6.25 (ddd, J = 56.6, 7.2, 1.9 Hz, 1H), 5.71 (td, J = 8.0, 3.0 Hz, 1H), 3.71 (dddd, J = 25.6, 15.4, 8.4, 7.1 Hz, 1H), 2.72-2.55 (m, 1H), 2.55-2.50 (m, 3H). | 284.1 2.95 min |
| 0.19 Method 47 | 68 | (5S,7S)-7-fluoro-5-phenyl-2-(1,2,4-triazol-1-yl)-6,7-dihydro-5H-pyrrolo[1,2-b][1,2,4]triazole | Single Unknown Stereoisomer | NO NMR | 271.1 4.01 min |

TABLE 1-continued

| Ki (μM) METHOD | Ex No. | Structure | Stereo | ¹H NMR | MS (m/z) R.T. |
|---|---|---|---|---|---|
| 0.086 Method 47 | 69 | 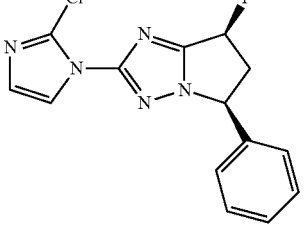<br>(5S,7S)-2-(2-chloroimidazol-1-yl)-7-fluoro-5-phenyl-6,7-dihydro-5H-pyrrolo[1,2-b][1,2,4]triazole | Single Unknown Stereoisomer | ¹H NMR (400 MHz, DMSO-$d_6$) δ 7.73 (d, J = 1.7 Hz, 1H), 7.51-7.34 (m, 4H), 7.32-7.24 (m, 2H), 7.09 (d, J = 1.7 Hz, 1H), 6.42-6.18 (m, 1H), 5.75 (ddd, J = 8.3, 7.2, 3.0 Hz, 1H), 3.73 (dddd, J = 25.6, 15.4, 8.5, 7.2 Hz, 1H), 2.75-2.55 (m, 1H). | 304.1 4.50 min |
| 0.18 Method 47 | 70 | 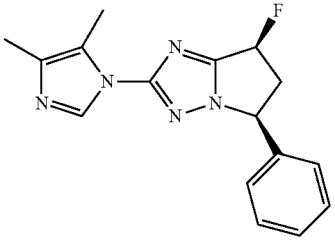<br>(5S,7S)-2-(4,5-dimethylimidazol-1-yl)-7-fluoro-5-phenyl-6,7-dihydro-5H-pyrrolo[1,2-b][1,2,4]triazole | Single Unknown Stereoisomer | ¹H NMR (400 MHz, DMSO-d6) δ 7.97 (s, 1H), 7.47-7.33 (m, 3H), 7.30-7.23 (m, 2H), 6.24 (ddd, J = 56.6, 7.2, 1.9 Hz, 1H), 5.70 (td, J = 7.9, 2.9 Hz, 1H), 3.70 (dddd, J = 25.7, 15.4, 8.4, 7.2 Hz, 1H), 2.63 (dddd, J = 26.6, 15.2, 3.0, 1.9 Hz, 1H), 2.29 (d, J = 0.9 Hz, 3H), 2.08 (d, J = 0.9 Hz, 3H). | 298.2 3.21 min |
| 0.82 Method 47 | 71 | 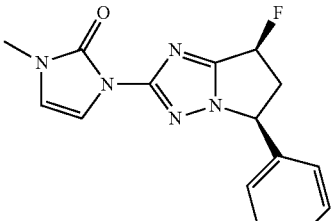<br>1-[(5S,7S)-7-fluoro-5-phenyl-6,7-dihydro-5H-pyrrolo[1,2-b][1,2,4]triazol-2-yl]-3-methyl-imidazol-2-one | Single Unknown Stereoisomer | ¹H NMR (400 MHz, DMSO-d6) δ 7.47-7.33 (m, 3H), 7.37-7.21 (m, 2H), 6.37 (d, J = 3.2 Hz, 1H), 6.71 (d, J = 3.2 Hz, 1H), 6.19 (ddd, J = 56.9, 7.2, 1.8 Hz, 1H), 5.64 (td, J = 8.0, 2.9 Hz, 1H), 3.68 (dddd, J = 25.7, 15.3, 8.4, 7.1 Hz, 1H), 3.15 (s, 3H), 2.61 (dddd, J = 26.6, 15.3, 3.0, 1.8 Hz, 1H). | 300.1 3.78 min |
| <0.005 Method 47 | 72 | 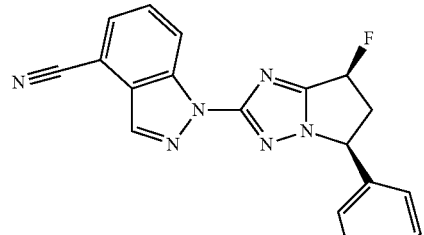<br>1-[(5S,7S)-7-fluoro-5-phenyl-6,7-dihydro-5H-pyrrolo[1,2-b][1,2,4]triazol-2-yl]indazole-4-carbonitrile | Single Unknown Stereoisomer | ¹H NMR (500 MHz, DMSO-d6) δ 8.68 (d, J = 0.8 Hz, 1H), 8.60 (d, J = 8.7 Hz, 1H), 7.97-7.92 (m, 1H), 7.77 (dd, J = 8.6, 7.3 Hz, 1H), 7.48-7.42 (m, 2H), 7.42-7.37 (m, 1H), 7.37-7.31 (m, 2H), 6.32 (ddd, J = 56.7, 7.2, 1.8 Hz, 1H), 5.77 (td, J = 8.0, 2.9 Hz, 1H), 3.84-3.69 (m, 1H), 2.76-2.65 (m, 1H). | 345.1 5.54 min |

TABLE 1-continued

| Ki (μM) METHOD | Ex No. | Structure | Stereo | ¹H NMR | MS (m/z) R.T. |
|---|---|---|---|---|---|
| 0.0062 Method 47 | 73 | 1-[rac-(5S,7S)-7-fluoro-5-phenyl-6,7-dihydro-5H-pyrrolo[1,2-b][1,2,4]triazol-2-yl]indazole | Single Unknown Stereoisomer | ¹H NMR (500 MHz, DMSO-d6) δ 8.43 (d, J = 0.7 Hz, 1H), 8.27 (dd, J = 8.5, 0.8 Hz, 1H), 7.91 (d, J = 8.0 Hz, 1H), 7.58 (ddd, J = 8.3, 7.0, 1.0 Hz, 1H), 7.48-7.42 (m, 2H), 7.42-7.36 (m, 1H), 7.36-7.30 (m, 3H), 6.31 (ddd, J = 56.9, 7.1, 1.7 Hz, 1H), 5.74 (td, J = 8.0, 2.8 Hz, 1H), 3.83-3.68 (m, 1H), 2.75-2.62 (m, 1H). | 320.1 5.47 min |
| 0.07 Method 49 | 74 | (5S,7S)-7-fluoro-2-(5-methyl-1,2,4-triazol-1-yl)-5-phenyl-6,7-dihydro-5H-pyrrolo[1,2-b][1,2,4]triazole | Single Unknown Stereoisomer | NO NMR | 285.1 4.03 min |
| 0.1 Method 47 | 75 | (5S,7S)-2-(4-chloroimidazol-1-yl)-7-fluoro-5-phenyl-6,7-dihydro-5H-pyrrolo[1,2-b][1,2,4]triazole | Single Unknown Stereoisomer | ¹H NMR (400 MHz, DMSO-d6) δ 8.32 (d, J = 1.5 Hz, 1H), 7.87 (d, J = 1.5 Hz, 1H), 7.50-7.34 (m, 3H), 7.33-7.25 (m, 2H), 6.25 (ddd, J = 56.7, 7.2, 2.0 Hz, 1H), 5.68 (td, J = 7.9, 3.1 Hz, 1H), 3.72 (dddd, J = 24.8, 15.4, 8.4, 7.3 Hz, 1H), 2.64 (dddd, J = 27.0, 15.1, 3.1, 1.9 Hz, 1H). | 304.1 4.99 min |
| 0.064 Method 47 | 76 | (5S,7S)-7-fluoro-2-(4-fluoroimidazol-1-yl)-5-phenyl-6,7-dihydro-5H-pyrrolo[1,2-b][1,2,4]triazole | Single Unknown Stereoisomer | ¹H NMR (400 MHz, DMSO-d6) δ 8.11 (t, J = 1.7 Hz, 1H), 7.50 (dd, J = 8.1, 1.7 Hz, 1H), 7.47-7.35 (m, 3H), 7.33-7.25 (m, 2H), 6.24 (ddd, J = 56.5, 7.3, 2.0 Hz, 1H), 5.68 (td, J = 8.0, 3.1 Hz, 1H), 3.72 (dddd, J = 24.9, 15.4, 8.4, 7.3 Hz, 1H), 2.64 (dddd, J = 27.0, 15.1, 3.1, 2.0 Hz, 1H). | 288.1 4.84 min |

| Ki (μM) METHOD | Ex No. | Structure | Stereo | ¹H NMR | MS (m/z) R.T. |
|---|---|---|---|---|---|
| 0.26 Method 50 | 77 | 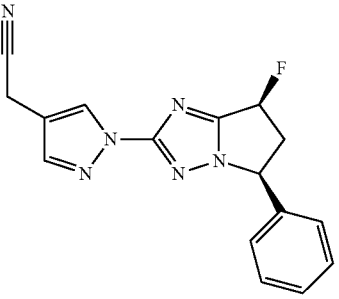 2-[1-[(5S,7S)-7-fluoro-5-phenyl-6,7-dihydro-5H-pyrrolo[1,2-b][1,2,4]triazol-2-yl]pyrazol-4-yl]acetonitrile | Single Unknown Stereoisomer | ¹H NMR (400 MHz, DMSO-$d_6$) δ 8.36 (q, J = 0.9 Hz, 1H), 7.79 (d, J = 0.7 Hz, 1H), 7.48-7.33 (m, 3H), 7.33-7.25 (m, 2H), 6.2.4 (ddd, J = 56.7, 7.2, 1.9 Hz, 1H), 5.68 (td, J = 8.0, 3.0 Hz, 1H), 3.97-3.86 (m, 2H), 3.83-3.56 (m, 1H), 2.65 (dddd, J = 26.9, 15.2, 3.1, 1.9 Hz, 1H). | 309.1 4.42 min |
| 0.13 Method 47 | 78 | 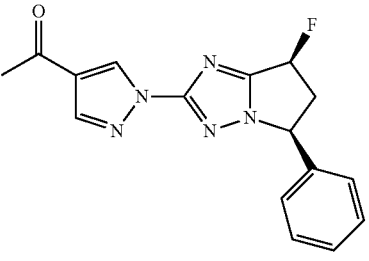 1-[1-[rac-(5S,7S)-7-fluoro-5-phenyl-6,7-dihydro-5H-pyrrolo[1,2-b][1,2,4]triazol-2-yl]pyrazol-4-yl]ethanone | Single Unknown Stereoisomer | ¹H NMR (400 MHz, DMSO-$d_6$) δ 9.04 (s, 1H), 8.18 (s, 1H), 7.48-7.37 (m, 3H), 7.34-7.26 (m, 2H), 6.43-6.16 (m, 1H), 5.71 (td, J = 7.9, 3.1 Hz, 1H), 3.83-3.63 (m, 1H), 2.76-2.63 (m, 1H), 2.47 (s, 3H). | 312.1 4.56 min |
| 0.013 Method 47 | 79 | 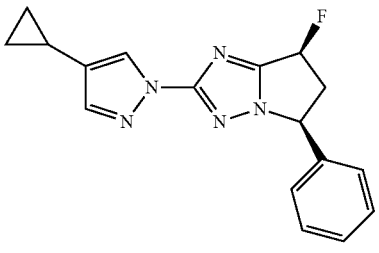 (5S,7S)-2-(4-cyclopropylpyrazol-1-yl)-7-fluoro-5-phenyl-6,7-dihydro-5H-pyrrolo[1,2-b][1,2,4]triazole | Single Unknown Stereoisomer | ¹H NMR (400 MHz, DMSO-d6) δ 8.09 (d, J = 0.7 Hz, 1H), 7.59 (d, J = 0.8 Hz, 1H), 7.47-7.35 (m, 3H), 7.37-7.24 (m, 2H), 6.22 (ddd, J = 56.8, 7.2, 1.9 Hz, 1H), 5.65 (td, J = 8.0, 3.0 Hz, 1H), 3.70 (dddd, J = 25.3, 15.4, 8.4, 7.2 Hz, 1H), 2.63 (dddd, J = 26.8, 15.2, 3.0, 1.9 Hz, 1H), 1.76 (tt, J = 8.4, 5.1 Hz, 1H), 0.91-0.77 (m, 2H), 0.67-0.55 (m, 2H). | 310.2 5.40 min |

TABLE 1-continued

| Ki (μM) METHOD | Ex No. | Structure | Stereo | ¹H NMR | MS (m/z) R.T. |
|---|---|---|---|---|---|
| 0.19 Method 47 | 80 | (5S,7S)-7-fluoro-2-(4-methylsulfonylpyrazol-1-yl)-5-phenyl-6,7-dihydro-5H-pyrrolo[1,2-b][1,2,4]triazole | Single Unknown Stereoisomer | ¹H NMR (400 MHz, DMSO-d6) δ 8.98 (s, 1H), 8.23 (s, 1H), 7.48-7.34 (m, 3H), 7.34-7.26 (m, 2H), 6.28 (ddd, J = 56.5, 7.3, 1.9 Hz, 1H), 5.73 (td, J = 7.9, 3.1 Hz, 1H), 3.83-3.64 (m, 1H), 2.76-2.60 (m, 1H). | 348.1 4.45 min |
| 0.005 Method 47 | 81 | 1-[(5S,7S)-7-fluoro-5-phenyl-6,7-dihydro-5H-pyrrolo[1,2-b][1,2,4]triazol-2-yl]benzotriazole | Single Unknown Stereoisomer | ¹H NMR (400 MHz, DMSO-d₆) δ 8.26-8.13 (m, 2H), 7.75 (ddd, J = 8.3, 7.1, 1.1 Hz, 1H), 7.57 (ddd, J = 8.2, 7.0, 1.1 Hz, 1H), 7.54-7.3.3 (m, 6H), 5.36 (ddd, J = 56.5, 7.2, 2.0 Hz, 1H), 5.82 (td, J = 7.9, 3.0 Hz, 1H), 3.80 (dddd, J = 25.1, 15.4, 8.4, 7.2 Hz, 1H), 2.82-2.66 (m, 1H). | 321.1 5.29 min |
| 0.0092 Method 47 | 82 | 5-chloro-1-[rac-(5S,7S)-7-fluoro-5-phenyl-6,7-dihydro-5H-pyrrolo[1,2-b][1,2,4]triazol-2-yl]benzotriazole | Single Unknown Stereoisomer | ¹H NMR (400 MHz, DMSO-d6) δ 8.48-8.09 (m, 2H), 7.70 (ddd, J = 66.7, 8.8, 1.9 Hz, 1H), 7.51-7.33 (m, 5H), 6.50-6.23 (m, 1H), 5.51-5.74 (m, 1H), 3.79 (dddd, J = 25.3, 15.4, 8.2, 7.1 Hz, 1H), 2.85-2.63 (m, 1H). | 355.1 5.81 min |

TABLE 1-continued

| Ki (μM) METHOD | Ex No. | Structure | Stereo | ¹H NMR | MS (m/z) R.T. |
|---|---|---|---|---|---|
| 0.036 Method 47 | 83 | 3-[(5S,7S)-7-fluoro-5-phenyl-6,7-dihydro-5H-pyrrolo[1,2-b][1,2,4]triazol-2-yl]triazolo[4,5-c]pyridine | Single Unknown Stereoisomer | NO NMR | 322.2 4.27 min |
| 0.029 Method 47 | 84 | 1-[(5S,7S)-7-fluoro-5-phenyl-6,7-dihydro-5H-pyrrolo[1,2-b][1,2,4]triazol-2-yl]pyrazolo[4,3-b]pyridine | Single Unknown Stereoisomer | ¹H NMR (500 MHz, DMSO-d6) δ 8.70 (dd, J = 4.4, 1.3 Hz, 1H), 8.67 (d, J = 0.7 Hz, 1H), 8.61 (dd, J = 8.5, 0.9 Hz, 1H), 7.61 (dd, J = 8.6, 4.4 Hz, 1H), 7.45 (dd, J = 7.9, 6.6 Hz, 2H), 7.42-7.36 (m, 1H), 7.36-7.31 (m, 2H), 6.31 (ddd, J = 56.8, 7.2, 1.7 Hz, 1H), 5.75 (td, J = 8.0, 2.9 Hz, 1H), 3.76 (ddt, J = 25.3, 15.4, 7.4 Hz, 1H), 2.69 (ddt, J = 26.7, 15.1, 2.0 Hz, 1H). | 321.2 4.51 min |
| 0.019 Method 47 | 85 | 1-[rac-(5S,7S)-7-fluoro-5-phenyl-6,7-dihydro-5H-pyrrolo[1,2-b][1,2,4]triazol-2-yl]benzotriazole-5-carbonitrile | Single Unknown Stereoisomer | NO NMR | 346.1 5.49 min |

TABLE 1-continued

| Ki (μM) METHOD | Ex No. | Structure | Stereo | ¹H NMR | MS (m/z) R.T. |
|---|---|---|---|---|---|
| 0.018 Method 47 | 86 | 1-[rac-(5S,7S)-7-fluoro-5-phenyl-6,7-dihydro-5H-pyrrolo[1,2-b][1,2,4]triazol-2-yl]-4,5,6,7-tetrahydrobenzotriazole | Single Unknown Stereoisomer | NO NMR | 325.2 5.16 min |
| 0.16 Method 47 | 87 | 1-[rac-(5S,7S)-7-fluoro-5-phenyl-6,7-dihydro-5H-pyrrolo[1,2-b][1,2,4]triazol-2-yl]pyrazolo[3,4-c]pyridine | Single Unknown Stereoisomer | ¹H NMR (400 MHz, DMSO-$d_6$) δ 9.63 (d, J = 1.1 Hz, 1H), 8.58 (d, J = 0.8 Hz, 1H), 8.46 (d, J = 5.5 Hz, 1H), 7.93 (dd, J = 5.5, 1.3 Hz, 1H), 7.50-7.31 (m, 5H), 6.33 (ddd, J = 56.7, 7.2, 1.9 Hz, 1H), 5.77 (td, J = 8.0, 3.0 Hz, 1H), 3.77 (dddd, J = 25.3, 15.4, 8.3, 7.1 Hz, 1H), 2.71 (dddd, J = 26.7, 15.1, 3.0, 1.9 Hz, 1H). | 321.2 4.02 min |
| 0.045 Method 47 | 88 | 5-methyl-1-[rac-(5S,7S)-7-fluoro-5-phenyl-6,7-dihydro-5H-pyrrolo[1,2-b][1,2,4]triazol-2-yl]benzotriazole | Single Unknown Stereoisomer | ¹H NMR (400 MHz, DMSO-$d_6$) δ 8.08 (dd, J = 10.3, 8.4 Hz, 1H), 7.93 (dq, J = 9.6, 1.2 Hz, 1H), 7.65-7.32 (m, 6H), 6.36 (ddt, J = 56.5, 7.3, 2.0 Hz, 1H), 5.87-5.77 (m, 1H), 3.79 (ddddd, J = 25.0, 15.5, 8.4, 7.2, 1.3 Hz, 1H), 2.82-2.66 (m, 1H), 2.55 (d, J = 0.9 Hz, 3H). | 335.2 5.78 min |

| Ki (μM) METHOD | Ex No. | Structure | Stereo | ¹H NMR | MS (m/z) R.T. |
|---|---|---|---|---|---|
| 0.81 Method 47 | 89 | 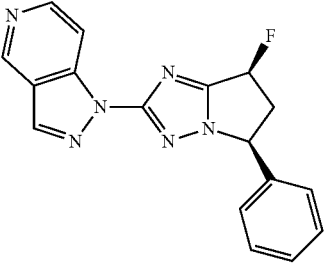<br>1-[(5S,7S)-7-fluoro-5-phenyl-6,7-dihydro-5H-pyrrolo[1,2-b][1,2,4]triazol-2-yl]pyrazolo[4,3-c]pyridine | Single Unknown Stereoisomer | ¹H NMR (400 MHz, DMSO-d6) δ 9.23 (d, J = 1.2 Hz, 1H), 8.65 (d, J = 0.9 Hz, 1H), 8.58 (d, J = 5.9 Hz, 1H), 8.15 (dt, J = 6.0, 1.1 Hz, 1H), 7.51-7.36 (m, 3H), 7.36-7.29 (m, 2H), 6.32 (ddd, J = 56.7, 7.2, 1.9 Hz, 1H), 5.76 (td, J = 7.9, 3.0 Hz, 1H), 3.76 (dddd, J = 25.3, 15.4, 8.4, 7.2 Hz, 1H), 2.84-2.58 (m, 1H). | 321.2 3.13 min |
| 0.055 Method 47 | 90 | 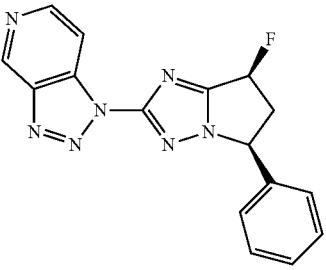<br>1-[(5S,7S)-7-fluoro-5-phenyl-6,7-dihydro-5H-pyrrolo[1,2-b][1,2,4]triazol-2-yl]triazolo[4,5-c]pyridine | Single Unknown Stereoisomer | NO NMR | 322.1 4.36 min |
| 0.013 Method 47 | 91 | 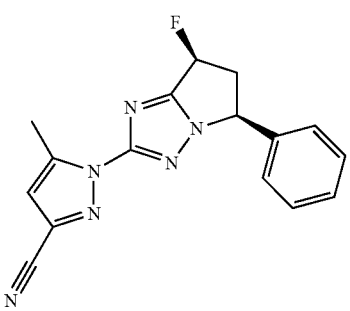<br>1-[(5S,7S)-7-fluoro-5-phenyl-6,7-dihydro-5H-pyrrolo[1,2-b][1,2,4]triazol-2-yl]-5-methyl-pyrazole-3-carbonitrile | Single Unknown Stereoisomer | ¹H NMR (500 MHz, DMSO-d6) δ 7.47-7.41 (m, 2H), 7.41-7.35 (m, 1H), 7.32-7.26 (m, 2H), 7.03 (d, J = 0.8 Hz, 1H), 6.30 (ddd, J = 56.4, 7.2, 1.9 Hz, 1H), 5.76 (td, J = 8.1, 3.0 Hz, 1H), 3.82-3.66 (m, 1H), 2.75-2.63 (m, 1H), 2.47 (d, J = 0.6 Hz, 3H). | 309.1 5.05 min |

TABLE 1-continued

| Ki (μM) METHOD | Ex No. | Structure | Stereo | ¹H NMR | MS (m/z) R.T. |
|---|---|---|---|---|---|
| 0.25 Method 49 | 92 | 1-[(5S,7S)-7-fluoro-5-phenyl-6,7-dihydro-5H-pyrrolo[1,2-b][1,2,4]triazol-2-yl]-3-methyl-pyrazole-4-carbonitrile | Single Unknown Stereoisomer | ¹H NMR (400 MHz, DMSO-d6) δ 9.14 (s, 1H), 7.48-7.34 (m, 3H), 7.33-7.25 (m, 2H), 6.26 (ddd, J = 56.5, 7.2, 2.0 Hz, 1H), 5.69 (td, J = 8.0, 3.1 Hz, 1H), 3.72 (dddd, J = 24.9, 15.5, 8.3, 7.2 Hz, 1H), 2.67 (dddd, J = 27.0, 15.2, 3.1, 2.0 Hz, 1H), 2.36 (s, 3H). | 309.1 4.99 min |
| 0.005 Method 49 | 93 | 1-[(5S,7S)-7-fluoro-5-phenyl-6,7-dihydro-5H-pyrrolo[1,2-b][1,2,4]triazol-2-yl]-5-methyl-pyrazole-4-carbonitrile | Single Unknown Stereoisomer | ¹H NMR (400 MHz, DMSO-d6) δ 8.25 (s, 1H), 7.48-7.34 (m, 3H), 7.33-7.21 (m, 2H), 6.29 (ddd, J = 56.4, 7.2, 2.0 Hz, 1H), 5.75 (ddd, J = 8.3, 7.2, 3.1 Hz, 1H), 3.73 (dddd, J = 25.2, 15.4, 8.4, 7.2 Hz, 1H), 2.76-2.61 (m, 1H), 2.59 (s, 3H) | 309.1 4.91 min |
| 0.016 Method 34 | 94 | (5S,7S)-2-(cyclobutylmethyl)-7-fluoro-5-phenyl-6,7-dihydro-5H-pyrrolo[1,2-b][1,2,4]triazole | Single Known Stereoisomer | 1H NMR (400 MHz, DMSO-d6) δ 7.50-7.29 (m, 3H), 7.25-7.10 (m, 2H), 6.09 (ddd, J = 57.1, 7.1, 1.7 Hz, 1H), 5.54 (ddd, J = 8.4, 7.1, 2.8 Hz, 1H), 4.09 (d, J = 5.4 Hz, 1H), 3.64 (dddd, J = 26.7, 15.3, 8.4, 7.0 Hz, 1H), 3.17 (d, J = 4.0 Hz, 1H), 2.78-2.55 (m, 3H), 2.05-1.96 (m, 1H), 1.88-1.62 (m, 3H), 1.06 (t, J = 6.4 Hz, 1H), | 272.1 5.08 min |
| 0.039 Method 51 | 95 | (5S,7S)-7-fluoro-5-phenyl-2-[rac-(1S,2S)-2-methylcyclopropyl]-6,7-dihydro-5H-pyrrolo[1,2-b][1,2,4]triazole | Single Unknown Stereoisomer | ¹H NMR (400 MHz, CD₃OD) δ 7.44-7.30 (m, 3H), 7.22-7.20 (m, 2H), 6.06-5.87 (m, 1H), 5.47-5.42 (m, 1H), 3.73-3.58 (m, 1H), 2.75-2.60 (m, 1H), 1.73-1.68 (m, 1H), 1.32-1.24 (m, 1H), 1.16 (d, J = 6.0 Hz, 3H), 1.15-1.09 (m, 1H), 0.82-0.74 (m, 1H). | 258.0 0.858 min, |

TABLE 1-continued

| Ki (μM) METHOD | Ex No. | Structure | Stereo | ¹H NMR | MS (m/z) R.T. |
|---|---|---|---|---|---|
| 0.063 Method 51 | 96 | (5S,7S)-7-fluoro-5-phenyl-2-[rac-(1R,2R)-2-methylcyclopropyl]-6,7-dihydro-5H-pyrrolo[1,2-b][1,2,4]triazole | Single Unknown Stereoisomer | ¹H NMR (400 MHz, CD₃OD) δ 7.47-7.30 (m, 3H), 7.25-7.17 (m, 2H), 6.07-5.86 (m, 1H), 5.46-5.42 (m, 1H), 3.74-3.60 (m, 1H), 2.75-2.59 (m, 1H), 1.73-1.68 (m, 1H), 1.34-1.29 (m, 1H), 1.16 (d, J = 6.0 Hz, 3H), 1.12-1.08 (m, 1H), 0.79-0.74 (m, 1H). | 258.0 0.851 min |
| 0.2 Method 52 | 97 | (5S,7S)-7-fluoro-2-(1-methylenepropyl)-5-phenyl-6,7-dihydro-5H-pyrrolo[1,2-b][1,2,4]triazole | Single Unknown Stereoisomer | ¹H NMR (400 MHz, CD₃OD) δ 7.44-7.33 (m, 3H), 7.26-7.22 (m, 2H), 6.15-6.11 (m, 1H), 6.00-5.98 (m, 1H), 5.58-5.50 (m, 1H), 5.32 (s, 1H), 3.79-3.64 (m, 1H), 2.80-2.67 (m, 1H), 2.51 (q, J = 7.6 Hz, 2H), 1.13 (t, J = 7.6 Hz, 3H). | 0.890 min 257.9 |
| 0.19 Method 53 | 98 | (5S)-2-(cyclopropylmethyl)-5-(2-fluorophenyl)-6,7-dihydro-5H-pyrrolo[1,2-b][1,2,4]triazole | Single Unknown Stereoisomer | ¹H NMR (400 MHz, CD₃OD) δ 7.43-7.36 (m, 1H), 7.22-7.12 (m, 2H), 7.12-7.06 (m, 1H), 5.72-5.65 (m, 1H), 3.30-3.22 (m, 1H), 3.14-2.97 (m, 2H), 2.68-2.59 (m, 1H), 2.59-2.55 (m, 2H), 1.14-1.03 (m, 1H), 0.52-0.46 (m, 2H), 0.23-0.18 (m, 2H). | 258.1 0.659 min |
| 0.14 Method 54 | 99 | 4-[(5S,7S)-7-fluoro-5-phenyl-6,7-dihydro-5H-pyrrolo[1,2-b][1,2,4]triazol-2-yl]isoxazole | Single Unknown Stereoisomer | ¹H NMR (400 MHz, CD₃OD) δ 9.20 (s, 1H), 8.82 (s, 1H), 7.44-7.37 (m, 3H), 7.29-7.28 (m, 2H), 6.19-6.01 (m, 1H), 5.61-5.56 (m, 1H), 3.82-3.68 (m, 1H), 2.85-2.72 (m, 1H). | 270.9 0.828 min |

TABLE 1-continued

| Ki (μM) METHOD | Ex No. | Structure | Stereo | ¹H NMR | MS (m/z) R.T. |
|---|---|---|---|---|---|
| 0.25 Method 55 | 100 | 1-[(5S,7S)-7-fluoro-5-phenyl-6,7-dihydro-5H-pyrrolo[1,2-b][1,2,4]triazol-2-yl]azetidine-3-carbonitrile | Single Unknown Stereoisomer | ¹H NMR (400 MHz, CDCl₃) δ 7.42-7.35 (m, 3H), 7.23-7.21 (m, 2H), 5.98-5.81 (m, 1H), 5.30-5.29 (m, 1H), 4.35-4.22 (m, 4H), 3.63-3.51 (m, 2H), 2.81-2.70 (m, 1H). | 283.9 1.852 min |
| 0.009 Method 56 | 101 | (5S,7S)-2-[cyclopropyl(deuterio)methyl]-7-fluoro-5-phenyl-6,7-dihydro-5H-pyrrolo[1,2-b][1,2,4]triazole | Mixture of Diastereomers | ¹H NMR (400 MHz, CDCl₃) δ 7.40-7.35 (m, 3H), 7.23-7.21 (m, 2H), 6.05-6.03 (m, 0.5H), 5.91-5.88 (m, 0.5H), 5.40-5.37 (m, 1H), 3.60-3.54 (m, 1H), 2.89-2.79 (m, 1H), 2.68-2.63 (m, 1H), 1.16-1.13 (m, 1H), 0.56-0.50 (m, 2H), 0.26-0.23 (m, 2H). | 259.2 1.712 min |
| 0.73 Method 57 | 102 | 2-[rac-(5S,7S)-7-fluoro-5-phenyl-6,7-dihydro-5H-pyrrolo[1,2-b][1,2,4]triazol-2-yl]acetonitrile | Mixture of Enantiomers | ¹H NMR (400 MHz, CD₃OD) δ 7.43-7.36 (m, 3H), 7.26-7.23 (m, 2H), 6.13-6.10 (m, 0.5H), 5.99-5.96 (m, 0.5H), 5.56-5.51 (m, 1H), 3.74-3.67 (m, 1H), 3.33-3.32 (m, 2H), 2.81-2.70 (m, 1H), | 243.2 0.870 min |
| 0.22 Method 58 | 103 | 2-methyl-2-[rac-(5S,7S)-7-fluoro-5-phenyl-6,7-dihydro-5H-pyrrolo[1,2-b][1,2,4]triazol-2-yl]propanenitrile | Mixture of Enantiomers | ¹H NMR (400 MHz, CD₃OD) δ 7.42-7.36 (m, 3H), 7.26-7.23 (m, 2H), 6.13-6.10 (m, 0.5H), 5.93-5.96 (m, 0.5H), 5.55-5.51 (m, 1H), 3.74-3.65 (m, 1H), 2.81-2.73 (m, 1H), 1.76 (s, 6H). | 271.2 0.999 min |

TABLE 1-continued

| Ki (μM) METHOD | Ex No. | Structure | Stereo | ¹H NMR | MS (m/z) R.T. |
|---|---|---|---|---|---|
| 0.004 Method 59 | 104 | (5S,7S)-2-[cyclopropyl(difluoro)methyl]-7-fluoro-5-(2-fluorophenyl)-6,7-dihydro-5H-pyrrolo[1,2-b][1,2,4]triazole | Single Unknown Stereoisomer | ¹H NMR (400 MHz, CD₃OD) δ 7.45-7.42 (m, 1H), 7.24-7.21 (m, 2H), 7.11-7.08 (m, 1H), 6.18-6.02 (m, 1H), 5.88-5.75 (m, 1H), 3.83-3.73 (m, 1H), 2.88-2.80 (m, 1H), 1.81-1.75 (m, 1H), 0.75-0.70 (m, 4H). | 312.1 0.809 min |
| 0.35 Method 60 | 105 | (R)-(1-methylcyclopropyl)-[rac-(5S,7S)-7-fluoro-5-phenyl-6,7-dihydro-5H-pyrrolo[1,2-b][1,2,4]triazol-2-yl]methanol | Single Unknown Stereoisomer | ¹H NMR (400 MHz, CDCl₃) δ 7.42-7.36 (m, 3H), 7.21-7.19 (m, 2H), 6.07-5.90 (m, 1H), 5.45-5.41 (m, 1H), 4.30-4.28 (m, 1H), 3.68-3.53 (m, 1H), 2.91-2.76 (m, 2H), 1.07 (s, 3H), 0.82-0.78 (m, 1H), 0.64-0.60 (m, 1H), 0.44-0.37 (m, 2H). | 288.2 0.918 min |
| 0.11 Method 61 | 106 | [(1R,2S)-2-fluorocyclopropyl]-[(5S,7S)-7-fluoro-5-phenyl-6,7-dihydro-5H-pyrrolo[1,2-b][1,2,4]triazol-2-yl]methanol | Mixture of Diastereomers | ¹H NMR (400 MHz, CDCl₃) δ 7.45-7.35 (m, 3H), 7.24-7.21 (m, 2H), 6.10-5.86 (m, 1H), 5.50-5.41 (m, 1H), 4.81-4.44 (m, 2H), 3.71-3.51 (m, 1H), 2.98-2.81 (m, 1H), 2.73-2.57 (m, 1H), 1.99-1.62 (m, 1H), 1.19-1.06 (m, 1H), 0.91-0.84 (m, 1H). | 292.0 0.766 min |

TABLE 1-continued

| Ki (μM) METHOD | Ex No. | Structure | Stereo | ¹H NMR | MS (m/z) R.T. |
|---|---|---|---|---|---|
| 0.0035 Method 62 | 107 | (5S,7S)-7-fluoro-5-phenyl-2-[rac-(R)-cyclopropyl(fluoro)methyl-6,7-dihydro-5H-pyrrolo[1,2-b][1,2,4]triazole | Single Unknown Stereoisomer | ¹H NMR (400 MHz, CDCl₃) δ 7.39-7.34 (m, 3H), 7.23-7.20 (m, 2H), 6.05-5.88 (m, 1H), 5.41-5.37 (m, 1H), 4.86-4.71 (m, 1H), 3.60-3.52 (m, 1H), 2.92-2.81 (m, 1H), 1.65-1.61 (m, 1H), 0.75-0.70 (m, 1H), 0.62-0.57 (m, 2H), 0.45-0.39 (m, 1H). | 276.1 0.764 min |
| 0.12 Method 63 | 108 | [(1S,2R)-2-fluorocyclopropyl]-[(5S,7S)-7-fluoro-5-phenyl-6,7-dihydro-5H-pyrrolo[1,2-b][1,2,4]triazol-2-yl]methanol | Mixture of Diastereomers | ¹H NMR (400 MHz, CDCl₃) δ 7.43-7.33 (m, 3H), 7.25-7.20 (m, 2H), 6.02-5.90 (m, 1H), 5.46-5.34 (m, 1H), 4.79-4.44 (m, 2H), 3.63-3.56 (m, 1H), 2.93-2.82 (m, 1H), 1.86-1.83 (m, 1H), 1.19-1.04 (m, 1H), 0.92-0.78 (m, 1H). | 292.0 0.769 min |
| 0.012 Method 62 | 109 | (5S,7S)-7-fluoro-5-phenyl-2-[rac-(S)-cyclopropyl(fluoro)methyl]-6,7-dihydro-5H-pyrrolo[1,2-b][1,2,4]triazole | Single Unknown Stereoisomer | ¹H NMR (400 MHz, CDCl₃) δ 7.42-7.37 (m, 3H), 7.27-7.23 (m, 2H), 6.08-5.92 (m, 1H), 5.46-5.42 (m, 1H), 4.91-4.76 (m, 1H), 3.69-3.54 (m, 1H), 2.96-2.84 (m, 1H), 1.70-1.67 (m, 1H), 0.79-0.75 (m, 1H), 0.70-0.62 (m, 2H), 0.52-0.45 (m, 1H). | 276.2 1.018 min |

TABLE 1-continued

| Ki (μM) METHOD | Ex No. | Structure | Stereo | ¹H NMR | MS (m/z) R.T. |
|---|---|---|---|---|---|
| 0.0031 Method 64 | 110 | 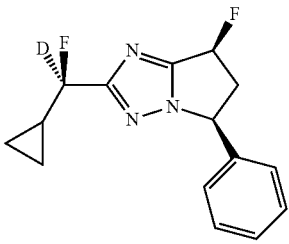<br>(5S,7S)-7-fluoro-5-phenyl-2-[rac-(R)-cyclopropyl-deuterio-fluoro-methyl]-6,7-dihydro-5H-pyrrolo[1,2-b][1,2,4]triazole | Single Unknown Stereoisomer | ¹H NMR (400 MHz, CD₃OD) δ 7.44-7.37 (m, 3H), 7.24-7.22 (m, 2H), 6.14-6.12 (m, 0.5H), 5.99-5.97 (m, 0.5H), 5.55-5.51 (m, 1H), 3.77-3.67 (m, 1H), 2.80-2.69 (m, 1H), 1.59-1.52 (m, 1H), 0.74-0.72 (m, 1H), 0.61-0.56 (m, 2H), 0.39-0.33 (m, 1H). | 277.1 0.762 min |
| 0.0049 Method 64 | 111 | 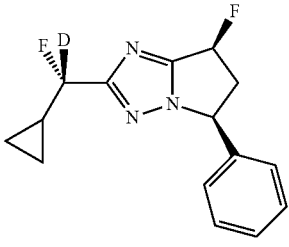<br>(5S,7S)-7-fluoro-5-phenyl-2-[rac-(S)-cyclopropyl-deuterio-fluoro-methyl]-6,7-dihydro-5H-pyrrolo[1,2-b][1,2,4]triazole | Single Unknown Stereoisomer | ¹H NMR (400 MHz, DMSO-d₆) δ 7.44-7.36 (m, 3H), 7.24-7.21 (m, 2H), 6.25-6.24 (m, 0.5H), 6.11-6.09 (m, 0.5H), 5.65-5.62 (m, 1H), 3.77-3.64 (m, 1H), 2.75-2.62 (m, 1H), 1.61-1.58 (m, 1H), 0.74-0.67 (m, 1H), 0.60-0.54 (m, 2H), 0.40-0.37 (m, 1H). | 277.1 0.761 min |
| 0.0045 Method 65 | 112 | 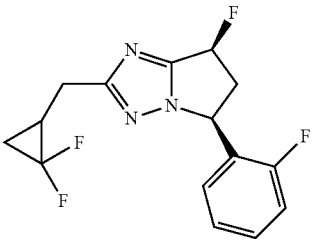<br>(5S,7S)-2-[(2,2-difluorocyclopropyl)methyl]-7-fluoro-5-(2-fluorophenyl)-6,7-dihydro-5H-pyrrolo[1,2-b][1,2,4]triazole | Mixture of Diastereomers | ¹H NMR (400 MHz, CD₃OD) δ 7.47-7.37 (m, 1H), 7.23-7.17 (m, 2H), 7.07-7.02 (m, 1H), 6.15-5.95 (m, 1H), 5.83-5.74 (m, 1H), 3.84-3.66 (m, 1H), 3.05-2.94 (m, 1H), 2.88-2.69 (m, 2H), 2.09-1.94 (m, 1H), 1.54-1.51 (m, 1H), 1.25-1.11 (m, 1H). | 312.1 0.769 min |

TABLE 1-continued

| Ki (μM) METHOD | Ex No. | Structure | Stereo | ¹H NMR | MS (m/z) R.T. |
|---|---|---|---|---|---|
| 0.0048 Method 66 | 113 | (1S,2S)-2-[difluoro-[rac-(5S,7S)-7-fluoro-5-phenyl-6,7-dihydro-5H-pyrrolo[1,2-b][1,2,4]triazol-2-yl]methyl]cyclopropanecarbonitrile | Mixture of Diastereomers | ¹H NMR (400 MHz, CD₃OD) δ 7.44-7.38 (m, 3H), 7.27-7.26 (m, 2H), 6.18-6.15 (m, 0.5H), 6.04-6.01 (m, 0.5H), 5.63-5.60 (m, 1H), 3.80-3.70 (m, 1H), 2.86-2.76 (m, 1H), 2.59-2.57 (m, 1H), 2.08-2.03 (m, 1H), 1.49-1.45 (m, 2H). | 319.1 1.785 min |
| 0.1 Method 67 | 114 | (R)-cyclopropyl-[rac-(4R,6R)-4-fluoro-6-phenyl-5,6-dihydro-4H-pyrrolo[1,2-b]pyrazol-2-yl]methanol | Single Unknown Stereoisomer | ¹H NMR (400 MHz, CDCl₃) δ 7.37-7.31 (m, 3H), 7.19-7.17 (m, 2H), 6.45 (d, J = 2.4 Hz, 1H), 6.04 (d, J = 5.2 Hz, 0.5H), 5.91-5.89 (m, 0.5H), 5.40-5.39 (m, 1H), 4.15-4.11 (m, 1H), 3.51-3.41 (m, 1H), 2.80-2.71 (m, 1H), 2.43 (d, J = 3.6 Hz, 1H), 1.29-1.27 (m, 1H), 0.63-0.56 (m, 2H), 0.48-0.38 (m, 2H). | 273.0 0.816 min |
| 0.081 Method 67 | 115 | (S)-cyclopropyl-[rac-(4R,6R)-4-fluoro-6-phenyl-5,6-dihydro-4H-pyrrolo[1,2-b]pyrazol-2-yl]methanol | Single Unknown Stereoisomer | ¹H NMR (400 MHz, CDCl₃) δ 7.37-7.31 (m, 3H), 7.19-7.17 (m, 2H), 6.45 (d, J = 2.4 Hz, 1H), 6.04 (d, J = 5.2 Hz, 0.5H), 5.91-5.89 (m, 0.5H), 5.41-5.39 (m, 1H), 4.15-4.12 (m, 1H), 3.50-3.41 (m, 1H), 2.81-2.71 (m, 1H), 2.39 (d, J = 3.6 Hz, 1H), 1.29-1.27 (m, 1H), 0.63-0.58 (m, 2H), 0.47-0.39 (m, 2H). | 272.9 0.808 min |
| 0.0073 Method 68 | 116 | (5S,7S)-2-[cyclopropyl(dideuterio)methyl]-7-fluoro-5-phenyl-6,7-dihydro-5H-pyrrolo[1,2-b][1,2,4]triazole | Single Unknown Stereoisomer | ¹H NMR (400 MHz, CD₃OD) δ 7.44-7.33 (m, 3H), 7.24-7.22 (m, 2H), 6.15-5.92 (m, 1H), 5.55-5.44 (m, 1H), 3.78-3.61 (m, 1H), 2.80-2.64 (m, 1H), 1.15-1.03 (m, 1H), 0.53-0.45 (m, 2H), 0.26-0.17 (m, 2H). | 260.2 0.995 min |

TABLE 1-continued

| Ki (μM) METHOD | Ex No. | Structure | Stereo | ¹H NMR | MS (m/z) R.T. |
|---|---|---|---|---|---|
| 0.42 Method 69 | 117 | 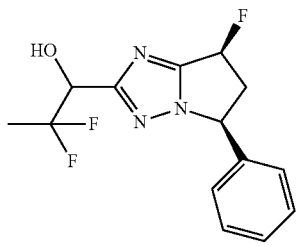<br>2,2-difluoro-1-[rac-(5S,7S)-7-fluoro-5-phenyl-6,7-dihydro-5H-pyrrolo[1,2-b][1,2,4]triazol-2-yl]propan-1-ol | Mixture of Diastereomers | ¹H NMR (400 MHz, CDCl$_3$) δ 7.40-7.36 (m, 3H), 7.23-7.15 (m, 2H), 6.06-5.90 (m, 1H), 5.49-5.37 (m, 1H), 5.00-4.84 (m, 1H), 3.69-3.52 (m, 1H), 3.30-3.13 (m, 1H), 3.00-2.81 (m, 1H), 1.77-1.66 (m, 3H). | 298.1 0.722 min |
| 0.18 Method 70 | 118 | 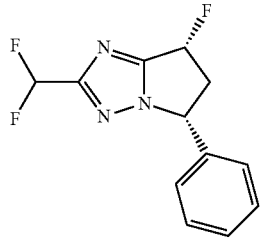<br>(5R,7R)-2-(difluoromethyl)-7-fluoro-5-phenyl-6,7-dihydro-5H-pyrrolo[1,2-b][1,2,4]triazole | Single Unknown Stereoisomer | ¹H NMR (400 MHz, CDCl$_3$) δ 7.43-7.39 (m, 3H), 7.27-7.24 (m, 2H), 6.69 (t, J = 53.6 Hz, 1H), 6.11-5.95 (m, 1H), 5.49-5.45 (m, 1H), 3.70-3.60 (m, 1H), 3.01-2.90 (m, 1H). | 254.1 1.649 min |

All of the U.S. patents, U.S. patent application publications, U.S. patent applications, foreign patents, foreign patent applications and non-patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

We claim:

1. A compound of formula

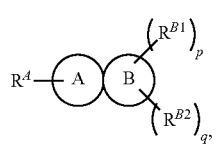

(I)

or a pharmaceutically acceptable salt thereof, wherein:

$R^A$ is selected from the group consisting of:

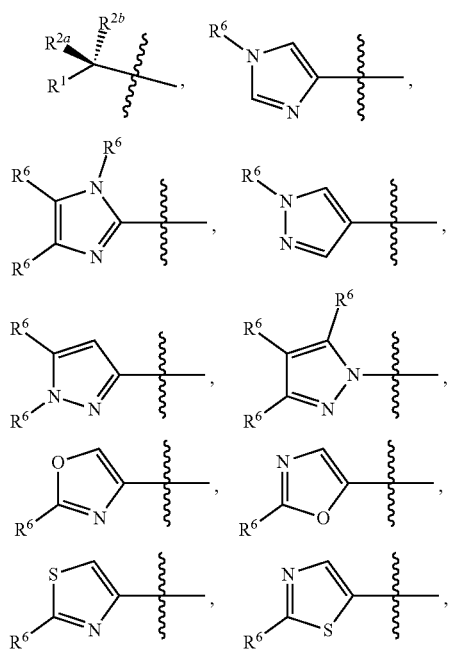

-continued

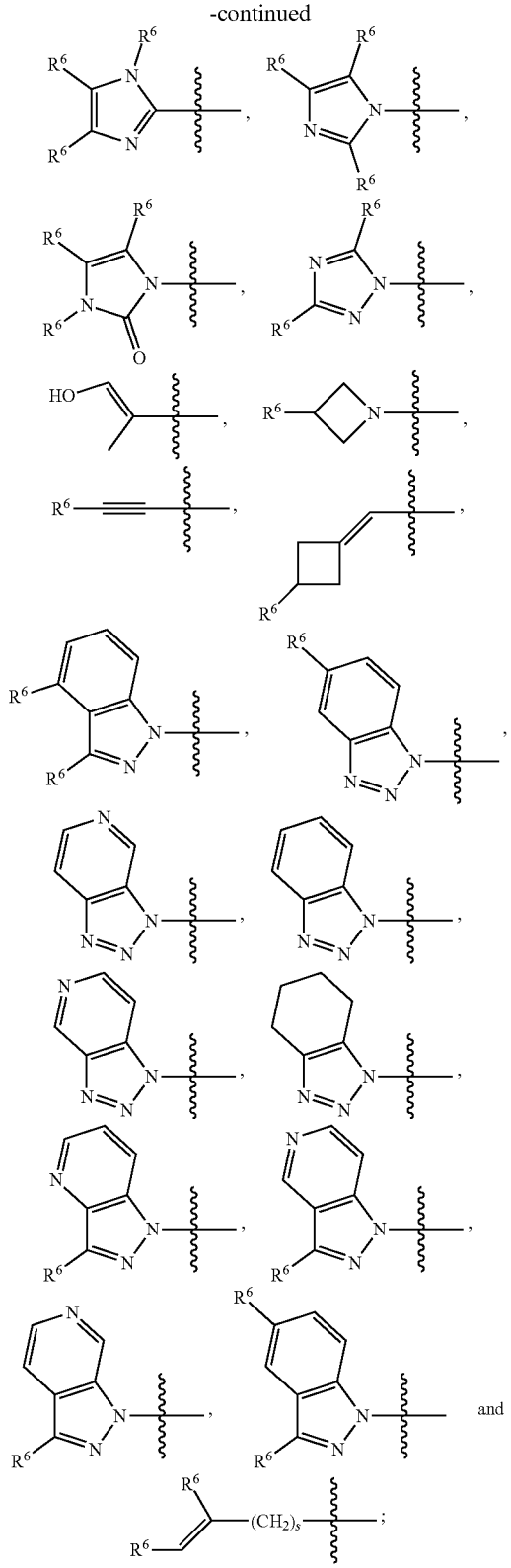

s is 0 or 1;

R$^1$ is selected from the group consisting of hydrogen, deutero, fluoro, hydroxyl, cyano, C$_1$-C$_6$ alkyl, C$_3$-C$_6$ cycloalkyl, C$_1$-C$_6$ alkoxy, C$_1$-C$_6$ haloalkyl, C$_1$-C$_6$ haloalkoxy, C$_1$-C$_6$ alkyl substituted with one (R$^N$)$_2$N substituent, C$_1$-C$_6$ cyanoalkyl, C$_1$-C$_6$ alkylsulfonyl, phenyl, benzyl, 4 to 6 membered heterocyclyl, and 5 to 6 membered heteroaryl;

wherein, when R$^1$ is phenyl, benzyl, C$_1$-C$_6$ alkyl, C$_1$-C$_6$ alkoxy or C$_3$-C$_6$ cycloalkyl, the phenyl, C$_1$-C$_6$ alkoxy or cycloalkyl ring is optionally substituted with 1 to 2 substituents selected from the group consisting of fluoro, chloro, cyano, C$_1$-C$_3$ alkyl, cyclopropyl, C$_1$-C$_3$ alkoxy, C$_1$-C$_3$ hydroxyalkyl, C$_1$-C$_3$ haloalkyl, C$_1$-C$_6$ alkoxycarbonyl, C$_1$-C$_3$ alkoxy-C$_1$-C$_3$ alkyl and C$_1$-C$_3$ haloalkoxy;

R$^{2a}$ and R$^{2b}$ are each independently selected from the group consisting of hydrogen, deutero, fluoro, hydroxyl, C$_1$-C$_3$ alkyl, and C$_1$-C$_3$ fluoroalkyl; provided that both R$^{2a}$ and R$^{2b}$ cannot be hydroxyl; or R$^1$ is selected from the group consisting of hydrogen, deutero, fluoro, methyl, and cyano; and R$^{2a}$ and R$^{2b}$ together with the carbon atom to which they are both attached form a 4 to 6 membered heterocyclic ring or a 3 to 5 membered carbocyclic ring, each optionally substituted by 1 to 2 substituents selected from the group consisting of fluoro, chloro, hydroxyl, cyano, C$_1$-C$_3$ alkyl, hydroxymethyl, methoxymethyl, C$_1$-C$_4$ alkoxycarbonyl, trifluoromethyl, difluoromethoxy, and trifluoromethoxy;

each R$^N$ is independently selected from the group consisting of C$_1$-C$_6$ alkyl, C$_3$-C$_6$ cycloalkyl, C$_1$-C$_6$ alkoxy, and C$_1$-C$_6$ haloalkyl; or two R$^N$ together with the nitrogen atom to which they are both attached form a 4-6 membered heterocyclic ring;

each R$^6$ is independently selected from the group consisting of hydrogen, halogen, C$_1$-C$_6$ alkyl, C$_3$-C$_6$ cycloalkyl, C$_1$-C$_3$ cyanoalkyl, C$_1$-C$_3$ alkylcarbonyl, methylsulfonyl, C$_1$-C$_6$ alkoxy, C$_1$-C$_6$ haloalkyl, formyl, C$_1$-C$_6$ haloalkoxy, cyano, 1-methyl-pyrazol-4-yl and pyrimidinyl;

the A ring, the B ring, R$^{B1}$, R$^{B2}$, q and p together are selected from the group consisting of:

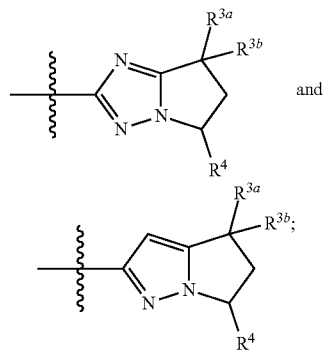

one of R$^{3a}$ and R$^{3b}$ is H, and the other is selected from the group consisting of hydrogen, deutero, fluoro, chloro, hydroxyl, cyano, C$_1$-C$_4$ alkyl, C$_1$-C$_4$ haloalkyl, cyclopropyl, C$_1$-C$_4$ alkoxy and C$_1$-C$_4$ haloalkoxy; or each of R$^{i}$a and R$^{3b}$ is independently selected from the group consisting of deutero, fluoro, chloro, hydroxyl, cyano, and methyl, provided that R$^i$a and R$^{3b}$ cannot both be OH or CN; or R$^{3a}$ and R$^{3b}$, together with the carbon atom to which they are both attached, form 1,1-cyclopropylene; and $R^4$ is selected from the group consisting of $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, phenyl, benzyl, $CH_2$—($C_3$-$C_6$ cycloalkyl), $CH_2CH_2$—($C_3$-$C_6$ cycloalkyl), $CH_2$-(4 to 6 membered heterocyclyl), $CH_2CH_2$-(4 to 6 membered heterocyclyl), 5 to 6 membered heteroaryl, and $CH_2$-(5 to 6 membered heteroaryl); wherein when a phenyl ring is present it may be substituted by 1 to 3 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano;

provided that, when $R^4$ is

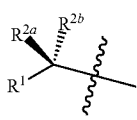

and $R^{2a}$ and $R^{2b}$ are each hydrogen, $R^1$ is not hydrogen, halogen or methyl.

2. The compound of claim 1, or a pharmaceutically acceptable salt thereof, wherein the A ring, the B ring, $R^{B1}$, $R^{B2}$, q and p together are:

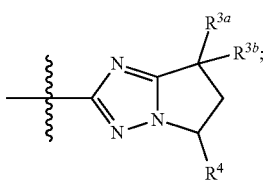

wherein:
one of $R^{3a}$ and $R^{3b}$ is H, and the other is selected from the group consisting of hydrogen, deutero, fluoro, chloro, hydroxyl, cyano, $C_1$-$C_4$ alkyl, $C_1$-$C_4$ haloalkyl, cyclopropyl, $C_1$-$C_4$ alkoxy and $C_1$-$C_4$ haloalkoxy; or each of $R^{3a}$ and $R^{3b}$ is independently selected from the group consisting of deutero, fluoro, chloro, hydroxyl, cyano, and methyl, provided that $R^{3a}$ and $R^{3b}$ cannot both be OH or CN; or $R^{3a}$ and $R^{3b}$, together with the carbon atom to which they are both attached, form 1,1-cyclopropylene; and $R^4$ is selected from the group consisting of $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, phenyl, benzyl, $CH_2$—($C_3$-$C_6$ cycloalkyl), $CH_2CH_2$—($C_3$-$C_6$ cycloalkyl), $CH_2$-(4 to 6 membered heterocyclyl), $CH_2CH_2$-(4 to 6 membered heterocyclyl), 5 to 6 membered heteroaryl, and $CH_2$-(5 to 6 membered heteroaryl); wherein when a phenyl ring is present it may be substituted by 1 to 3 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano.

3. The compound of claim 1, or a pharmaceutically acceptable salt thereof, wherein the A ring, the B ring, $R^{B1}$, $R^{B2}$, q and p together are selected from the group consisting of:

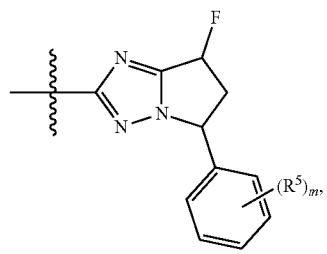

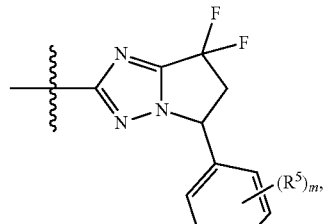

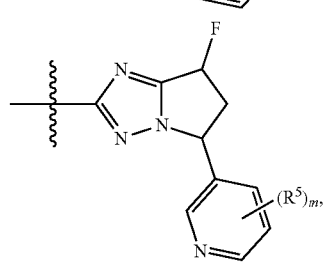

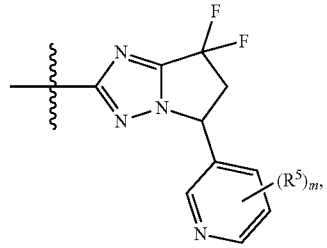

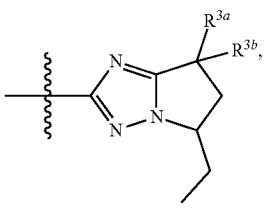 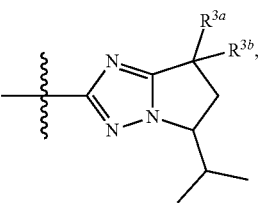

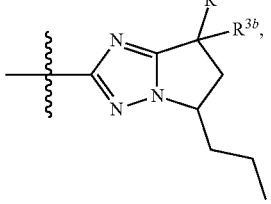 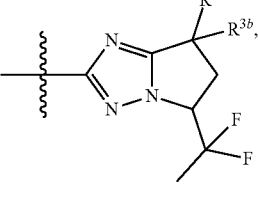

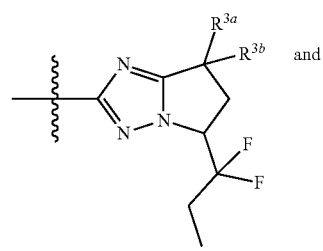

and

-continued

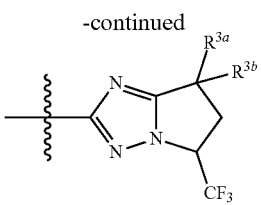

wherein:
one of $R^{3a}$ and $R^{3b}$ is H, and the other is selected from the group consisting of hydrogen, deutero, fluoro, chloro, hydroxyl, cyano, $C_1$-$C_4$ alkyl, $C_1$-$C_4$ haloalkyl, cyclopropyl, $C_1$-$C_4$ alkoxy and $C_1$-$C_4$ haloalkoxy; or
each of $R^{3a}$ and $R^{3b}$ is independently selected from the group consisting of deutero, fluoro, chloro, hydroxyl, cyano, and methyl, provided that $R^{3a}$ and $R^{3b}$ cannot both be OH or CN; or
$R^{3a}$ and $R^{3b}$, together with the carbon atom to which they are both attached, form 1,1-cyclopropylene;
each $R^5$ is independently selected from the group consisting of H, F, Cl, $C_1$-$C_6$ alkyl, $C_1$-$C_6$ haloalkyl, $C_1$-$C_6$ alkoxy, and $C_1$-$C_6$ haloalkoxy; and
m is 0, 1, 2 or 3.

4. The compound of claim 1, or a pharmaceutically acceptable salt thereof, wherein the A ring, the B ring, $R^{B1}$, $R^{B2}$, q and p together are:

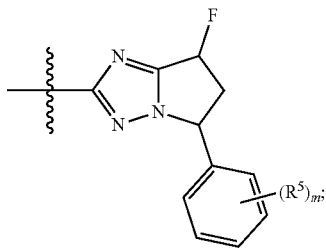

wherein:
each $R^5$ is selected from the group consisting of hydrogen, fluoro, chloro, $C_1$-$C_6$ alkyl, $C_1$-$C_6$ haloalkyl, $C_1$-$C_6$ alkoxy, and $C_1$-$C_6$ haloalkoxy; and
m is 0, 1, 2 or 3.

5. The compound of claim 1, or a pharmaceutically acceptable salt thereof, wherein the A ring, the B ring, $R^{B1}$, $R^{B2}$, q and p together are:

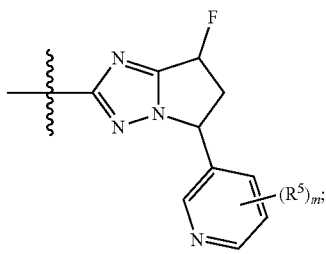

wherein:
each $R^5$ is selected from the group consisting of hydrogen, fluoro, chloro, $C_1$-$C_6$ alkyl, $C_1$-$C_6$ haloalkyl, $C_1$-$C_6$ alkoxy, and $C_1$-$C_6$ haloalkoxy; and
m is 0, 1, 2 or 3.

6. The compound of claim 3, or a pharmaceutically acceptable salt thereof, wherein $R^5$ is selected from the group consisting of H, F, Cl, $CH_3$, $CH_2CH_3$, $OCH_3$, $CF_3$, $OCF_3$, $CF_2H$, and $OCF_2H$.

7. The compound of claim 1, or a pharmaceutically acceptable salt thereof, wherein:
$R^1$ is selected from the group consisting of hydrogen, fluoro, hydroxyl, cyano, $CH_2CN$, $C_1$-$C_7$ alkyl, $C_3$-$C_6$ cycloalkyl, $C_1$-$C_6$ alkoxy, $C_1$-$C_6$ haloalkyl, $C_1$-$C_6$ haloalkoxy, and 4 to 5 membered heterocyclyl; and
$R^{2a}$ and $R^{2b}$ are each independently selected from the group consisting of hydrogen, deutero, fluoro, hydroxyl, $C_1$-$C_3$ alkyl, $C_1$-$C_3$ fluoroalkyl; or
$R^1$ is hydrogen, deutero, fluoro, methyl or cyano, and $R^{2a}$ and $R^{2b}$, together with the carbon atom to which they are both attached, form 1,1-cyclopropylene that is optionally substituted by one or two substituents selected from the group consisting of F, $C_{1-3}$ alkyl, hydroxyl, hydroxymethyl, methoxymethyl, cyano, $CO_2$—$C_{1-3}$ alkyl, trifluoromethyl, difluoromethoxy, and trifluoromethoxy.

8. The compound of claim 1, or a pharmaceutically acceptable salt thereof, wherein $R^A$ is

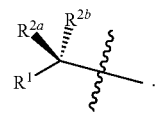

9. The compound of claim 8, or a pharmaceutically acceptable salt thereof, wherein

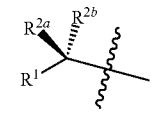

is selected from the group consisting of:

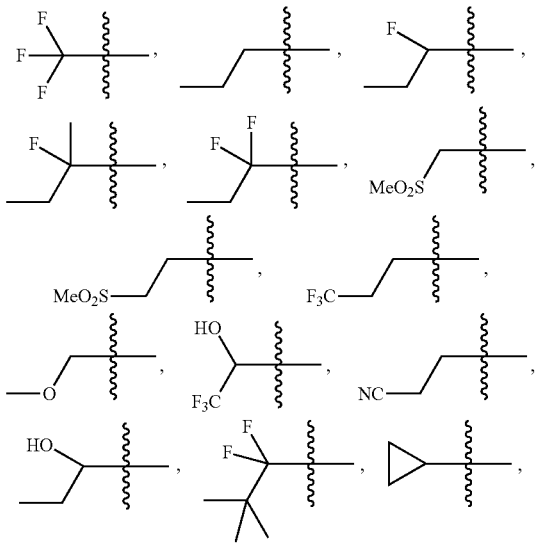

-continued

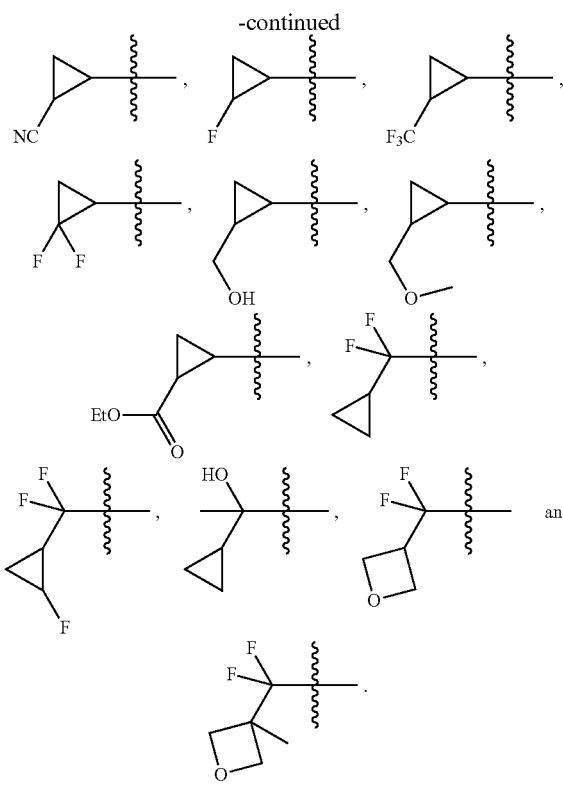

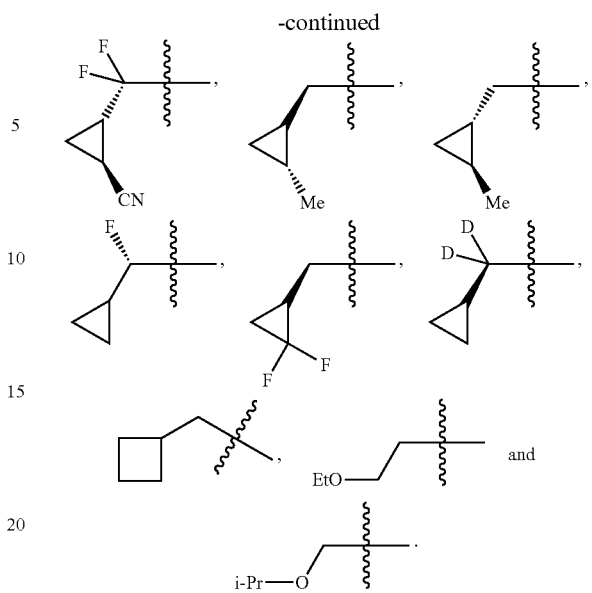

10. The compound of claim 8, or a pharmaceutically acceptable salt thereof, wherein

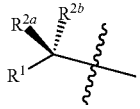

is selected from the group consisting of:

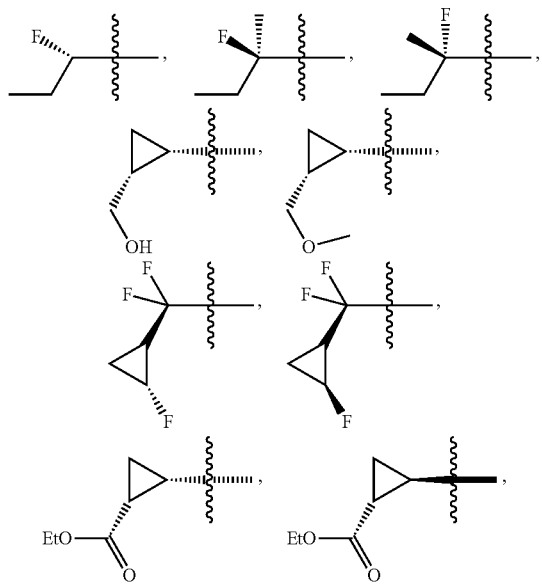

11. The compound of claim 1, or a pharmaceutically acceptable salt thereof, wherein the compound is selected from the group consisting of:

(1S,2S)-2-[difluoro-[rac-(5S,7S)-7-fluoro-5-phenyl-6,7-dihydro-5H-pyrrolo[1,2-b][1,2,4]triazol-2-yl]methyl]cyclopropanecarbonitrile;

(5S,7S)-2-(2-ethoxyethyl)-7-fluoro-5-phenyl-6,7-dihydro-5H-pyrrolo[1,2-b][1,2,4]triazole;

(5S,7S)-7-fluoro-2-(isopropoxymethyl)-5-phenyl-6,7-dihydro-5H-pyrrolo[1,2-b][1,2,4]triazole;

rac-(5S,7S)-2-[(2,2-difluorocyclopropyl)methyl]-7-fluoro-5-(2-fluorophenyl)-6,7-dihydro-5H-pyrrolo[1,2-b][1,2,4]triazole;

(5S,7S)-2-(cyclobutylmethyl)-7-fluoro-5-phenyl-6,7-dihydro-5H-pyrrolo[1,2-b][1,2,4]triazole;

(5S,7S)-7-fluoro-5-phenyl-2-[(S)-cyclopropyl(fluoro)methyl]-6,7-dihydro-5H-pyrrolo[1,2-b][1,2,4]triazole;

(5S,7S)-7-fluoro-5-phenyl-2-[(R)-cyclopropyl(fluoro)methyl]-6,7-dihydro-5H-pyrrolo[1,2-b][1,2,4]triazole;

(5S,7S)-7-fluoro-5-phenyl-2-[(S)-cyclopropyl-deuteriofluoro-methyl]-6,7-dihydro-5H-pyrrolo[1,2-b][1,2,4]triazole;

(5S,7S)-7-fluoro-5-phenyl-2-[(R)-cyclopropyl-deuteriofluoro-methyl]-6,7-dihydro-5H-pyrrolo[1,2-b][1,2,4]triazole;

(5S,7S)-2-[cyclopropyl(difluoro)methyl]-7-fluoro-5-(2-fluorophenyl)-6,7-dihydro-5H-pyrrolo[1,2-b][1,2,4]triazole;

(5S,7S)-2-[cyclopropyl(deuterio)methyl]-7-fluoro-5-phenyl-6,7-dihydro-5H-pyrrolo[1,2-b][1,2,4]triazole;

(5S,7S)-2-[1-bicyclo[1.1.1]pentanyl(difluoro)methyl]-7-fluoro-5-phenyl-6,7-dihydro-5H-pyrrolo[1,2-b][1,2,4]triazole;

(5S,7S)-7-fluoro-5-phenyl-2-[(1S,2S)-2-methylcyclopropyl]-6,7-dihydro-5H-pyrrolo[1,2-b][1,2,4]triazole; and (5S,7S)-7-fluoro-5-phenyl-2-[(1R,2R)-2-methylcyclopropyl]-6,7-dihydro-5H-pyrrolo[1,2-b][1,2,4]triazole.

12. A compound, wherein the compound is a compound of formula (II):

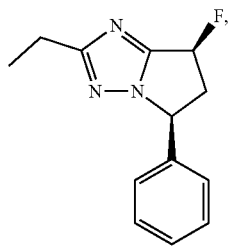

(II)

or pharmacologically acceptable salt thereof.

13. The compound of claim 1, wherein the compound is a compound of formula (III):

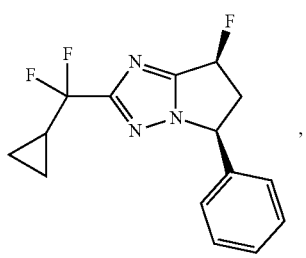

(III)

or pharmacologically acceptable salt thereof.

14. The compound of claim 1, wherein the compound is a compound of formula (IV):

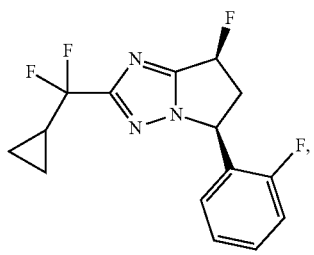

(IV)

or pharmacologically acceptable salt thereof.

15. The compound of claim 1, wherein the compound is a compound of formula (V):

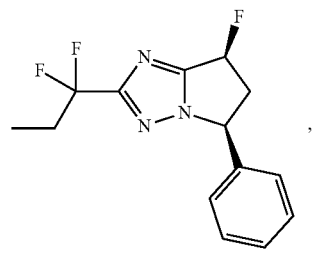

(V)

or pharmacologically acceptable salt thereof.

16. The compound of claim 1, wherein the compound is a compound of formula (VI):

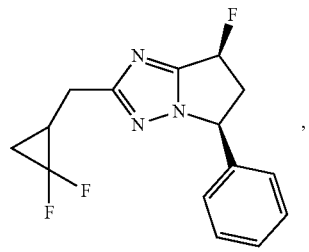

(VI)

or pharmacologically acceptable salt thereof.

17. The compound of claim 1, wherein the compound is a compound of formula (VII):

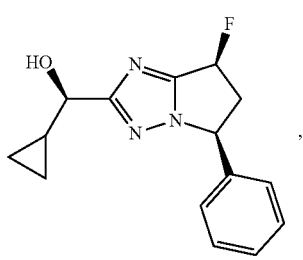

(VII)

or pharmacologically acceptable salt thereof.

18. The compound of claim 1, wherein the compound is a compound of formula (VIII):

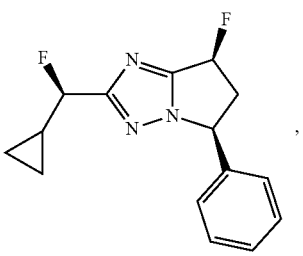

(VIII)

or pharmacologically acceptable salt thereof.

19. The compound of claim 1, wherein the compound is a compound of formula (IX):

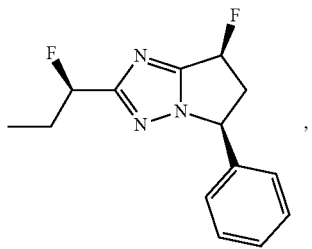

(IX)

or pharmacologically acceptable salt thereof.

20. The compound of claim 1, wherein the compound is a compound of formula (X):

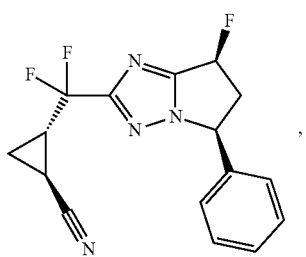

(X)

or pharmacologically acceptable salt thereof.

21. The compound of claim 1, or a pharmaceutically acceptable salt thereof, wherein the compound is selected from the group consisting of:
cis-7-fluoro-5-phenyl-6,7-dihydro-5H-pyrrolo[1,2-b][1,2,4]triazol-2-yl]propan-1-ol;
cis-2-(1,1-difluoropropyl)-7-fluoro-5-phenyl-6,7-dihydro-5H-pyrrolo[1,2-b][1,2,4]triazole;
cis-7-fluoro-2-(1-fluoropropyl)-5-phenyl-6,7-dihydro-5H-pyrrolo[1,2-b][1,2,4]triazole;
cis-2,2,2-trifluoro-1-(7-fluoro-5-phenyl-6,7-dihydro-5H-pyrrolo[1,2-b][1,2,4]triazol-2-yl)ethanol;
cis-2-[cyclopropyl(difluoro)methyl]-7-fluoro-5-phenyl-6,7-dihydro-5H-pyrrolo[1,2-b][1,2,4]triazole;
cis-7-fluoro-2-(1-fluoro-1-methyl-propyl)-5-phenyl-6,7-dihydro-5H-pyrrolo[1,2-b][1,2,4]triazole;
(5S,7S)-7-fluoro-5-phenyl-2-[(1R)-1-fluoropropyl]-6,7-dihydro-5H-pyrrolo[1,2-b][1,2,4]triazole;
(5S,7S)-7-fluoro-2-((S)-1-fluoropropyl)-5-phenyl-6,7-dihydro-5H-pyrrolo[1,2-b][1,2,4]triazole;
cis-2-(1,1-difluoro-2,2-dimethyl-propyl)-7-fluoro-5-phenyl-6,7-dihydro-5H-pyrrolo[1,2-b][1,2,4]triazole;
cis-7-fluoro-5-phenyl-2-propyl-6,7-dihydro-5H-pyrrolo[1,2-b][1,2,4]triazole;
cis-2-cyclopropyl-7-fluoro-5-phenyl-6,7-dihydro-5H-pyrrolo[1,2-b][1,2,4]triazole;
cis-7-fluoro-5-phenyl-2-(trifluoromethyl)-6,7-dihydro-5H-pyrrolo[1,2-b][1,2,4]triazole;
(5S,7S)-2-[cyclopropyl(difluoro)methyl]-7-fluoro-5-phenyl-6,7-dihydro-5H-pyrrolo[1,2-b][1,2,4]triazole;
(5S,7S)-7-fluoro-5-phenyl-2-propyl-6,7-dihydro-5H-pyrrolo[1,2-b][1,2,4]triazole;
(5R,7R)-7-fluoro-5-phenyl-2-(3,3,3-trifluoropropyl)-6,7-dihydro-5H-pyrrolo[1,2-b][1,2,4]triazole;
trans-2-[(5S,7S)-7-fluoro-5-phenyl-6,7-dihydro-5H-pyrrolo[1,2-b][1,2,4]triazol-2-yl]cyclopropanecarbonitrile;
(5S,7S)-2-[difluoro-(3-methyloxetan-3-yl)methyl]-7-fluoro-5-phenyl-6,7-dihydro-5H-pyrrolo[1,2-b][1,2,4]triazole;
(5S,7S)-7-fluoro-5-phenyl-2-(3,3,3-trifluoropropyl)-6,7-dihydro-5H-pyrrolo[1,2-b][1,2,4]triazole;
(5S,7S)-7-fluoro-2-(1-methylpyrazol-3-yl)-5-phenyl-6,7-dihydro-5H-pyrrolo[1,2-b][1,2,4]triazole;
(5S,7S)-2-[(2,2-difluorocyclopropyl)methyl]-7-fluoro-5-phenyl-6,7-dihydro-5H-pyrrolo[1,2-b][1,2,4]triazole;
ethyl rac-(1R,2R)-2-[(5S,7S)-7-fluoro-5-phenyl-6,7-dihydro-5H-pyrrolo[1,2-b][1,2,4]triazol-2-yl]cyclopropanecarboxylate;
3-[(5S,7S)-7-fluoro-5-phenyl-6,7-dihydro-5H-pyrrolo[1,2-b][1,2,4]triazol-2-yl]propanenitrile;
(5S,7S)-2-[difluoro-[rac-(1R,2R)-2-fluorocyclopropyl]methyl]-7-fluoro-5-phenyl-6,7-dihydro-5H-pyrrolo[1,2-b][1,2,4]triazole;
(5S,7S)-7-fluoro-5-phenyl-2-[rac-(1R,2R)-2-(methoxymethyl)cyclopropyl]-6,7-dihydro-5H-pyrrolo[1,2-b][1,2,4]triazole;
(5S,7S)-7-fluoro-2-(4-methylpyrazol-1-yl)-5-phenyl-6,7-dihydro-5H-pyrrolo[1,2-b][1,2,4]triazole;
(5S)-5-(2-fluorophenyl)-2-propyl-6,7-dihydro-5H-pyrrolo[1,2-b][1,2,4]triazole;
(5S,7S)-7-fluoro-2((S)-2-fluorobutan-2-yl)-5-phenyl-6,7-dihydro-5H-pyrrolo[1,2-b][1,2,4]triazole;
(5S,7S)-2-(2,2-difluorocyclopropyl)-7-fluoro-5-phenyl-6,7-dihydro-5H-pyrrolo[1,2-b][1,2,4]triazole;
(5S,7S)-2-(3,3-difluoropropyl)-7-fluoro-5-phenyl-6,7-dihydro-5H-pyrrolo[1,2-b][1,2,4]triazole;
(5S,7S)-2-(2,2-dimethylcyclopropyl)-7-fluoro-5-phenyl-6,7-dihydro-5H-pyrrolo[1,2-b][1,2,4]triazole;
(5S,7S)-7-fluoro-5-phenyl-2-pyrazol-1-yl-6,7-dihydro-5H-pyrrolo[1,2-b][1,2,4]triazole;
(5S,7S)-7-fluoro-2((R)-2-fluorobutan-2-yl)-5-phenyl-6,7-dihydro-5H-pyrrolo[1,2-b][1,2,4]triazole;
(5S,7S)-7-fluoro-5-phenyl-2-[2-(trifluoromethyl)cyclopropyl]-6,7-dihydro-5H-pyrrolo[1,2-b][1,2,4]triazole;
(S)-cyclopropyl-[(5S,7S)-7-fluoro-5-phenyl-6,7-dihydro-5H-pyrrolo[1,2-b][1,2,4]triazol-2-yl]methanol;
(R)-cyclopropyl-[(5S,7S)-7-fluoro-5-phenyl-6,7-dihydro-5H-pyrrolo[1,2-b][1,2,4]triazol-2-yl]methanol;
(5S,7S)-7-fluoro-2-(isopropoxymethyl)-5-phenyl-6,7-dihydro-5H-pyrrolo[1,2-b][1,2,4]triazole;
(5S,7S)-2-(2-ethoxyethyl)-7-fluoro-5-phenyl-6,7-dihydro-5H-pyrrolo[1,2-b][1,2,4]triazole;
(5S,7S)-7-fluoro-2-(4-isopropylpyrazol-1-yl)-5-phenyl-6,7-dihydro-5H-pyrrolo[1,2-b][1,2,4]triazole;
1-[(5S,7S)-7-fluoro-5-phenyl-6,7-dihydro-5H-pyrrolo[1,2-b][1,2,4]triazol-2-yl]pyrazole-4-carbaldehyde;
(5S,7S)-7-fluoro-5-phenyl-2-(4-pyrimidin-4-ylpyrazol-1-yl)-6,7-dihydro-5H-pyrrolo[1,2-b][1,2,4]triazole;
(5S,7S)-2-[1-bicyclo[1.1.1]pentanyl(difluoro)methyl]-7-fluoro-5-phenyl-6,7-dihydro-5H-pyrrolo[1,2-b][1,2,4]triazole;
(5S,7S)-2-(2-cyclopropylethynyl)-7-fluoro-5-phenyl-6,7-dihydro-5H-pyrrolo[1,2-b][1,2,4]triazole;
(5S,7S)-7-fluoro-5-phenyl-2-prop-1-ynyl-6,7-dihydro-5H-pyrrolo[1,2-b][1,2,4]triazole;
(5S,7S)-2-((R)-bicyclo[1.1.1]pentan-1-ylfluoromethyl)-7-fluoro-5-phenyl-6,7-dihydro-5H-pyrrolo[1,2-b][1,2,4]triazole;
(5S,7S)-2((S)-bicyclo[1.1.1]pentan-1-ylfluoromethyl)-7-fluoro-5-phenyl-6,7-dihydro-5H-pyrrolo[1,2-b][1,2,4]triazole;
1-[[(5S,7S)-7-fluoro-5-phenyl-6,7-dihydro-5H-pyrrolo[1,2-b][1,2,4]triazol-2-yl]methyl]cyclopropanecarbonitrile;
2-fluoro-2-[rac-(5S,7S)-7-fluoro-5-phenyl-6,7-dihydro-5H-pyrrolo[1,2-b][1,2,4]triazol-2-yl]acetonitrile;
(5S,7S)-7-fluoro-2- [(E)-2-(1-methylpyrazol-4-yl)vinyl]-5-phenyl-6, 7-dihydro-5H-pyrrolo[1,2-b] [1,2,4]triazole;
(5S,7S)-7-fluoro-5-phenyl-2-vinyl-6,7-dihydro-5H-pyrrolo[1,2-b][1,2,4]triazole;
2-[(rac-(5S,7S)-7-fluoro-5-phenyl-6,7-dihydro-5H-pyrrolo[1,2-b][1,2,4]triazol-2-yl)methoxy]acetonitrile;
(5S,7S)-2-allyl-7-fluoro-5-phenyl-6,7-dihydro-5H-pyrrolo[1,2-b][1,2,4]triazole;
1-[(5S,7S)-7-fluoro-5-phenyl-6,7-dihydro-5H-pyrrolo[1,2-b] [1,2,4]triazol-2-yl]pyrazole-3-carbonitrile;

1-[(5S,7S)-7-fluoro-5-phenyl-6,7-dihydro-5H-pyrrolo[1,2-b][1,2,4]triazol-2-yl]pyrazole-4-carbonitrile;
3-[[(5S,7S)-7-fluoro-5-phenyl-6,7-dihydro-5H-pyrrolo[1,2-b][1,2,4]triazol-2-yl]methylene]cyclobutanecarbonitrile;
(5S,7S)-7-fluoro-5-phenyl-2-[4-(trifluoromethyl)pyrazol-1-yl]-6, 7-dihydro-5H-pyrrolo[1,2-b][1,2,4]triazole;
(5S,7S)-7-fluoro-2-(4-methoxypyrazol-1-yl)-5-phenyl-6,7-dihydro-5H-pyrrolo[1,2-b][1,2,4]triazole;
(5S,7S)-7-fluoro-2-(4-fluoropyrazol-1-yl)-5-phenyl-6,7-dihydro-5H-pyrrolo[1,2-b]-[1,2,4]triazole;
(5S,7S)-2-(4-ethylpyrazol-1-yl)-7-fluoro-5-phenyl-6,7-dihydro-5H-pyrrolo[1,2-b][1,2,4]triazole;
(5S,7S)-2-(4-chloropyrazol-1-yl)-7-fluoro-5-phenyl-6,7-dihydro-5H-pyrrolo[1,2-b][1,2,4]triazole;
(5S,7S)-7-fluoro-2-(1-methylimidazol-2-yl)-5-phenyl-6,7-dihydro-5H-pyrrolo[1,2-b][1,2,4]triazole;
(5S,7S)-7-fluoro-5-phenyl-2-[4-(trifluoromethyl)imidazo]-1-yl]-6, 7-dihydro-5H-pyrrolo[1,2-b] [1,2,4]triazole;
(5S,7S)-7-fluoro-2-(5-methylpyrazol-1-yl)-5-phenyl-6,7-dihydro-5H-pyrrolo[1,2-b][1,2,4]triazole;
(5S,7S)-7-fluoro-5-phenyl-2-[3-(trifluoromethyl)pyrazol-1-yl]-6, 7-dihydro-5H-pyrrolo[1,2-b] [1,2,4]triazole;
5-amino-1-[(5S,7S)-7-fluoro-5-phenyl-6,7-dihydro-5H-pyrrolo[1,2-b][1,2,4]triazol-2-yl]-3-methyl-pyrazole-4-carbonitrile;
(5S,7S)-7-fluoro-2-imidazol-1-yl-5-phenyl-6,7-dihydro-5H-pyrrolo[1,2-b] [1,2,4]triazole;
(5S,7S)-7-fluoro-2-(2-methylimidazol-1-yl)-5-phenyl-6, 7-dihydro-5H-pyrrolo[1,2-b][1,2,4]triazole;
(5S,7S)-7-fluoro-5-phenyl-2-(1,2,4-triazol-1-yl)-6,7-dihydro-5H-pyrrolo[1,2-b][1,2,4]triazole;
(5S,7S)-2-(2-chloroimidazol-1-yl)-7-fluoro-5-phenyl-6, 7-dihydro-5H-pyrrolo[1,2-b][1,2,4]triazole;
(5S,7S)-2-(4, 5-dimethylimidazol-1-yl)-7-fluoro-5-phenyl-6,7-dihydro-5H-pyrrolo[1,2-b][1,2,4]triazole;
1-[(5S,7S)-7-fluoro-5-phenyl-6,7-dihydro-5H-pyrrolo[1,2-b] [1,2,4]triazol-2-yl]-3-methyl-imidazol-2-one;
1-[(5S,7S)-7-fluoro-5-phenyl-6,7-dihydro-5H-pyrrolo[1,2-b][1,2,4]triazol-2-yl]indazole-4-carbonitrile;
1-[(5S,7S)-7-fluoro-5-phenyl-6,7-dihydro-5H-pyrrolo[1,2-b][1,2,4]triazol-2-yl]indazole;
(5S,7S)-2-(4-methyl-1,2,4-triazol-1-yl)-5-phenyl-6,7-dihydro-5H-pyrrolo[1,2-b][1,2,4]triazole;
(5S,7S)-2-(4-chloroimidazol-1-yl)-7-fluoro-5-phenyl-6,7-dihydro-5H-pyrrolo[1,2-b][1,2,4]triazole;
(5S,7S)-7-fluoro-2-(4-fluoroimidazol-1-yl)-5-phenyl-6, 7-dihydro-5H-pyrrolo[1,2-b][1,2,4]triazole;
2-[1-[(5S,7S)-7-fluoro-5-phenyl-6,7-dihydro-5H-pyrrolo[1,2-b][1,2,4]triazol-2-yl]pyrazol-4-yl]acetonitrile;
1-[1-[(5S,7S)-7-fluoro-5-phenyl-6,7-dihydro-5H-pyrrolo[1,2-b][1,2,4]triazol-2-yl]pyrazol-4-yl]ethanone;
(5S,7S)-2-(4-cyclopropylpyrazol-1-yl)-7-fluoro-5-phenyl-6,7-dihydro-5H-pyrrolo[1,2-b][1,2,4]triazole;
(5S,7S)-7-fluoro-2-(4-methylsulfonylpyrazol-1-yl)-5-phenyl-6,7-dihydro-5H-pyrrolo[1,2-b][1,2,4]triazole;
1-[(5S,7S)-7-fluoro-5-phenyl-6,7-dihydro-5H-pyrrolo[1,2-b][1,2,4]triazol-2-yl]benzotriazole;
5-chloro-1-[rac-(5S,7S)-7-fluoro-5-phenyl-6,7-dihydro-5H-pyrrolo[1,2-b][1,2,4]triazol-2-yl]benzotriazole;
3-[(5S,7S)-7-fluoro-5-phenyl-6,7-dihydro-5H-pyrrolo[1,2-b][1,2,4]triazol-2-yl]triazolo[4,5-c]pyridine;
1-[(5S,7S)-7-fluoro-5-phenyl-6,7-dihydro-5H-pyrrolo[1,2-b][1,2,4]triazol-2-yl]pyrazolo[4,3-b]pyridine;
1-[(5S,7S)-7-fluoro-5-phenyl-6,7-dihydro-5H-pyrrolo[1,2-b][1,2,4]triazol-2-yl]benzotriazole-5-carbonitrile;
1-[(5S,7S)-7-fluoro-5-phenyl-6,7-dihydro-5H-pyrrolo[1,2-b][1,2,4]triazol-2-yl]-4,5,6,7-tetrahydrobenzotriazole;
1-[(5S,7S)-7-fluoro-5-phenyl-6,7-dihydro-5H-pyrrolo[1,2-b][1,2,4]triazol-2-yl]pyrazolo[3,4-c]pyridine;
5-methyl-1-[(5S,7S)-7-fluoro-5-phenyl-6,7-dihydro-5H-pyrrolo[1,2-b][1,2,4]triazol-2-yl]benzotriazole;
1-[(5S,7S)-7-fluoro-5-phenyl-6,7-dihydro-5H-pyrrolo[1,2-b][1,2,4]triazol-2-yl]pyrazolo[4,3-c]pyridine;
1-[(5S,7S)-7-fluoro-5-phenyl-6,7-dihydro-5H-pyrrolo[1,2-b][1,2,4]triazol-2-yl]triazolo[4,5-c]pyridine;
1-[(5S,7S)-7-fluoro-5-phenyl-6,7-dihydro-5H-pyrrolo[1,2-b][1,2,4]triazol-2-yl]-5-methyl-pyrazole-3-carbonitrile;
1-[(5S,7S)-7-fluoro-5-phenyl-6,7-dihydro-5H-pyrrolo[1,2-b][1,2,4]triazol-2-yl]-3-methyl-pyrazole-4-carbonitrile;
1-[(5S,7S)-7-fluoro-5-phenyl-6,7-dihydro-5H-pyrrolo[1,2-b][1,2,4]triazol-2-yl]-5-methyl-pyrazole-4-carbonitrile;
(5S,7S)-2-(cyclobutylmethyl)-7-fluoro-5-phenyl-6,7-dihydro-5H-pyrrolo[1,2-b][1,2,4]triazole;
(5S,7S)-7-fluoro-5-phenyl-2-[(1S,2S)-2-methylcyclopropyl]-6,7-dihydro-5H-pyrrolo[1,2-b][1,2,4]triazole;
(5S,7S)-7-fluoro-5-phenyl-2-[(1R,2R)-2-methylcyclopropyl]-6,7-dihydro-5H-pyrrolo[1,2-b][1,2,4]triazole;
(5S,7S)-7-fluoro-2-(1-methylenepropyl)-5-phenyl-6,7-dihydro-5H-pyrrolo[1,2-b][1,2,4]triazole;
(5S)-2-(cyclopropylmethyl)-5-(2-fluorophenyl)-6,7-dihydro-5H-pyrrolo[1,2-b][1,2,4]triazole;
4-[(5S,7S)-7-fluoro-5-phenyl-6,7-dihydro-5H-pyrrolo[1,2-b][1,2,4]triazol-2-yl]isoxazole;
1-[(5S,7S)-7-fluoro-5-phenyl-6,7-dihydro-5H-pyrrolo[1,2-b][1,2,4]triazol-2-yl]azetidine-3-carbonitrile;
(5S,7S)-2-[cyclopropyl(deuterio)methyl]-7-fluoro-5-phenyl-6,7-dihydro-5H-pyrrolo[1,2-b][1,2,4]triazole;
2-[rac-(5S,7S)-7-fluoro-5-phenyl-6,7-dihydro-5H-pyrrolo[1,2-b][1,2,4]triazol-2-yl]acetonitrile;
2-methyl-2-[rac-(5S,7S)-7-fluoro-5-phenyl-6,7-dihydro-5H-pyrrolo[1,2-b][1,2,4]triazol-2-yl]propanenitrile;
(5S,7S)-2-[cyclopropyl(difluoro)methyl]-7-fluoro-5-(2-fluorophenyl)-6,7-dihydro-5H-pyrrolo[1,2-b][1,2,4]triazole;
(R)-(1-methylcyclopropyl)-[(5S,7S)-7-fluoro-5-phenyl-6,7-dihydro-5H-pyrrolo[1,2-b][1,2,4]triazol-2-yl]methanol;
[rac-(1R,2S)-2-fluorocyclopropyl]-[rac-(5S,7S)-7-fluoro-5-phenyl-6,7-dihydro-5H-pyrrolo[1,2-b][1,2,4]triazol-2-yl]methanol;
(5S,7S)-7-fluoro-5-phenyl-2-[(R)-cyclopropyl(fluoro)methyl]-6,7-dihydro-5H-pyrrolo[1,2-b][1,2,4]triazole;
[rac-(1S,2R)-2-fluorocyclopropyl]-[rac-(5S,7S)-7-fluoro-5-phenyl-6,7-dihydro-5H-pyrrolo[1,2-b][1,2,4]triazol-2-yl]methanol;
(5S,7S)-7-fluoro-5-phenyl-2-[(S)-cyclopropyl(fluoro)methyl]-6,7-dihydro-5H-pyrrolo[1,2-b][1,2,4]triazole;
(5S,7S)-7-fluoro-5-phenyl-2-[(R)-cyclopropyl-deuterio-fluoro-methyl]-6,7-dihydro-5H-pyrrolo[1,2-b][1,2,4]triazole;
(5S,7S)-7-fluoro-5-phenyl-2-[(S)-cyclopropyl-deuterio-fluoro-methyl]-6,7-dihydro-5H-pyrrolo[1,2-b][1,2,4]triazole;
rac-(5S,7S)-2-[(2,2-difluorocyclopropyl)methyl]-7-fluoro-5-(2-fluorophenyl)-6,7-dihydro-5H-pyrrolo[1,2-b][1,2,4]triazole;

(1S,2S)-2-[difluoro-[rac-(5S,7S)-7-fluoro-5-phenyl-6,7-dihydro-5H-pyrrolo[1,2-b][1,2,4]triazol-2-yl]methyl]cyclopropanecarbonitrile;

(R)-cyclopropyl-[(4R,6R)-4-fluoro-6-phenyl-5,6-dihydro-4H-pyrrolo[1,2-b]pyrazol-2-yl]methanol;

(S)-cyclopropyl-[(4R,6R)-4-fluoro-6-phenyl-5,6-dihydro-4H-pyrrolo[1,2-b]pyrazol-2-yl]methanol;

(5S,7S)-2-[cyclopropyl(dideuterio)methyl]-7-fluoro-5-phenyl-6,7-dihydro-5H-pyrrolo[1,2-b][1,2,4]triazole;

2,2-difluoro-1-[rac-(5S,7S)-7-fluoro-5-phenyl-6,7-dihydro-5H-pyrrolo[1,2-b][1,2,4]triazol-2-yl]propan-1-ol; and (5R,7R)-2-(difluoromethyl)-7-fluoro-5-phenyl-6,7-dihydro-5H-pyrrolo[1,2-b][1,2,4]triazole.

22. A pharmaceutical composition comprising a compound of claim 1, or a pharmaceutically acceptable salt thereof, and a pharmaceutically acceptable carrier.

23. A method for the treatment of a disease or disorder in a human, the method comprising administration to the human of an effective treatment amount of a compound of claim 1, or a pharmaceutically acceptable salt thereof, wherein the disease or disorder is selected from the group consisting of Parkinson's Disease, Lewy body dementia, multiple system atrophy, Parkinson-plus syndromes, tauopathies, Alzheimer's Disease, frontotemporal dementia, amyotrophic lateral sclerosis, spinal muscular atrophy, primary lateral sclerosis, Huntington's disease, ischemia, stroke, intracranial hemorrhage, cerebral hemorrhage, muscular dystrophy, progressive muscular atrophy, pseudobulbar palsy, progressive bulbar palsy, spinal muscular atrophy, inherited muscular atrophy, peripheral neuropathies, progressive supranuclear palsy, corticobasal degeneration and demyelinating disease.

24. The method of claim 23, wherein the disease or disorder is Alzheimer's disease.

25. The method of claim 23, wherein the disease or disorder is multiple sclerosis.

26. The method of claim 23, wherein the disease or disorder is Parkinson's disease.

27. The method of claim 23, wherein the disease or disorder is amyotrophic lateral sclerosis.

28. The method of claim 23, wherein the disease or disorder is Huntington's disease.

29. The method of claim 23, wherein the disease or disorder is spinal muscular atrophy.

* * * * *